United States Patent
Rau et al.

(10) Patent No.: US 10,519,226 B2
(45) Date of Patent: Dec. 31, 2019

(54) VEGF NEUTRALIZING PRODRUGS FOR THE TREATMENT OF OCULAR CONDITIONS

(71) Applicant: Ascendis Pharma Ophthalmology Division A/S, Hellerup (DK)

(72) Inventors: Harald Rau, Dossenheim (DE); Thomas Knappe, Heidelberg (DE); Burkhardt Laufer, Dossenheim (DE); Romy Reimann, Heidelberg (DE); Samuel Weisbrod, Heidelberg (DE); Kennett Sprogøe, Palo Alto, CA (US); Nicola Bisek, Heidelberg (DE); Sebastian Stark, Heidelberg (DE); Tobias Voigt, Bensheim (DE)

(73) Assignee: Ascendis Pharma Opthalmology Division A/S, Hellerup (DK)

( * ) Notice: Subject to any disclaimer, the term of this patent is extended or adjusted under 35 U.S.C. 154(b) by 0 days.

(21) Appl. No.: 14/435,350

(22) PCT Filed: Oct. 8, 2013

(86) PCT No.: PCT/EP2013/070959
§ 371 (c)(1),
(2) Date: Apr. 13, 2015

(87) PCT Pub. No.: WO2014/056923
PCT Pub. Date: Apr. 17, 2014

(65) Prior Publication Data
US 2015/0297740 A1    Oct. 22, 2015

(30) Foreign Application Priority Data

Oct. 11, 2012  (EP) .................................... 12188226

(51) Int. Cl.
| | | |
|---|---|---|
| C07K 16/22 | (2006.01) | |
| A61K 9/00 | (2006.01) | |
| A61K 39/44 | (2006.01) | |
| A61K 45/06 | (2006.01) | |
| A61K 47/60 | (2017.01) | |
| A61K 47/69 | (2017.01) | |

(52) U.S. Cl.
CPC ............ C07K 16/22 (2013.01); A61K 9/0048 (2013.01); A61K 39/44 (2013.01); A61K 45/06 (2013.01); A61K 47/60 (2017.08); A61K 47/6903 (2017.08); A61K 47/6921 (2017.08); C07K 2317/24 (2013.01); C07K 2317/76 (2013.01); C07K 2317/90 (2013.01)

(58) Field of Classification Search
CPC ............... C07K 16/22; C07K 2317/76; A61K 47/6921; A61K 47/6903; A61K 47/60
See application file for complete search history.

(56) References Cited

U.S. PATENT DOCUMENTS

| | | | | |
|---|---|---|---|---|
| 2008/0027371 A1* | 1/2008 | Higuchi | ................ | A61F 9/0017 604/20 |
| 2012/0156259 A1* | 6/2012 | Rau | ....................... | A61K 9/0024 424/400 |
| 2012/0260968 A1 | 10/2012 | Enrile Medina et al. | | |

FOREIGN PATENT DOCUMENTS

| | | |
|---|---|---|
| WO | WO 03/092665 | 11/2003 |
| WO | WO 2005/020972 | 3/2005 |
| WO | WO 2005/099768 | 10/2005 |
| WO | WO 2005/110489 | 11/2005 |
| WO | WO 2006/003014 | 1/2006 |
| WO | WO 2007/016380 | 2/2007 |
| WO | WO 2007/130134 | 11/2007 |
| WO | WO 2009/095479 | 8/2009 |
| WO | WO 2011/012715 | 2/2011 |
| WO | WO 2011/012721 | 2/2011 |
| WO | WO 2011/012755 | 2/2011 |
| WO | WO 2011/089214 | 7/2011 |
| WO | WO 2011/089215 | 7/2011 |
| WO | WO 2011/089216 | 7/2011 |
| WO | WO 2011/123591 | 10/2011 |
| WO | WO 2013/024053 | 2/2013 |
| WO | WO 2013/160340 | 10/2013 |

OTHER PUBLICATIONS

Carrasquillo et al., "Controlled Delivery of the Anti-VEGF Aptamer EYE001 with Poly(lactic-co-glycolic) Acid Microspheres"Invest Ophthalmol VisSci. 2003;44:290-299.*
The CATT research group NEJM 364:30:1897-908.*
The CATT research group NEJM 364:30:1897-908—Protocol that appears in appendix.*
Gude et al., An Accurate Method for the Quantitation of Fmoc-Derivatized Solid Phase Supports, Letters in Peptide Science vol. 9, No. 4 (2002) pp. 203-206.
Carrasquillo K. G. et al.: "Controlled delivery of the anti-VEGF aptamer EYE001with poly(lactic-coglyocolic) acid microspheres", Investigative Ophthalmology & Visual Science, Association for Research in Vision and Ophthalmology, US, vol. 44, No. 1, Jan. 1, 2003, pp. 290-299.
Eugen Barbu et al.: "Hybrid polymeric hydrogels for ocular drug delivery: nanoparticulate systems from copolymers of acrylic acid-functionalized chitosan and Nisopropylacrylamide or 2-hydroxyethyl methacrylate", Nanotechnology, IOP, Bristol, GB, vol. 20, No. 22, Jun. 3, 2009, p. 225108.
Benny O. et al., Broad Spectrum Antiangiogenic Treatment for Ocular Neovascular Diseases. Plos One., vol. 5, No. 9, e12525., Sep. 1, 2010, p. 2.
International Search Report for Application No. PCT/EP2013/070959 dated Nov. 11, 2013.

(Continued)

*Primary Examiner* — Ruixiang Li
(74) *Attorney, Agent, or Firm* — Haug Partners LLP

(57) ABSTRACT

The present invention relates to a pharmaceutical composition comprising one or more pharmaceutically acceptable excipient(s) and a VEGF neutralizing prodrug, which comprises a VEGF neutralizing biologically active moiety, for use in a method for the treatment of one or more ocular conditions.

21 Claims, No Drawings

(56) References Cited

OTHER PUBLICATIONS

Carolyn K. Pan et al., *Comparison of Long-Acting Bevacizumab Formulations in the Treatment of Choroidal Neovascularization in a Rat Model*, 27(3) J. Ocular Pharmacology and Therapeutics 219-224 (Jun. 2011).

Christine Schmucker et al., *A Safety Review and Meta-Analyses of Bevacizumab and Ranibizumab: Off-Label versus Goldstandard*, 7(8) PLos ONE 1-15, www.plosone.org, e42701 (Aug. 2012).

* cited by examiner

VEGF NEUTRALIZING PRODRUGS FOR THE TREATMENT OF OCULAR CONDITIONS

The present application claims priority from PCT Patent Application No. PCT/EP2013/070959 filed on Oct. 8, 2013, which claims priority from European Patent Application No. EP 12188226.0 filed on Oct. 11, 2012, the disclosures of which are incorporated herein by reference in their entirety.

The present invention relates to pharmaceutical compositions for use in a method for the treatment of one or more ocular conditions.

A leading cause of blindness is the inability to sufficiently treat certain diseases of the eye. A major limitation is the lack of suitable options of introducing drugs or therapeutic agents into the eye and maintain these drugs or agents at a therapeutically effective concentration therein for the necessary duration. Systemic administration may not be an ideal solution because, often, unacceptably high levels of systemic dosing are needed to achieve effective intraocular concentrations, with the increased incidence of unacceptable side effects of the drugs. Simple ocular instillation or application is not an acceptable alternative in many cases because the drug may be quickly washed out by tear-action or is depleted from within the eye into the general circulation. Topical eye drop therapy is limited by poor absorption, a need for frequent and/or chronic dosing over periods of days to years, rapid turnover of aqueous humor, production and movement of the tear film and other causes, which may effectively remove therapeutic agents long before therapy has been completed or the proper dose delivered.

Intraocular injections have the advantage that they can provide enhanced bioavailability to a target location (e.g., the retina) of the eye relative to other delivery mechanisms such as topical delivery. However, they also have drawbacks and can present various different complications. For example, intravitreal injections can result in delivery of undesirably high concentrations of therapeutic agent to a target location or elsewhere particularly when the therapeutic agent is relatively soluble. In addition, intraocular injections are highly unpleasant for the patient. Furthermore, as the intraocular injection itself may cause complications, such as endophthalmitis and retinal detachment, it is highly desirable to have the longest possible duration between injections, while retaining therapeutic levels of drug in the eye.

In addition to the above, therapeutic agents delivered by intravitreal injections can lack duration of action since the agents can often rapidly disperse within the eye after injection. Such lack of duration is particularly undesirable since it can necessitate greater injection frequency. Ranibizumab and pegaptanib, for example, are administered to a patient via intraocular injection every 4 and 6 weeks, respectively, which is a highly unpleasant experience for the patient.

Thus, there is widespread recognition that the field of ophthalmology would benefit from longer lasting formulations. They would benefit patient care and ocular health by providing extended delivery of therapeutic agents to the eye while minimizing the problems associated with patient compliance to prescribed therapeutic medical regimens.

Expression of vascular endothelial growth factor (VEGF), a signal protein produced by cells that stimulates vasculogenesis and angiogenesis, plays an important role in various ocular conditions, such as in certain forms of macular degeneration and retinopathies.

Various medicaments to treat such ocular conditions are on the market, such as ranibizumab, aflibercept and pegaptanib. Application to the patient occurs via intraocular injections every 4 and 8 weeks.

In view of the above, there exists a need to provide a form of administration that overcomes these drawbacks at least partially.

This objective is achieved with a pharmaceutical composition comprising one or more pharmaceutically acceptable excipient(s) and a VEGF neutralizing prodrug, the prodrug comprising a covalently bound VEGF neutralizing biologically active moiety, for use in a method for the treatment of one or more ocular conditions.

Within the present invention the terms are used with the meaning as follows.

As used herein, the term "VEGF neutralizing drug" means a drug which exhibits it pharmaceutical effect through neutralizing the effect of vascular endothelial growth factor (VEGF). The effect of VEGF may be neutralized by the drug binding to the VEGF receptor or binding to VEGF itself, thus blocking or reducing effective binding of VEGF to its receptor. Alternatively the neutralizing effect may be obtained by inhibiting or interfering with expression and production of VEGF, or interfering with VEGF signaling.

As used herein, the term "hydrogel" means a hydrophilic or amphiphilic polymeric network composed of homopolymers or copolymers, which is insoluble due to the presence of covalent chemical crosslinks. The crosslinks provide the network structure and physical integrity. Hydrogels exhibit a thermodynamic compatibility with water which allows them to swell in aqueous media.

As used herein, the term "reagent" means a chemical compound which comprises a functional group for reaction with another functional group.

As used herein, the term "backbone reagent" means a reagent, which is suitable as a starting material for forming hydrogels. As used herein, a backbone reagent preferably does not comprise biodegradable bonds.

As used herein, the term "crosslinker reagent" means a linear or branched reagent, which is suitable as a starting material for crosslinking backbone reagents. Preferably, the crosslinker reagent is a linear chemical compound. A crosslinker reagent as used herein comprises at least one biodegradable bond.

As used herein, the term "moiety" means a part of a molecule, which lacks one or more atom(s) compared to the corresponding reagent. If, for example, a reagent of the formula "H—X—H" reacts with another reagent and becomes part of the reaction product, the corresponding moiety of the reaction product has the structure "H—X—" or "—X—", whereas each "—" indicates attachment to another moiety.

Accordingly, the phrase "in bound form" is used to refer to the corresponding moiety of a reagent, i.e. "lysine in bound form" refers to a lysine moiety which lacks one or more atom(s) of the lysine reagent and is part of a molecule.

As used herein, the term "functional group" means a group of atoms which can react with other functional groups. Functional groups include but are not limited to the following groups: carboxylic acid (—(C=O)OH) or an activated form thereof, like a carboxylic ester or acid halide; primary or secondary amine (—NH$_2$, —NH—); maleimide; thiol (—SH); sulfonic acid (—(O=S=O)OH); carbonate; carbamate (—O(C=O)N<); hydroxy (—OH); aldehyde (—(C=O)H); ketone (—(C=O)—); hydrazine (>N—N<); isocyanate; isothiocyanate; phosphoric acid (—O(P=O)

OHOH); phosphonic acid (—O(P=O)OHH); haloacetyl; alkyl halide; acryloyl; aryl fluoride; hydroxylamine; disulfide; vinyl sulfone; vinyl ketone; diazoalkane; oxirane; and aziridine.

If a functional group is coupled to another functional group, the resulting structure is referred to as "linkage". For example, the reaction of an amine group with a carboxyl group results in an amide linkage.

As used herein, the term "activated functional group" means a functional group, which is connected to an activating group. Preferred activated functional groups include but are not limited to activated ester groups, activated carbamate groups, activated carbonate groups and thiocarbonate groups.

As used herein, the term "capping group" means a moiety which is irreversibly, i.e. permanently, connected to a functional group to render it incapable of reacting with functional groups of other reagents or moieties.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. It is understood that a polymer may for example also comprise functional groups or capping moieties. Preferably, a polymer has a molecular weight of at least 0.5 kDa, e.g. a molecular weight of at least 1 kDa, a molecular weight of at least 2 kDa, a molecular weight of at least 3 kDa or a molecular weight of at least 5 kDa.

As used herein, the term "polymeric" means a reagent or a moiety comprising one or more polymer(s).

As used herein, the term "number average molecular weight" means the ordinary arithmetic mean of the molecular weights of the individual polymers. The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers.

As used herein, the term "polymerization" means the process of reacting monomer or macromonomer reagents in a chemical reaction to form polymer chains or networks, including but not limited to hydrogels.

As used herein, the term "macromonomer" means a molecule that was obtained from the polymerization of monomer reagents.

As used herein, the term "condensation polymerization" or "condensation reaction" means a chemical reaction, in which the functional groups of two reagents react to form one single molecule, the reaction product, and a low molecular weight molecule, for example water, is released.

As used herein, the term "suspension polymerization" means a heterogeneous and/or biphasic polymerization reaction, wherein the monomer reagents are dissolved in solvent A, forming the disperse phase which is emulsified in solvent B, forming the continuous phase. In the present invention, the monomer reagents are the backbone reagent and the crosslinker reagent. Both solvent A and the monomer reagents are not soluble in solvent B. Such emulsion is formed by stirring, shaking, exposure to ultrasound or Microsieve™ emulsification, more preferably by stirring or Microsieve™ emulsification and more preferably by stirring. This emulsion is stabilized by an appropriate emulsifier. The polymerization is initiated by addition of an initiator which is soluble in solvent A. A suitable commonly known initiator may be a tertiary base, such as tetramethylethylenediamine (TMEDA).

As used herein, the term "inert" refers to a moiety which is not chemically reactive, i.e. it does not react with other moieties or reagents. The person skilled in the art understands that the term "inert" does not per se exclude the presence of functional groups, but understands that the functional groups potentially present in an inert moiety are not reactive with functional groups of moieties/reagents brought in contact with the inert moiety in, for example, subsequent reactions. In particular, the inert moiety Z does not react with $A^{x0}$ or $A^{x2}$ or with functional groups present, for example, in reversible prodrug linker reagents, drugs, reversible prodrug linker moiety-biologically active moiety conjugate reagents or spacer reagents which may be covalently conjugated to the hydrogel of the present invention to obtain the hydrogel-linked prodrug of the present invention.

As used herein, the term "immiscible" means the property where two substances are not capable of combining to form a homogeneous mixture.

As used herein, the term "polyamine" means a reagent or moiety comprising more than one amine group (—NH— or —NH$_2$), e.g. from 2 to 64 amine groups, from 4 to 48 amine groups, from 6 to 32 amine groups, from 8 to 24 amine groups, from 10 to 16 amine groups. Particularly preferred polyamines comprise from 2 to 32 amine groups.

As used herein, the term "PEG-based comprising at least X % PEG" in relation to a moiety or reagent means that said moiety or reagent comprises at least X % (w/w) ethylene glycol units (—CH$_2$CH$_2$O—), wherein the ethylene glycol units may be arranged blockwise, alternating or may be randomly distributed within the moiety or reagent and preferably all ethylene glycol units of said moiety or reagent are present in one block; the remaining weight percentage of the PEG-based moiety or reagent are other moieties especially selected from the following substituents and linkages:

$C_{1-50}$ alkyl, $C_{2-50}$ alkenyl, $C_{2-50}$ alkynyl, $C_{3-10}$ cycloalkyl, 4- to 7-membered heterocyclyl, 8- to 11-membered heterobicyclyl, phenyl; naphthyl; indenyl; indanyl; and tetralinyl; and linkages selected from the group comprising

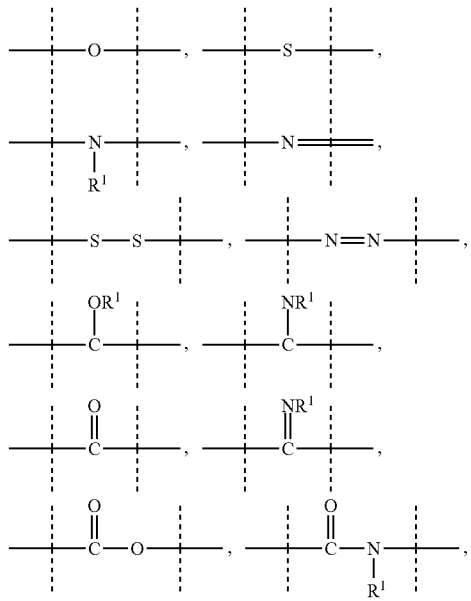

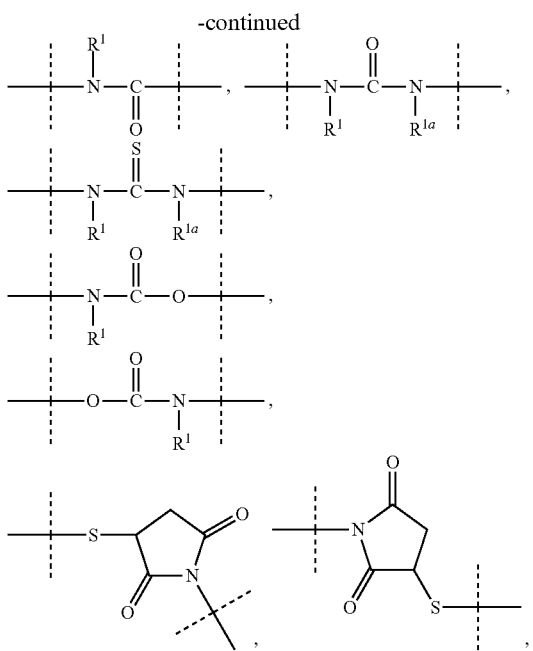

wherein
dashed lines indicate attachment to the remainder of the molecule, moiety or reagent, and
$R^1$ and $R^{1a}$ are independently of each other selected from H and $C_{1-6}$ alkyl.

As used herein, the term "$C_{1-4}$ alkyl" alone or in combination means a straight-chain or branched alkyl group having 1 to 4 carbon atoms. If present at the end of a molecule, examples of straight-chain and branched $C_{1-4}$ alkyl groups are methyl, ethyl, n-propyl, isopropyl, n-butyl, isobutyl, sec-butyl and tert-butyl. When two moieties of a molecule are linked by the $C_{1-4}$ alkyl group, then examples for such $C_{1-4}$ alkyl groups are —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, —$CH_2$—$CH_2$—$CH_2$—$CH_2$—, and —$CH_2$—$CH_2$—$CH_2(CH_3)$—. Each hydrogen atom of a $C_{1-4}$ alkyl group may be replaced by a substituent as defined below.

As used herein, the term "$C_{1-6}$ alkyl" alone or in combination means a straight-chain or branched alkyl group having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such C1-6 alkyl groups are —$CH_2$—, —$CH_2$—$CH_2$—, —$CH(CH_3)$—, —$CH_2$—$CH_2$—$CH_2$—, —$CH(C_2H_5)$— and —$C(CH_3)_2$—. Each hydrogen atom of a $C_{1-6}$ alkyl group may be replaced by a substituent as defined below.

Accordingly, as used herein, the term "$C_{1-20}$ alkyl" alone or in combination means a straight-chain or branched alkyl group having 1 to 20 carbon atoms. The term "$C_{8-18}$ alkyl" alone or in combination means a straight-chain or branched alkyl group having 8 to 18 carbon atoms. Accordingly, as used herein, the term "$C_{1-50}$ alkyl" alone or in combination means a straight-chain or branched alkyl group having 1 to 50 carbon atoms. Each hydrogen atom of a $C_{1-20}$ alkyl group, a $C_{8-18}$ alkyl group and $C_{1-50}$ alkyl group may be replaced by a substituent. In each case the alkyl group may be present at the end of a molecule or two moieties of a molecule may be linked by the alkyl group.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are —CH=$CH_2$, —CH=CH—$CH_3$, —$CH_2$—CH=$CH_2$, —CH=CH$CH_2$—$CH_3$ and —CH=CH—CH=$CH_2$. When two moieties of a molecule are linked by the $C_{2-6}$ alkenyl group, then an example for such $C_{2-6}$ alkenyl is —CH=CH—. Each hydrogen atom of a $C_{2-6}$ alkenyl group may be replaced by a substituent as defined below. Optionally, one or more triple bond(s) may occur.

Accordingly, as used herein, the term "$C_{2-20}$ alkenyl" alone or in combination means a straight-chain or branched hydrocarbon residue comprising at least one carbon-carbon double bond having 2 to 20 carbon atoms. The term "$C_{2-50}$ alkenyl" alone or in combination means a straight-chain or branched hydrocarbon residue comprising at least one carbon-carbon double bond having 2 to 50 carbon atoms. If present at the end of a molecule, examples are —CH=$CH_2$, —CH=CH—$CH_3$, —$CH_2$—CH=$CH_2$, —CH=CH$CH_2$—$CH_3$ and —CH=CH—CH=$CH_2$. When two moieties of a molecule are linked by the alkenyl group, then an example is e.g. —CH=CH—. Each hydrogen atom of a $C_{2-20}$ alkenyl or $C_{2-50}$ alkenyl group may be replaced by a substituent as defined below. Optionally, one or more triple bond(s) may occur.

As used herein, the term "$C_{2-6}$ alkynyl" alone or in combination means straight-chain or branched hydrocarbon residue comprising at least one carbon-carbon triple bond having 2 to 6 carbon atoms. If present at the end of a molecule, examples are —C≡CH, —$CH_2$—C≡CH, $CH_2$—$CH_2$—C≡CH and $CH_2$—C≡C—$CH_3$. When two moieties of a molecule are linked by the alkynyl group, then an example is: —C≡C—. Each hydrogen atom of a $C_{2-6}$ alkynyl group may be replaced by a substituent as defined below. Optionally, one or more double bond(s) may occur.

Accordingly, as used herein, the term "$C_{2-20}$ alkynyl" alone or in combination means a straight-chain or branched hydrocarbon residue comprising at least one carbon-carbon triple bond having 2 to 20 carbon atoms and "$C_{2-50}$ alkynyl" alone or in combination means a straight-chain or branched hydrocarbon residue comprising at least one carbon-carbon triple bond having 2 to 50 carbon atoms. If present at the end of a molecule, examples are —C≡CH, —$CH_2$—C≡CH, $CH_2$—$CH_2$—C≡CH and $CH_2$—C≡C—$CH_3$. When two moieties of a molecule are linked by the alkynyl group, then an example is —C≡C—. Each hydrogen atom of a $C_{2-20}$ alkynyl or $C_{2-50}$ alkynyl group may be replaced by a substituent as defined below. Optionally, one or more double bond(s) may occur.

As used herein, the terms "$C_{3-7}$ cycloalkyl" or "$C_{3-7}$ cycloalkyl ring" means a cyclic alkyl chain having 3 to 7 carbon atoms, which may be saturated or unsaturated, e.g. cyclopropyl, cyclobutyl, cyclopentyl, cyclohexyl, cyclohexenyl, cycloheptyl. Each hydrogen atom of a cycloalkyl carbon may be replaced by a substituent as defined below. The term "$C_{3-7}$ cycloalkyl" or "$C_{3-7}$ cycloalkyl ring" also includes bridged bicycles like norbonane or norbonene. Accordingly, "$C_{3-5}$ cycloalkyl" means a cycloalkyl having 3 to 5 carbon atoms and $C_{3-10}$ cycloalkyl having 3 to 10 carbon atoms.

Accordingly, as used herein, the term "$C_{3-10}$ cycloalkyl" means a carbocyclic ring system having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl, cyclodecyl. The term "$C_{3-10}$ cycloalkyl" also includes at least partially saturated carbomono- and -bicycles.

As used herein, the term "halogen" means fluoro, chloro, bromo or iodo. Particularly preferred is fluoro or chloro.

As used herein, the term "4- to 7-membered heterocyclyl" or "4- to 7-membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 4- to 7-membered heterocycles include but are not limited to azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 4- to 7-membered heterocyclyl or 4- to 7-membered heterocyclic group may be replaced by a substituent as defined below.

As used herein, the term "8- to 11-membered heterobicyclyl" or "8- to 11-membered heterobicycle" means a heterocyclic system of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

The term "substituted" means that one or more H atom(s) of a molecule are replaced by a different atom or a group of atoms, which are referred to as "substituent" or "substituents". Suitable substituents are selected from the group consisting of halogen; CN; COOR$^9$; OR$^9$; C(O)R$^9$; C(O)N(R$^9$R$^{9a}$); S(O)$_2$N(R$^9$R$^{9a}$); S(O)N(R$^9$R$^{9a}$); S(O)$_2$R$^9$; S(O)R$^9$; N(R$^9$)S(O)$_2$N(R$^{9a}$R$^{9b}$); SR$^9$; N(R$^9$R$^{9a}$); NO$_2$; OC(O)R$^9$; N(R$^9$)C(O)R$^{9a}$; N(R$^9$)S(O)$_2$R$^{9a}$; N(R$^9$)S(O)R$^{9a}$; N(R$^9$)C(O) OR$^{9a}$; N(R$^9$)C(O)N(R$^{9a}$R$^{9b}$); OC(O)N(R$^9$R$^{9a}$); T; C$_{1-50}$ alkyl; C$_{2-50}$ alkenyl; or C$_{2-50}$ alkynyl, wherein T; C$_{1-50}$ alkyl; C$_{2-50}$ alkenyl; and C$_{2-50}$ alkynyl are optionally substituted with one or more R$^{10}$, which are the same or different and wherein C$_{1-50}$ alkyl; C$_2$-50 alkenyl; and C$_{2-50}$ alkynyl are optionally interrupted by one or more group(s) selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

wherein

R$^9$, R$^{9a}$, R$^{9b}$ are independently selected from the group consisting of H; T; and C$_{1-50}$ alkyl; C$_{2-50}$ alkenyl; or C$_{2-50}$ alkynyl, wherein T; C$_{1-50}$ alkyl; C$_{2-50}$ alkenyl; and C$_{2-50}$ alkynyl are optionally substituted with one or more R$^{10}$, which are the same or different and wherein C$_{1-50}$ alkyl; C$_{2-50}$ alkenyl; and C$_{2-50}$ alkynyl are optionally interrupted by one or more group(s) selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

T is selected from the group consisting of phenyl; naphthyl; indenyl; indanyl; tetralinyl; C$_{3-10}$ cycloalkyl; 4 to 7 membered heterocyclyl; or 8- to 11-membered heterobicyclyl, wherein T is optionally substituted with one or more R$^{10}$, which are the same or different;

R$^{10}$ is halogen; CN; oxo (=O); COOR$^{12}$; OR$^{12}$; C(O)R$^{12}$; C(O)N(R$^{12}$R$^{12a}$); S(O)$_2$N(R$^{12}$R$^{12a}$); S(O)N(R$^{12}$R$^{12a}$); S(O)$_2$R$^{12}$; S(O)R$^{12}$; N(R$^{12}$)S(O)$_2$N(R$^{12a}$R$^{12b}$); SR$^{12}$; N(R$^{12}$R$^{12a}$), NO$_2$; OC(O)R$^{12}$; N(R$^{12}$)C(O)R$^{12a}$; N(R$^{12}$)S(O)$_2$R$^{12a}$; N(R$^{12}$)S(O)R$^{12a}$; N(R$^{12}$)C(O) (OR$^{12a}$; N(R$^{12}$)C(O)N(R$^{12a}$R$^{12b}$); OC(O)N(R$^{12}$R$^{12a}$); or C$_{1-6}$ alkyl, wherein C$_{1-6}$ alkyl is optionally substituted with one or more halogen, which are the same or different;

R$^{11}$, R$^{11a}$, R$^{12}$, R$^{12a}$, R$^{12b}$ are independently selected from the group consisting of H; or C$_{1-6}$ alkyl, wherein C$_{1-6}$ alkyl is optionally substituted with one or more halogen, which are the same or different.

In one embodiment R$^9$, R$^{9a}$, R$^{9b}$ may be independently of each other H.

In one embodiment R$^{10}$ is C$_{1-6}$ alkyl.

In one embodiment T is phenyl.

As used herein, the term "interrupted" means that between two carbon atoms or at the end of a carbon chain between the respective carbon atom and the hydrogen atom one or more atom(s) are inserted.

As used herein, the term "prodrug" means a compound that undergoes biotransformation before exhibiting its pharmacological effects. Prodrugs can thus be viewed as biologically active moieties connected to specialized non-toxic protective groups used in a transient manner to alter or to eliminate undesirable properties in the parent molecule. This also includes the enhancement of desirable properties in the drug and the suppression of undesirable properties.

As used herein, the term "carrier-linked prodrug" means a prodrug that contains a temporary linkage of a biologically active moiety with a transient carrier group that produces improved physicochemical or pharmacokinetic properties and that can be easily removed in vivo, usually by a hydrolytic cleavage. Upon administration of such carrier-linked prodrugs to a mammal, preferably to a human, drug molecules are released. Accordingly, a carrier-linked prodrug comprises a biologically active moiety, a reversible prodrug linker moiety and a carrier group, wherein the biologically active moiety is reversibly connected to the carrier group through a reversible prodrug linker. It is understood that the biologically active moiety is reversibly and covalently linked to the reversible prodrug linker which reversible prodrug linker is covalently linked to the carrier group. Preferably, the linkage between the reversible prodrug linker and the carrier group is a stable covalent linkage.

As used herein, the term "reversible prodrug linker moiety" means a moiety which on its one end is attached to a biologically active moiety D, i.e. a VEGF neutralizing biologically active moiety, through a reversible linkage and on another end is attached through a permanent bond to a carrier, thereby linking the VEGF neutralizing biologically active moiety to the carrier. Such reversible prodrug linkers are non-enzymatically hydrolytically degradable, i.e. cleavable, under physiological conditions (aqueous buffer at pH 7.4, 37° C.) with half-lives ranging from, for example, one hour to twelve months. Reversible linkages are, for example, aconityls, acetals, amides, carboxylic anhydrides, esters, imines, hydrazones, maleamic acid amides, ortho esters, phosphamides, phosphoesters, phosphosilyl esters, silyl esters, sulfonic esters, aromatic carbamates, and combinations thereof.

In contrast, permanent linkages are non-enzymatically hydrolytically degradable under physiological conditions (aqueous buffer at pH 7.4, 37° C.) with half-lives of more than twelve months.

As used herein, the term "traceless prodrug linker moiety" means a reversible prodrug linker moiety which upon cleavage releases the drug in its free form. As used herein, the term "free form" of a drug means the drug in its unmodified, pharmacologically active form.

As used herein, the term "peptide" means a short polymer of amino acid monomers linked by peptide bonds. The term "polypeptide" means a peptide comprising up to and including 50 amino acid monomers. The term "protein" means a peptide of more than 50 amino acid monomers.

As used herein, the term "pharmaceutical composition" means one or more active ingredient(s), and one or more inert ingredient(s), as well as any product which results, directly or indirectly, from combination, complexation or aggregation of any two or more of the ingredients, or from dissociation of one or more of the ingredient(s), or from other types of reactions or interactions of one or more of the ingredients. Accordingly, the pharmaceutical compositions of the present invention encompass any composition made by admixing the VEGF neutralizing prodrug and one or more pharmaceutically acceptable excipient(s).

As used herein, the term "excipient" refers to a diluent, adjuvant, or vehicle with which the therapeutic, i.e. the VEGF neutralizing prodrug, is administered. Such pharmaceutical excipient can be water; oils and petroleum of animal, vegetable or synthetic origin, including but not limited to peanut oil, soybean oil, mineral oil, sesame oil and the like; starch; glucose; lactose; sucrose; mannitol; trehalose; gelatin; malt; rice; flour; chalk; silica gel; sodium stearate; glycerol monostearate; talc; sodium chloride; dried skim milk; glycerol; propylene; glycol; ethanol; acetate; succinate; tris; carbonate; phosphate; HEPES (4-(2-hydroxyethyl)-1-piperazineethanesulfonic acid); MES (2-(N-morpholino)ethanesulfonic acid); Tween®; poloxamers; poloxamines; CHAPS; Igepal®; amino acids like, for example, glycine, lysine, or histidine; triglycerides; mannitol; lactose; starch; magnesium stearate; sodium saccharine; cellulose; and magnesium carbonate. Examples of suitable pharmaceutical excipients are described in "Remington's Pharmaceutical Sciences" by E. W. Martin. The formulation should suit the mode of administration.

As used herein, the term "pharmaceutically acceptable" means that a molecule or reagent is approved by a regulatory agency, such as the EMA (Europe) and/or the FDA (US) and/or any other national regulatory agency, for use in animals, preferably in humans.

As used herein, the term "intraocular injection" means an injection into the aqueous humor (anterior or posterior chamber), the vitreous body, lens or the suprachoroidal space of the eye. In general the term "comprise" or "comprising" also encompasses "consist of" or "consisting of".

As used herein, the term "modulators of the activity of protein X" refers to molecules that are agonists, antagonists or otherwise neutralize or enhance the activity of protein X.

The present invention relates to a pharmaceutical composition comprising one or more pharmaceutically acceptable excipient(s) and a VEGF neutralizing prodrug, the prodrug comprising a covalently bound VEGF neutralizing biologically active moiety, for use in a method for the treatment of one or more ocular conditions.

In a preferred embodiment the pharmaceutical composition comprising a VEGF neutralizing prodrug is administered intraocularly, preferably via intraocular injection.

In a preferred embodiment the time period between two intraocular administrations of the VEGF neutralizing prodrug is at least one month, e.g. the time period between two intraocular administrations of the VEGF neutralizing prodrug is at least one month, or at least five weeks, or at least six weeks, or at least eight weeks, or at least ten weeks, or at least twelve weeks, or at least sixteen weeks, or at least twenty weeks, or at least twenty-four weeks, or at least twenty-eight weeks, or at least thirty-two weeks, or at least thirty-six weeks, or at least forty weeks, or at least forty-four weeks, or at least forty-eight weeks. The maximum period between two intraocular administrations preferably is no longer then four years, i.e. no longer than three years, no longer than two years, or no longer than one year. Preferably, the pharmaceutical composition comprising VEGF neutralizing prodrug is administered every two to twelve months, more preferably every four to ten months and most preferably every six months.

Thus, a preferred aspect of the invention is the pharmaceutical composition, wherein the prodrug comprised in the pharmaceutical composition has a concentration of 5 to 200 mg prodrug/ml pharmaceutical composition, e.g. a concentration of 5 to 180 mg prodrug/ml pharmaceutical composition, a concentration of 10 to 170 mg prodrug/ml pharmaceutical composition, a concentration of 15 to 160 mg prodrug/ml pharmaceutical composition, a concentration of 20 to 150 mg prodrug/ml pharmaceutical composition, a concentration of 25 to 140 mg prodrug/ml pharmaceutical composition, a concentration of 30 to 130 mg prodrug/ml pharmaceutical composition, a concentration of 40 to 120 mg prodrug/ml pharmaceutical composition, a concentration of 50 to 110 mg prodrug/ml pharmaceutical composition or a concentration of 60 to 100 mg prodrug/ml pharmaceutical composition.

In one embodiment the pharmaceutical composition comprises 5 to 80 weight percent of VEGF neutralizing biologically active moiety based on the total weight of the prodrug, e.g. 10 to 70 weight percent of VEGF neutralizing biologically active moiety based on the total weight of the prodrug, 15 to 65 weight percent of the VEGF neutralizing biologically active moiety based on the total weight of the prodrug, 20 to 65 weight percent of the VEGF neutralizing biologically active moiety based on the total weight of the prodrug or 30 to 65 weight percent of the VEGF neutralizing biologically active moiety based on the total weight of the prodrug.

In one embodiment the injection is carried out with an injection volume ranging from 10 to 200 µl, e.g. ranging from 15 to 150 µl, ranging from 20 to 100 µl, ranging from 30 to 80 µl, or ranging from 40 to 70 µl. Preferably, the injection volume is 50 µl.

The VEGF neutralizing prodrug is preferably a carrier-linked prodrug.

In the VEGF neutralizing prodrugs various stoichiometries regarding drug and carrier are included.

In one embodiment one VEGF neutralizing biologically active moiety is connected through one reversible prodrug linker moiety to one carrier moiety. Attachment of the VEGF neutralizing biologically active moiety to the reversible prodrug linker moiety occurs through a functional group of the corresponding drug. Optionally, there is a spacer moiety between the carrier moiety and the reversible prodrug linker moiety.

In another embodiment, the VEGF neutralizing biologically active moiety is connected to more than one reversible prodrug linker moieties through more than one functional groups of the VEGF neutralizing biologically active moiety. Each of the more than one reversible prodrug linker moieties are connected to a different carrier moiety, optionally through a spacer moiety. Therefore, in this embodiment one VEGF neutralizing biologically active moiety is connected to more than one carrier moiety.

In another embodiment, one carrier moiety is connected to more than one reversible prodrug linker moieties, either directly or via an optional spacer moiety. Each of the reversible prodrug linker moieties is connected to one or more, preferably one, VEGF neutralizing biologically active moiety/moieties.

In one embodiment the carrier is a soluble carrier. Preferably, the soluble carrier comprises at least one polymer selected from the group of polymers comprising poly(acrylic acids), poly(acrylates), poly(acrylamides), poly(alkyloxy) polymers, poly(amides), poly(amidoamines), poly(amino acids), poly(anhydrides), poly(aspartamide), poly(butyric acid), poly(caprolacton), poly(carbonates), poly(cyanoacrylates), poly(dimethylacrylamide), poly(esters), poly(ethylene), poly(ethylene glycol), poly(ethylene oxide), poly(ethyloxazoline), poly(glycolic acid), poly(hydroxyethyl acrylate), poly(hydroxyethyloxazoline), poly(hydroxypropylmethacrylamide), poly(hydroxypropyl methacrylate), poly(hydroxypropyloxazoline), poly(iminocarbonates), poly(N-isopropylacrylamide), poly(lactic acid), poly(lactic-co-glycolic acid), poly(methacrylamide), poly(methacrylates), poly(methyloxazoline), poly(propylene fumarate), poly(organophosphazenes), poly(ortho esters), poly(oxazolines), poly(propylene glycol), poly(siloxanes), poly(urethanes), poly(vinylalcohols), poly(vinylamines), poly(vinylmethylether), poly(vinylpyrrolidone), silicones, ribonucleic acids, desoxynucleic acid, albumins, antibodies and fragments thereof, blood plasma protein, collagens, elastin, fascin, fibrin, keratins, polyaspartate, polyglutamate, prolamins, transferrins, cytochromes, flavoprotein, glycoproteins, hemoproteins, lipoproteins, metalloproteins, phytochromes, phosphoproteins, opsins, agar, agarose, alginate, arabinans, arabinogalactans, carrageenan, cellulose, carbomethyl cellulose, hydroxypropyl methylcellulose and other carbohydrate-based polymers, chitosan, dextran, dextrin, gelatin, hyaluronic acid and derivatives, mannan, pectins, rhamnogalacturonans, starch, hydroxyalkyl starch, xylan, and copolymers and functionalized derivatives thereof.

In another embodiment the carrier is an insoluble carrier, more preferably the carrier of the carrier-linked prodrug is a hydrogel.

Preferably, the hydrogel of the VEGF neutralizing prodrug is a biodegradable hydrogel.

The hydrogel comprises at least one polymer which is preferably selected from the group of polymers comprising poly(acrylic acids), poly(acrylates), poly(acrylamides), poly(alkyloxy) polymers, poly(amides), poly(amidoamines), poly(amino acids), poly(anhydrides), poly(aspartamide), poly(butyric acid), poly(caprolacton), poly(carbonates), poly(cyanoacrylates), poly(dimethylacrylamide), poly(esters), poly(ethylene), poly(ethylene glycol), poly(ethylene oxide), poly(ethyloxazoline), poly(glycolic acid), poly(hydroxyethyl acrylate), poly(hydroxyethyloxazoline), poly(hydroxypropylmethacrylamide), poly(hydroxypropyl methacrylate), poly(hydroxypropyloxazoline), poly(iminocarbonates), poly(N-isopropylacrylamide), poly(lactic acid), poly(lactic-co-glycolic acid), poly(methacrylamide), poly(methacrylates), poly(methyloxazoline), poly(propylene fumarate), poly(organophosphazenes), poly(ortho esters), poly(oxazolines), poly(propylene glycol), poly(siloxanes), poly(urethanes), poly(vinylalcohols), poly(vinylamines), poly(vinylmethylether), poly(vinylpyrrolidone), silicones, ribonucleic acids, desoxynucleic acid, albumins, antibodies and fragments thereof, blood plasma protein, collagens, elastin, fascin, fibrin, keratins, polyaspartate, polyglutamate, prolamins, transferrins, cytochromes, flavoprotein, glycoproteins, hemoproteins, lipoproteins, metalloproteins, phytochromes, phosphoproteins, opsins, agar, agarose, alginate, arabinans, arabinogalactans, carrageenan, cellulose, carbomethyl cellulose, hydroxypropyl methylcellulose and other carbohydrate-based polymers, chitosan, dextran, dextrin, gelatin, hyaluronic acid and derivatives, mannan, pectins, rhamnogalacturonans, starch, hydroxyalkyl starch, xylan, and copolymers and functionalized derivatives thereof.

Preferably, the hydrogel of VEGF neutralizing prodrug is a biodegradable poly(ethylene glycol) (PEG)-based hydrogel comprising at least 10% PEG, more preferably, comprising at least 20% PEG and most preferably 30% PEG.

The hydrogel of the VEGF neutralizing prodrug is a shaped article, preferably in the shape of microparticles. More preferably, the hydrogel is in the shape of microparticulate beads. Even more preferably, such microparticulate beads have a diameter of 1 to 1000 μm, more preferably of 5 to 500 μm, more preferably of 10 to 100 μm, more preferably of 20 to 100 μm, and even more preferably of 20 to 80 μm. Bead diameters are measured when the microparticulate beads are suspended in an isotonic aqueous buffer.

The hydrogel of the VEGF neutralizing prodrug is preferably a hydrogel as disclosed in WO2006/003014A2 and WO2011/012715A1, which are hereby enclosed by reference in their entirety.

Even more preferably, the hydrogel of the VEGF neutralizing prodrug is a hydrogel obtainable by a process comprising the steps of:

(a) providing a mixture comprising
  - (a-i) at least one backbone reagent, wherein the at least one backbone reagent has a molecular weight ranging from 1 to 100 kDa, and comprises at least three amines ($—NH_2$ and/or —NH—);
  - (a-ii) at least one crosslinker reagent, wherein the at least one crosslinker reagent has a molecular weight ranging from 6 to 40 kDa, the at least one crosslinker reagent comprising (i) at least two carbonyloxy groups (—(C=O)—O— or —O—(C=O)—), and additionally (ii) at least two activated functional end groups selected from the group consisting of activated ester groups, activated carbamate groups, activated carbonate groups and activated thiocarbonate groups, and being PEG-based comprising at least 70% PEG; and (a-iii) a first solvent and at least a second solvent, which second solvent is immiscible in the first solvent, in a weight ratio of the at least one backbone reagent to the at least one crosslinker reagent ranging from 1:99 to 99:1;

(b) polymerizing the mixture of step (a) in a suspension polymerization to a hydrogel; and (c) optionally working-up the hydrogel.

The mixture of step (a) comprises a first solvent and at least a second solvent. Said first solvent is preferably selected from the group comprising dichloromethane, chloroform, tetrahydrofuran, ethyl acetate, dimethylformamide, acetonitrile, dimethyl sulfoxide, propylene carbonate, N-methylpyrrolidone, methanol, ethanol, isopropanol and water and mixtures thereof.

The at least one backbone reagent and at least one crosslinker reagent are dissolved in the first solvent, i.e. the disperse phase of the suspension polymerization. In one embodiment the backbone reagent and the crosslinker reagent are dissolved separately, i.e. in different containers, using either the same or different solvent and preferably using the same solvent for both reagents. In another embodiment, the backbone reagent and the crosslinker reagent are dissolved together, i.e. in the same container and using the same solvent.

A suitable solvent for the backbone reagent is an organic solvent. Preferably, the solvent is selected from the group consisting of dichloromethane, chloroform, tetrahydrofuran, ethyl acetate, dimethylformamide, acetonitrile, dimethyl sulfoxide, propylene carbonate, N-methylpyrrolidone, methanol, ethanol, isopropanol and water and mixtures thereof. More preferably, the backbone reagent is dissolved in a solvent selected from the group comprising acetonitrile, dimethyl sulfoxide, methanol or mixtures thereof. Most preferably, the backbone reagent is dissolved in dimethylsulfoxide.

In one embodiment the backbone reagent is dissolved in the solvent in a concentration ranging from 1 to 300 mg/ml, more preferably from 5 to 60 mg/ml and most preferably from 10 to 40 mg/ml.

A suitable solvent for the crosslinker reagent is an organic solvent. Preferably, the solvent is selected from the group comprising dichloromethane, chloroform, tetrahydrofuran, ethyl acetate, dimethylformamide, acetonitrile, dimethyl sulfoxide, propylene carbonate, N-methylpyrrolidone, methanol, ethanol, isopropanol, water or mixtures thereof. More preferably, the crosslinker reagent is dissolved in a solvent selected from the group comprising dimethylformamide, acetonitrile, dimethyl sulfoxide, methanol or mixtures thereof. Most preferably, the crosslinker reagent is dissolved in dimethylsulfoxide.

In one embodiment the crosslinker reagent is dissolved in the solvent in a concentration ranging from 5 to 500 mg/ml, more preferably from 25 to 300 mg/ml and most preferably from 50 to 200 mg/ml.

The at least one backbone reagent and the at least one crosslinker reagent are mixed in a weight ratio ranging from 1:99 to 99:1, e.g. in a ratio ranging from 2:98 to 90:10, in a weight ratio ranging from 3:97 to 88:12, in a weight ratio ranging from 3:96 to 85:15, in a weight ratio ranging from 2:98 to 90:10 and in a weight ratio ranging from 5:95 to 80:20; particularly preferred in a weight ratio from 5:95 to 80:20, wherein the first number refers to the backbone reagent and the second number to the crosslinker reagent.

Preferably, the ratios are selected such that the mixture of step (a) comprises a molar excess of amine groups from the backbone reagent compared to the activated functional end groups of the crosslinker reagent. Consequently, the hydrogel resulting from the process of the present invention has free amine groups which can be used to couple a prodrug linker reagent to the hydrogel, either directly or through a spacer moiety.

The at least one second solvent, i.e. the continuous phase of the suspension polymerization, is preferably an organic solvent, more preferably an organic solvent selected from the group comprising linear, branched or cyclic $C_{5-30}$ alkanes; linear, branched or cyclic $C_{5-30}$ alkenes; linear, branched or cyclic $C_{5-30}$ alkynes; linear or cyclic poly(dimethylsiloxanes); aromatic $C_{6-20}$ hydrocarbons; and mixtures thereof. Even more preferably, the at least second solvent is selected from the group comprising linear, branched or cyclic $C_{5-16}$ alkanes; toluene; xylene; mesitylene; hexamethyldisiloxane; or mixtures thereof. Most preferably, the at least second solvent selected from the group comprising linear $C_{7-11}$ alkanes, such as heptane, octane, nonane, decane and undecane.

Preferably, the mixture of step (a) further comprises a detergent. Preferred detergents are Cithrol DPHS, Hypermer 70A, Hypermer B246, Hypermer 1599A, Hypermer 2296, and Hypermer 1083.

Preferably, the detergent has a concentration of 0.1 g to 100 g per 1 L total mixture, i.e. disperse phase and continuous phase together. More preferably, the detergent has a concentration of 0.5 g to 10 g per 1 L total mixture, and most preferably, the detergent has a concentration of 0.5 g to 5 g per 1 L total mixture.

Preferably, the mixture of step (a) is an emulsion.

The polymerization in step (b) is initiated by adding a base. Preferably, the base is a non-nucleophilic base soluble in alkanes, more preferably the base is selected from N,N,N',N'-tetramethylethylene diamine (TMEDA), 1,4-dimethylpiperazine, 4-methylmorpholine, 4-ethylmorpholine, 1,4-diazabicyclo[2.2.2]octane, 1,1,4,7,10,10-hexamethyltriethylenetetramine, 1,4,7-trimethyl-1,4,7-triazacyclononane, tris[2-(dimethylamino)ethyl]amine, triethylamine, DIPEA, trimethylamine, N,N-dimethylethylamine, N,N,N',N'-tetramethyl-1,6-hexanediamine, N,N,N',N'',N''-pentamethyldiethylenetriamine, 1,8-diazabicyclo[5.4.0]undec-7-ene, 1,5-diazabicyclo[4.3.0]non-5-ene, and hexamethylenetetramine. Even more preferably, the base is selected from TMEDA, 1,4-dimethylpiperazine, 4-methylmorpholine, 4-ethylmorpholine, 1,4-diazabicyclo[2.2.2]octane, 1,1,4,7,10,10-hexamethyltriethylenetetramine, 1,4,7-trimethyl-1,4,7-triazacyclononane, tris[2-(dimethylamino)ethyl]amine, 1,8-diazabicyclo[5.4.0]undec-7-ene, 1,5-diazabicyclo[4.3.0]non-5-ene, and hexamethylenetetramine. Most preferably, the base is TMEDA.

The base is added to the mixture of step (a) in an amount of 1 to 500 equivalents per activated functional end group in the mixture, preferably in an amount of 5 to 50 equivalents, more preferably in an amount of 5 to 25 equivalents and most preferably in an amount of 10 equivalents.

In process step (b), the polymerization of the hydrogel of the present invention is a condensation reaction, which preferably occurs under continuous stirring of the mixture of step (a). Preferably, the tip speed (tip speed=π×stirrer rotational speed×stirrer diameter) ranges from 0.2 to 10 meter per second (m/s), more preferably from 0.5 to 4 m/s and most preferably from 1 to 2 m/s.

In a preferred embodiment of step (b), the polymerization reaction is carried out in a cylindrical vessel equipped with baffles. The diameter to height ratio of the vessel may range from 4:1 to 1:2, more preferably the diameter to height ratio of the vessel ranges from 2:1 to 1:1.

Preferably, the reaction vessel is equipped with an axial flow stirrer selected from the group comprising pitched blade stirrer, marine type propeller, or Lightnin A-310. More preferably, the stirrer is a pitched blade stirrer.

Step (b) can be performed in a broad temperature range, preferably at a temperature from −10° C. to 100° C., more preferably at a temperature of 0° C. to 80° C., even more preferably at a temperature of 10° C. to 50° C. and most preferably at ambient temperature. "Ambient temperature" refers to the temperature present in a typical laboratory environment and preferably means a temperature ranging from 17 to 25° C.

Preferably, the hydrogel obtained from the polymerization is a shaped article, such as a coating, mesh, stent, nanoparticle or a microparticle. More preferably, the hydrogel is in the form of microparticular beads having a diameter from 1 to 500 micrometer, more preferably with a diameter from 10 to 300 micrometer, even more preferably with a diameter from 20 and 150 micrometer and most preferably with a diameter from 30 to 130 micrometer. The afore-mentioned diameters are measured when the hydrogel microparticles are fully hydrated in water.

Optional step (c) comprises one or more of the following step(s):
(c1) removing excess liquid from the polymerization reaction,
(c2) washing the hydrogel to remove solvents used during polymerization,
(c3) transferring the hydrogel into a buffer solution,
(c4) size fractionating/sieving of the hydrogel,
(c5) transferring the hydrogel into a container,
(c6) drying the hydrogel,
(c7) transferring the hydrogel into a specific solvent suitable for sterilization, and
(c8) sterilizing the hydrogel, preferably by gamma radiation Preferably, optional step (c) comprises all of the following steps
(c1) removing excess liquid from the polymerization reaction,
(c2) washing the hydrogel to remove solvents used during polymerization,
(c3) transferring the hydrogel into a buffer solution,
(c4) size fractionating/sieving of the hydrogel,
(c5) transferring the hydrogel into a container,
(c7) transferring the hydrogel into a specific solvent suitable for sterilization, and
(c8) sterilizing the hydrogel, preferably by gamma radiation.

The at least one backbone reagent has a molecular weight ranging from 1 to 100 kDa, preferably from 2 to 50 kDa, more preferably from 5 and 30 kDa, even more preferably from 5 to 25 kDa and most preferably from 5 to 15 kDa.

Preferably, the backbone reagent is PEG-based comprising at least 10% PEG, more preferably comprising at least 20% PEG, even more preferably comprising at least 30% PEG and most preferably comprising at least 40% PEG.

In one embodiment the backbone reagent is present in the form of its acidic salt, preferably in the form of an acid addition salt. Suitable acid addition salts are formed from acids which form non-toxic salts. Examples include but are not limited to the acetate, aspartate, benzoate, besylate, bicarbonate, carbonate, bisulphate, sulphate, borate, camsylate, citrate, edisylate, esylate, formate, fumarate, gluceptate, gluconate, glucuronate, hexafluorophosphate, hibenzate, hydrochloride, hydrobromide, hydroiodide, isethionate, lactate, malate, maleate, malonate, mesylate, methylsulphate, naphthylate, nicotinate, nitrate, orotate, oxalate, palmitate, pamoate, phosphate, hydrogen phosphate, dihydrogen phosphate, sacharate, stearate, succinate, tartrate and tosylate. Particularly preferred, the backbone reagent is present in the form of its hydrochloride salt.

In one embodiment, the at least one backbone reagent is selected from the group consisting of
a compound of formula (I)

$$B(-(A^0)_{x1}-(SP)_{x2}-A^1-P-A^2-Hyp^1)_x \qquad (I),$$

wherein
B is a branching core,
SP is a spacer moiety selected from the group consisting of $C_{1-6}$ alkyl, $C_{2-6}$ alkenyl and $C_{2-6}$ alkynyl,
P is a PEG-based polymeric chain comprising at least 80% PEG, preferably at least 85% PEG, more preferably at least 90% PEG and most preferably at least 95% PEG,
$Hyp^1$ is a moiety comprising an amine ($-NH_2$ and/or $-NH-$) or a polyamine comprising at least two amines ($-NH_2$ and/or $-NH-$),
x is an integer from 3 to 16,
x1, x2 are independently of each other 0 or 1, provided that x1 is 0, if x2 is 0,
$A^0$, $A^1$, $A^2$ are independently of each other selected from the group consisting of

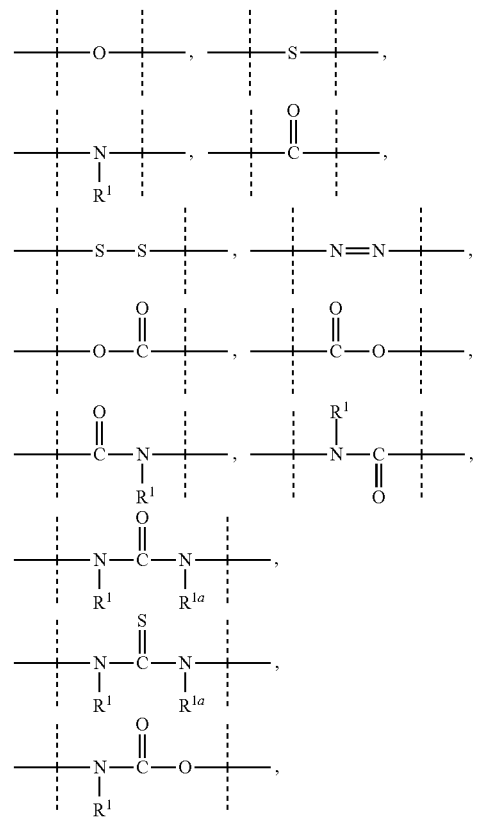

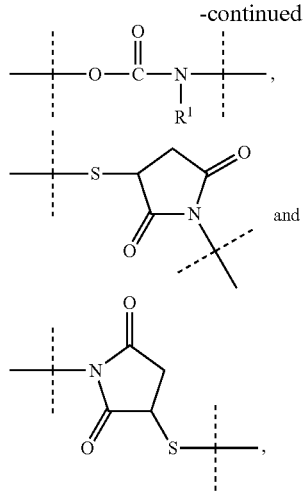

wherein $R^1$ and $R^{1a}$ are independently of each other selected from H and $C_{1-6}$ alkyl;

a compound of formula (II)

$$\text{Hyp}^2\text{-}A^3\text{-}P\text{-}A^4\text{-}\text{Hyp}^3 \qquad (II),$$

wherein

P is defined as above in the compound of formula (I), $\text{Hyp}^2$, $\text{Hyp}^3$ are independently of each other a polyamine comprising at least two amines (—$NH_2$ and/or —NH—), and $A^3$ and $A^4$ are independently selected from the group consisting of

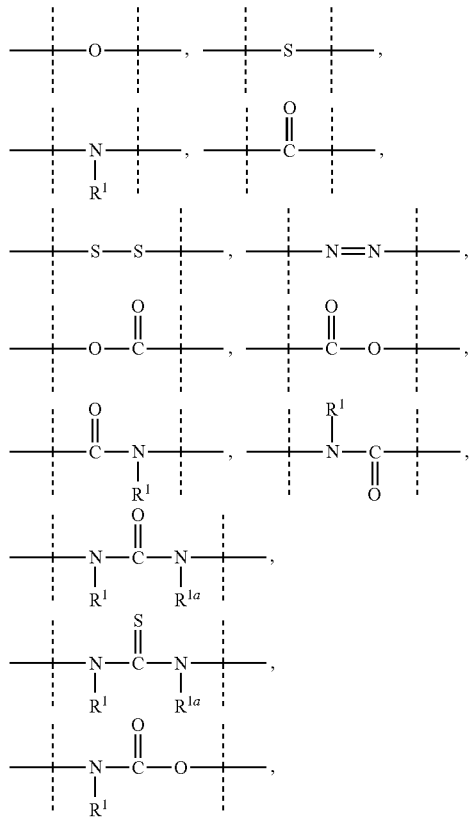

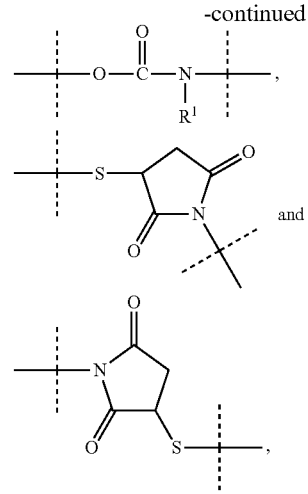

wherein $R^1$ and $R^{1a}$ are independently of each other selected from H and $C_{1-6}$ alkyl;

a compound of formula (III)

$$P^1\text{-}A^5\text{-}\text{Hyp}^4 \qquad (III),$$

wherein $P^1$ is a PEG-based polymeric chain comprising at least 80% PEG, preferably at least 85% PEG, more preferably at least 90% PEG and most preferably at least 95% PEG, $\text{Hyp}^4$ is a polyamine comprising at least three amines (—$NH_2$ and/or —NH), and $A^5$ is selected from the group consisting of

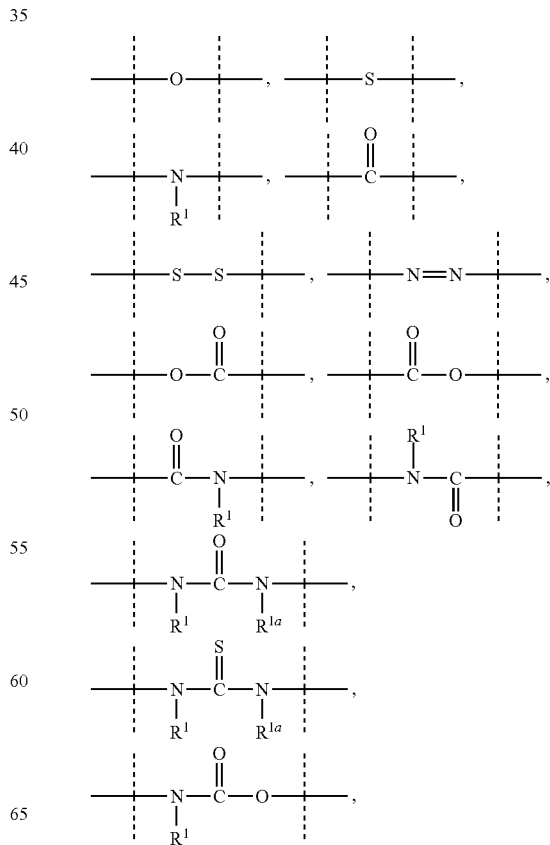

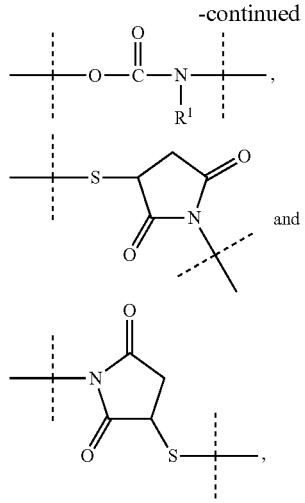

wherein $R^1$ and $R^{1a}$ are independently of each other selected from H and $C_{1-6}$ alkyl;

and a compound of formula (IV), $$T^1\text{-}A^6\text{-}Hyp^5 \quad (IV),$$

wherein $Hyp^5$ is a polyamine comprising at least three amines ($-NH_2$ and/or $-NH$), and $A^6$ is selected from the group consisting of

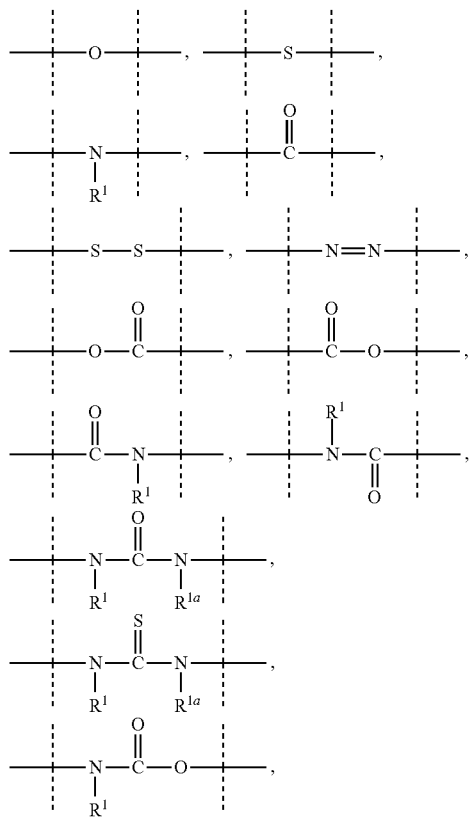

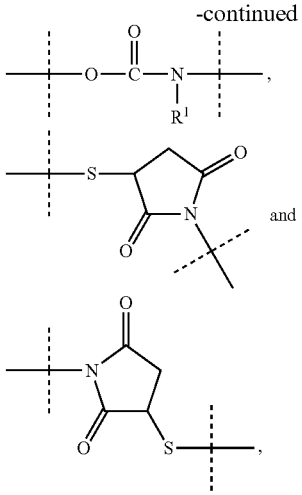

wherein $R^1$ and $R^{1a}$ are independently of each other selected from H and $C_{1-6}$ alkyl; and $T^1$ is selected from the group consisting of $C_{1-50}$ alkyl, $C_{2-50}$ alkenyl or $C_{2-50}$ alkynyl, which fragment is optionally interrupted by one or more group(s) selected from $-NH-$, $-N(C_{1-4}$ alkyl$)$-, $-O-$, $-S-$, $-C(O)-$, $-C(O)NH-$, $-C(O)N(C_{1-4}$ alkyl$)$-, $-O-C(O)-$, $-S(O)-$, $-S(O)_2-$, 4- to 7-membered heterocyclyl, phenyl or naphthyl.

In the following sections the term "$Hyp^x$" refers to $Hyp^1$, $Hype^2$, $Hyp^3$, $Hyp^4$ and $Hyp^5$ collectively.

Preferably, the backbone reagent is a compound of formula (I), (II) or (III), more preferably the backbone reagent is a compound of formula (I) or (III), and most preferably the backbone reagent is a compound of formula (I).

In a preferred embodiment, in a compound of formula (I), x is 4, 6 or 8. Preferably, in a compound of formula (I) x is 4 or 8, most preferably, x is 4.

In a preferred embodiment in the compounds of the formulas (I) to (IV), $A^0$, $A^1$, $A^2$, $A^3$, $A^4$, $A^5$ and $A^6$ are selected from the group comprising

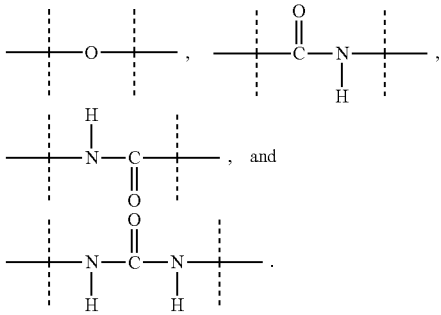

Preferably, in a compound of formula (I), $A^0$ is

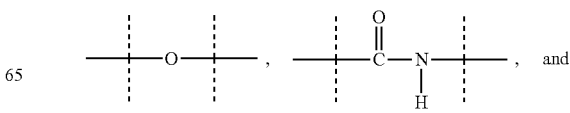

-continued

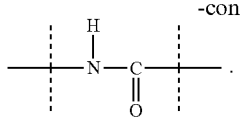

Preferably, in a compound of formula (I), $A^1$ is

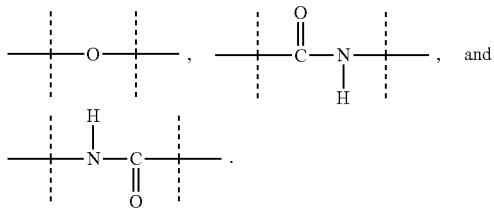

and

Preferably, in a compound of formula (I), $A^2$ is

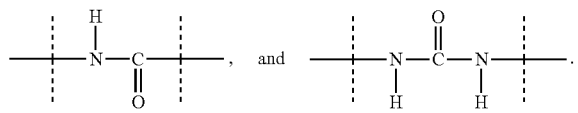

, and

Preferably, in a compound of formula (II), $A^3$

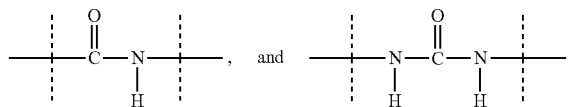

, and and $A^4$ is

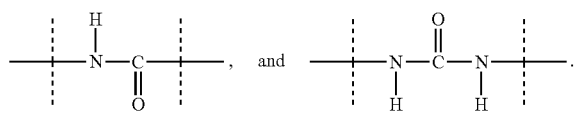

, and

Preferably, in a compound of formula (III), $A^5$

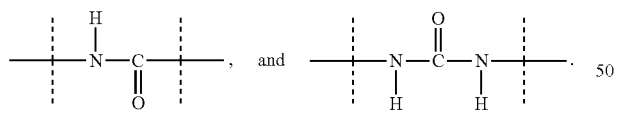

, and

Preferably, in a compound of formula (IV), $A^6$ is

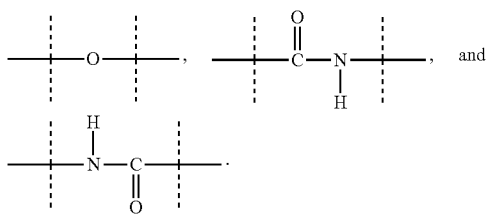

, and

Preferably, in a compound of formula (IV), $T^1$ is selected from H and $C_{1-6}$ alkyl.

In one embodiment, in a compound of formula (I), the branching core B is selected from the following structures:

(a-i)
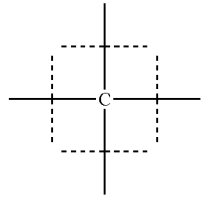

(a-ii)
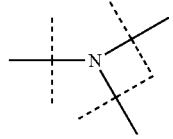

(a-iii)
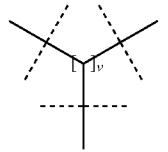

(a-iv)
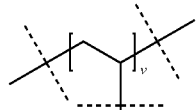

(a-v)
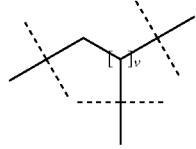

(a-vi)
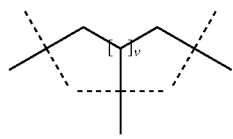

(a-vii)
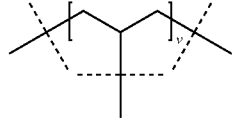

(a-viii)
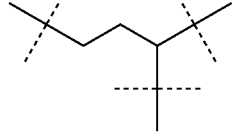

(a-ix)
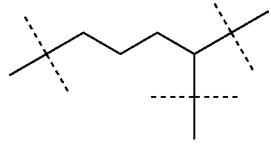

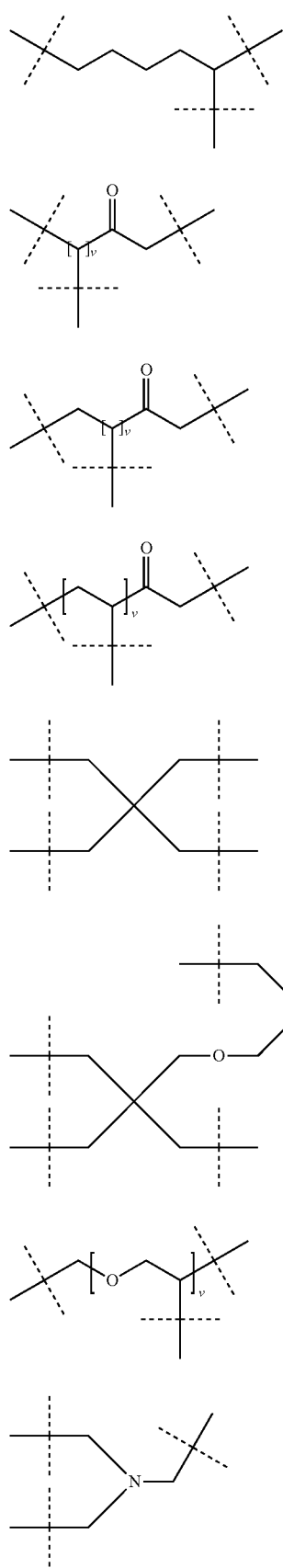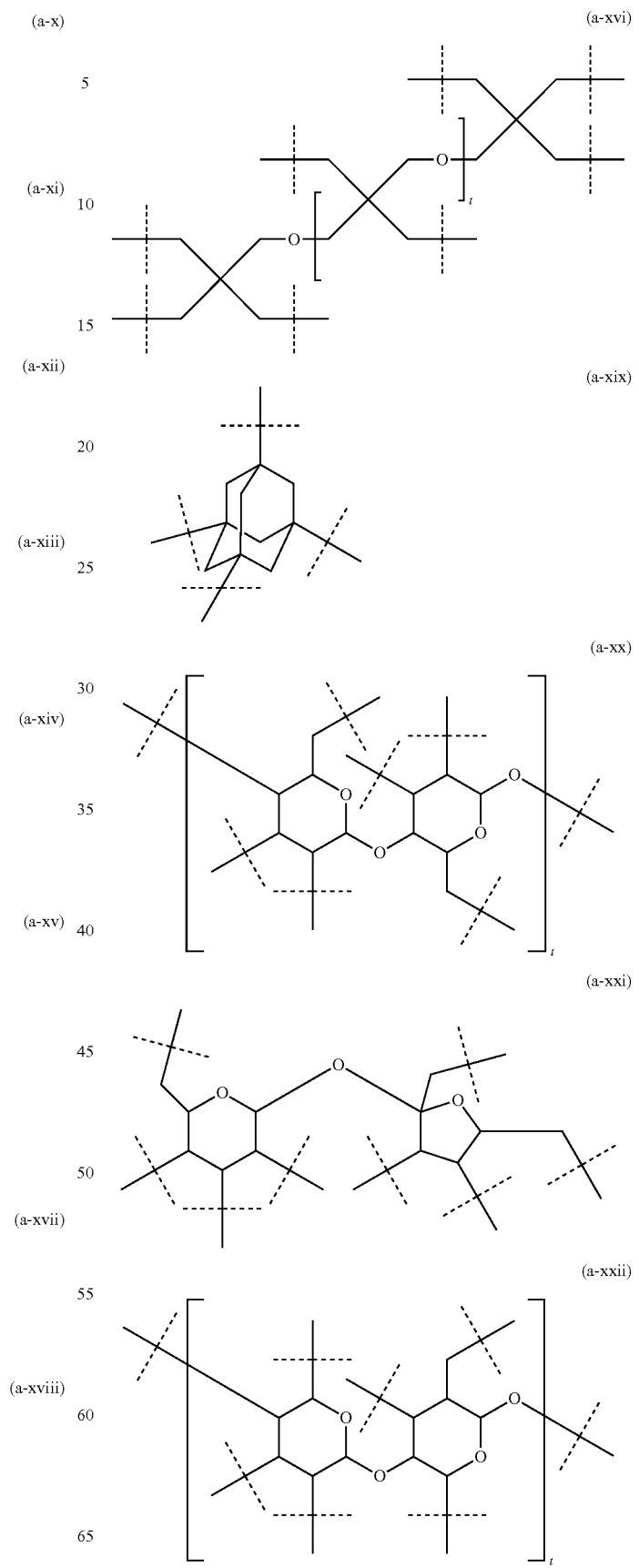

(a-xxiii)

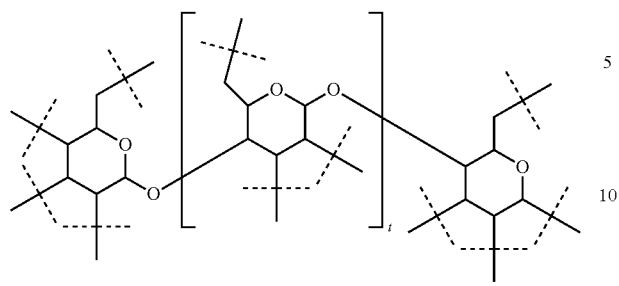

wherein
dashed lines indicate attachment to $A^0$ or, if x1 and x2 are both 0, to $A^1$,
t is 1 or 2; preferably t is 1,
v is 1, 2, 3, 4, 5, 6, 7, 8, 9, 10, 11, 12, 13 or 14; preferably, v is 2, 3, 4, 5, 6; more preferably, v is 2, 4 or 6; most preferably, v is 2.

In a preferred embodiment, B has a structure of formula (a-i), (a-ii), (a-iii), (a-iv), (a-v), (a-vi), (a-vii), (a-viii), (a-ix), (a-x), (a-xiv), (a-xv) or (a-xvi). More preferably, B has a structure of formula (a-iii), (a-iv), (a-v), (a-vi), (a-vii), (a-viii), (a-ix), (a-x) or (a-iv). Most preferably, B has a structure of formula (a-xiv).

A preferred embodiment is a combination of B and $A^0$, or, if x1 and x2 are both 0 a preferred combination of B and $A^1$, which is selected from the following structures:

(b-i)

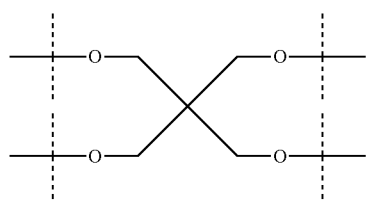

(b-ii)

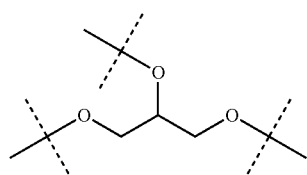

(b-iii)

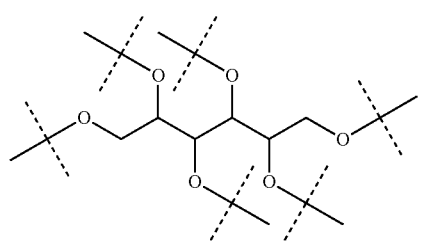

(b-iv)

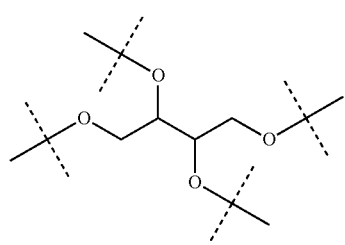

(b-v)

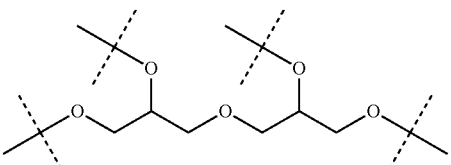

(b-vi)

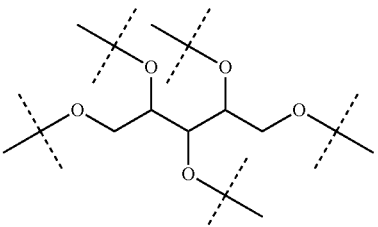

(b-vii)

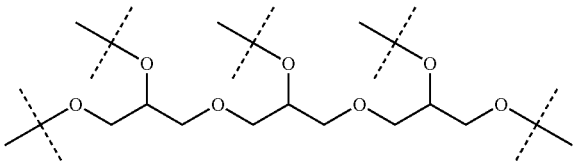

wherein
dashed lines indicate attachment to SP or, if x1 and x2 are both 0, to P.

More preferably, the combination of B and $A^0$ or, if x1 and x2 are both 0, the combination of B and $A^1$, has a structure of formula of formula (b-i), (b-iv), (b-vi) or (b-viii) and most preferably has a structure of formula of formula (b-i).

In one embodiment, x1 and x2 of formula (I) are 0.

In one embodiment, the PEG-based polymeric chain P has a molecular weight from 0.3 kDa to 40 kDa; e.g. from 0.4 to 35 kDa, from 0.6 to 38 kDA, from 0.8 to 30 kDa, from 1 to 25 kDa, from 1 to 15 kDa or from 1 to 10 kDa. Most preferably P has a molecular weight from 1 to 10 kDa.

In one embodiment, the PEG-based polymeric chain $P^1$ has a molecular weight from 0.3 kDa to 40 kDa; e.g. from 0.4 to 35 kDa, from 0.6 to 38 kDA, from 0.8 to 30 kDa, from 1 to 25 kDa, from 1 to 15 kDa or from 1 to 10 kDa. Most preferably $P^1$ has a molecular weight from 1 to 10 kDa.

In one embodiment, in the compounds of formulas (I) or (II), P has the structure of formula (c-i):

(c-i)

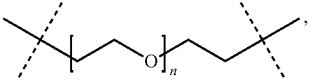

wherein n ranges from 6 to 900, more preferably n ranges from 20 to 700 and most preferably n ranges from 20 to 250.

In one embodiment, in the compounds of formulas (III), $P^1$ has the structure of formula (c-ii):

(c-ii)

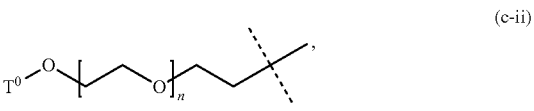

wherein
n ranges from 6 to 900, more preferably n ranges from 20 to 700 and most preferably n ranges from 20 to 250;
$T^o$ is selected from the group comprising $C_{1-6}$ alkyl, $C_{2-6}$ alkenyl and $C_{2-6}$ alkynyl, which is optionally interrupted by one or more group(s) selected from —NH—, —N($C_{1-4}$ alkyl)-, —O—, —S—, —C(O)—, —C(O)NH—, —C(O)N($C_{1-4}$ alkyl)-, —O—C(O)—, —S(O)— or —S(O)$_2$—.

In one embodiment, in the compounds of formulas (I) to (IV), the moiety $Hyp^x$ is a polyamine and preferably comprises in bound form and, where applicable, in R- and/or S-configuration a moiety of the formulas (d-i), (d-ii), (d-iii) and/or (d-iv):

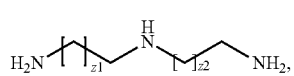
(d-i)

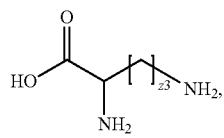
(d-ii)

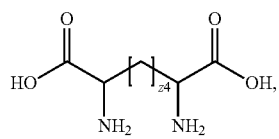
(d-iii)

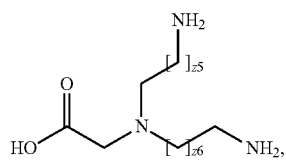
(d-iv)

wherein
z1, z2, z3, z4, z5, z6 are independently of each other 1, 2, 3, 4, 5, 6, 7 or 8.

More preferably, $Hyp^x$ comprises in bound form and in R- and/or S-configuration lysine, ornithine, diaminoproprionic acid and/or diaminobutyric acid. Most preferably, $Hyp^x$ comprises in bound form and in R- and/or S-configuration lysine.

$Hyp^x$ has a molecular weight from 40 Da to 30 kDa, preferably from 0.3 kDa to 25 kDa, more preferably from 0.5 kDa to 20 kDa, even more preferably from 1 kDa to 20 kDa and most preferably from 2 kDa to 15 kDa.

$Hyp^x$ is preferably selected from the group consisting of a moiety of formula (e-i)

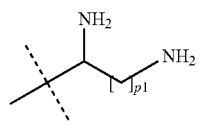
(e-i)

wherein
p1 is an integer from 1 to 5, preferably p1 is 4, and the dashed line indicates attachment to $A^2$ if the backbone reagent has a structure of formula (I) and to $A^3$ or $A^4$ if the backbone reagent has the structure of formula (II);

a moiety of formula (e-ii)

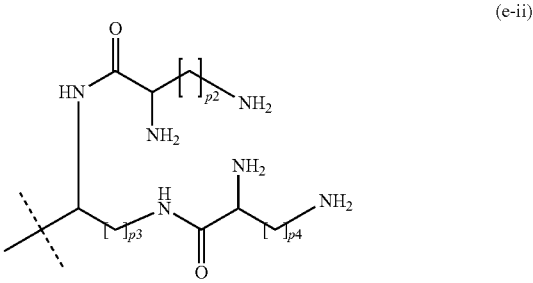
(e-ii)

wherein
p2, p3 and p4 are identical or different and each is independently of the others an integer from 1 to 5, preferably p2, p3 and p4 are 4, and
the dashed line indicates attachment to $A^2$ if the backbone reagent has a structure of formula (I), to $A^3$ or $A^4$ if the backbone reagent has a structure of formula (II), to $A^5$ if the backbone reagent has a structure of formula (III) and to $A^6$ if the backbone reagent has a structure of formula (IV);

a moiety of formula (e-iii)

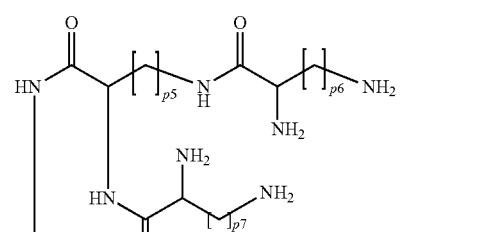
(e-iii)

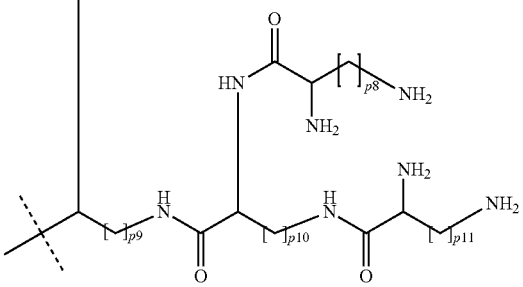

wherein
p5 to p11 are identical or different and each is independently of the others an integer from 1 to 5, preferably p5 to p11 are 4, and
the dashed line indicates attachment to $A^2$ if the backbone reagent is of formula (I), to $A^3$ or $A^4$ if the backbone reagent is of formula (II), to $A^5$ if the backbone reagent is of formula (III) and to $A^6$ if the backbone reagent is of formula (IV);

a moiety of formula (e-iv)

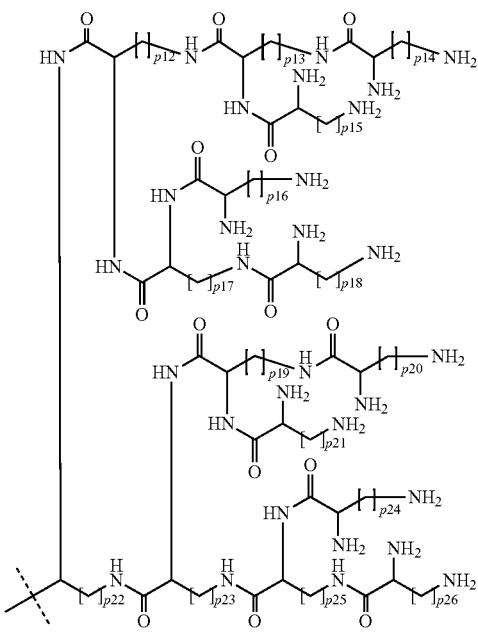

wherein
p12 to p26 are identical or different and each is independently of the others an integer from 1 to 5, preferably p12 to p26 are 4, and
the dashed line indicates attachment to $A^2$ if the backbone reagent has a structure of formula (I), to $A^3$ or $A^4$ if the backbone reagent has a structure of formula (II), to $A^5$ if the backbone reagent has a structure of formula (III) and to $A^6$ if the backbone reagent has a structure of formula (IV);

a moiety of formula (e-v)

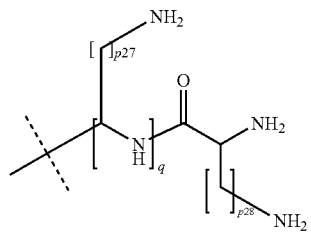

wherein
p27 and p28 are identical or different and each is independently of the other an integer from 1 to 5, preferably p27 and p28 are 4,
q is an integer from 1 to 8, preferably q is 2 or 6 and most preferably 1 is 6, and
the dashed line indicates attachment to $A^2$ if the backbone reagent has a structure of formula (I), to $A^3$ or $A^4$ if the backbone reagent has a structure of formula (II), to $A^5$ if the backbone reagent has a structure of formula (III) and to $A^6$ if the backbone reagent has a structure of formula (IV);

a moiety of formula (e-vi)

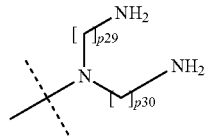

wherein
p29 and p30 are identical or different and each is independently of the other an integer from 2 to 5, preferably p29 and p30 are 3, and
the dashed line indicates attachment to $A^2$ if the backbone reagent has the structure of formula (I), to $A^3$ or $A^4$ if the backbone reagent has the structure of formula (II), to $A^5$ if the backbone reagent has the structure of formula (III) and to $A^6$ if the backbone reagent has the structure of formula (IV);

a moiety of formula (e-vii)

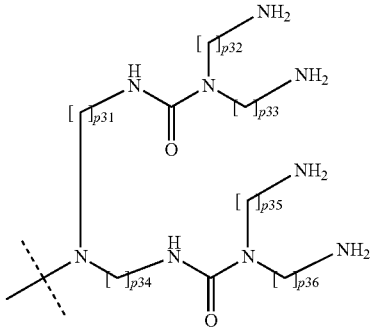

wherein
p31 to p36 are identical or different and each is independently of the others an integer from 2 to 5, preferably p31 to p36 are 3, and
the dashed line indicates attachment to $A^2$ if the backbone reagent has a structure of formula (I), to $A^3$ or $A^4$ if the backbone reagent has a structure of formula (II), to $A^5$ if the backbone reagent has a structure of formula (III) and to $A^6$ if the backbone reagent has a structure of formula (IV);

a moiety of formula (e-viii)

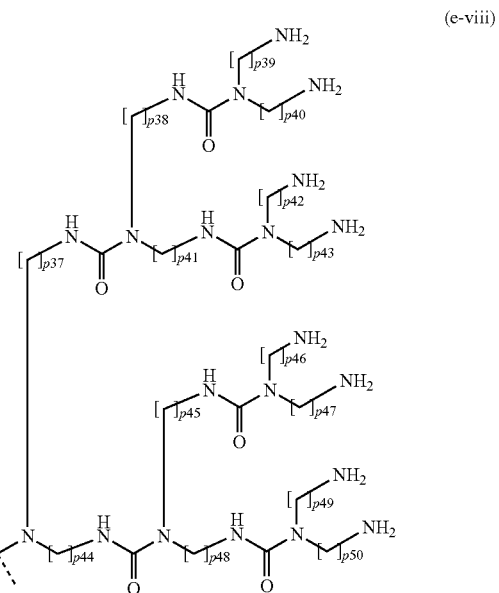

wherein
p37 to p50 are identical or different and each is independently of the others an integer from 2 to 5, preferably p37 to p50 are 3, and
the dashed line indicates attachment to $A^2$ if the backbone reagent has a structure of formula (I), to $A^3$ or $A^4$ if the backbone reagent has a structure of formula (II), to $A^5$ if the backbone reagent has a structure of formula (III) and to $A^6$ if the backbone reagent has a structure of formula (IV); and
a moiety of formula (e-ix):

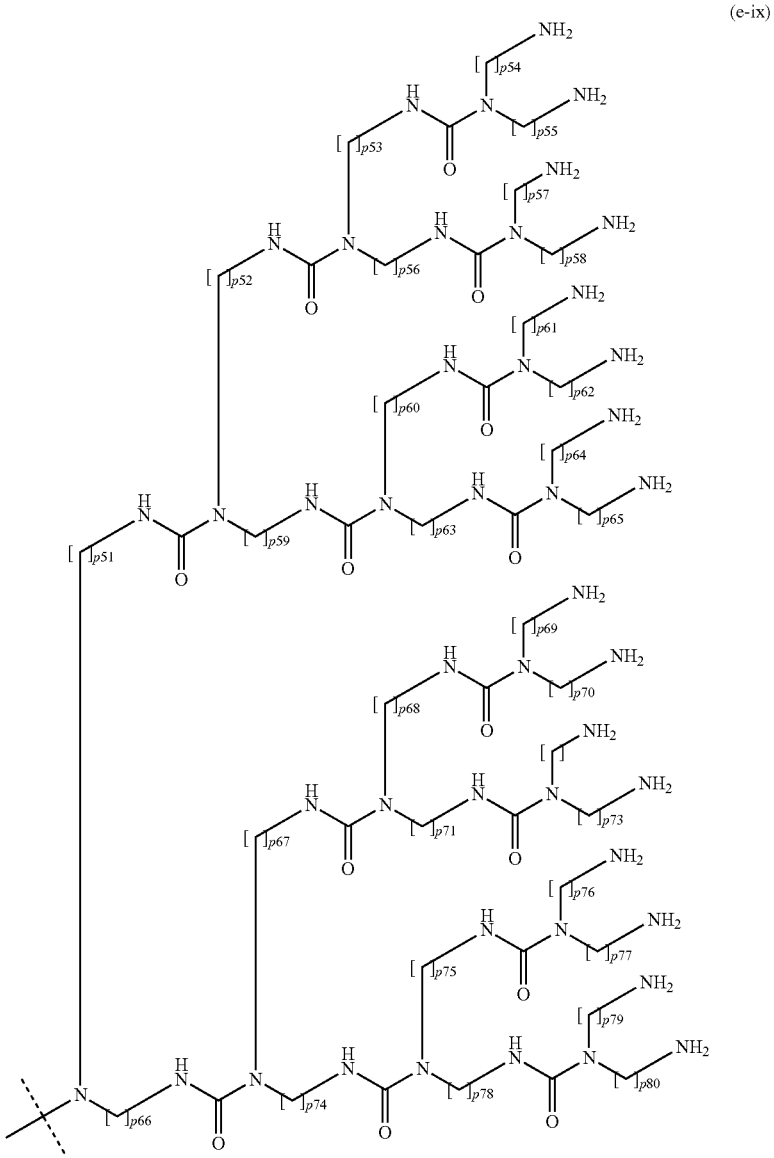

(e-ix)

wherein
p51 to p80 are identical or different and each is independently of the others an integer from 2 to 5, preferably p51 to p80 are 3, and
the dashed line indicates attachment to $A^2$ if the backbone reagent has a structure of formula (I), to $A^3$ or $A^4$ if the backbone reagent has a structure of formula (II), to $A^5$ if the backbone reagent has a structure of formula (III) and to $A^6$ if the backbone reagent has a structure of formula (IV); and
wherein the moieties (e-i) to (e-v) may at each chiral center be in either R- or S-configuration, preferably, all chiral centers of a moiety (e-i) to (e-v) are in the same configuration.

Preferably, $Hyp^x$ has a structure of formulas (e-i), (e-ii), (e-iii), (e-iv), (e-vi), (e-vii), (e-viii) or (e-ix). More preferably, $Hyp^x$ has a structure of formulas (e-ii), (e-iii), (e-iv), (e-vii), (e-viii) or (e-ix), even more preferably $Hyp^x$ has a structure of formulas (e-ii), (e-iii), (e-vii) or (e-viii) and most preferably $Hyp^x$ has the structure of formula (e-iii).

If the backbone reagent has a structure of formula (I), a preferred moiety -$A^2$-$Hyp^1$ is a moiety of the formula

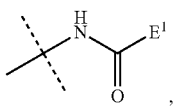

wherein
the dashed line indicates attachment to P; and
$E^1$ is selected from formulas (e-i) to (e-ix).

If the backbone reagent has a structure of formula (II) a preferred moiety $Hyp^2$-$A^3$- is a moiety of the formula

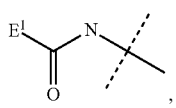

wherein
the dashed line indicates attachment to P; and
$E^1$ is selected from formulas (e-i) to (e-ix);
and a preferred moiety -$A^4$-$Hyp^3$ is a moiety of the formula

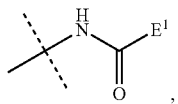

wherein
the dashed line indicates attachment to P; and
$E^1$ is selected from formulas (e-i) to (e-ix).
If the backbone reagent has a structure of formula (III), a preferred moiety -$A^5$-$Hyp^4$ is a moiety of the formula

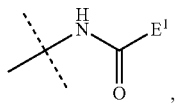

wherein
the dashed line indicates attachment to $P^1$; and
$E^1$ is selected from formulas (e-i) to (e-ix).

More preferably, the backbone reagent has a structure of formula (I) and B is has a structure of formula (a-xiv).

Even more preferably, the backbone reagent has the structure of formula (I), B has the structure of formula (a-xiv), x1 and x2 are 0, and $A^1$ is —O—.

Even more preferably, the backbone reagent has the structure of formula (I), B has the structure of formula (a-xiv), $A^1$ is —O—, and P has a structure of formula (c-i).

Even more preferably, the backbone reagent is formula (I), B is of formula (a-xiv), x1 and x2 are 0, $A^1$ is —O—, P is of formula (c-i), $A^2$ is —NH—(C=O)— and $Hyp^1$ is of formula (e-iii).

Most preferably, the backbone reagent has the following formula:

wherein
n ranges from 10 to 40, preferably from 10 to 30, more preferably from 10 to 20.

Equally preferably, n ranges from 20 to 30 kDa and most preferably n is 28.

SP is a spacer moiety selected from the group comprising $C_{1-6}$ alkyl, $C_{2-6}$ alkenyl and $C_{2-6}$ alkynyl, preferably SP is —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, —CH=CH— or —CH=CH—, most preferably SP is —$CH_2$—, —$CH_2$—$CH_2$— or —CH=CH—.

The at least one crosslinker reagent comprises at least two carbonyloxy groups (—(C=O)—O— or —O—(C=O)—), which are biodegradable linkages. These biodegradable linkages are necessary to render the hydrogel biodegradable. Additionally, the at least one crosslinker reagent comprises at least two activated functional end groups which during the polymerization of step (b) react with the amines of the at least one backbone reagent.

The crosslinker reagent has a molecular weight ranging from 6 to 40 kDa, more preferably ranging from 6 to 30 kDa, even more preferably ranging from 6 to 20 kDa, even more preferably ranging from 6 to 15 kDa and most preferably ranging from 6 to 10 kDa.

The crosslinker reagent comprises at least two activated functional end groups selected from the group comprising activated ester groups, activated carbamate groups, activated carbonate groups and activated thiocarbonate groups, which during polymerization react with the amine groups of the backbone reagents, forming amide bonds.

In one preferred embodiment, the crosslinker reagent is a compound of formula (V-I):

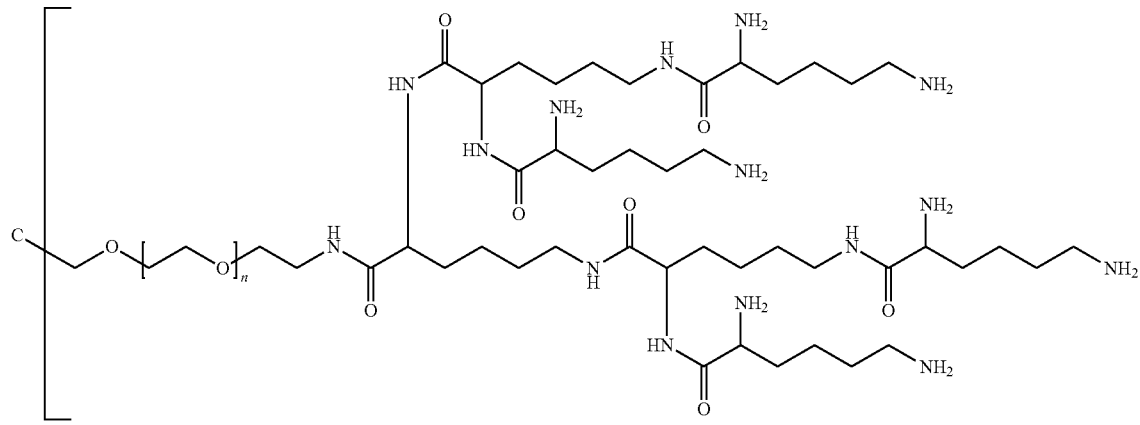

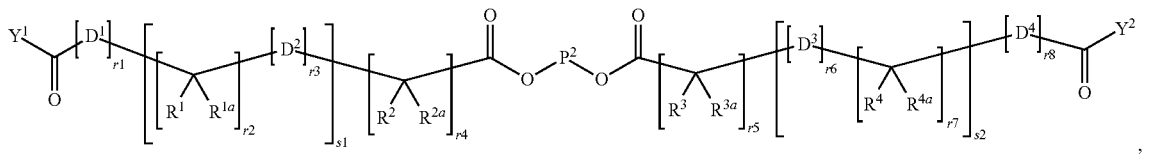

(V-I)

wherein
each $D^1$, $D^2$, $D^3$ and $D^4$ are identical or different and each is independently of the others selected from the group comprising —O—, —$NR^5$—, —S— and —$CR^6R^{6a}$—;
each $R^1$, $R^{1a}$, $R^2$, $R^{2a}$, $R^3$, $R^{3a}$, $R^4$, $R^{4a}$, $R^6$ and $R^{6a}$ are identical or different and each is independently of the others selected from the group comprising —H, —$OR^7$, —$NR^7R^{7a}$, —$SR^7$ and $C_{1-6}$ alkyl; optionally, each of the pair(s) $R^1/R^2$, $R^3/R^4$, $R^{1a}/R^{2a}$, and $R^{3a}/R^{4a}$ may independently form a chemical bond and/or each of the pairs $R^1/R^{1a}$, $R^2/R^{2a}$, $R^3/R^{3a}$, $R^4/R^{4a}$, $R^6/R^{6a}$, $R^1/R^2$, $R^3/R^4$, $R^{1a}/R^{2a}$, and $R^{3a}/R^{4a}$ are independently of each other joined together with the atom to which they are attached to form a $C_{3-8}$ cycloalkyl or to form a ring A or are joined together with the atom to which they are attached to form a 4- to 7-membered heterocyclyl or 8- to 11-membered heterobicyclyl or adamantyl;
each $R^5$ is independently selected from —H and $C_{1-6}$ alkyl; optionally, each of the pair(s) $R^1/R^5$, $R^2/R^5$, $R^3/R^5$, $R^4/R^5$ and $R^5/R^6$ may independently form a chemical bond and/or are joined together with the atom to which they are attached to form a 4- to 7-membered heterocyclyl or 8- to 11-membered heterobicyclyl;
each $R^7$, $R^{7a}$ is independently selected from H and $C_{1-6}$ alkyl;
A is selected from the group consisting of indenyl, indanyl and tetralinyl;
$P^2$ is

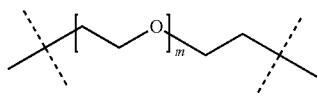

m ranges from 120 to 920, preferably from 120 to 460 and more preferably from 120 to 230;
r1, r2, r7, r8 are independently 0 or 1;
r3, r6 are independently 0, 1, 2, 3, or 4;
r4, r5 are independently 1, 2, 3, 4, 5, 6, 7, 8, 9 or 10;
s1, s2 are independently 1, 2, 3, 4, 5 or 6;
$Y^1$, $Y^2$ are identical or different and each is independently of the other selected from formulas (f-i) to (f-vi):

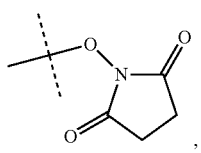
(f-i)

-continued

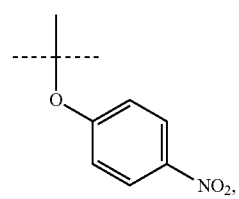
(f-ii)

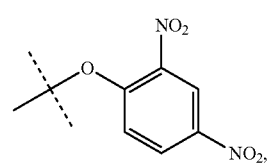
(f-iii)

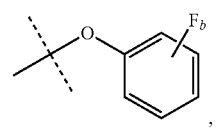
(f-iv)

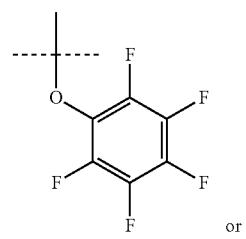
(f-v)

or

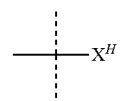
(f-vi)

wherein
the dashed lines indicate attachment to the rest of the molecule,
b is 1, 2, 3 or 4
$X^H$ is Cl, Br, I, or F.
Preferably, the crosslinker reagent is a compound of formula (V-II):

(V-II)

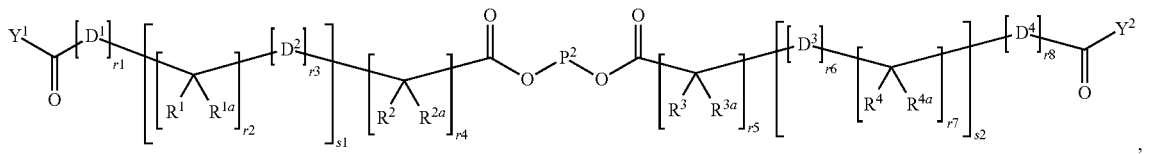

wherein
$D^1$, $D^2$, $D^3$ and $D^4$ are identical or different and each is independently of the others selected from the group comprising O, $NR^5$, S and $CR^5R^{5a}$;
$R^1$, $R^{1a}$, $R^2$, $R^{2a}$, $R^3$, $R^{3a}$, $R^4$, $R^{4a}$, $R^5$ and $R^{5a}$ are identical or different and each is independently of the others selected from the group comprising H and $C_{1-6}$ alkyl; optionally, one or more of the pair(s) $R^1/R^{1a}$, $R^2/R^{2a}$, $R^3/R^{3a}$, $R^4/R^{4a}$, $R^1/R^2$, $R^3/R^4$, $R^{1a}/R^{2a}$, and $R^{3a}/R^{4a}$ form a chemical bond or are joined together with the atom to which they are attached to form a $C_{3-8}$ cycloalkyl or to form a ring A or are joined together with the atom to which they are attached to form a 4- to 7-membered heterocyclyl or 8- to 11-membered heterobicyclyl or adamantyl;
A is selected from the group consisting of phenyl, naphthyl, indenyl, indanyl and tetralinyl;
$P^2$ is

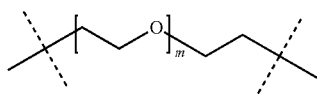

m ranges from 120 to 920, preferably from 120 to 460 and more preferably from 120 to 230;
r1, r2, r7, r8 are independently 0 or 1;
r3, r6 are independently 0, 1, 2, 3, or 4;
r4, r5 are independently 1, 2, 3, 4, 5, 6, 7, 8, 9 or 10;
s1, s2 are independently 1, 2, 3, 4, 5 or 6;
$Y^1$, $Y^2$ are identical or different and each is independently of the other selected from formulas (f-i) to (f-vi):

(f-i)

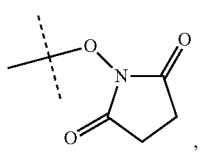

(f-ii)

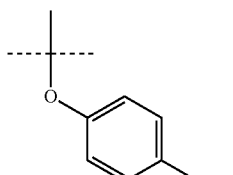

(f-iii)

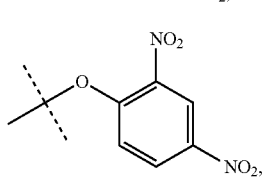

(f-iv)

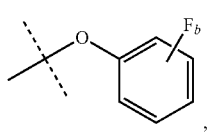

(f-v)

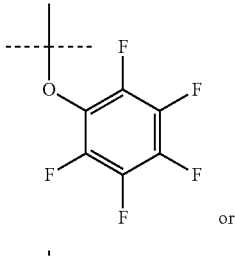

or (f-vi)

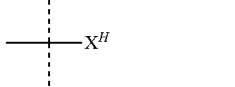

wherein
the dashed lines indicate attachment to the rest of the molecule,
b is 1, 2, 3 or 4
$X^H$ is Cl, Br, I, or F.
It is understood that the moieties

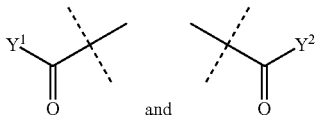
and represent the at least two activated functional end groups.
Preferably, $Y^1$ and $Y^2$ of formula (V-I) or (V-II) have a structure of formula (f-i), (f-ii) or (f-v). More preferably, $Y^1$ and $Y^2$ have a structure of formula (f-i) or (f-ii) and most preferably, $Y^1$ and $Y^2$ have a structure of formula (f-i).
Preferably, both moieties $Y^1$ and $Y^2$ of formula (V-I) or (V-II) have the same structure. More preferably, both moieties $Y^1$ and $Y^2$ have the structure of formula (f-i).
Preferably, r1 of formula (V-I) or (V-II) is 0.
Preferably, r1 and s1 of formula (V-I) or (V-II) are both 0.
Preferably, one or more of the pair(s) $R^1/R^{1a}$, $R^2/R^{2a}$, $R^3/R^{3a}$, $R^4/R^{4a}$, $R^1/R^2$, $R^3/R^4$, $R^{1a}/R^{2a}$, and $R^{3a}/R^{4a}$ of formula (V-I) or (V-II) form a chemical bond or are joined together with the atom to which they are attached to form a $C_{3-8}$ cycloalkyl or form a ring A.
Preferably, one or more of the pair(s) $R^1/R^2$, $R^{1a}/R^{2a}$, $R^3/R^4$, $R^{3a}/R^{4a}$ of formula (V-I) or (V-II) are joined together with the atom to which they are attached to form a 4- to 7-membered heterocyclyl or 8- to 11-membered heterobicyclyl.
Preferably, the crosslinker reagent of formula (V-I) or (V-II) is symmetric, i.e. the moiety

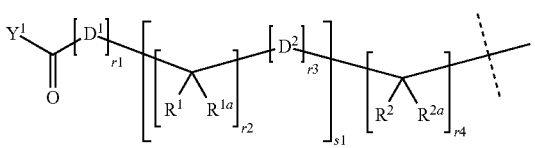

has the same structure as the moiety
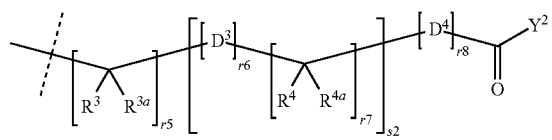
In one preferred embodiment s1, s2, r1 and r8 of formula (V-I) and (V-II) are 0.
In another preferred embodiment s1, s2, r1 and r8 of formula (V-I) and (V-II) are 0 and r4 of formula (V-I) and (V-II) and r5 are 1.
Preferred crosslinker reagents are of formula (V-1) to (V-54):
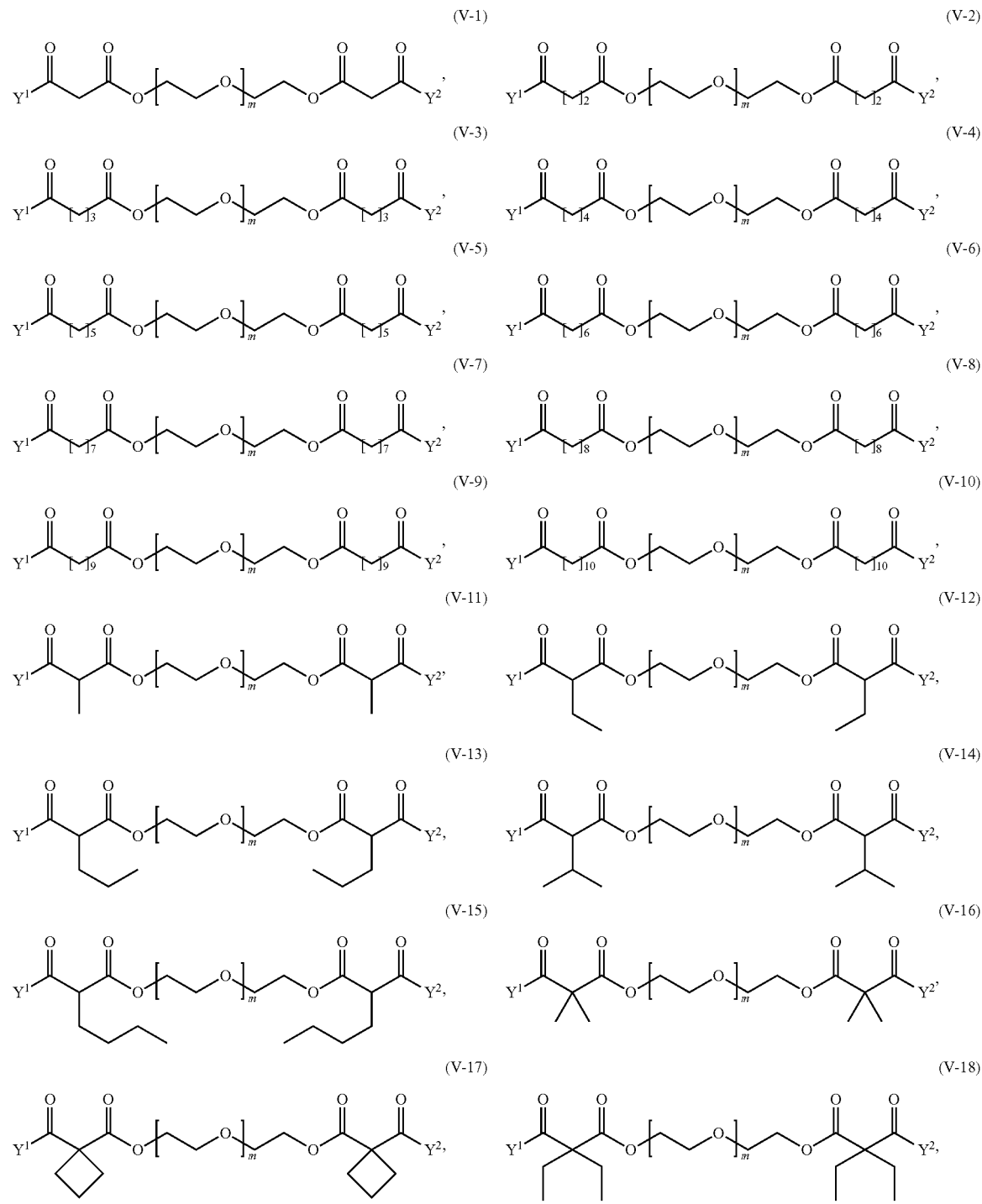

-continued
(V-19)
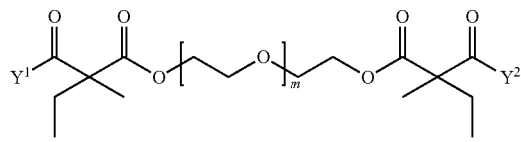
(V-20)
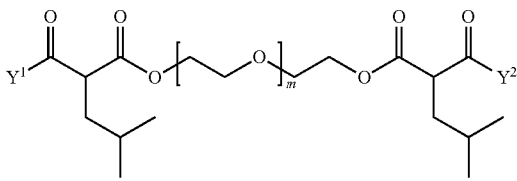
(V-21)
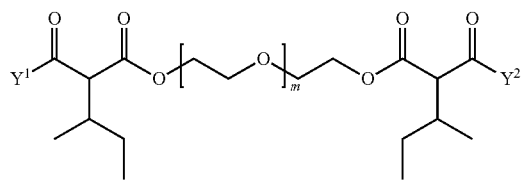
(V-22)
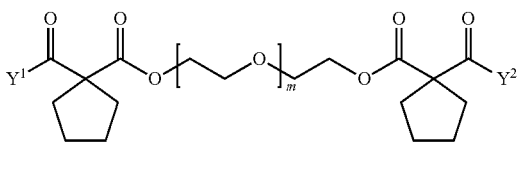
(V-23)
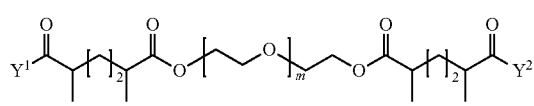
(V-24)
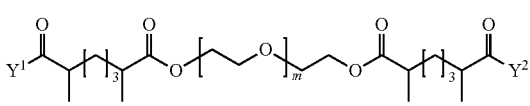
(V-25)
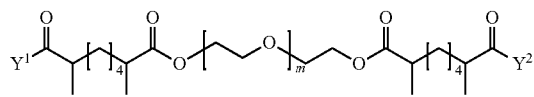
(V-26)
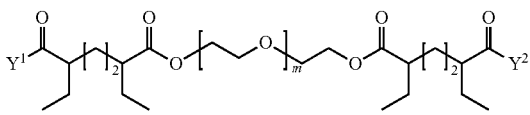
(V-27)
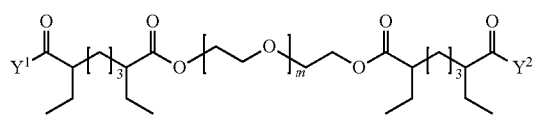
(V-28)
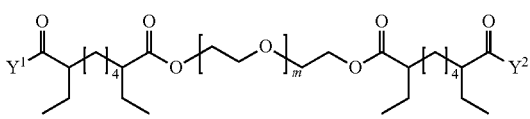
(V-29)
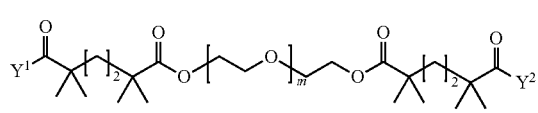
(V-30)
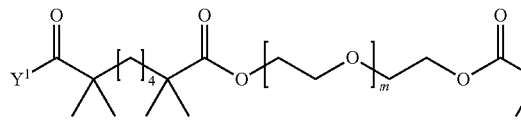
(V-31)
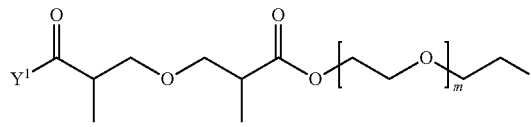
(V-32)
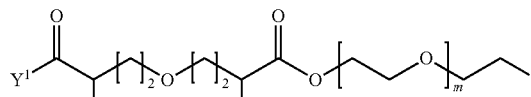
(V-33)
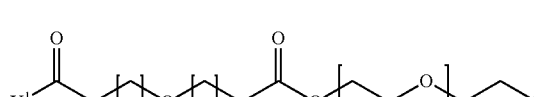
(V-34)
(V-35)

-continued
(V-36) (V-37)
(V-38) (V-39)
(V-40) (V-41)
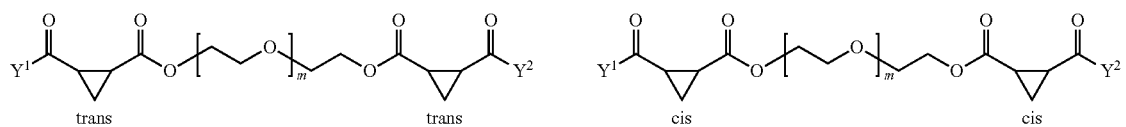
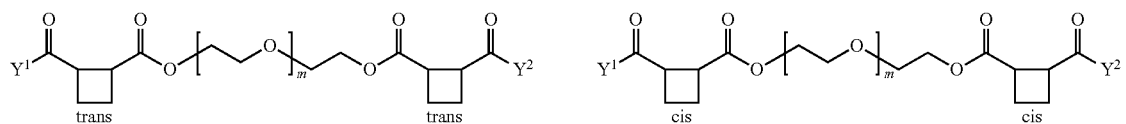
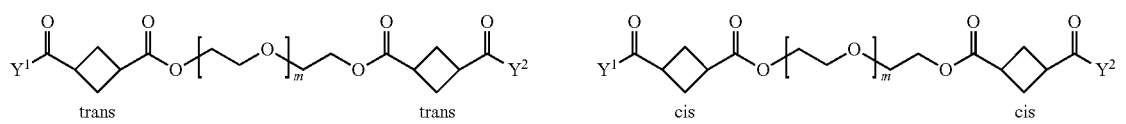
(V-42) (V-43)
(V-44) (V-45)
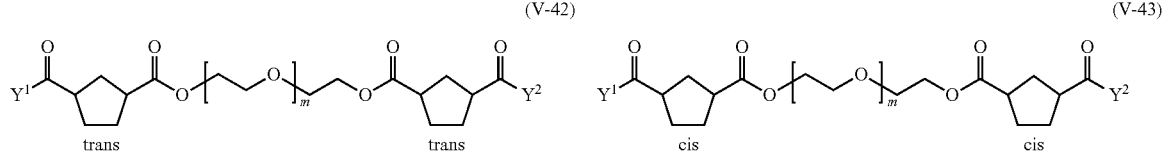
(V-46)
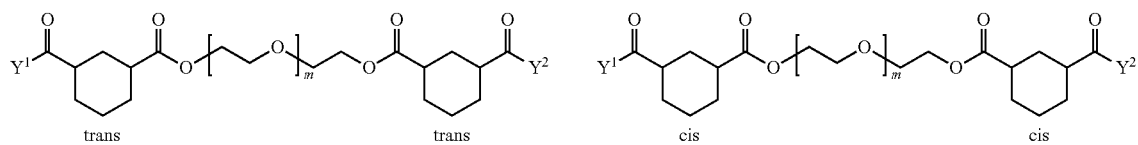
(V-47)
(V-48)
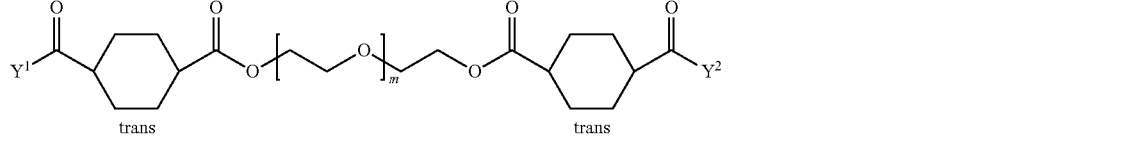
(V-49)
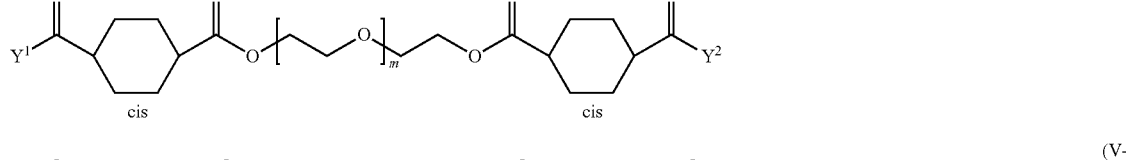

-continued
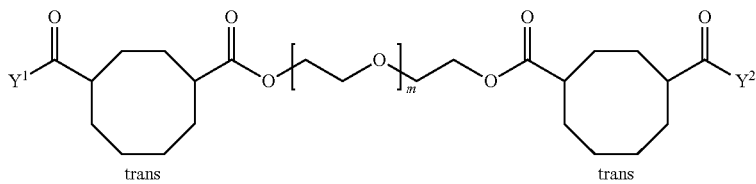 (V-50)
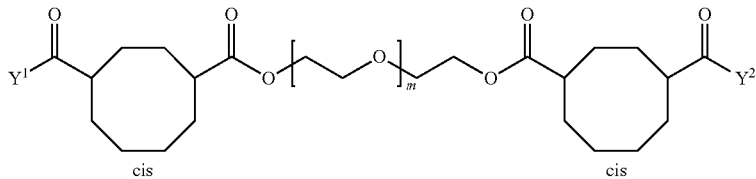 (V-51)
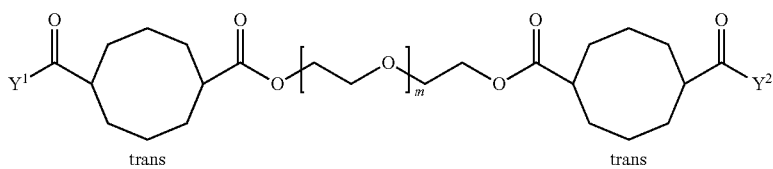 (V-52)
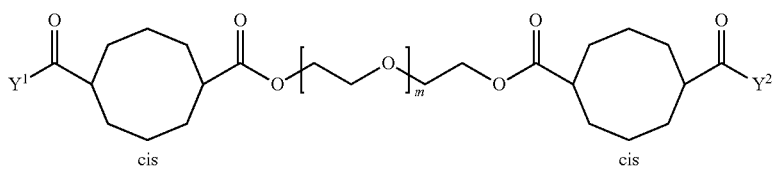 (V-53)
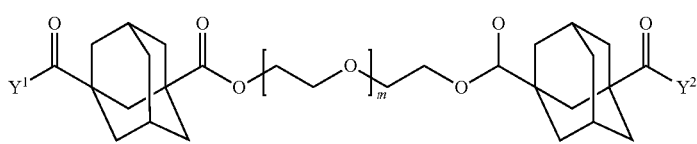 (V-54)
wherein
each crosslinker reagent may be in the form of its racemic mixture, where applicable; and
m, $Y^1$ and $Y^2$ are defined as above.
Even more preferred crosslinker reagents are of formula (Va-1) to (Va-54):
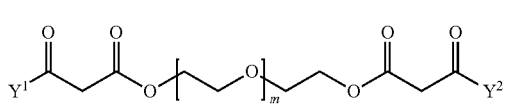 (Va-1)  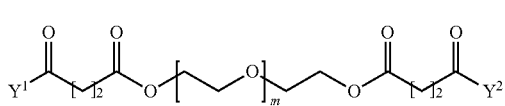 (Va-2)
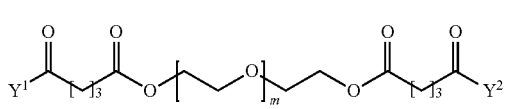 (Va-3)  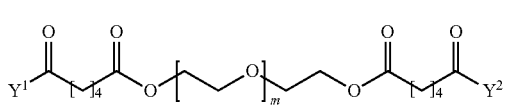 (Va-4)
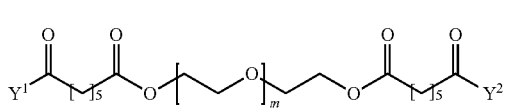 (Va-5)  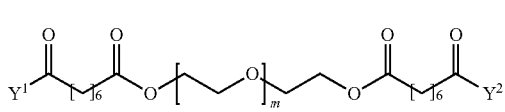 (Va-6)
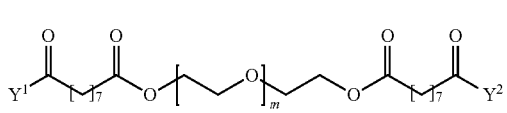 (Va-7)  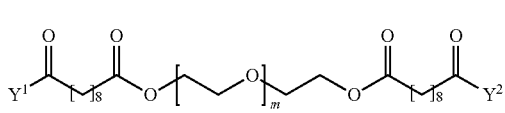 (Va-8)

-continued
(Va-9)
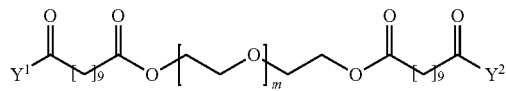
(Va-10)
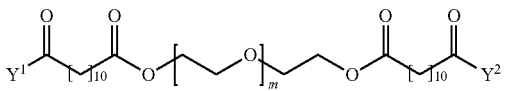
(Va-11)
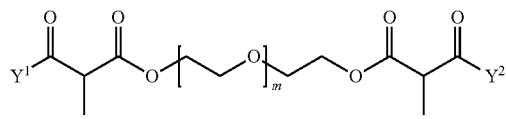
(Va-12)
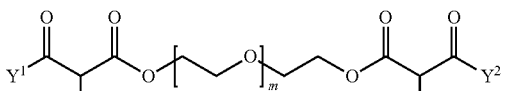
(Va-13)
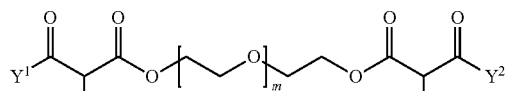
(Va-14)
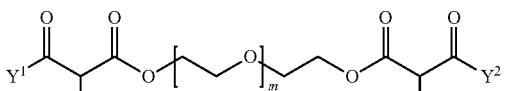
(Va-15)
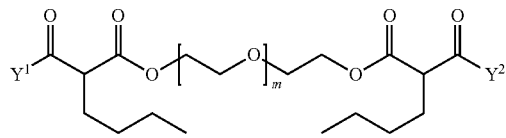
(Va-16)
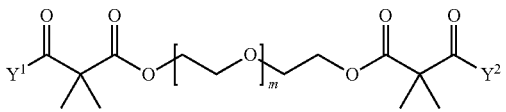
(Va-17)
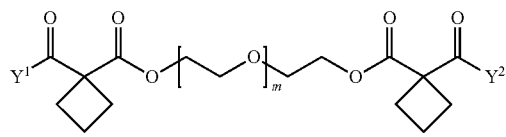
(Va-18)
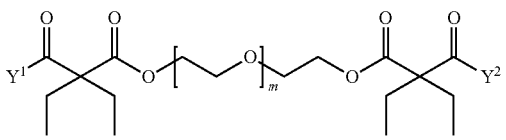
(Va-19)
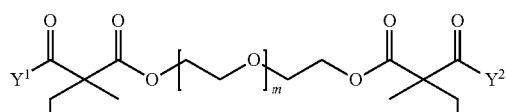
(Va-20)
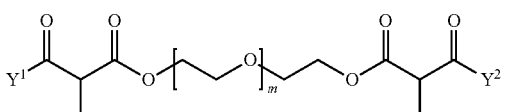
(Va-21)
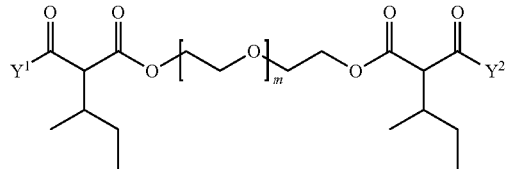
(Va-22)
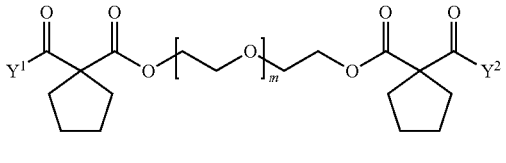
(Va-23)
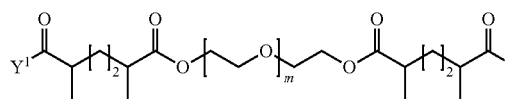
(Va-24)
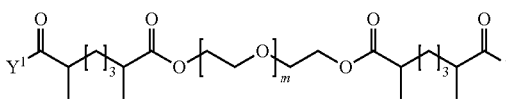
(Va-25)
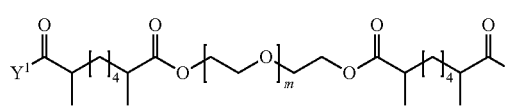
(Va-26)
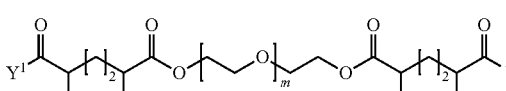
(Va-27)
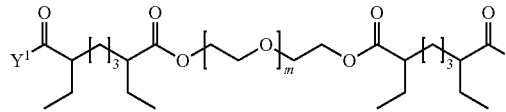
(Va-28)
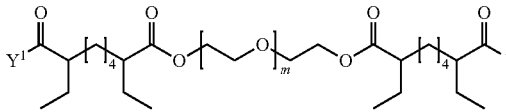

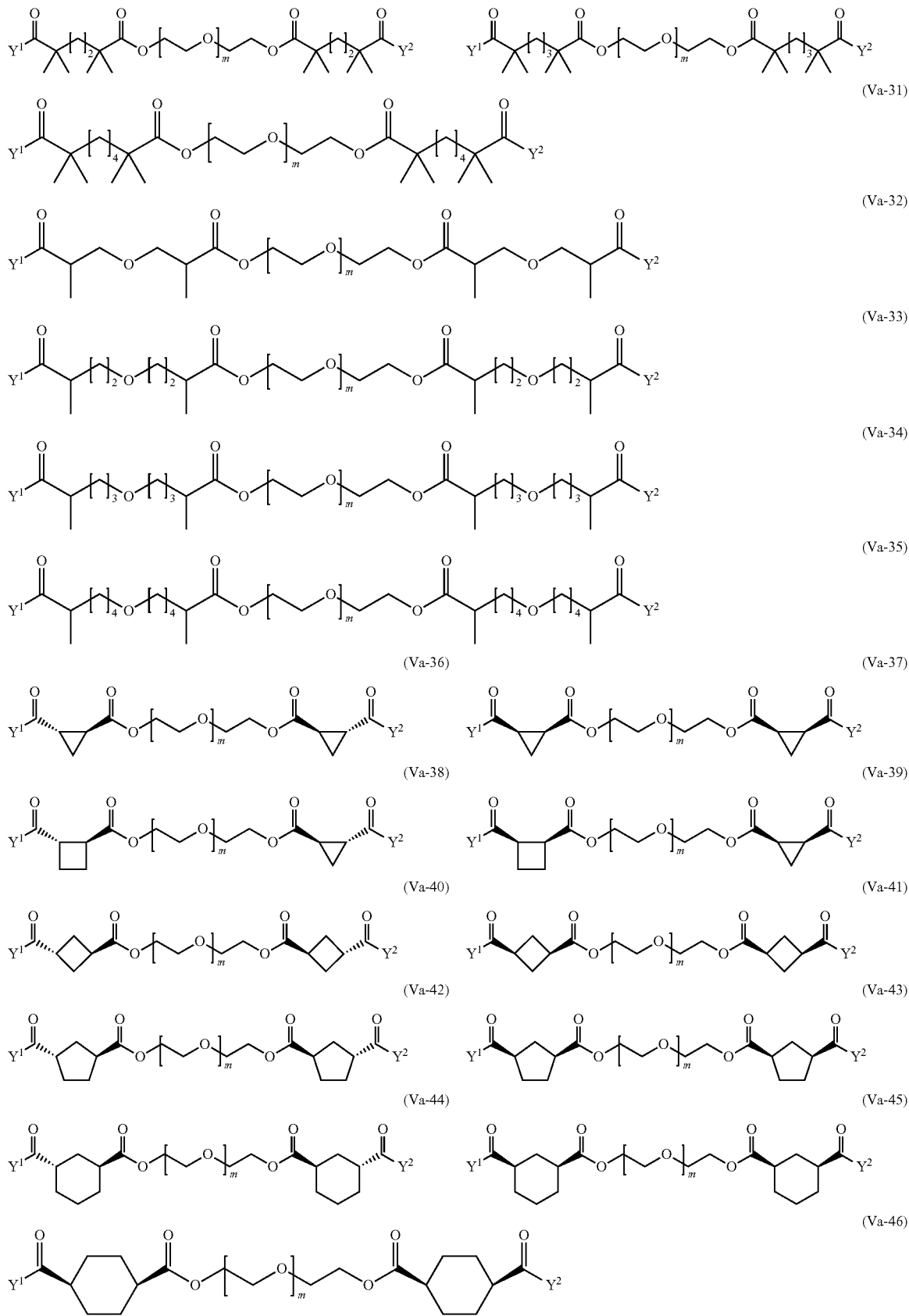

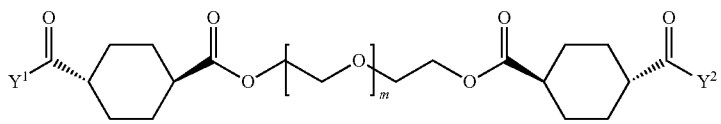
(Va-47)

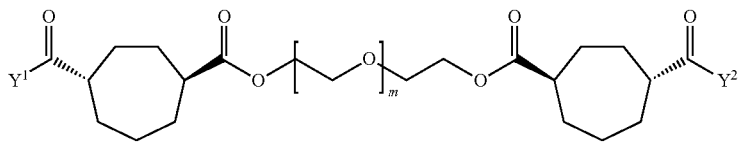
(Va-48)

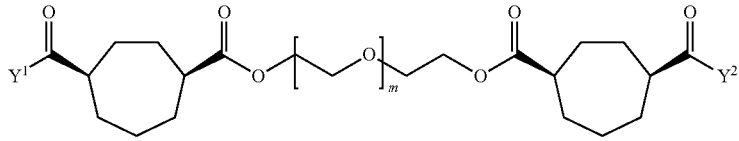
(Va-49)

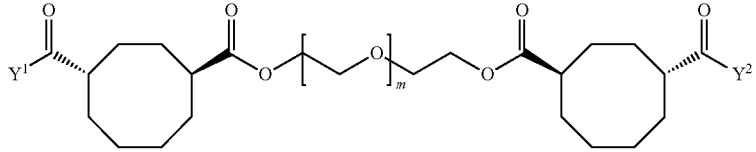
(Va-50)

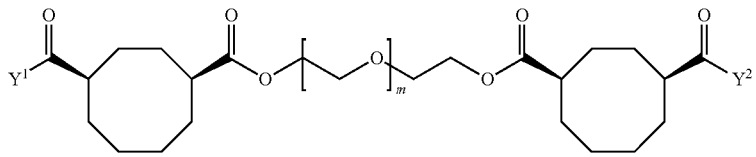
(Va-51)

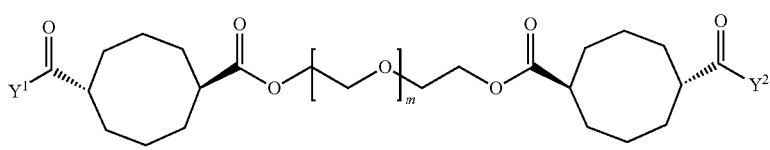
(Va-52)

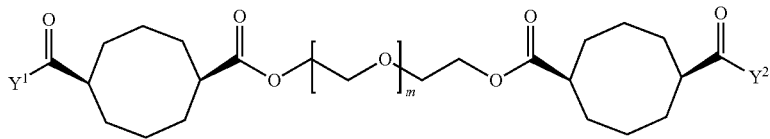
(Va-53)

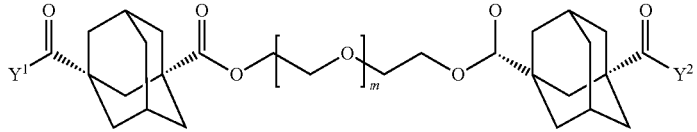
(Va-54)

wherein
each crosslinker reagent may be in the form of its racemic mixture, where applicable; and
m, $Y^1$ and $Y^2$ are defined as above.

It was surprisingly found that the use of crosslinker reagents with branches, i.e. residues other than H, at the alpha carbon of the carbonyloxy group lead to the formation of hydrogels which are more resistant against enzymatic degradation, such as degradation through esterases.

Similarly, it was surprisingly found that the fewer atoms there are between the (C=O) of a carbonyloxy group and the (C=O) of the adjacent activated ester, activated carbamate, activated carbonate or activated thiocarbamate, the more resistant against degradation the resulting hydrogels are, such as more resistant against degradation through esterases.

Accordingly, crosslinker reagents V-11 to V-54, V-1, V-2, Va-11 to Va-54, Va-1 and Va-2 are preferred crosslinker reagents. Crosslinker reagents Va-11 to Va-54, Va-1 and Va-2 are most preferred crosslinker reagents. Most preferred is crosslinker reagent Va-14.

In another embodiment, crosslinker reagents V-1, V-2, V-5, V-6, V-7, V-8, V-9, V-10, V-11, V-12, V-13, V-14, V-15, V-16, V-17, V-18, V-19, V-20, V-21, V-22, V-23, V-24, V-25, V-26, V-27, V-28, V-29, V-30, V-31, V-32, V-33, V-34, V-35, V-36, V-37, V-38, V-39, V-40, V-41, V-42, V-43, V-44, V-45, V-46, V-47, V-48, V-49, V-50, V-51, V-52, V-53 an V-54 are preferred crosslinker reagents. More preferably, the at least one crosslinker reagent is of formula V-5, V-6, V-7, V-8, V-9, V-10, V-14, V-22, V-23, V-43, V-44, V-45 or V-46, and most preferably, the at least one crosslinker reagent is of formula V-5, V-6, V-9 or V-14.

In another embodiment, crosslinker reagents Va-1, Va-2, Va-5, Va-6, Va-7, Va-8, Va-9, Va-10, Va-11, Va-12, Va-13, Va-14, Va-15, Va-16, Va-17, Va-18, Va-19, Va-20, Va-21, Va-22, Va-23, Va-24, Va-25, Va-26, Va-27, Va-28, Va-29, Va-30, Va-31, Va-32, Va-33, Va-34, Va-35, Va-36, Va-37, Va-38, Va-39, Va-40, Va-41, Va-42, Va-43, Va-44, Va-45, Va-46, Va-47, Va-48, Va-49, Va-50, Va-51, Va-52, Va-53 an Va-54 are even more preferred crosslinker reagents. More preferably, the at least one crosslinker reagent is of formula Va-5, Va-6, Va-7, Va-8, Va-9, Va-10, Va-14, Va-22, Va-23, Va-43, Va-44, Va-45 or Va-46, and most preferably, the at least one crosslinker reagent is of formula Va-5, Va-6, Va-9 or Va-14.

The preferred embodiments of the compound of formula (V-I) and (V-II) as mentioned above apply accordingly to the preferred compounds of formulas (V-1) to (V-53).

In another aspect, the present invention relates to a hydrogel obtainable by a process of the present invention as defined above.

The hydrogel contains from 0.01 to 1 mmol/g primary amine groups (—$NH_2$), more preferably, from 0.02 to 0.5 mmol/g primary amine groups and most preferably from 0.05 to 0.3 mmol/g primary amine groups. The term "X mmol/g primary amine groups" means that 1 g of dry hydrogel comprises X mmol primary amine groups. Measurement of the amine content of the hydrogel may be carried out according to Gude et al. (Letters in Peptide Science, 2002, 9(4): 203-206, which is incorporated by reference in its entirety).

Preferably, the term "dry" as used herein means having a residual water content of a maximum of 10%, preferably less than 5% and more preferably less than 2% (determined according to Karl Fischer). The preferred method of drying is lyophilization.

In one embodiment the hydrogel of the VEGF neutralizing prodrug is further modified before a reversible prodrug linker-VEGF neutralizing biologically active moiety is conjugated to the hydrogel.

Preferably, the hydrogel is modified by a process comprising the steps of
(A) providing a hydrogel having groups $A^{x0}$, wherein groups $A^{x0}$ represent the same or different, preferably same, functional groups;
(B) optionally covalently conjugating a spacer reagent of formula (VI)

$$A^{x1}\text{-}SP^2\text{-}A^{x2} \quad (VI),$$

wherein
$SP^2$ is $C_{1-50}$ alkyl, $C_{2-50}$ alkenyl or $C_{2-50}$ alkynyl, which $C_{1-50}$ alkyl, $C_{2-50}$ alkenyl and $C_{2-50}$ alkynyl is optionally interrupted by one or more group(s) selected from the group consisting of —NH—, —N($C_{1-4}$ alkyl)-, —O—, —S, —C(O)—, —C(O)NH, —C(O)N($C_{1-4}$ alkyl)-, —O—C(O)—, —S(O)—, —S(O)$_2$—, 4- to 7-membered heterocyclyl, phenyl and naphthyl;
$A^{x1}$ is a functional group for reaction with $A^{x0}$ of the hydrogel; and
$A^{x2}$ is a functional group;
to $A^{x0}$ of the hydrogel from step (A); and
(C) reacting the hydrogel of step (A) or step (B) with a reagent of formula (VII)

$$A^{x3}\text{-}Z \quad (VII),$$

wherein
$A^{x3}$ is a functional group; and
Z is an inert moiety having a molecular weight ranging from 10 Da to 1000 kDa;
such that at most 99 mol-% of $A^{x0}$ or $A^{x2}$ react with $A^{x3}$.

Preferably, $A^{x0}$ of step (A) is selected from the group consisting of maleimide, amine (—$NH_2$ or —NH—), hydroxyl (—OH), carboxyl (—COOH) and activated carboxyl (—$COY^1$, wherein $Y^1$ is selected from formulas (f-i) to (f-vi):

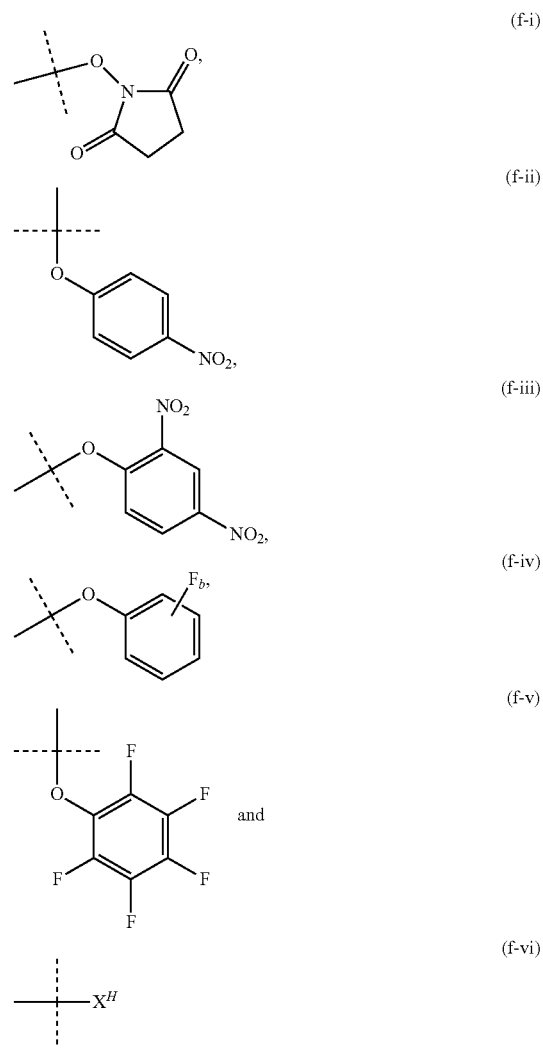

wherein
the dashed lines indicate attachment to the rest of the molecule,
b is 1, 2, 3 or 4;
$X^H$ is Cl, Br, I, or F).

More preferably, $A^{x0}$ of step (A) is an amine or maleimide.

It is understood that the functional groups $A^{x0}$ of step (A) correspond to the amines of the at least one backbone reagent, if the hydrogel of the VEGF neutralizing prodrug is obtained by the process described above.

In a preferred embodiment $A^{x0}$ of step (A) is an amine and $A^{x1}$ of step (B) is ClSO$_2$—, $R^1$(C=O)—, I—, Br—, Cl—, SCN—, CN—, O=C=N—, $Y^1$—(C=O)—, $Y^1$—(C=O)—NH—, or $Y^1$—(C=O)—O—, wherein
R¹ is H, $C_{1-6}$ alkyl, $C_{2-6}$ alkenyl, $C_{2-6}$ alkynyl, $C_{3-8}$ cycloalkyl, 4- to 7-membered heterocyclyl, 8- to 11-membered heterobicyclyl, phenyl, naphthyl, indenyl, indanyl, or tetralinyl; and
Y¹ is selected from formulas (f-i) to (f-vi):

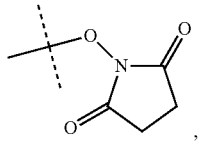
(f-i)

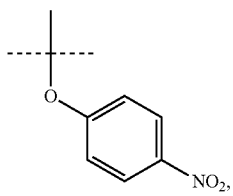
(f-ii)

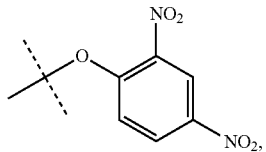
(f-iii)

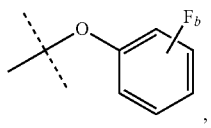
(f-iv)

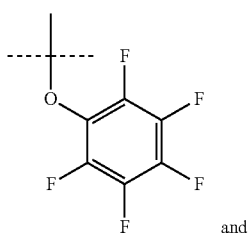
(f-v)

and

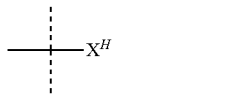
(f-vi)

wherein
the dashed lines indicate attachment to the rest of the molecule,
b is 1, 2, 3 or 4,
$X^H$ is Cl, Br, I, or F.

In another preferred embodiment $A^{x0}$ of step (A) is a hydroxyl group (—OH) and $A^{x1}$ of step (B) is O=C=N—, I—, Br—, SCN—, or Y¹—(C=O)—NH—,
wherein Y¹ is selected from formulas (f-i) to (f-vi):

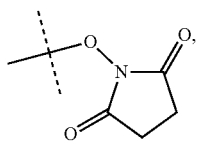
(f-i)

-continued

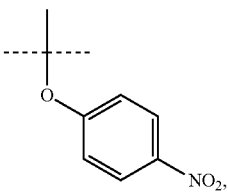
(f-ii)

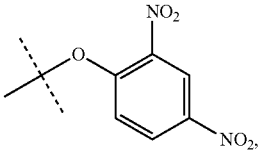
(f-iii)

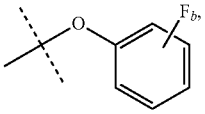
(f-iv)

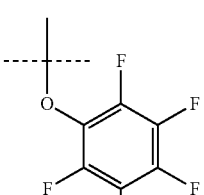
(f-v)

and

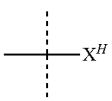
(f-vi)

wherein
the dashed lines indicate attachment to the rest of the molecule,
b is 1, 2, 3 or 4,
$X^H$ is Cl, Br, I, or F.

In another preferred embodiment $A^{x0}$ of step (A) is a carboxylic acid (—(C=O)OH) and $A^{x1}$ of step (B) is a primary amine or secondary amine.

In another preferred embodiment $A^{x0}$ of step (A) is a maleimide and $A^{x1}$ of step (B) is a thiol.

More preferably, $A^{x0}$ of step (A) is an amine and $A^{x1}$ of step (B) is Y¹—(C=O)—, Y¹—(C=O)—NH—, or Y¹—(C=O)—O— and most preferably $A^{x0}$ of step (A) is an amine and $A^{x1}$ of step (B) is Y¹—(C=O)—.

$A^{x1}$ of step (B) may optionally be present in protected form.

Suitable activating reagents to obtain the activated carboxylic acid are for example N,N'-dicyclohexyl-carbodiimide (DCC), 1-ethyl-3-carbodiimide (EDC), benzotriazol-1-yl-oxytripyrrolidinophosphonium hexafluorophosphate (PyBOP), bromotripyrrolidinophosphonium hexafluorophosphate (PyBrOP), 1-cyano-2-ethoxy-2-oxoethylidenaminooxy)dimethylamino-morpholino-carbenium hexafluorophosphate (COMU), 1-hydroxybenzotriazole (HOBT), 1-hydroxy-7-azabenzotriazole (HOAT), O-(6-chlorobenzotriazol-1-yl)-N,N,N',N'-tetramethyluronium hexafluorophosphate (HCTU), 1-H-benzotriazolium (HBTU), (0-(7-azabenzotriazol-1-yl)-N,N,N',N'-tetramethyluronium hexafluorophosphate (HATU), and O-(benzotriazol-1-yl)-N,N,N',N'-tetramethyluronium tetrafluoroborate (TBTU). These reagents are commercially available and well-known to the skilled person.

Preferably, $A^{x2}$ of step (B) is selected from the group consisting of -maleimide, —SH, —NH$_2$, —SeH, —N$_3$, —C≡CH, —CR$^1$=CR$^{1a}$R$^{1b}$, —OH, —(CH=X)R$^1$, —(C=O)SR$^1$, —(C=O)—H, —NH—NH$_2$, —O—NH$_2$, —Ar—X$^0$, —Ar—Sn(R$^1$)(R$^{1a}$)(R$^{1b}$), —Ar—B(OH)(OH), Br, I, Y$^1$—(C=O)—, Y$^1$—(C=O)—NH—, Y$^1$—(C=O)—O—,

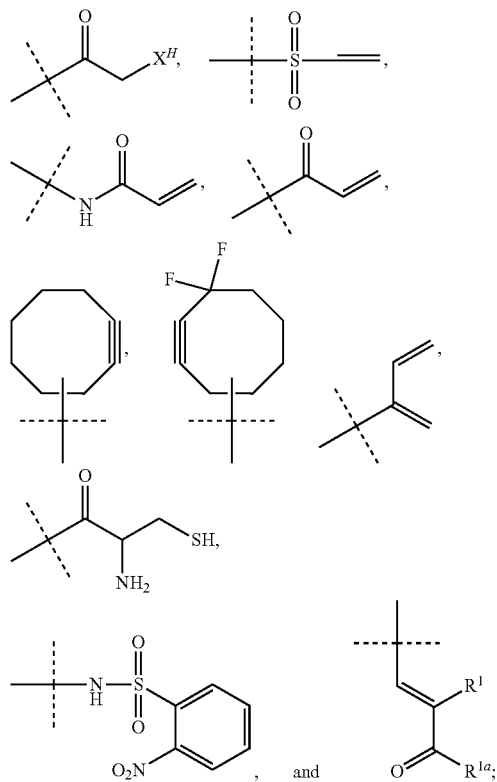

with optional protecting groups;
wherein
dashed lines indicate attachment to SP$^2$;
X is O, S, or NH,
X$^0$ is —OH, —NR$^1$R$^{1a}$, —SH, or —SeH,
X$^H$ is Cl, Br, I or F;
Ar is phenyl, naphthyl, indenyl, indanyl, or tetralinyl;
R$^1$, R$^{1a}$, R$^{1b}$ are independently of each other H, C$_{1-6}$ alkyl, C$_{2-6}$ alkenyl, C$_{2-6}$ alkynyl, C$_{3-8}$ cycloalkyl, 4- to 7-membered heterocyclyl, 8- to 11-membered heterobicyclyl, phenyl, naphthyl, indenyl, indanyl, or tetralinyl; and
Y$^1$ is selected from formulas (f-i) to (f-vi):

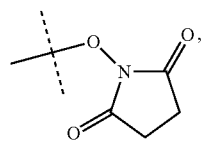
(f-i)

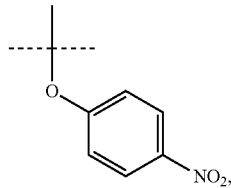
(f-ii)

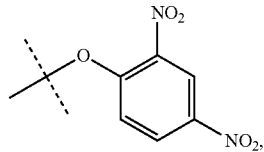
(f-iii)

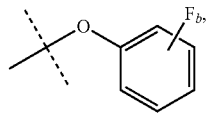
(f-iv)

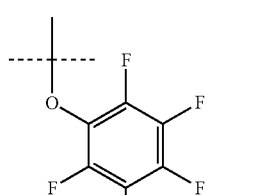
(f-v)

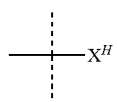
(f-vi)

wherein
the dashed lines indicate attachment to the rest of the molecule,
b is 1, 2, 3 or 4,
X$^H$ is Cl, Br, I, or F.

More preferably, $A^{x2}$ of step (B) is NH$_2$, maleimide or thiol and most preferably $A^{x2}$ of step (B) is maleimide. Equally preferable, $A^{x2}$ of step (B) is thiol.

$A^{x2}$ of step (B) may optionally be present in protected form.

If the hydrogel of step (A) is covalently conjugated to a spacer moiety, the resulting hydrogel-spacer moiety conjugate is of formula (VIII):

(VIII), wherein
the dashed line indicates attachment to the hydrogel of step (A);
$A^{y1}$ is the linkage formed between $A^{x0}$ and $A^{x1}$; and
SP$^2$ and $A^{x2}$ are used as in formula (VI).

Preferably, $A^{y1}$ of formula (VIII) is a stable linkage.
Preferably, $A^{y1}$ of formula (VIII) is selected from the group consisting of

-continued

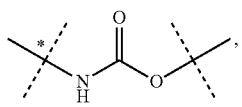

wherein dashed lines marked with an asterisk indicate attachment to the hydrogel; and unmarked dashed lines indicate attachment to $SP^2$.

Suitable reaction conditions are described in the Examples sections and are known to the person skilled in the art.

Process step (B) may be carried out in the presence of a base. Suitable bases include customary inorganic or organic bases. These preferably include alkaline earth metal or alkali metal hydrides, hydroxides, amides, alkoxides, acetates, carbonates or bicarbonates such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN), N,N-diisopropylethylamine (DIPEA), diazabicycloundecene (DBU) or collidine.

Process step (B) may be carried out in the presence of a solvent. Suitable solvents for carrying out the process step (B) of the invention include organic solvents. These preferably include water and aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, carbon tetrachloride, dichloroethane or trichloroethane; alcohols such as methanol, ethanol, n- or i-propanol, n-, i-, sec- or tert-butanol, ethanediol, propane-1,2-diol, ethoxyethanol, methoxyethanol, diethylene glycol monomethyl ether, dimethylether, diethylene glycol; acetonitrile, N-methyl-2-pyrrolidone (NMP), dimethylformamide (DMF), dimethyl sulfoxide (DMSO), N,N-dimethylacetamide, nitromethane, nitrobenzene, hexamethylphosphoramide (HMPT), 1,3-dimethyl-2-imidazolidinone (DMI), 1,3-dimethyl-3,4,5,6-tetrahydro-2(1H)-pyrimidinone (DMPU), ethyl acetate, acetone, butanone; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; or mixtures thereof. Preferably, the solvent is selected from the group consisting of water, acetonitrile and N-methyl-2-pyrrolidone.

Preferably, $A^{x3}$ of step (C) is selected from the group consisting of SH, —$NH_2$, —SeH, -maleimide, —C≡CH, —$N_3$, —$CR^1$=$CR^{1a}R^{1b}$, —(C=X)—$R^1$, —OH, —(C=O)—S—$R^1$, —NH—$NH_2$, —O—$NH_2$, —Ar—Sn$(R^1)(R^{1a})(R^{1b})$, —Ar—B(OH)(OH), —Ar—$X^0$,

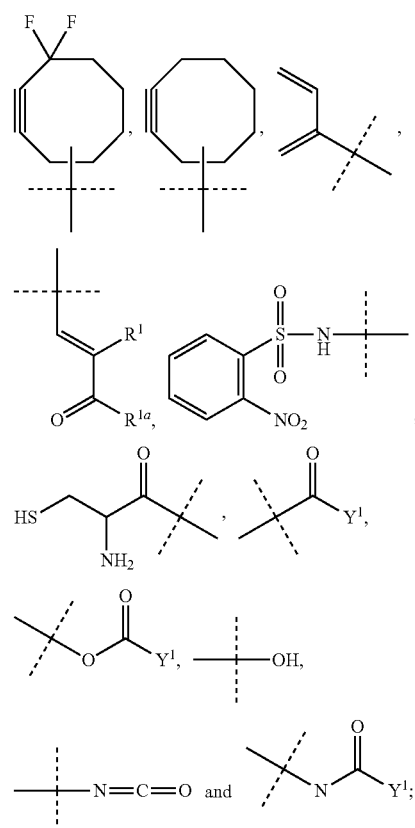

wherein dashed lines indicate attachment to Z;

X is O, S, or NH, $X^0$ is —OH, —$NR^1R^{1a}$, —SH, or SeH;

$R^1$, $R^{1a}$, $R^{1b}$ are independently of each other H, $C_{1-6}$ alkyl, $C_{2-6}$ alkenyl, $C_{2-6}$ alkynyl, $C_{3-8}$ cycloalkyl, 4- to 7-membered heterocyclyl, 8- to 11-membered heterobicyclyl, phenyl, naphthyl, indenyl, indanyl, or tetralinyl; and Ar is phenyl, naphthyl, indenyl, indanyl, or tetralinyl.

$Y^1$ is an activated carboxylic acid, activated carbonate or activated carbamate, preferably $Y^1$ is selected from formulas (f-i) to (f-vi):

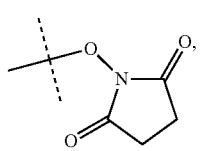

(f-i)

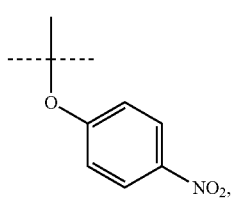

(f-ii)

wherein
the dashed lines indicate attachment to the rest of the molecule,
b is 1, 2, 3 or 4,
$X^H$ is Cl, Br, I, or F In a preferred embodiment, $Y^1$ is selected from formulas (f-i) to (f-vi):

(f-i) N-hydroxysuccinimide ester structure (f-ii) 4-nitrophenyl ether structure (f-iii) 2,4-dinitrophenyl ether structure (f-iv) fluorophenyl ether structure with $F_b$ (f-v) pentafluorophenyl ether structure (f-vi) —$X^H$ wherein
the dashed lines, b and $X^H$ are used as above.

More preferably, $A^{x3}$ of step (C) is —SH or -maleimide and most preferably $A^{x3}$ of step (C) is —SH.

In another preferred embodiment $A^{x3}$ is of formula (aI)

$$PG^0\text{-}S\text{---}\quad\quad (aI),$$

wherein
the dashed line indicates attachment to Z of formula (VII);
$PG^0$ is a sulfur-activating moiety; and
S is sulfur.

Preferably, $PG^0$ of formula (aI) is selected from the group consisting of (i) Ar—S—

(ii) Ar—S(O)$_2$—

(iii) $R^{01}$—S(O)$_2$—

(iv) $R^{03}(R^{02})$N—C(O)—S—

(v) $R^{04}$—O—C(O)—S—

(vi) triphenylmethyl (trityl), and

-continued (vii)

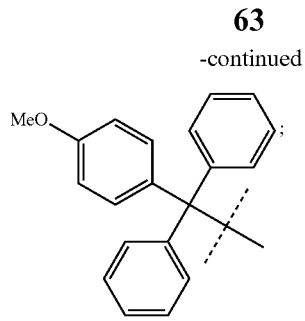

wherein the dashed lines indicate attachment to the sulfur of formula (aI);

Ar is an aromatic moiety which is optionally further substituted;

$R^{01}$, $R^{02}$, $R^{03}$, $R^{04}$ are independently of each other —H; $C_{1-50}$ alkyl; $C_{2-50}$ alkenyl; or $C_{2-50}$ alkynyl, wherein $C_{1-50}$ alkyl; $C_{2-50}$ alkenyl; and $C_{2-50}$ alkynyl are optionally substituted with one or more $R^3$, which are the same or different and wherein $C_{1-50}$ alkyl; $C_{2-50}$ alkenyl; and $C_{2-50}$ alkynyl are optionally interrupted by one or more groups selected from the group consisting of -Q-, —C(O)O—; —O—; —C(O)—; —C(O)N($R^4$)—; —S(O)$_2$N($R^4$)—; —S(O)N($R^4$)—; —S(O)$_2$—; —S(O)—; —N($R^4$)S(O)$_2$N($R^{4a}$)—; —S—; —N($R^4$)—; —OC(O)$R^4$; —N($R^4$)C(O)—; —N($R^4$)S(O)$_2$—; —N($R^4$)S(O)—; —N($R^4$)C(O)O—; —N($R^4$)C(O)N($R^{4a}$)—; and —OC(O)N($R^4R^{4a}$);

Q is selected from the group consisting of phenyl; naphthyl; indenyl; indanyl; tetralinyl; $C_{3-10}$ cycloalkyl; 4- to 7-membered heterocyclyl; and 8- to 11-membered heterobicyclyl, wherein T is optionally substituted with one or more $R^3$, which are the same or different;

$R^3$ is halogen; —CN; oxo (=O); —COO$R^5$; —OR$^5$; —C(O)$R^5$; —C(O)N($R^5R^{5a}$); —S(O)$_2$N($R^5R^{5a}$); —S(O)N($R^5R^{5a}$); —S(O)$_2R^5$; —S(O)$R^5$; —N($R^5$)S(O)$_2$N($R^{5a}R^{5b}$); —S$R^5$; —N($R^5R^{5a}$); —NO$_2$; —OC(O)$R^5$; —N($R^5$)C(O)$R^{5a}$; —N($R^5$)S(O)$_2R^{5a}$; —N($R^5$)S(O)$R^{5a}$; —N($R^5$)C(O)O$R^{5a}$; —N($R^5$)C(O)N($R^{5a}R^{5b}$); —OC(O)N($R^5R^{5a}$); or $C_{1-6}$ alkyl, wherein $C_{1-6}$ alkyl is optionally substituted with one or more halogen, which are the $R^4$, $R^{4a}$, $R^5$, $R^{5a}$, $R^{5b}$ are independently selected from the group consisting of —H; or $C_{1-6}$ alkyl, wherein $C_{1-6}$ alkyl is optionally substituted with one or more halogen, which are the same or different.

Preferably, $R^{01}$, $R^{03}$ and $R^{04}$ are independently of each other $C_{1-6}$ alkyl.

Preferably, $R^{02}$ is selected from H and $C_{1-6}$ alkyl.

Preferably, Ar is selected from the group consisting of

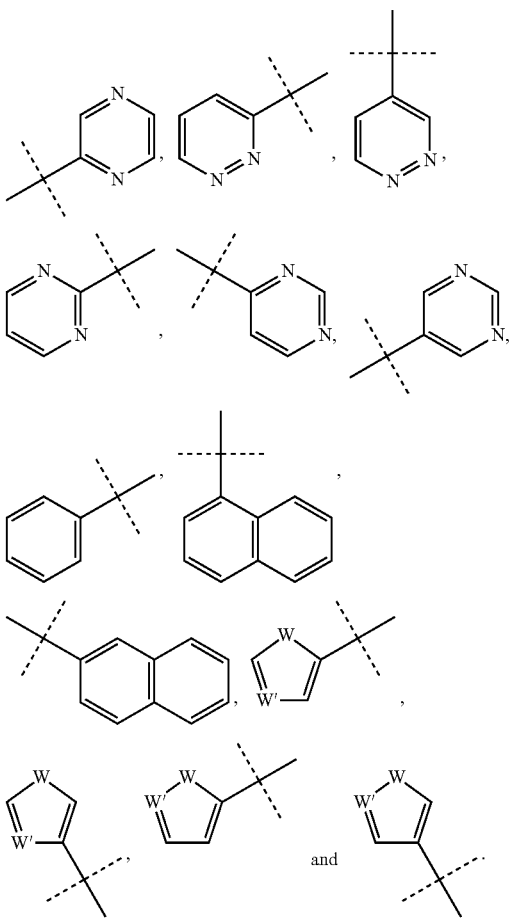

wherein dashed lines indicate attachment to the rest of $PG^0$ of formula (aI);

W is independently of each other O, S, or N;

W' is N; and wherein Ar is optionally substituted with one or more substituent(s) independently selected from the group consisting of NO$_2$, Cl and F.

More preferably, $PG^0$ of formula (aI) is selected from the group consisting of

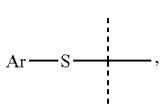

(i)

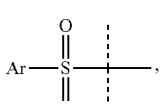

(ii)

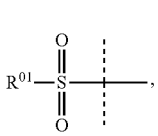

(iii)

-continued

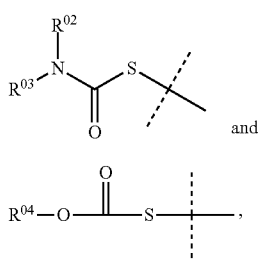

and

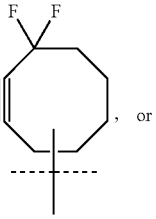

wherein
the dashed lines indicate attachment to the sulfur of formula (aI); and
Ar, $R^{01}$, $R^{02}$, $R^{03}$ and $R^{04}$ are used as above.

More preferably, $PG^0$ of formula (aI) is

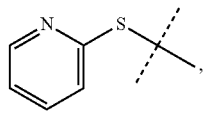

(iv)

wherein
the dashed line indicates attachment to the sulfur of formula (aI).

$A^{x3}$ of step (C) may optionally be present in protected form.

Preferred combinations of $A^{x2}$ of step (B) and $A^{x3}$ of step (C) are the following:

| $A^{x2}$ | $A^{x3}$ |
|---|---|
| -maleimide | HS—, H$_2$N—, or HSe— |
| —SH, —NH$_2$, or —SeH | maleimide- |
| —NH$_2$, | $Y^1$—(C=O)—, $Y^1$—(C=O)—NH—, or $Y^1$—(C=O)—O— |
| —N$_3$ | HC≡C—, 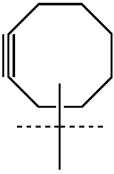, or 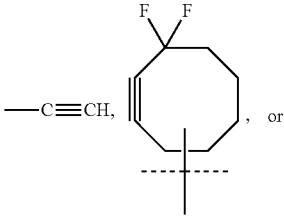 |
| —C≡CH, 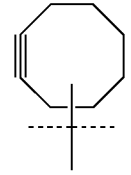, or 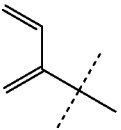 | N$_3$— |
| —CR$^{1a}$=CR$^{1a}$R$^{1b}$ | R$^{1b}$R$^{1a}$=CR$^1$— or R$^{1b}$R$^{1a}$C=CR$^1$— 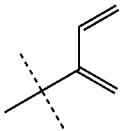 |

-continued

| $A^{x2}$ | $A^{x3}$ |
|---|---|
| 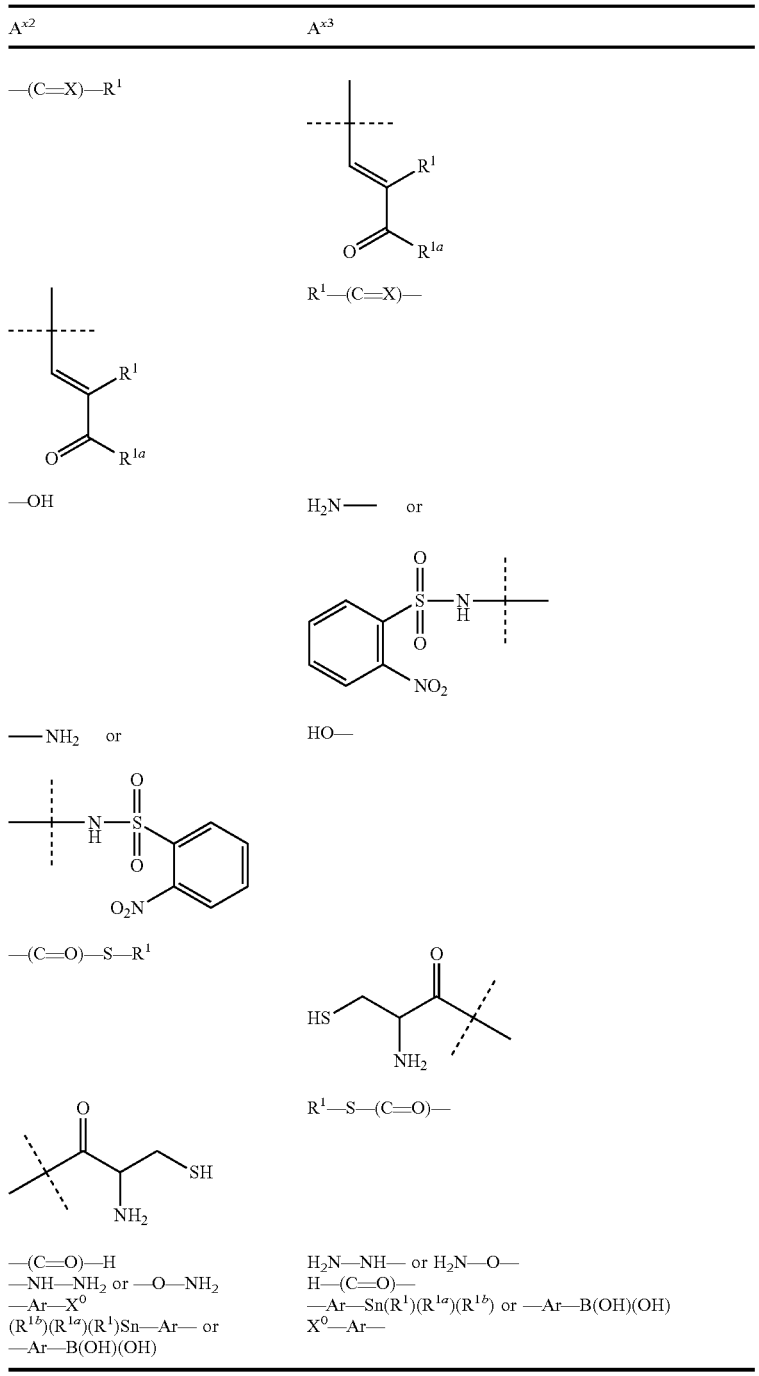 | |
| —(C=O)—H | H$_2$N—NH— or H$_2$N—O— |
| —NH—NH$_2$ or —O—NH$_2$ | H—(C=O)— |
| —Ar—X$^0$ | —Ar—Sn(R$^1$)(R$^{1a}$)(R$^{1b}$) or —Ar—B(OH)(OH) |
| (R$^{1b}$)(R$^{1a}$)(R$^1$)Sn—Ar— or | X$^0$—Ar— |
| —Ar—B(OH)(OH) | | wherein
X is O, S, or NH;
X$^0$ is —OH, —NR$^1$R$^{1a}$, —SH, or SeH;
R$^1$, R$^{1a}$, R$^{1b}$ are independently of each other selected from the group consisting of H, C$_{1-6}$ alkyl, C$_{2-6}$ alkenyl, C$_{2-6}$ alkynyl, C$_{3-8}$ cycloalkyl, 4- to 7-membered heterocyclyl, 8- to 11-membered heterobicyclyl, phenyl, naphthyl, indenyl, indanyl, and tetralinyl; and
Ar is phenyl, naphthyl, indenyl, indanyl, or tetralinyl.

In another preferred embodiment $A^{x2}$ is SH and $A^{x3}$ is of formula (aI), wherein PG$^0$ is of formula (i), (ii), (iii), (iv), (v), (vi) or (viii). More preferably, PG$^0$ of formula (aI) is of formula (i), (ii), (iii), (iv) or (v) and even more preferably, PG$^0$ of formula (aI) is of formula (i). Most preferably, PG$^0$ of formula (aI) is of formula

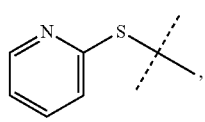
, wherein
the dashed line indicates attachment to the sulfur of formula (aI).

In one preferred embodiment, $A^{x2}$ of step (B) is an amine and $A^{x3}$ of step (C) is $Y^1$—(C=O)—, $Y^1$—(C=O)—NH—, or $Y^1$—(C=O)—O— and most preferably $A^{x2}$ of step (B) is an amine and $A^{x3}$ of step (C) is $Y^1$—(C=O)—.

In another preferred embodiment $A^{x2}$ of step (B) is maleimide and $A^{x3}$ of step (C) is SH.

In one embodiment the optional step (B) is omitted, $A^{x0}$ of step (A) is an amine and $A^{x3}$ of step (C) is ClSO$_2$—, $R^1$(C=O)—, I—, Br—, Cl—, SCN—, CN—, O=C=N—, $Y^1$—(C=O)—, $Y^1$—(C=O)—NH—, or $Y^1$—(C=O)—O—,
wherein
$R^1$ is H, $C_{1-6}$ alkyl, $C_{2-6}$ alkenyl, $C_{2-6}$ alkynyl, $C_{3-8}$ cycloalkyl, 4- to 7-membered heterocyclyl, 8- to 11-membered heterobicyclyl, phenyl, naphthyl, indenyl, indanyl, or tetralinyl; and
$Y^1$ is selected from formulas (f-i) to (f-vi):

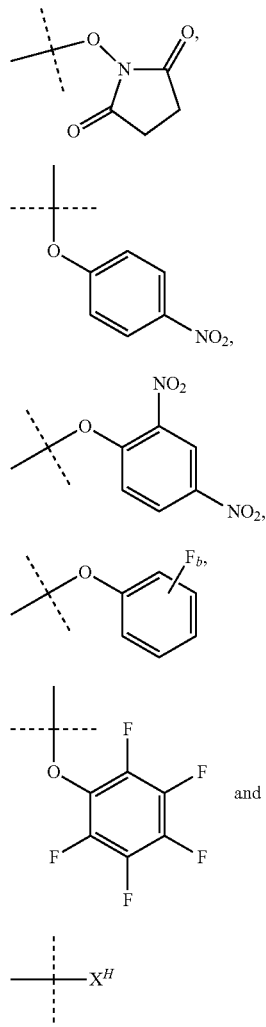

wherein
the dashed lines indicate attachment to the rest of the molecule,
b is 1, 2, 3 or 4,
$X^H$ is Cl, Br, I, or F.

In another embodiment the optional step (B) is omitted, $A^{x0}$ of step (A) is a hydroxyl group (—OH) and $A^{x3}$ of step (C) is O=C=N—, I—, Br—, SCN—, or $Y^1$—(C=O)—NH—,
wherein $Y^1$ is selected from formulas (f-i) to (f-vi):

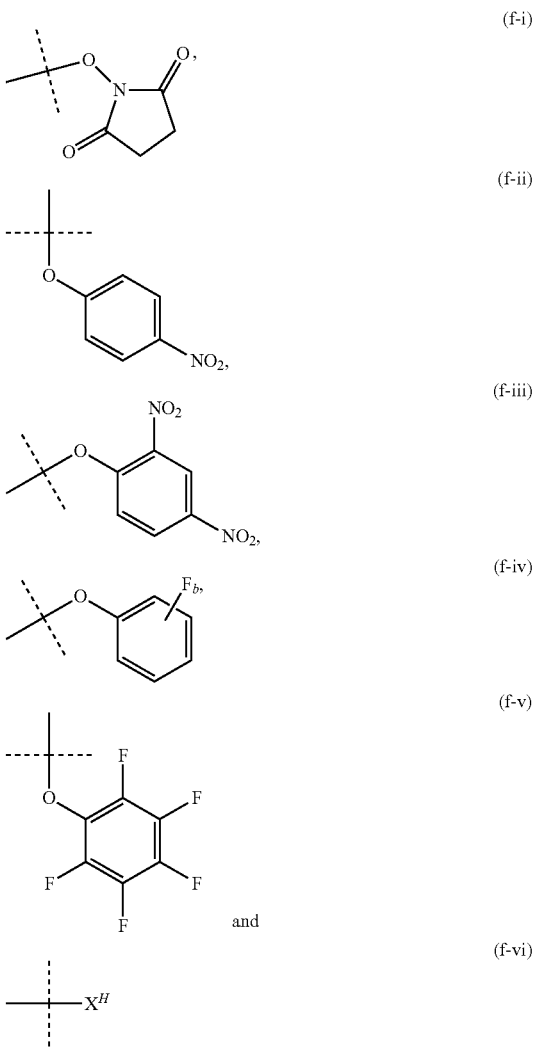

wherein
the dashed lines indicate attachment to the rest of the molecule,
b is 1, 2, 3 or 4,
$X^H$ is Cl, Br, I, or F.

In another embodiment the optional step (B) is omitted, $A^{x0}$ of step (A) is a carboxylic acid (—(C=O)OH) and $A^{x3}$ of step (C) is a primary amine or secondary amine.

In another embodiment the optional step (B) is omitted, $A^{x0}$ of step (A) is an amine and $A^{x3}$ of step (C) is $Y^1$—(C=O)—, $Y^1$—(C=O)—NH—, or $Y^1$—(C=O)—O—.

In another embodiment the optional step (B) is omitted, $A^{x0}$ of step (A) is a maleimide and $A^{x3}$ of step (C) is thiol.

In a preferred embodiment the optional step (B) is omitted, $A^{x0}$ of step (A) is an amine and $A^{x3}$ of step (C) is $Y^1$—(C=O)—.

In another preferred embodiment the optional step (b) is omitted, $A^{x0}$ is SH and $A^{x3}$ is of formula (aI), wherein $PG^0$ is of formula (i), (ii), (iii), (iv), (v), (vi) or (viii). More preferably, $PG^0$ of formula (aI) is of formula (i), (ii), (iii), (iv) or (v) and even more preferably, $PG^0$ of formula (aI) is of formula (i). Most preferably, $PG^0$ of formula (aI) is of formula

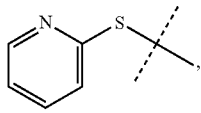

wherein
the dashed line indicates attachment to the sulfur of formula (aI).

The hydrogel obtained from step (C) has the structure of formula (IXa) or (IXb):

wherein
the dashed line indicates attachment to the hydrogel of step (A);
$A^{x0}$ is the linkage formed between $A^{x0}$ and $A^{x3}$;
$A^{y1}$ is used as in formula (VIII);
$A^{y2}$ is the linkage formed between $A^{x2}$ and $A^{x3}$;
$SP^2$ is used as in formula (VI); and
Z is used as in formula (VII).

Preferably, $A^{y0}$ of step (A) and $A^{y2}$ of formula (IXb) are selected from the group consisting of amide, carbamate,

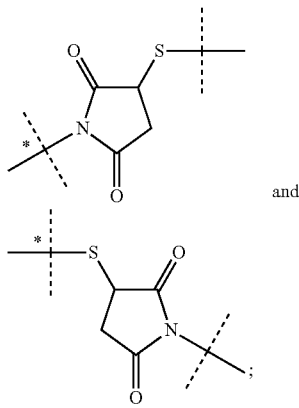

wherein
the dashed lines marked with an asterisk indicate attachment to the hydrogel or $SP^2$, respectively; and
the unmarked dashed lines indicate attachment to Z of formula (VII).

In one embodiment, Z of step (C) is selected from the group consisting of $C_{1-50}$ alkyl, $C_{2-50}$ alkenyl, $C_{2-50}$ alkynyl, $C_{3-10}$ cycloalkyl, 4- to 7-membered heterocyclyl, 8- to 11-membered heterobicyclyl, phenyl; naphthyl; indenyl; indanyl; and tetralinyl; which $C_{1-50}$ alkyl, $C_{2-50}$ alkenyl, $C_{2-50}$ alkynyl, $C_{3-10}$ cycloalkyl, 4- to 7-membered heterocyclyl, 8- to 11-membered heterobicyclyl, phenyl; naphthyl; indenyl; indanyl; and tetralinyl are optionally substituted with one or more $R^{10}$, which are the same or different and wherein $C_{1-50}$ alkyl; $C_{2-50}$ alkenyl; and $C_{2-50}$ alkynyl are optionally interrupted by one or more group(s) selected from the group consisting of T, —C(O)O—; —O—; —C(O)—; —C(O)N($R^9$)—; —S(O)$_2$N($R^9$)—; —S(O)N($R^9$)—; —S(O)$_2$—; —S(O)—; —N($R^9$)S(O)$_2$N($R^{9a}$)—; —S—; —N($R^9$)—; —OC(O)$R^9$; —N($R^9$)C(O)—; —N($R^9$)S(O)$_2$—; —N($R^9$)S(O)—; —N($R^9$)C(O)O—; —N($R^9$)C(O)N($R^{9a}$)—; and —OC(O)N($R^9R^{9a}$);
wherein
$R^9$, $R^{9a}$ are independently selected from the group consisting of H; T; $C_{1-50}$ alkyl; $C_{2-50}$ alkenyl; and $C_{2-50}$ alkynyl, which T; $C_{1-50}$ alkyl; $C_{2-50}$ alkenyl; and $C_{2-50}$ alkynyl are optionally substituted with one or more $R^{10}$, which are the same or different and which $C_{1-50}$ alkyl; $C_{2-50}$ alkenyl; and $C_{2-50}$ alkynyl are optionally interrupted by one or more group(s) selected from the group consisting of T, —C(O)O—; —O—; —C(O)—; —C(O)N($R^{11}$)—; —S(O)$_2$N($R^{11}$)—; —S(O)N($R^{11}$)—; —S(O)$_2$—; —S(O)—; —N($R^{11}$)S(O)$_2$N($R^{11a}$)—; —S—; —N($R^{11}$)—; —OC(O)$R^{11}$; —N($R^{11}$)C(O)—; —N($R^{11}$)S(O)$_2$—; —N($R^{11}$)S(O)—; —N($R^{11}$)C(O)O—; —N($R^{11}$)C(O)N($R^{11a}$)—; and —OC(O)N($R^{11}R^{11a}$);
T is selected from the group consisting of phenyl; naphthyl; indenyl; indanyl; tetralinyl; $C_{3-10}$ cycloalkyl; 4- to 7-membered heterocyclyl; and 8- to 11-membered heterobicyclyl, wherein T is optionally substituted with one or more $R^{10}$, which are the same or different;
$R^{10}$ is halogen; CN; oxo (=O); COOR$^{12}$; OR$^{12}$; C(O)R$^{12}$; C(O)N(R$^{12}$R$^{12a}$); S(O)$_2$N(R$^{12}$R$^{12a}$); S(O)N(R$^{12}$R$^{12a}$); S(O)$_2$R$^{12}$; S(O)R$^{12}$; N(R$^{12}$)S(O)$_2$N(R$^{12a}$R$^{12b}$); SR$^{12}$; N(R$^{12}$R$^{12a}$); NO$_2$; OC(O)R$^{12}$; N(R$^{12}$)C(O)R$^{12a}$; N(R$^{12}$)S(O)$_2$R$^{12a}$; N(R$^{12}$)S(O)R$^{12a}$; N(R$^{12}$)C(O)OR$^{12a}$; N(R$^{12}$)C(O)N(R$^{12a}$R$^{12b}$); OC(O)N(R$^{12}$R$^{12a}$); or $C_{1-6}$ alkyl, which $C_{1-6}$ alkyl is optionally substituted with one or more halogen, which are the same or different;
$R^{11}$, $R^{11a}$, $R^{12}$, $R^{12a}$, $R^{12b}$ are independently of each other selected from the group consisting of H; and $C_{1-6}$ alkyl, which $C_{1-6}$ alkyl is optionally substituted with one or more halogen, which are the same or different.

In another embodiment Z of step (C) is an inert polymer having a molecular weight ranging from 0.5 kDa to 1000 kDa, preferably having a molecular weight ranging from 0.5 to 500 kDa, more preferably having a molecular weight ranging from 0.75 to 250 kDa, even more preferably ranging from 1 to 100 kDa, even more preferably ranging from 5 to 60 kDa, even more preferably from 10 to 50 and most preferably Z has a molecular weight of 40 kDa.

Preferably, Z of step (C) is an inert polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(imino carbonates), poly(lactic acids), poly(lactic-co-glycolic acids), poly(methacrylamides), poly(methacrylates), poly(methyloxazolines), poly(organophosphazenes), poly(ortho esters), poly(oxazolines), polypropylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In a preferred embodiment Z of step (C) is an inert linear or branched PEG-based polymer comprising at least 70% PEG or a hyaluronic acid-based polymer comprising at least 70% hyaluronic acid. More preferably, Z of step (C) is an inert linear or branched PEG-based polymer comprising at least 70% PEG, even more preferably comprising at least 80% PEG and most preferably comprising at least 90% PEG.

In another preferred embodiment Z of step (C) is a zwitterionic polymer. Preferably, such zwitterionic polymer comprises poly(amino acids) and/or poly(acrylates).

As used herein, the terms "zwitterion" and "zwitterionic" refer to a neutral molecule or moiety with positive and negative charges at different locations within that molecule or moiety at the same time.

According to Zhang et al. (Nature Biotechnology, 2013, volume 31, number 6, pages 553-557) hydrogels made of zwitterionic polymers resist the foreign body response.

Step (C) comprises reacting the hydrogel of step (A) or step (B) with a reagent of formula (VII) in such manner that no more than 99 mol-% of $A^{x0}$ or $A^{x2}$ react with $A^{x3}$. This can be achieved, for example, by reacting at most 0.99 chemical equivalents of the reagent of formula (VII) relative to $A^{x0}$ or $A^{x2}$ with the hydrogel of step (A) or (B).

In order to prevent the reaction of more than 0.99 chemical equivalents, the reagent of formula (VII) can be used in an amount of at most 0.99 chemical equivalents relative to $A^{x0}$ or $A^{x2}$ or, alternatively, the reaction rate is monitored and the reaction is interrupted when at most 0.99 chemical equivalents relative to $A^{x0}$ or $A^{x2}$ have reacted, especially when more than 0.99 chemical equivalents are used. It is understood that also due to physical constraints, such as steric hindrance, hydrophobic properties or other characteristics of the inert moiety Z, no more than 0.99 chemical equivalents may be capable of reacting with $A^{x0}$ or $A^{x2}$, even if more chemical equivalents are added to the reaction.

Preferably, step (C) comprises reacting the hydrogel of step (A) or step (B) with a reagent of formula (VII) in such manner that no more than 80 mol-% of $A^{x0}$ or $A^{x2}$ react with $A^{x3}$, even more preferably, such that no more than 60 mol-% of $A^{x0}$ or $A^{x2}$ react with $A^{x3}$, even more preferably, such that no more than 40 mol-% of $A^{x0}$ or $A^{x2}$ react with $A^{x3}$, even more preferably, such that no more than 20 mol-% of $A^{x0}$ or $A^{x2}$ react with $A^{x3}$ and most preferably, such that no more than 15 mol-% of $A^{x0}$ or $A^{x2}$ react with $A^{x3}$.

This can be achieved, for example, by reacting at most 0.8, 0.6, 0.4, 0.2 or 0.15 chemical equivalents of the reagent of formula (VII) relative to $A^{x0}$ or $A^{x2}$ with the hydrogel of step (A) or (B), respectively.

Methods to prevent the reaction of more chemical equivalents are described above.

Based on the measurements of the amount of substance of $A^{x0}$ of step (A) and after step (C) the amount of substance of reacted $A^{x0}$ can be calculated with equation (1):

$$\text{Amount of substance of reacted } A^{x0} \text{ in mmol/g} = (A^{x0}_1 - A^{x0}_2)/(A^{x0}_2 \times MW_Z + 1), \quad (1)$$

wherein $A^{x0}_1$ is the amount of substance of functional groups $A^{x0}$ of the hydrogel of step (A) in mmol/g;

$A^{x0}_2$ is the amount of substance of functional groups $A^{x0}$ of the hydrogel after step (C) in mmol/g; and $MW_Z$ is the molecular weight of Z in g/mmol.

If the optional spacer reagent was covalently conjugated to the hydrogel of step (A), the calculation of the number of reacted $A^{x2}$ is done accordingly.

The percentage of reacted functional groups $A^{x0}$ relative to the functional groups $A^{x0}$ of the hydrogel of step (A) is calculated according to equation (2):

$$\text{mol-\% of reacted } A^{x0} = 100 \times [(A^{x0}_1 - A^{x0}_2)/(A^{x0}_2 \times MW_Z + 1)]/A^{x0}_1, \quad (2)$$

wherein the variables are used as above.

In one embodiment Z of step (C) is conjugated to the surface of the hydrogel. This can be achieved by selecting the size and structure of the reagent $A^{x3}$-Z such that it is too large to enter the pores or network of the hydrogel. Accordingly, the minimal size of $A^{x3}$-Z depends on the properties of the hydrogel. The person skilled in the art however knows methods how to test whether a reagent $A^{x3}$-Z is capable of entering into the hydrogel using standard experimentation, for example by using size exclusion chromatography with the hydrogel as stationary phase.

A prodrug linker moiety comprised in the VEGF neutralizing prodrug may have the structure of any prodrug linker moiety known in the art.

A preferred prodrug linker is disclosed and can be obtained as described in WO 2005/099768 A2. Accordingly, a preferred reversible prodrug linker-VEGF neutralizing biologically active moiety has the structure of formula (A) or (B):

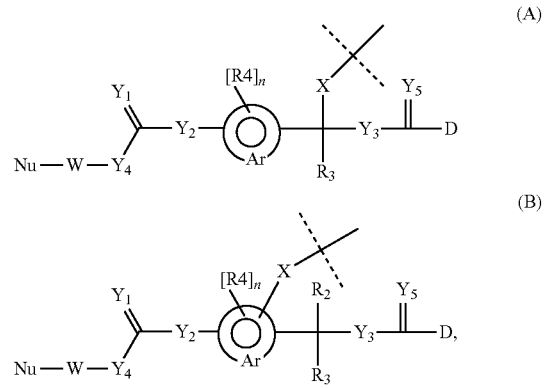

wherein the dashed line indicates attachment to the rest of the prodrug, i.e. to the carrier moiety or to the optional spacer moiety;

D is a VEGF neutralizing biologically active moiety which is connected to the rest of the moiety via an amine-group of the corresponding VEGF neutralizing drug;

X is a spacer moiety such as $R_5$—$Y_6$;

$Y_1$, $Y_2$ are independently O, S or $NR_6$;

$Y_3$, $Y_5$ are independently O or S;

$Y_4$ is O, $NR_6$ or $C(R_7)(R_8)$—;

$Y_6$ is O, S, $NR_6$, succinimide, maleimide, unsaturated carbon-carbon bonds or any heteroatom containing a free electron pair or is absent;

$R_2$, $R_3$ are independently of each other selected from hydrogel, substituted or non-substituted linear, branched or cyclical alkyl or heteroalkyl, aryls, substituted aryls, substituted or non-substituted heteroaryl, cyano, nitro, halogen, carboxy, carboxylalkyl, alkylcarbonyl or carboxamidoalkyl;

R4 is selected from hydrogen, substituted or non-substituted linear, branched or cyclical alkyl or heteroalkyl, aryl, substituted aryl, substituted or non-substituted heteroaryl, substituted or non-substituted linear, branched or cyclical alkoxy, substituted or non-substituted linear, branched or cyclical heteroalkyloxy, aryloxy or heteroaryloxy, cyano, halogen;

$R_5$ is selected from substituted or non-substituted linear, branched or cyclical alkyl or heteroalkyl, aryls, substituted aryls, substituted or non-substituted heteroaryls;

$R_6$ is selected from hydrogel, substituted or non-substituted linear, branched or cyclical alkyl or heteroalkyl, aryls, substituted or non-substituted heteroaryls;

$R_7$, $R_8$ are independently selected from hydrogen, substituted or non-substituted linear, branched or cyclical alkyl or heteroalkyl, aryls, substituted aryls, substituted or non-substituted heteroaryls, carboxyalkyl, alkylcarbonyl, carboxamidoalkyl, cyano or halogen;

W is selected from substituted or non-substituted linear, branched or cyclical alkyl, aryls, substituted aryls, substituted or non-substituted linear, branched or cyclical heteroalkyl, substituted or non-substituted heteroaryls;

Nu is a nucleophile;

n is zero or a positive integer; and

Ar is a multi-substituted aromatic hydrocarbon or a multi-substituted aromatic heterocycle.

Preferably, $R_2$, $R_3$, R4, $R_5$, $R_6$, $R_7$ and $R_8$ of formula (A) and (B) are independently selected from H, $C_{1-6}$ alkyl, $C_{2-6}$ alkenyl and $C_{2-6}$ alkynyl.

Preferably, $Y_6$ of formula (A) and (B) is $C_{1-20}$ alkyl, $C_{2-20}$ alkenyl or $C_{2-20}$ alkynyl.

Preferably, Nu of formula (A) and (B) is selected from the group of nucleophiles consisting of primary, secondary and tertiary amino groups, thiol, carboxylic acid, hydroxylamine, hydrazine and nitrogen containing heteroaryl.

Preferably, W of formula (A) and (B) is $-(CR_9R_{10})_b-$, wherein $R_9$ and $R_{10}$ are independently selected from H, $C_{1-6}$ alkyl, $C_{2-6}$ alkenyl and $C_{2-6}$ alkynyl and wherein b is 1, 2, 3, 4 or 5.

Preferably, n of formula (A) and (B) is 0, 1 or 2, more preferably, n is 0 or 1 and most preferably n is 0.

Preferably, Ar of formula (A) and (B) is selected from

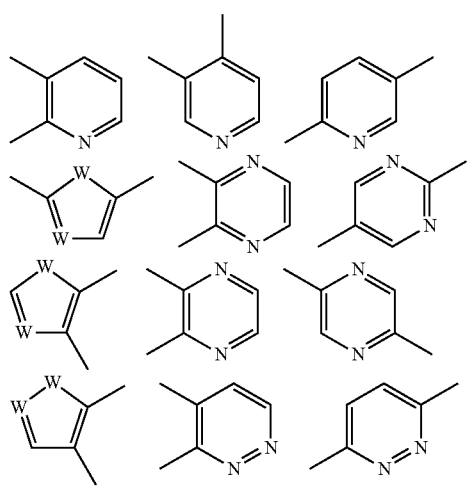

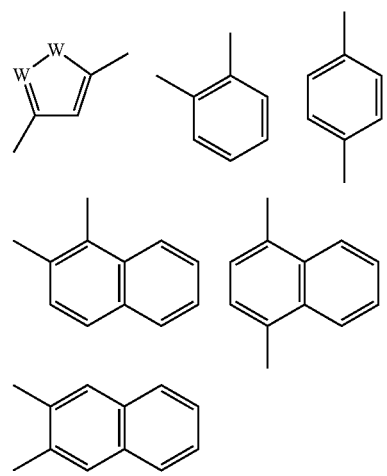

Other preferred prodrug linkers are disclosed and can be obtained as described in WO 2006/136586 A2. Accordingly, a preferred reversible prodrug linker-VEGF neutralizing biologically active moiety has the structure of formula (C), (D) or (E):

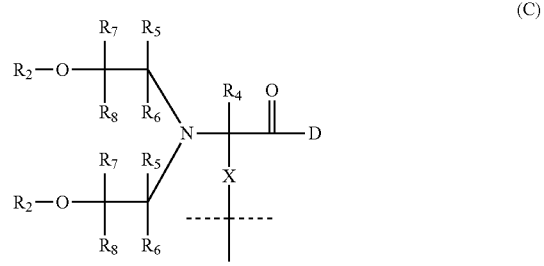

(C)

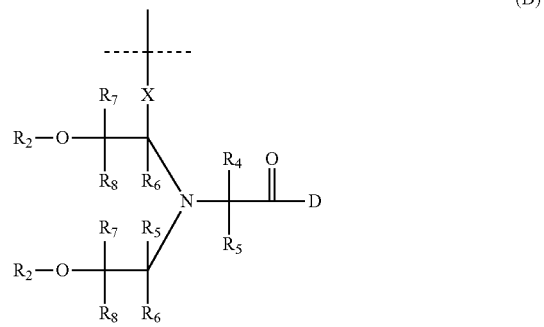

(D)

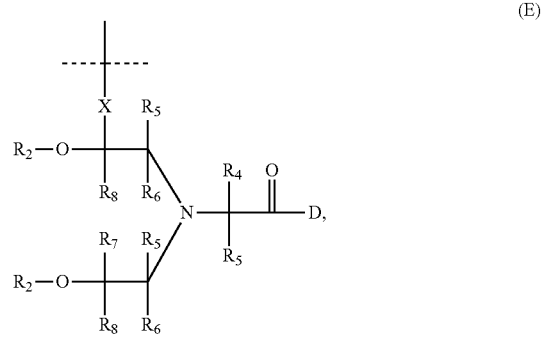

(E)

wherein
the dashed line indicates attachment to the rest of the prodrug, i.e. to the carrier moiety or to the optional spacer moiety;
D is a VEGF neutralizing biologically active moiety which is connected to the rest of the molecule via an amine-group of the corresponding VEGF neutralizing drug forming an amide linkage;
X is a spacer moiety such as R13-Y1;
Y1 is O, S, NR6, succinimide, maleimide, unsaturated carbon-carbon bonds or any heteroatom-containing a free electron pair or is absent;
$R_{13}$ is selected from substituted or non-substituted linear, branched or cyclical alkyl or heteroalkyl, aryls, substituted aryls, substituted or non-substituted heteroaryls;
$R_2$ and $R_3$ are selected independently from hydrogen, acyl groups, or protecting groups for hydroxyl groups;
$R_4$ to $R_{12}$ are selected independently from hydrogen, substituted or non-substituted linear, branched or cyclical alkyl or heteroalkyl, aryls, substituted aryls, substituted or non-substituted heteroaryls, cyano, nitro, halogen, carboxy, carboxamide.
Preferably, $R_2$, $R_3$, $R_4$, $R_5$, $R_6$, $R_7$, $R_8$, $R_9$, $R_{10}$, $R_{11}$ and $R_{12}$ of formula (C), (D) and (E) are independently selected from H, $C_{1-6}$ alkyl, $C_{2-6}$ alkenyl and $C_{2-6}$ alkynyl.
Preferably, in the formulas (C), (D) and (E) Y1 is $C_{1-20}$ alkyl, $C_{2-20}$ alkenyl or $C_{2-20}$ alkynyl.
Another preferred prodrug linker is disclosed and can be obtained as described in WO 2009/095479 A2. Accordingly, a preferred reversible prodrug linker-VEGF neutralizing biologically active moiety has the structure of formula (F):

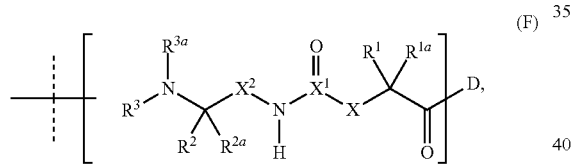

(F)

wherein
the dashed line indicates attachment to the rest of the prodrug, i.e. to the carrier moiety or to the optional spacer moiety;
D is a VEGF neutralizing biologically active moiety which is connected to the rest of the molecule via an aromatic amine of the corresponding VEGF neutralizing drug by forming an amide linkage;
X is $C(R^4R^{4a})$; $N(R^4)$; O; $C(R^4R^{4a})$—$C(R^5R^{5a})$; $C(R^5R^{5a})$—$C(R^4R^{4a})$; $C(R^4R^{4a})$—$N(R^6)$; $N(R^6)$—$C(R^4R^{4a})$; $C(R^4R^{4a})$—O; or O—$C(R^4R^{4a})$;
$X^1$ is C; or S(O);
$X^2$ is $C(R^7, R^{7a})$; or $C(R^7, R^{7a})$—$C(R^8, R^{8a})$;
$R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, $R^{8a}$ are independently selected from the group consisting of H; and $C_{1-4}$ alkyl;
optionally, one or more of the pair(s) $R^{1a}/R^{4a}$, $R^{1a}/R^{5a}$, $R^{4a}/R^{5a}$, $R^{4a}/R^{5a}$, $R^{7a}/R^{8a}$ form a chemical bond;
optionally, one or more of the pair(s) $R^1/R^{1a}$, $R^2/R^{2a}$, $R^4/R^{4a}$, $R^5/R^{5a}$, $R^7/R^{7a}$, $R^8/R^{8a}$ are joined together with the atom to which they are attached to form a $C_{3-7}$ cycloalkyl; or 4- to 7-membered heterocyclyl;
optionally, one or more of the pair(s) $R^1/R^4$, $R^1/R^5$, $R^1/R^6$, $R^4/R^5$, $R^7/R^8$, $R^2/R^3$ are joined together with the atoms to which they are attached to form a ring A;

optionally, $R^3/R^{3a}$ are joined together with the nitrogen atom to which they are attached to form a 4- to 7-membered heterocycle;
A is selected from the group consisting of phenyl; naphthyl; indenyl; indanyl; tetralinyl; $C_{3-10}$ cycloalkyl; 4- to 7-membered heterocyclyl; and 8- to 11-membered heterobicyclyl;
provided that one hydrogen of $R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$ or $R^{8a}$ is replaced with a bond to connect the moiety of formula (F) with the rest of the VEGF neutralizing prodrug, i.e. to the carrier moiety or to the optional spacer moiety.

Optionally, the reversible prodrug linker moiety of formula (F) is further substituted, provided that the hydrogen of the nitrogen of the moiety

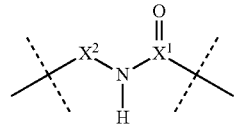

is not replaced and that that $R^3$ and $R^{3a}$ are independently of each other H or are connected to N through an $SP^3$-hybridized carbon atom.

Another preferred prodrug linker is disclosed and can be obtained as described in WO 2011/012721 A1 and WO 2011/012722 A1. Accordingly, a preferred reversible prodrug linker-VEGF neutralizing biologically active moiety has the structure of formula (G):

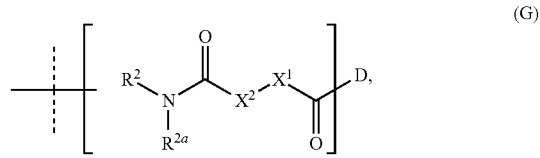

(G)

wherein
the dashed line indicates attachment to the rest of the prodrug, i.e. to the carrier moiety or to the optional spacer moiety;
D is a VEGF neutralizing biologically active moiety which is connected to the rest of the molecule via an aromatic amine of the corresponding VEGF neutralizing drug by forming an amide linkage;
$X^1$ is $C(R^1R^{1a})$ or a cyclic fragment selected from $C_{3-7}$ cycloalkyl, 4- to 7-membered heterocyclyl, phenyl, naphthyl, indenyl, indanyl, tetralinyl, or 8- to 11-membered heterobicyclyl,
wherein
in case $X^1$ is a cyclic fragment, said cyclic fragment is incorporated into $L^1$ via two adjacent ring atoms and the ring atom of $X^1$, which is adjacent to the carbon atom of the amide bond, is also a carbon atom;
$X^2$ is a chemical bond or selected from $C(R^3R^{3a})$, $N(R^3)$, O, $C(R^3R^{3a})$—$C(R^4R^{4a})$, $C(R^3R^{3a})$—$N(R^4)$, $N(R^3)$—$C(R^4R^{4a})$, $C(R^3R^{3a})$—O, or O—$C(R^3R^{3a})$,
wherein
in case $X^1$ is a cyclic fragment, $X^2$ is a chemical bond, $C(R^3R^{3a})$, $N(R^3)$ or O;
optionally, in case $X^1$ is a cyclic fragment and $X^2$ is $C(R^3R^{3a})$, the order of the $X^1$ fragment and the $X^2$ fragment within $L^1$ may be changed and the cyclic fragment is incorporated into $L^1$ via two adjacent ring atoms;

$R^1$, $R^3$ and $R^4$ are independently selected from the group consisting of H, $C_{1-4}$ alkyl and —$N(R^5R^{5a})$;

$R^{1a}$, $R^2$, $R^{3a}$, $R^{4a}$ and $R^{5a}$ are independently selected from the group consisting of H, and $C_{1-4}$ alkyl;

$R^5$ is $C(O)R^6$;

$R^6$ is $C_{1-4}$ alkyl;

optionally, one of the pairs $R^{1a}/R^{4a}$, $R^{3a}/R^{4a}$ or $R^{1a}/R^{3a}$ form a chemical bond;

provided that one hydrogen of $R^1$, $R^{1a}$, $R^2$, $R^{2a}$, $R^3$, $R^{3a}$, $R^4$, $R^{4a}$, $R^5$, $R^{5a}$ or $R^6$ is replaced with a bond to connect the moiety of formula (G) with the rest of the VEGF neutralizing prodrug, i.e. to the carrier moiety or to the optional spacer moiety.

Another preferred prodrug linker is disclosed and can be obtained as described in WO 2011/089214 A1. Accordingly, a preferred reversible prodrug linker-VEGF neutralizing biologically active moiety has the structure of formula (H):

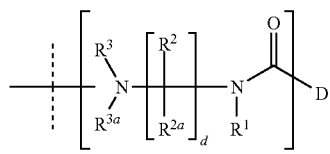

(H)

wherein the dashed line indicates attachment to the rest of the prodrug, i.e. to the carrier moiety or to the optional spacer moiety;

D is a VEGF neutralizing biologically active moiety which is connected to the rest of the molecule via an aromatic hydroxyl (—OH) of the corresponding VEGF neutralizing drug by forming a carbamate linkage;

$R^1$ is selected from the group consisting of $C_{1-4}$ alkyl; heteroalkyl; $C_{3-7}$ cycloalkyl; and

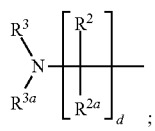

$R^2$, $R^{2a}$, and $R^{3a}$ are independently selected from hydrogen, substituted or non-substituted linear, branched or cyclic $C_{1-4}$ alkyl or heteroalkyl;

each d is independently 2, 3 or 4;

provided that one hydrogen of $R^1$, $R^2$, $R^{2a}$, $R^3$, or $R^{3a}$ is replaced with a bond to connect the moiety of formula (H) with the rest of the VEGF neutralizing prodrug, i.e. to the carrier moiety or to the optional spacer moiety.

Another preferred prodrug linker is disclosed and can be obtained as described in WO 2011/089216 A1. Accordingly, a preferred reversible prodrug linker-VEGF neutralizing biologically active moiety has the structure of formula (J):

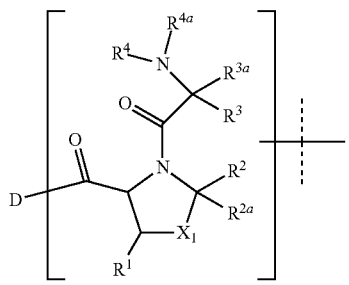

(J)

wherein the dashed line indicates attachment to the rest of the prodrug, i.e. to the carrier moiety or to the optional spacer moiety;

D is a VEGF neutralizing biologically active moiety which is connected to the rest of the molecule via an aliphatic amine of the corresponding drug by forming an amide linkage;

$X_1$ is selected from O, S or CH—$R^{1a}$;

$R^1$ and $R^{1a}$ are independently selected from H, OH, $CH_3$;

$R^2$, $R^{2a}$, $R^4$ and $R^{4a}$ are independently selected from H and $C_{1-4}$ alkyl, $R^3$ and $R^{3a}$ are independently selected from H, $C_{1-4}$ alkyl, and $R^5$;

$R^5$ is selected from

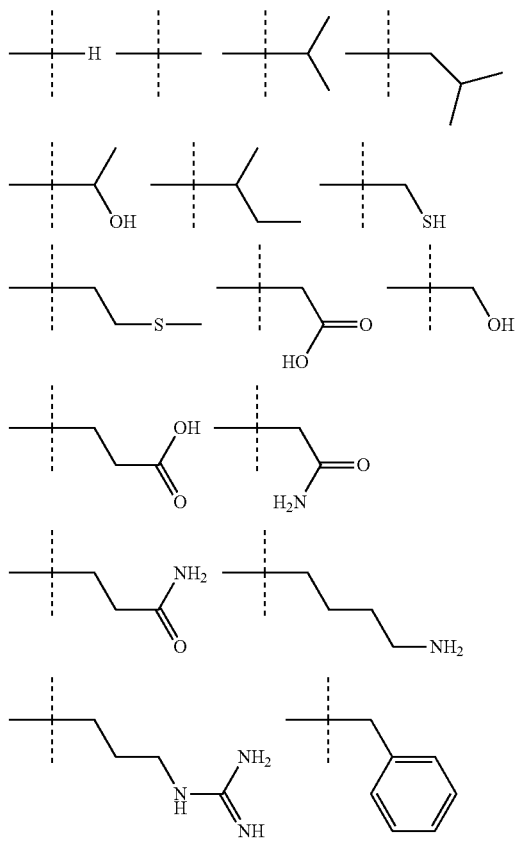

-continued

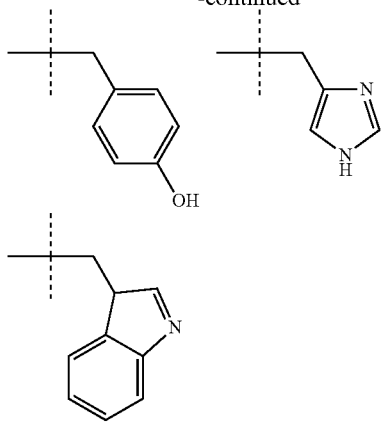

wherein dashed lines indicate attachment to the rest of the moiety;

provided that one hydrogen of $R^1$, $R^{1a}$, $R^2$, $R^{2a}$, $R^3$, $R^{3a}$, $R^4$, $R^{4a}$ and $R^5$ is replaced with a bond to connect the moiety of formula (J) with the rest of the VEGF neutralizing prodrug, i.e. to the carrier moiety or to the optional spacer moiety.

Preferably, $R^3$ of formula (J) is H and $R^{3a}$ of formula (J) is $R^5$.

Preferably, one of $R^4/R^{4a}$ of formula (J) is H.

Optionally, one or more of the pair(s) $R^3/R^{3a}$, $R^4/R^{4a}$, $R^3/R^4$ of formula (J) may independently form one or more cyclic fragment(s) selected from $C_{3-7}$ cycloalkyl, 4- to 7-membered heterocyclyl, or 8- to 11-membered heterobicyclyl.

Optionally, $R^3$, $R^{3a}$, $R^4$ and $R^{4a}$ of formula (J) are further substituted with $C_{1-6}$ alkyl, $C_{2-6}$ alkenyl, $C_{2-6}$ alkynyl, phenyl, 4- to 7-membered heterocycle or halogen.

Another preferred prodrug linker is disclosed and can be obtained as described in WO 2011/089215 A1. Accordingly, a preferred reversible prodrug linker-VEGF neutralizing biologically active moiety has the structure of formula (K):

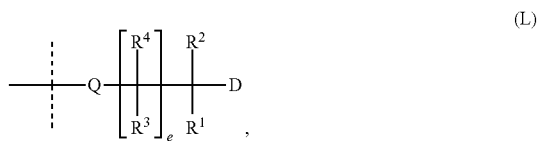

(K)

wherein the dashed line indicates attachment to the rest of the prodrug, i.e. to the carrier moiety or to the optional spacer moiety;

D is a VEGF neutralizing biologically active moiety which is connected to the rest of the molecule via an aromatic amine of the corresponding VEGF neutralizing drug by forming an amide linkage;

$R^1$, $R^{1a}$, $R^2$, $R^3$, $R^{3a}$, $R^4$ and $R^{4a}$ are independently selected from H and $C_{1-4}$ alkyl;

optionally, any two of $R^1$, $R^{1a}$, $R^2$, $R^3$, $R^{3a}$, $R^4$ and $R^{4a}$ may independently form one or more cyclic fragment(s) selected from $C_{3-7}$ cycloalkyl, 4- to 7-membered heterocyclyl, phenyl, naphthyl, indenyl, indanyl, tetralinyl, or 8- to 11-membered heterobicyclyl;

optionally, $R^1$, $R^{1a}$, $R^2$, $R^3$, $R^{3a}$, $R^4$ and $R^{4a}$ are further substitute with a substituent selected from the group comprising $C_{1-6}$ alkyl, $C_{2-6}$ alkenyl, $C_{2-6}$ alkynyl, $C_{3-7}$ cycloalkyl, 4- to 7-membered heterocyclyl, phenyl, naphthyl, indenyl, indanyl, tetralinyl, or 8- to 11-membered heterobicyclyl;

provided that one hydrogen of $R^1$, $R^{1a}$, $R^2$, $R^3$, $R^{3a}R^4$ and $R^{4a}$ is replaced with a bond to connect the moiety of formula (J) with the rest of the VEGF neutralizing prodrug, i.e. to the carrier moiety or to the optional spacer moiety.

Another preferred prodrug linker is disclosed and can be obtained as described in PCT/EP2012/065748. Accordingly, a preferred reversible prodrug linker-VEGF neutralizing biologically active moiety has the structure of formula (L):

(L)

wherein the dashed line indicates attachment to the rest of the prodrug, i.e. to the carrier moiety or to the optional spacer moiety;

D is a VEGF neutralizing biologically active moiety which is connected to the rest of the molecule via a carboxylic acid group (—(C═O)—OH) of the corresponding VEGF neutralizing drug by forming a carboxylic ester linkage;

$R^1$ is selected from the group of unsubstituted alkyl; substituted alkyl; unsubstituted phenyl; substituted phenyl; unsubstituted naphthyl; substituted naphthyl; unsubstituted indenyl; substituted indenyl; unsubstituted indanyl; substituted indanyl; unsubstituted tetralinyl; substituted tetralinyl; unsubstituted $C_{3-10}$ cycloalkyl; substituted $C_{3-10}$ cycloalkyl; unsubstituted 4- to 7-membered heterocyclyl; substituted 4- to 7-membered heterocyclyl; unsubstituted 8- to 11-membered heterobicyclyl; and substituted 8- to 11-membered heterobicyclyl;

$R^2$ is selected from H, unsubstituted alkyl, and substituted alkyl $R^3$ and $R^4$ are independently selected from the group consisting of H, unsubstituted alkyl, and substituted alkyl;

e is 0 or 1;

optionally, $R^1$ and $R^3$ are joined together with the atoms to which they are attached to form a ring A;

A is selected from the group consisting of $C_{3-10}$ cycloalkyl; 4- to 7-membered aliphatic heterocyclyl; and 8- to 11-membered aliphatic heterobicyclyl, wherein A is unsubstituted or substituted;

Q is selected from the group comprising $C_{1-50}$ alkyl, $C_{2-50}$ alkenyl or $C_{2-50}$ alkinyl, which fragment is optionally interrupted by one or more group(s) selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4- to 7-membered heterocyclyl, phenyl or naphthyl.

Another preferred prodrug linker is disclosed and can be obtained as described in EP12165516. Accordingly, a preferred reversible prodrug linker-VEGF neutralizing biologically active moiety has the structure of formula (M):

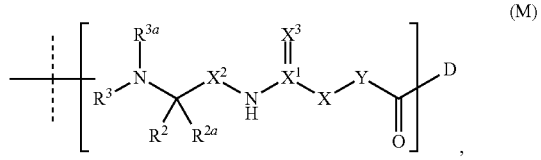
(M)

wherein
the dashed line indicates attachment to the rest of the prodrug, i.e. to the carrier moiety or to the optional spacer moiety;
D is a VEGF neutralizing biologically active moiety which is connected to the rest of the molecule via a hydroxyl group of the corresponding VEGF neutralizing drug by forming an ester or carbamate linkage
Y is —C($R^1$)($R^{1a}$)—; or —N($R^1$)—;
X is —C($R^4$)($R^{4a}$); —N($R^4$)—; —O—; —C($R^4$)($R^{4a}$)—C($R^5$)($R^{5a}$)—; —C($R^4$)($R^{4a}$)—N($R^6$)—; —N($R^6$)—C($R^4$)($R^{4a}$)—; ($R^4$)($R^{4a}$)—O—; O—C($R^4$)($R^{4a}$)—; —C(O)—N($R^6$); or —N($R^6$)—C(O)—;

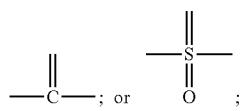

$X^1$ is
$X^2$ is —C($R^7$)($R^{7a}$)—; or —C($R^7$)($R^{7a}$)—C($R^8$)($R^{8a}$)—;
$X^3$ is =O; =S; or =N—CN;
$R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, $R^{8a}$ are independently selected from the group consisting of H; $C_{1-6}$ alkyl, $C_{2-6}$ alkenyl, $C_{2-6}$ alkynyl, $C_{1-20}$ heteroalkyl and $Y_1$-T; and independently none, one or more of the pair(s) $R^{1a}/R^{4a}$, $R^{1a}/R^{5a}$, $R^{4a}/R^{5a}$, $R^{7a}/R^{8a}$ are absent and the corresponding carbon atoms to which they are attached form a cis double bond;
$Y^1$ is a chemical bond or $C_{1-6}$ alkyl, $C_{2-6}$ alkenyl, $C_{2-6}$ alkynyl;
T is selected from the group consisting of phenyl; naphthyl; indenyl; indanyl; tetralinyl; $C_{3-10}$ cycloalkyl; 4- to 7-membered heterocyclyl; or 8- to 11-membered heterobicyclyl, wherein T is optionally substituted with one or more $R^9$, which are the same or different;
$R^9$ is halogen; —CN; oxo (=O); —C(O)OH; —OH; —S(O)$_2$NH$_2$; —S(O)NH$_2$; —S(O)$_2$OH; —S(O)OH; —SH; —NH$_2$; —NO$_2$; $C_{1-6}$ alkyl, or $C_{1-10}$ heteroalkyl;
optionally, one or more of the pairs $R^1/R^{1a}$, $R^1/R^4$, $R^1/R^6$, $R^1/R^5$, $R^2/R^{2a}$, $R^2/R^3$, $R^4/R^{4a}$, $R^4/R^5$, $R^5/R^{5a}$, $R^7/R^{7a}$, $R^7/R^8$, $R^8/R^{8a}$ are joined together with the atom to which they are attached to form a ring T;
optionally, $R^3/R^{3a}$ are joined together with the nitrogen atom to which they are attached to form a 4- to 7-membered heterocycle;
provided that one hydrogen of $R^1$, $R^{1a}$, $R^2$, $R^{2a}$, $R^3$, $R^{3a}$, $R^4$, $R^{4a}$, $R^5$, $R^{5a}$, $R^6$, $R^{7a}$, $R^8$ or $R^{8a}$ is replaced with a bond to connect the moiety of formula (M) with the rest of the VEGF neutralizing prodrug, i.e. to the carrier moiety or to the optional spacer moiety.

More preferably, the VEGF neutralizing prodrug comprises a reversible prodrug linker moiety-VEGF neutralizing biologically active moiety of formula (F).

Even more preferably, the VEGF neutralizing prodrug comprises a reversible prodrug linker moiety-VEGF neutralizing biologically active moiety o formula (F) and attachment to the rest of the prodrug, i.e. to the carrier or to the optional spacer which is connected to the carrier, occurs through $R^4$ of X or $R^3$ of formula (F), most preferably through $R^4$ of formula (F).

Even more preferably, the VEGF neutralizing prodrug comprises a moiety of formula (F-i):

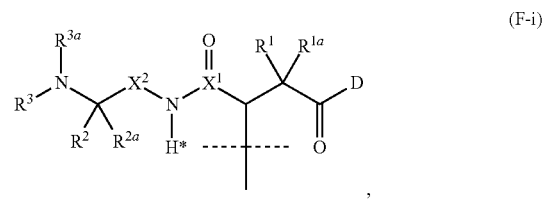
(F-i)

wherein
the dashed line indicates attachment to the carrier or to the optional spacer moiety;
$R^1$, $R^{1a}$, $R^2$, $R^{2a}$, $R^3$, $R^{3a}$, $X^1$, $X^2$ and D are used as in formula (F);
optionally, the moiety of formula (F-i) is further substituted, provided that the hydrogel marked with the asterisk in formula (F-i) is not replaced by a substituent and that $R^3$ and $R^{3a}$ are independently of each other H or are connected to N through an $SP^3$-hybridized carbon atom.
Preferably, $X^1$ of formula (F-i) is C.
In one embodiment, $X^2$ of formula (F-i) is C($R^7R^{7a}$).
In another embodiment $X^2$ of formula (F-i) is C($R^7R^{7a}$)—C($R^8R^{8a}$).
Preferably, $R^1$ of formula (F-i) is H.
Preferably, $R^{1a}$ of formula (F-i) is H.
Preferably, $R^1$ and $R^{1a}$ of formula (F-i) are both H.
Preferably, $R^2$ of formula (F-i) is H.
Preferably, $R^{2a}$ of formula (F-i) is H.
Preferably, $R^2$ and $R^{2a}$ of formula (F-i) are H.
Preferably, $R^3$ of formula (F-i) is H or methyl, ethyl or propyl.
Preferably, $R^{3a}$ of formula (F-i) is H or methyl, ethyl or propyl.
In one preferred embodiment $R^3$ and $R^{3a}$ of formula (F-i) are both H.
In another preferred embodiment $R^3$ of formula (F-i) is H and $R^{3a}$ of formula (F-i) is methyl.
In another preferred embodiment $R^3$ and $R^{3a}$ of formula (F-i) are both methyl.
Preferably, D of formula (F-i) is ranibizumab.
Preferably, the carrier of formula (F-i) is a hydrogel, more preferably a PEG-based hydrogel.
In a preferred embodiment the VEGF neutralizing prodrug comprises a moiety of formula (f-ii)

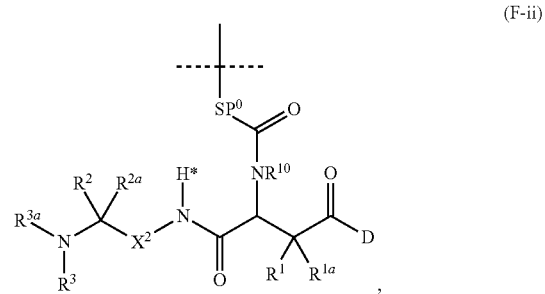
(F-ii)

wherein the dashed line indicates attachment to the carrier;

$R^1$, $R^{1a}$, $R^2$, $R^{2a}$, $R^3$, $R^{3a}$, $X^2$ and D are used as defined in formula (F);

$R^{10}$ is selected from H and $C_{1-6}$ alkyl;

$SP^0$ is a spacer moiety;

and wherein the moiety of formula (F-ii) is optionally further substituted, provided that the hydrogel marked with the asterisk in formula (F-ii) is not replaced by a substituent and that $R^3$ and $R^{3a}$ are independently of each other H or are connected to N through an $SP^3$-hybridized carbon atom.

In one embodiment, $X^2$ of formula (F-ii) is $C(R^7R^{7a})$.

In another embodiment $X^2$ of formula (F-ii) is $C(R^7R^{7a})$—$C(R^8R^{8a})$.

Preferably, $R^1$ of formula (F-ii) is H.
Preferably, $R^{1a}$ of formula (F-ii) is H.
Preferably, $R^1$ and $R^{1a}$ of formula (F-ii) are both H.
Preferably, $R^2$ of formula (F-ii) is H.
Preferably, $R^{2a}$ of formula (F-ii) is H.
Preferably, $R^2$ and $R^{2a}$ of formula (F-ii) are H.
Preferably, $R^3$ of formula (F-ii) is H or methyl, ethyl or propyl.
Preferably, $R^{3a}$ of formula (F-ii) is H or methyl, ethyl or propyl.

In one preferred embodiment $R^3$ and $R^{3a}$ of formula (F-ii) are both H.

In another preferred embodiment $R^3$ of formula (F-ii) is H and $R^{3a}$ of formula (F-ii) is methyl.

In another preferred embodiment $R^3$ and $R^{3a}$ of formula (F-ii) are both methyl.

In one embodiment $R^{10}$ of formula (F-ii) is H.

In another preferred embodiment $R^{10}$ of formula (F-ii) is methyl, ethyl, propyl, isopropyl, butyl, isobutyl or tert-butyl. More preferably, $R^{10}$ of formula (F-ii) is methyl, ethyl, propyl or isopropyl. Even more preferably, $R^{10}$ of formula (F-ii) is methyl or ethyl and most preferably, $R^{10}$ of formula (F-ii) is methyl.

Preferably, $SP^0$ of formula (F-ii) is selected from $C_{1-50}$ alkyl; $C_{2-50}$ alkenyl; and $C_{2-50}$ alkynyl which $C_{1-50}$ alkyl; $C_{2-50}$ alkenyl; and $C_{2-50}$ alkynyl are optionally substituted with one or more $R^{a10}$, which are the same or different and wherein $C_{1-50}$ alkyl; $C_{2-50}$ alkenyl; and $C_{2-50}$ alkynyl are optionally interrupted by one or more group(s) selected from the group consisting of T, —C(O)O—; —O—; —C(O)—; —C(O)N($R^{a11}$)—; —S(O)$_2$N($R^{a11}$)—; —S(O)N($R^{a11}$)—; —S(O)$_2$—; —S(O)—; —N($R^{a11}$)S(O)$_2$N($R^{a11a}$)—; —S—; —N($R^{a11}$)—; —OC(O)$R^{a11}$; —N($R^{a11}$)C(O)—; —N($R^{a11}$)S(O)$_2$—; —N($R^{a11}$)S(O)—; —N($R^{a11}$)C(O)O—; —N($R^{a11}$)C(O)N($R^{a11a}$)—; and —OC(O)N($R^{a11}R^{a11a}$);

T is selected from the group consisting of phenyl; naphthyl; indenyl; indanyl; tetralinyl; $C_{3-10}$ cycloalkyl; 4- to 7-membered heterocyclyl; or 8- to 11-membered heterobicyclyl, wherein T is optionally substituted with one or more $R^{a10}$, which are the same or different;

$R^{a10}$ is halogen; CN; oxo (=O); $COOR^{a12}$; $OR^{a12}$; C(O)$R^{a12}$; C(O)N($R^{a12}R^{a12a}$); S(O)$_2$N($R^{a12}R^{a12a}$); S(O)N($R^{a12}R^{a12a}$); S(O)$_2R^{a12}$; S(O)$R^{a12}$; N($R^{a12}$)S(O)$_2$N($R^{a12a}R^{a12b}$); $SR^{a12}$; N($R^{a12}R^{a12a}$); NO$_2$; OC(O)$R^{a12}$; N($R^{a12}$)C(O)$R^{a12a}$; N($R^{a12}$)S(O)$_2R^{a12a}$; N($R^{a12}$)S(O)$R^{a12a}$; N($R^{a12}$)C(O)O$R^{a12a}$; N($R^{a12}$)C(O)N($R^{a12a}R^{a12b}$); OC(O)N($R^{a12}R^{a12a}$); or $C_{1-6}$ alkyl, wherein $C_{1-6}$ alkyl is optionally substituted with one or more halogen, which are the same or different;

$R^{a11}$, $R^{a11a}$, $R^{a12}$, $R^{a12a}$, $R^{a12b}$ are independently selected from the group consisting of H; or $C_{1-6}$ alkyl, wherein $C_{1-6}$ alkyl is optionally substituted with one or more halogen, which are the same or different.

Preferably, $SP^0$ of formula (F-ii) is $C_{1-20}$ alkyl, which $C_{1-20}$ alkyl is optionally interrupted by one or more groups independently selected from —O—; and —C(O)N($R^{1aa}$)—; and which $C_{1-20}$ alkyl chain is optionally substituted with one or more groups independently selected from OH; and —C(O)N($R^{1aa}R^{1aaa}$); wherein $R^{1aa}$, $R^{1aaa}$ are independently selected from the group consisting of H; and $C_{1-4}$ alkyl.

Preferably, $SP^0$ of formula (F-ii) has a molecular weight in the range of from 14 g/mol to 750 g/mol.

Preferably, $SP^0$ of formula (F-ii) is attached to the carrier via a terminal group selected from

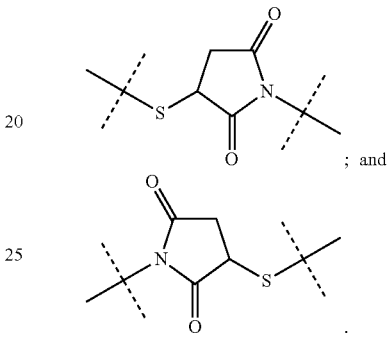

; and

In case $SP^0$ of formula (F-ii) has such terminal group it is furthermore preferred that $SP^0$ has a molecular weight in the range of from 14 g/mol to 500 g/mol calculated without such terminal group.

Preferably, D of formula (F-ii) is ranibizumab.

Preferably, the carrier of formula (F-ii) is a hydrogel, more preferably a PEG-based hydrogel.

Even more preferably, the VEGF neutralizing prodrug comprises a moiety of formula (F-iiia) or (F-iiib):

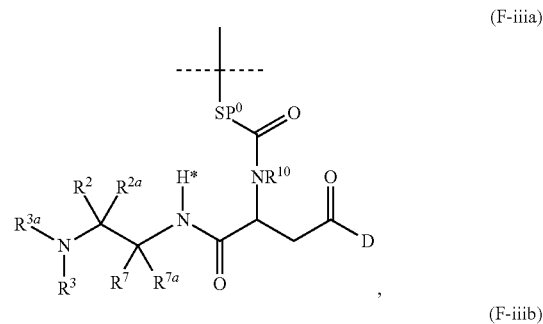

(F-iiia)

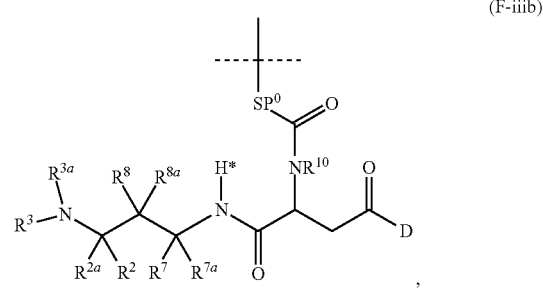

(F-iiib)

wherein the dashed line indicates attachment to the carrier;

$R^2$, $R^{2a}$, $R^3$, $R^{3a}$, $R^7$, $R^{7a}$, $R^8$, $R^{8a}$, $X^2$ and D are used as defined in formula (F);

$R^{10}$ and $SP^0$ are used as defined in formula (F-ii);

and wherein the moiety of formula (F-iiia) or (F-iiib) is optionally further substituted, provided that the hydrogen marked with the asterisk in formula (F-iiia) and (F-iiib) is not replaced by a substituent and that $R^3$ and $R^{3a}$ are independently of each other H or are connected to N through an $SP^3$-hybridized carbon atom.

Preferably, $SP^0$ of formula (F-iiia) or (F-iiib) is $C_{1-20}$ alkyl, which $C_{1-20}$ alkyl is optionally interrupted by one or more groups independently selected from —O—; and —C(O)N($R^{1aa}$)—; and which $C_{1-20}$ alkyl chain is optionally substituted with one or more groups independently selected from OH; and —C(O)N($R^{1aa}R^{1aaa}$); wherein $R^{1aa}$, $R^{1aaa}$ are independently selected from the group consisting of H; and $C_{1-4}$ alkyl.

Preferably, $SP^0$ of formula (F-iiia) or (F-iiib) has a molecular weight in the range of from 14 g/mol to 750 g/mol.

Preferably, $SP^0$ of formula (F-iiia) or (F-iiib) is attached to the carrier via a terminal group selected from

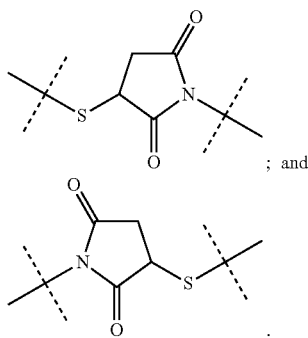

; and

In case $SP^0$ of formula (F-iiia) or (F-iiib) has such terminal group it is furthermore preferred that $SP^0$ has a molecular weight in the range of from 14 g/mol to 500 g/mol calculated without such terminal group.

Preferably, $R^2$ of formula (F-iiia) or (F-iiib) is H.
Preferably, $R^{2a}$ of formula (F-iiia) or (F-iiib) is H.
Preferably, $R^2$ and $R^{2a}$ of formula (F-iiia) or (F-iiib) are H.
Preferably, $R^3$ of formula (F-iii) is H or methyl, ethyl or propyl.
Preferably, $R^{3a}$ of formula (F-iii) is H or methyl, ethyl or propyl.
In one preferred embodiment $R^3$ and $R^{3a}$ of formula (F-iii) are both H.
In another preferred embodiment $R^3$ of formula (F-iii) is H and $R^{3a}$ of formula (F-iii) is methyl.
In another preferred embodiment $R^3$ and $R^{3a}$ of formula (F-iii) are both methyl.
Preferably, $R^7$ of formula (F-iiia) or (F-iiib) is H.
Preferably, $R^{7a}$ of formula (F-iiia) or (F-iiib) is H.
Preferably, $R^8$ of formula (F-iiib) is H.
Preferably, $R^{8a}$ of formula (F-iiib) is H.
Preferably, $R^8$ and $R^{8a}$ of formula (F-iiib) are both H.
Preferably, $R^{10}$ of formula (F-iiia) is H.
Preferably, $R^{10}$ of formula (F-iiib) is methyl, ethyl or propyl. Most preferably, $R^{10}$ of formula (F-iiib) is methyl.
Preferably, D of formula (F-iiia) or (F-iiib) is ranibizumab.
Preferably, the carrier of formula (F-iiia) or (F-iiib) is a hydrogel, more preferably a PEG-based hydrogel.
Even more preferably, the VEGF neutralizing prodrug comprises a moiety of formula (F-iva) or (F-ivb):

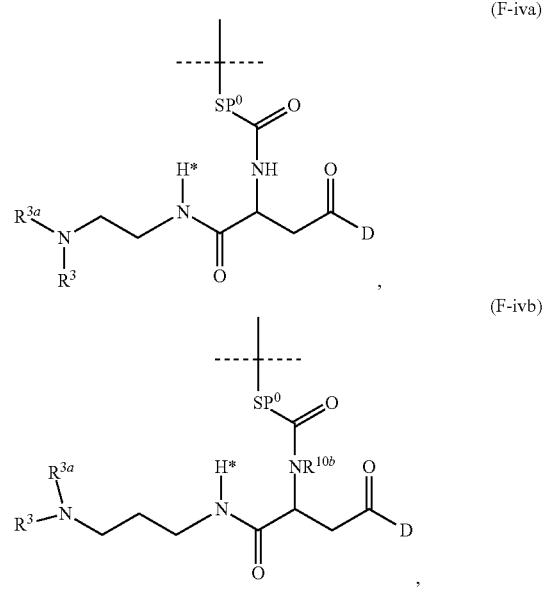

wherein
the dashed line indicates attachment to the carrier;
$R^3$ and $R^{3a}$ are used as defined in formula (I);
$R^{10b}$ is $C_{1-6}$ alkyl;
and wherein the moiety of formula (F-iva) or (F-ivb) is optionally further substituted, provided that the hydrogen marked with the asterisk is not replaced by a substituent and that $R^3$ and $R^{3a}$ are independently of each other H or are connected to N through an $SP^3$-hybridized carbon atom.

Preferably, $SP^0$ of formula (F-iva) and (F-ivb) is $C_{1-20}$ alkyl, which $C_{1-20}$ alkyl is optionally interrupted by one or more groups independently selected from —O—; and —C(O)N($R^{1aa}$)—; and which $C_{1-20}$ alkyl chain is optionally substituted with one or more groups independently selected from OH; and —C(O)N($R^{1aa}R^{1aaa}$); wherein $R^{1aa}$, $R^{1aaa}$ are independently selected from the group consisting of H; and $C_{1-4}$ alkyl.

Preferably, $SP^0$ of formula (F-iva) and (F-ivb) has a molecular weight in the range of from 14 g/mol to 750 g/mol.

Preferably, $SP^0$ of formula (F-iva) and (F-ivb) is attached to the carrier via a terminal group selected from

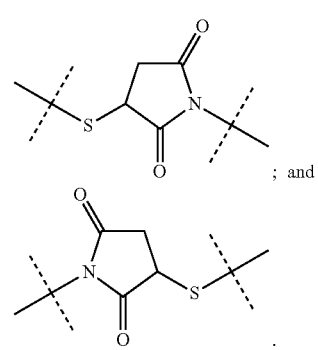

; and

In case $SP^0$ of formula (F-iva) and (F-ivb) has such terminal group it is furthermore preferred that $SP^0$ has a molecular weight in the range of from 14 g/mol to 500 g/mol calculated without such terminal group.

Preferably, $R^3$ of formula (F-iva) or (F-ivb) is H or methyl, ethyl or propyl.

Preferably, $R^{3a}$ of formula (F-iva) or (F-ivb) is H or methyl, ethyl or propyl.

In one preferred embodiment $R^3$ and $R^{3a}$ of formula (F-iva) or (F-ivb) are both H.

In another preferred embodiment $R^3$ of formula (F-iva) or (F-ivb) is H and $R^{3a}$ of formula (F-iva) or (F-ivb) is methyl.

In another preferred embodiment $R^3$ and $R^{3a}$ of formula (F-iva) or (F-ivb) are both methyl.

In another preferred embodiment $R^3$ of formula (F-iva) or (F-ivb) is H and $R^{3a}$ of formula (F-iva) or (F-ivb) is methyl.

Preferably $R^{10b}$ of formula (F-ivb) is methyl, ethyl or propyl. Most preferably, $R^{10b}$ is methyl.

Preferably, D of formula (F-iva) and (F-ivb) is ranibizumab.

Preferably, the carrier of formula (F-iva) and (F-ivb) is a hydrogel, more preferably a PEG-based hydrogel.

In one embodiment the VEGF neutralizing prodrug comprises in bound form a biologically active moiety selected from the group of drugs consisting of antisense RNA, antisense DNA, ribozymes or RNAi molecules targeting a VEGF nucleic acid; anti-VEGF aptamers, anti-VEGF antibodies, anti-VEGF antibody fragments, DARPins and soluble VEGF receptor decoys that prevent binding of a VEGF to its cognate receptor; antisense, ribozymes, and RNAi molecules targeting a cognate VEGF receptor (VEGFR) nucleic acid; anti-VEGFR aptamers or anti-VEGFR antibodies that bind to a cognate VEGFR receptor; anti-VEGFR antibody fragments that bind to a cognate VEGFR receptor and VEGFR tyrosine kinase inhibitors.

In a preferred embodiment the VEGF neutralizing prodrug comprises in bound form a biologically active moiety selected from the group of drugs consisting of antisense RNA, antisense DNA, ribozymes or RNAi molecules targeting a VEGF nucleic acid; anti-VEGF aptamers, anti-VEGF antibodies, DARPins and soluble VEGF receptor decoys that prevent binding of a VEGF to its cognate receptor; antisense, ribozymes, and RNAi molecules targeting a cognate VEGF receptor (VEGFR) nucleic acid; anti-VEGFR aptamers or anti-VEGFR antibodies that bind to a cognate VEGFR receptor; and VEGFR tyrosine kinase inhibitors.

Preferably, the VEGF neutralizing prodrug comprises in bound form a biologically active moiety selected from the group consisting of ranibizumab, bevacizumab, pegaptanib, aflibercept, MP0112, KH902, ESBA1008, AL 39324, ALG-1001, and bevasiranib and/or fragments thereof.

More preferably, the VEGF neutralizing prodrug is selected from the group consisting of ranibizumab, bevacizumab, pegaptanib, aflibercept and bevasiranib and/or fragments thereof.

Most preferably, the VEGF neutralizing prodrug is ranibizumab.

In one embodiment, the ocular condition to be treated with the pharmaceutical composition of the present invention is a disease characterized by ocular neovascularization.

The intraocular neovascularization is preferably selected from the group consisting of optic disc neovascularization, iris neovascularization, retinal neovascularization, choroidal neovascularization, corneal neovascularization, vitreal neovascularization, glaucoma, pannus, pterygium, macular edema, macular degeneration, age-related macular degeneration, diabetic retinopathy, diabetic retinal ischemia, diabetic macular edema, vascular retinopathy, retinal degeneration, retrolental fibroplasias, retinoblastoma, retinopathy of prematurity of macular degeneration, corneal graft neovascularization, central retinal vein occlusion (CRVO), pathological myopia, ocular tumors, uveitis, inflammatory diseases of the eye, and proliferative vitreoretinopathy.

In one embodiment the pharmaceutical composition further comprises one or more drug(s) in its/their free form selected from the list of drug classes comprising antisense RNA, antisense DNA, ribozymes or RNAi molecules targeting a VEGF nucleic acid; anti-VEGF aptamers, anti-VEGF antibodies, anti-VEGF antibody fragments, DARPins, anticalins, lipocalins, and soluble VEGF receptor decoys that prevent binding of a VEGF to its cognate receptor; antisense, ribozymes, and RNAi molecules targeting a cognate VEGF receptor (VEGFR) nucleic acid; anti-VEGFR aptamers or anti-VEGFR antibodies that bind to a cognate VEGFR receptor; anti-VEGFR antibody fragments that bind to a cognate VEGFR receptor and VEGFR tyrosine kinase inhibitors.

In a preferred embodiment the pharmaceutical composition further comprises one or more drug(s) in its/their free form selected from the list of drug classes comprising antisense RNA, antisense DNA, ribozymes or RNAi molecules targeting a VEGF nucleic acid; anti-VEGF aptamers, anti-VEGF antibodies, DARPins, anticalins, lipocalins, and soluble VEGF receptor decoys that prevent binding of a VEGF to its cognate receptor; antisense, ribozymes, and RNAi molecules targeting a cognate VEGF receptor (VEGFR) nucleic acid; anti-VEGFR aptamers or anti-VEGFR antibodies that bind to a cognate VEGFR receptor; and VEGFR tyrosine kinase inhibitors.

Preferably, the pharmaceutical composition further comprises one or more active ingredient(s) which can be a steroid, an anti-inflammatory compound, an antibiotic, and antiviral, an antifungal, or an anti-angiogenesis compound. The active ingredient can, for example, be methotrexate, retinoic acid, aspirin, diclofenac, flurbiprofen, ibuprofen, ketorolac, naproxen, uprofen, dexamethasone, cortisone, fluocinolone, hydrocortisone, methylprednisolone, prednisolone, prednisone, or triamcinolone.

In one preferred embodiment the pharmaceutical composition further comprises in its/their free form one or more modulator(s) of the activity of one or more protein(s) selected from the group comprising basic fibroblast growth factors (bFGF), acidic fibroblast growth factors (aFGF), transforming growth factors alpha (TGFa), transforming growth factors beta (TGFβ), platelet-derived growth factor (PDGF), angiogenin, platelet-derived endothelial cell growth factor (PD-ECGF), interleukin-1 (IL-1), interleukin-8 (IL-8), interleukin-12, vascular endothelial growth factor (VEGF), angiopoietin-I, Del-I, follistatin, granulocyte colony-stimulating factor (G-CSF), hepatocyte growth factor (HGF), leptin, midkine, placental growth factor, pleiotrophin (PTN), progranulin, proliferin, tumor necrosis factor-alpha (TNF-alpha), angioarrestin, angiostatin plasminogen fragment, antiangiogenic anti-thrombin III, cartilage-derived inhibitor (CDI), CDS9 complement fragment, endostatin collagen XVIII fragment, fibronectin fragment, gro-beta, heparinases, heparin hexasaccharide fragment, human chorionic gonadotropin (hCG), interferon alpha/beta/gamma, interferon inducible protein (IP-IO), kringle S plasminogen fragment, metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), retinoids, tetrahydrocortisol-S, thrombospondin-I (TSP-I), vasculostatin, vasostatin calreticulin fragment, prostaglandin receptor, growth hormone, insulin-like growth factor-I (IGF-I), sphingosine-1-phosphate, factor D, RTP801, inhibitors of complement, $\alpha_2$ adrenergic agonist, mTOR, ciliary neurotrophic factor (CNTF), brain-derived neurotrophic factor (BDNF), glial cell-derived neurotrophic factor (GDNF), lens epithelium derived growth factor (LEDGF), rod-derived cone viability factor (RdCVF), pigment epithelium-derived factor (PEDF), neutrophil-activating protein, monocyte chemoattractant protein, macrophage-inflammatory protein, small inducible secreted (SIS) proteins, platelet factor, platelet basic protein, melanoma growth stimulating activity, epidermal growth factor, nerve growth factor, bone morphogenic proteins, bone growth cartilage-inducing factor, interleukins, interleukin inhibitors, interleukin receptors, hematopoietic factors, granulocyte colony stimulating factor, macrophage colony stimulating factor, granulocyte-macrophage colony stimulating factor, inhibin, and activin.

Preferred inhibitors of complement are C1 inhibitor, C3 inhibitor and C5 inhibitor.

Preferred inhibitors of growth factors are platelet-derived growth factor (PDGF), ciliary neurotrophic factor (CNTF), brain-derived neurotrophic factor (BDNF), glial cell-derived neurotrophic factor (GDNF), lens epithelium derived growth factor (LEDGF), rod-derived cone viability factor (RdCVF), and pigment epithelium-derived factor (PEDF).

Preferred bone growth cartilage-inducing factor are bone growth cartilage-inducing factor alpha and bone growth cartilage-inducing factor beta.

A preferred hematopoietic factor is erythropoietin.

In another embodiment the pharmaceutical composition further comprises one or more prodrug(s), which one or more prodrug(s) comprise(s) in bound form a biologically active moiety selected from the group consisting of anti-sense RNA, antisense DNA, ribozymes or RNAi molecules targeting a VEGF nucleic acid; anti-VEGF aptamers, anti-VEGF antibodies, DARPins anticalins, lipocalins, and soluble VEGF receptor decoys that prevent binding of a VEGF to its cognate receptor; antisense, ribozymes, and RNAi molecules targeting a cognate VEGF receptor (VEGFR) nucleic acid; anti-VEGFR aptamers or anti-VEGFR antibodies that bind to a cognate VEGFR receptor; and VEGFR tyrosine kinase inhibitors.

In another preferred embodiment the pharmaceutical composition further comprises one or more additional prodrug(s) which one or more additional prodrug(s) comprise(s) in bound form a biologically active moiety, which biologically active moiety is a modulator of the activity of one or more protein(s) selected from the group comprising basic fibroblast growth factors (bFGF), acidic fibroblast growth factors (aFGF), transforming growth factors alpha (TGFa), transforming growth factors beta (TGFβ), platelet-derived growth factor (PDGF), angiogenin, platelet-derived endothelial cell growth factor (PD-ECGF), interleukin-1 (IL-1), interleukin-8 (IL-8), interleukin-12, vascular endothelial growth factor (VEGF), angiopoietin-I, Del-I, follistatin, granulocyte colony-stimulating factor (G-CSF), hepatocyte growth factor (HGF), leptin, midkine, placental growth factor, pleiotrophin (PTN), progranulin, proliferin, tumor necrosis factor-alpha (TNF-alpha), angioarrestin, angiostatin plasminogen fragment, antiangiogenic anti-thrombin III, cartilage-derived inhibitor (CDI), CDS9 complement fragment, endostatin collagen XVIII fragment, fibronectin fragment, gro-beta, heparinases, heparin hexasaccharide fragment, human chorionic gonadotropin (hCG), interferon alpha/beta/gamma, interferon inducible protein (IP-IO), kringle S plasminogen fragment, metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), retinoids, tetrahydrocortisol-S, thrombospondin-I (TSP-I), vasculostatin, vasostatin calreticulin fragment, prostaglandin receptor, growth hormone, insulin-like growth factor-I (IGF-I), sphingosine-1-phosphate, factor D, RTP801, inhibitors of complement, $\alpha_2$ adrenergic agonist, mTOR, ciliary neurotrophic factor (CNTF), brain-derived neurotrophic factor (BDNF), glial cell-derived neurotrophic factor (GDNF), lens epithelium derived growth factor (LEDGF), rod-derived cone viability factor (RdCVF), pigment epithelium-derived factor (PEDF), neutrophil-activating protein, monocyte chemoattractant protein, macrophage-inflammatory protein, small inducible secreted (SIS) proteins, platelet factor, platelet basic protein, melanoma growth stimulating activity, epidermal growth factor, nerve growth factor, bone morphogenic proteins, bone growth cartilage-inducing factor, interleukins, interleukin inhibitors, interleukin receptors, hematopoietic factors, granulocyte colony stimulating factor, macrophage colony stimulating factor, granulocyte-macrophage colony stimulating factor, inhibin, and activin.

In one embodiment, the one or more additional drug(s) are in the form of a prodrug.

The pharmaceutical composition of the present invention comprises one or more excipient(s). Excipients may be categorized as buffering agents, isotonicity modifiers, preservatives, stabilizers, anti-adsorption agents, oxidation protection agents, viscosifiers/viscosity enhancing agents, or other auxiliary agents. In some cases, these ingredients may have dual or triple functions. The pharmaceutical composition may comprise one or more excipients selected from the groups consisting of:

(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability;

(ii) Isotonicity modifiers: to minimize pain that can result from cell damage due to osmotic pressure differences at the injection side. Glycerin and sodium chloride are examples. Effective concentrations can be determined by osmometry;

(iii) Preservatives and/or antimicrobials: to minimize the risk of patients becoming infected upon injection. Typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride;

(iv) Stabilizers: Stabilization is achieved by strengthening of the protein-stabilizing forces, by destabilization of the denatured state, or by direct binding of excipients to the protein. Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, PEG or PVP or protamine or HSA may be used;

(v) Anti-adsorption agents: Mainly ionic or non-ionic surfactants or other proteins or soluble polymers are used to coat or adsorb competitively to, for example, the inner surface of the pharmaceutical composition's container. Suitable surfactants are e.g., alkyl sulfates, such as ammonium lauryl sulfate and sodium lauryl sulfate; alkyl ether sulfates, such as sodium laureth sulfate and sodium myreth sulfate; sulfonates such as dioctyl sodium sulfosuccinates, perfluorooctanesulfonates, perfluorobutanesulfonates, alkyl benzene sulfonates; phosphates, such as alkyl aryl ether phosphates and alkyl ether phosphates; carboxylates, such as fatty acid salts (soaps) or sodium stearate, sodium lauroyl sarcosinate, perfluorononanoate, perfluorooctanoate; octenidine dihydrochloride; quaternary ammonium cations such as cetyl trimethylammonium bromide, cetyl trimethylammonium chloride, cetylpyridinium chloride, polyethoxylated tallow amine, benzalkonium chloride, benzethonium chloride, 5-bromo-5-nitor-1,3-dioxane, dimethyldioctadecylammonium chloride, dioctadecyldimethylammonium bromide; zwitterionics, such as 3-[(3-cholamidopropyl)dimethylammonio]-1-propanesulfonate, cocamidopropyl hydroxysultaine, amino acids, imino acids, cocamidopropyl betaine, lecithin; fatty alcohols, such as cetyl alcohol, stearyl alcohol, cetostearyl alcohol, oleyl alcohol; polyoxyethylene glycol alkyl ethers, such as octaethylene glycol monododecyl ether, pentaethylene glycol monododecyl ether; polyoxypropylene glycol alkyl ethers; glucoside alkyl ethers, such as decyl glucoside, lauryl glucoside, octyl glucoside; polyoxyethylene glycol octylphenol ethers such as Triton X-100; polyoxyethylene glycol alkylphenol ethers such as nonoxynol-9; glycerol alkyl esters such as glyceryl laurate; polyoxyethylene glycol sorbitan alkyl esters such as polysorbates; sorbitan alkyl esters; cocamide MEA and cocamide DEA; dodecyl dimethylamine oxide; block copolymers of polyethylene glycol and polypropylene glycol, such as poloxamers (Pluronic F-68), PEG dodecyl ether (Brij 35), polysorbate 20 and 80; other anti-absorption agents are dextran, polyethylene glycol, PEG-polyhistidine, BSA and HSA and gelatines. Chosen concentration and type of excipient depends on the effect to be avoided but typically a monolayer of surfactant is formed at the interface just above the CMC value;

(vi) Lyo- and/or cryoprotectants: During freeze- or spray drying, excipients may counteract the destabilizing effects caused by hydrogen bond breaking and water removal. For this purpose sugars and polyols may be used, but corresponding positive effects have also been observed for surfactants, amino acids, non-aqueous solvents, and other peptides. Trehalose is particularly efficient at reducing moisture-induced aggregation and also improves thermal stability potentially caused by exposure of protein hydrophobic groups to water. Mannitol and sucrose may also be used, either as sole lyo/cryoprotectant or in combination with each other where higher ratios of mannitol:sucrose are known to enhance physical stability of a lyophilized cake. Mannitol may also be combined with trehalose. Trehalose may also be combined with sorbitol or sorbitol used as the sole protectant. Starch or starch derivatives may also be used;

(vii) Oxidation protection agents: antioxidants such as ascorbic acid, ectoine, methionine, glutathione, monothioglycerol, morin, polyethylenimine (PEI), propyl gallate, vitamin E, chelating agents such as citric acid, EDTA, hexaphosphate, thioglycolic acid;

(viii) Spreading or diffusing agent: modifies the permeability of connective tissue through the hydrolysis of components of the extracellular matrix in the intrastitial space such as but not limited to hyaluronic acid, a polysaccharide found in the intercellular space of connective tissue. A spreading agent such as but not limited to hyaluronidase temporarily decreases the viscosity of the extracellular matrix and promotes diffusion of injected drugs;

(ix) Other auxiliary agents: such as wetting agents, viscosity modifiers, antibiotics, hyaluronidase. Acids and bases such as hydrochloric acid and sodium hydroxide are auxiliary agents necessary for pH adjustment during manufacture;

The pharmaceutical composition may be provided in the form of a dry, liquid or suspension pharmaceutical composition.

The pharmaceutical composition in either dry, liquid or suspension form may be provided as a single or multiple dose pharmaceutical composition.

In one embodiment of the present invention, the dry, liquid or suspension pharmaceutical composition is provided as a single dose, meaning that the container in which it is supplied contains one pharmaceutical dose.

In another embodiment the dry, liquid or suspension pharmaceutical composition is a multiple dose pharmaceutical composition, meaning that the container in which it is supplied contains more than one therapeutic dose, i.e., a multiple dose composition contains at least 2 doses. Such multiple dose pharmaceutical composition can either be used for different patients in need thereof or can be used for one patient, wherein the remaining doses are stored after the application of the first dose until needed.

Preferably, the pharmaceutical composition is provided as a single dose.

In another aspect of the present invention the pharmaceutical composition is in a container. Suitable containers for dry, liquid or suspension pharmaceutical compositions are, for example, syringes, vials, vials with stopper and seal, ampoules, and cartridges. In particular, the dry, liquid or suspension pharmaceutical composition is provided in a syringe. If the pharmaceutical composition is a dry pharmaceutical composition the container preferably is a dual-chamber syringe. In such embodiment, said dry pharmaceutical composition is provided in a first chamber of the dual-chamber syringe and reconstitution solution is provided in the second chamber of the dual-chamber syringe.

Prior to applying the dry pharmaceutical composition to a patient in need thereof, the dry composition is reconstituted. Reconstitution can take place in the container in which the dry composition is provided, such as in a vial, syringe, dual-chamber syringe, ampoule, and cartridge. Reconstitution is done by adding a predefined amount of reconstitution solution to the dry composition. Reconstitution solutions are sterile liquids, such as water or buffer, which may contain further additives, such as preservatives and/or antimicrobials, such as, for example, benzylalcohol and cresol. Preferably, the reconstitution solution is sterile water. When a dry pharmaceutical composition is reconstituted, it is referred to as a "reconstituted pharmaceutical composition" or "reconstituted pharmaceutical composition" or "reconstituted composition".

Preferably, the pharmaceutical composition is a liquid or suspension.

Another aspect of the present invention is a kit of parts.

If the administration device is simply a hypodermic syringe then the kit may comprise the syringe, a needle and a container comprising dry pharmaceutical composition for use with the syringe and a second container comprising the reconstitution solution.

If the pharmaceutical composition is a liquid or suspension pharmaceutical composition then the kit may comprise the syringe, a needle and a container comprising the liquid or suspension pharmaceutical composition for use with the syringe.

EXAMPLES

Materials and Methods

Lucentis and Ranibizumab are used synonymously throughout the following examples.

Materials:

Amino 4-arm PEG5000 was obtained from JenKem Technology, Beijing, P. R. China. Cithrol™ DPHS was obtained from Croda International Pic, Cowick Hall, United Kingdom.

cis-1,4-cyclohexanedicaboxylic acid was obtained from TCI EUROPE N.V., Boerenveldseweg 6-Haven 1063, 2070 Zwijndrecht, Belgium.

Isopropylmalonic acid was obtained from ABCR GmbH & Co. KG, 76187 Karlsruhe, Germany.

N-(3-maleimidopropyl)-39-amino-4,7,10,13,16,19,22,25,28,31,34,37-dodecaoxa-nonatriacontanoic acid pentafluorophenyl ester (Mal-PEG12-PFE) was obtained from Biomatrik Inc., Jiaxing, P. R. China.

Oxyma pure, HATU, HOAt, HOBt, PyBOP, TBTU, COMU, Fmoc-L-Asp(OBzl)-OH, Fmoc-L-Asp(OtBu)-OH, Fmoc-L-His(OTrt)-OH, Fmoc-Ado-OH and Rink amide resin were purchased from Merck Biosciences GmbH, Schwalbach/Ts, Germany.

Boc-Lys(Boc)-OSu was purchased from Senn chemicals AG, Dielsdorf, Switzerland. Fmoc-N-Me-L-Asp(OtBu)-OH was purchased from Bachem, Bubendorf, Switzerland. Fmoc-N-Me-L-Asp(OBzl)-OH was purchased from Peptides International, Louisville, Ky., USA. 1,9-bis-Boc-1,5,9-triazanonan was purchased from PolyPeptide Laboratories A/S, Hillerød, Denmark.

(5-methyl-2-oxo-1,3-dioxol-4-yl)-methyl 4-nitrophenyl carbonate was purchased from Chemzon Scientific Inc., Lachine, QC, Canada.

α-[3-(o-pyridyldisulfido)propanoylamido]-ω-succinimidyl ester dodeca(ethylene glycol) (OPSS-PEG$_{12}$-NHS) was purchased from Iris Biotech GmbH, Marktredwitz, Germany.

All other chemicals were from Sigma-ALDRICH Chemie GmbH, Taufkirchen, Germany.

Methods:

Reactions were performed with dry solvents (DCM, THF, ACN, DMF, dioxane, MeOH, toluene) stored over molecular sieve purchased from Sigma-ALDRICH Chemie GmbH, Taufkirchen, Germany. Generally, reactions were stirred at room temperature and monitored by HPLC/MS or TLC.

RP-HPLC was done on a 100×20 mm or 100×40 mm C18 ReproSil-Pur 300 ODS-3 5µ column (Dr. Maisch, Ammerbuch, Germany) or XBridge BEH300 C18 OBD Prep 10 µm 30×150 mm or 5 µm 10×150 mm (Waters, Eschborn, Germany) connected to a Waters 600 or 2535 HPLC System and Waters 2487 or 2489 Absorbance detector, respectively. Linear gradients of solution A (0.1% TFA in H$_2$O) and solution B (0.1% TFA in acetonitrile) were used. HPLC fractions containing product were combined and lyophilized.

Flash chromatography purifications were performed on an Isolera One system from Biotage AB, Sweden, using Biotage KP-Sil silica cartridges and n-heptane, ethyl acetate, and methanol as eluents. Products were detected at 254 nm. For products showing no absorbance above 240 nm fractions were screened by LC/MS.

Analytical ultra-performance LC (UPLC) was performed on a Waters Acquity system equipped with a Waters BEH300 C18 column (2.1×50 mm, 1.7 µm particle size) coupled to a LTQ Orbitrap Discovery mass spectrometer from Thermo Scientific.

HPLC-Electrospray ionization mass spectrometry (HPLC-ESI-MS) was performed on a Waters Acquity UPLC with an Acquity PDA detector coupled to a Thermo LTQ Orbitrap Discovery high resolution/high accuracy mass spectrometer or Waters Micromass ZQ both equipped with a Waters ACQUITY UPLC BEH300 C18 RP column (2.1× 50 mm, 300 Å, 1.7 µm, flow: 0.25 mL/min; solvent A: UP-H$_2$O+0.04% TFA, solvent B: UP-Acetonitrile+0.05% TFA.

MS spectra of PEG products showed a series of (CH$_2$CH$_2$O) moieties due to polydispersity of PEG staring materials. For easier interpretation only one single representative m/z signal is given in the examples.

Buffer exchange was performed on a HiTrap or HiPrep column (GE Healthcare) connected to an Aekta Purifier 100 system.

Cationic ion exchange chromatography was performed either on a Source 15 S 6 mL column connected to an Aekta Purifier 100 system using 20 mM MES, pH 5.7 and 20 mM MES, 500 mM NaCl, pH 5.7 as mobile phase A and B, respectively.

Example 1

Synthesis of Backbone Reagent 1a and 1g

[PEG1250—DLys—DLys$_2$—DLys$_4$(NH$_2$)$_8$]$_4$ =

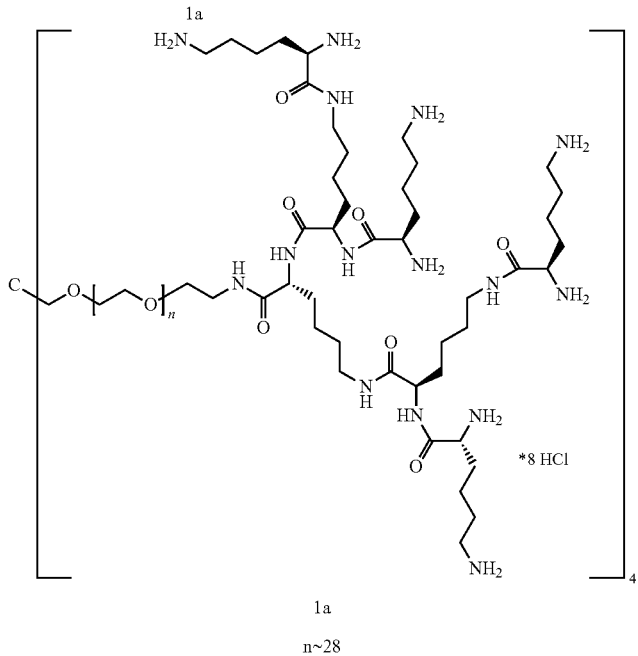

1a
n~28

Backbone reagent 1a was synthesized as described in example 1 of WO 2011/012715 A1 except for the use of Boc-DLys(Boc)-OH instead of Boc-LLys(Boc)-OH.

MS: m/z 888.50=[M+10H$^+$]$^{10+}$ (calculated=888.54)

[PEG1250-TAN-TAN$_2$-TAN$_4$(NH$_2$)$_8$]$_4$ =
1g

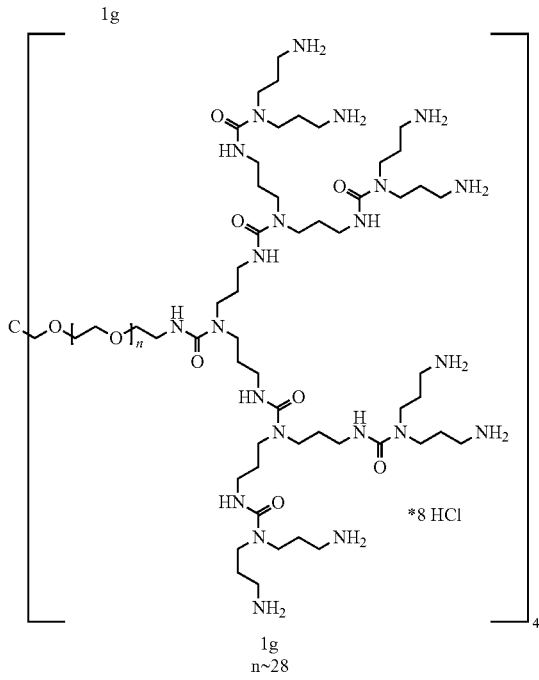

1g
n~28

Backbone reagent 1g was synthesized from amino 4-arm PEG5000 1b according to the following scheme:

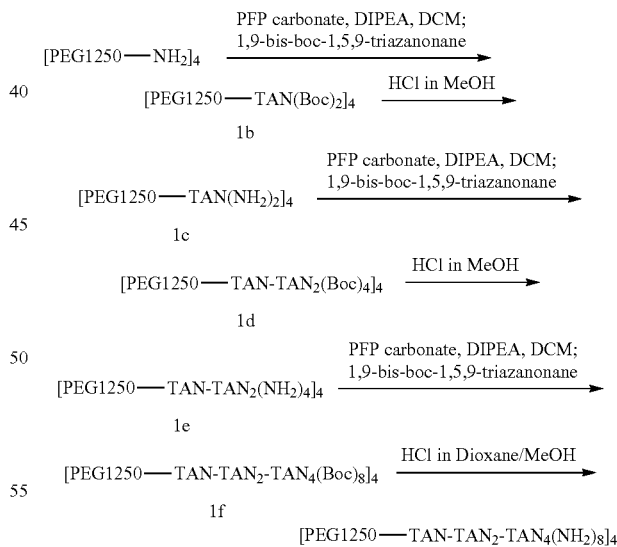

For synthesis of compound 1b, amino 4-arm PEG5000 (MW ca. 5350 g/mol, 10.7 g, 2.00 mmol, HCl salt) and bis(pentafluorophenyl)carbonate (4.73 g, 12.0 mmol) were dissolved in 43 mL of DCM (anhydrous) and DIPEA (3.10 g, 24.0 mmol, 4.18 mL) was added at room temperature. After 10 min, 1,9-bis-boc-1,5,9-triazanonane (5.30 g, 16.0 mmol) was added and the mixture was stirred for 15 min. Then additional 1,9-bis-boc-1,5,9-triazanonane (0.33 g, 1.0 mmol) was added. After complete dissolution, the reaction mixture was filtered and the solvent was evaporated at room temperature.

The residue was dissolved in 40 mL iPrOH and diluted with 320 mL MTBE. The product was precipitated over night at −20° C. The precipitate was collected by filtration through a glass filter Por. 3, and washed with 200 mL of cooled MTBE (0° C.). The product was dried in vacuo over night.

Yield 11.1 g (83%) white solid 1b.

MS: m/z 1112.86=[M+6H]$^{6+}$ (calculated=1113.04).

For synthesis of compound 1c, the boc-protected compound 1b (11.1 g, 1.66 mmol) was dissolved in 40 mL of 3 M HCl in MeOH and stirred for 20 min at 45° C., then for 10 min at 55° C. For precipitation, 10 mL MeOH and 200 mL of MTBE were added and the mixture was stored for 16 h at −20° C. The precipitate was collected by filtration through a glass filter Por. 3 and washed with 200 mL of cooled MTBE (0° C.). The product was dried in vacuo over night.

Yield 9.14 g (89%) white powder 1c (HCl salt).

MS: m/z 979.45=[M+6H]$^{6+}$ (calculated=979.55).

For synthesis of compound 1d, compound 1c (9.06 g, 1.47 mmol, HCl salt) and bis(pentafluorophenyl)carbonate (6.95 g, 17.6 mmol) were dissolved in 50 mL of DCM (anhydrous) and DIPEA (4.56 g, 35.3 mmol, 6.15 mL) was added at room temperature. After 10 min, 1,9-bis-boc-1,5,9-triazanonane (7.80 g, 23.5 mmol) was added and the mixture was stirred for 15 min. Then additional 1,9-bis-boc-1,5,9-triazanonane (0.49 g, 1.5 mmol) was added. After complete dissolution, the solvent was evaporated at room temperature.

The residue was dissolved in 35 mL iPrOH at 40° C. and diluted with 200 mL MTBE. The product was precipitated over night at −20° C. The precipitate was collected by filtration through a glass filter Por. 3, and washed with 200 mL of cooled MTBE (0° C.). The product was dried in vacuo over night to give 1d as a white solid.

Yield 11.6 g (90%) white solid 1d.

MS: m/z 1248.08=[M+7H]$^{7+}$ (calculated=1248.27).

For synthesis of compound 1e, the boc-protected compound 1d (11.4 g, 1.31 mmol) was dissolved in 40 mL of 3 M HCl in MeOH and stirred for 20 min at 45° C., then for 10 min at 55° C. For precipitation, 10 mL MeOH and 200 mL of MTBE were added and the mixture was stored for 16 h at −20° C. The precipitate was collected by filtration through a glass filter Por. 3 and washed with 200 mL of cooled MTBE (0° C.). The product was dried in vacuo over night to give white powder 1e.

Yield 7.60 g (75%) white powder 1e (HCl salt).

MS: m/z 891.96=[M+8H]$^{8+}$ (calculated=892.13).

For synthesis of compound 1f, compound 1e (7.56 g, 0.980 mmol, HCl salt) and bis(pentafluorophenyl)carbonate (9.27 g, 23.0 mmol) were dissolved in 250 mL of DCM (anhydrous) and DIPEA (6.08 g, 47.0 mmol, 8.19 mL) was added at 35° C. After 10 min, 1,9-bis-boc-1,5,9-triazanonane (5.30 g, 16.0 mmol) was added and the mixture was stirred for 15 min. Then additional 1,9-bis-boc-1,5,9-triazanonane (0.33 g, 1.0 mmol) was added. After complete dissolution, the solvent was evaporated at room temperature.

The residue was dissolved in 250 mL iPrOH at 60° C. and diluted with 1350 mL MTBE. The product was precipitated over night at −20° C. The precipitate was collected by filtration through a glass filter Por. 3, and washed with 400 mL of cooled MTBE (0° C.). The product was dried in vacuo over night to give 1f as a glassy solid.

Yield 11.1 g (83%) glassy solid 1f.

MS: m/z 1312.01=[M+10H]$^{10+}$ (calculated=1312.21).

For synthesis of backbone reagent 1g, the boc-protected compound 1f (7.84 g, 0.610 mmol) was dissolved in 16 mL of MeOH at 37° C. and 55 mL of a precooled solution of 4 M HCl (4° C.) in dioxane was added at room temperature. The mixture was stirred without cooling for 20 min. After 20 min 110 mL of 3M HCl in MeOH was added. The solution was partitioned in 24 Falcon tubes (50 mL) and precipitated by adding 40 mL cold MTBE (−20° C.) to each Falcon tube. After centrifugation at 3214 rcf for 1 min, the supernatant was decanted and the glassy solid was dissolved in 5 mL MeOH per Falcon tube and precipitated by adding 40 mL cold MTBE (−20° C.) to each Falcon tube again. The supernatant was discarded and the remaining solid was dried in vacuo over night.

Yield 5.74 g (87%) white glassy solid 1g (HCl salt).

MS: m/z 965.46=[M+10H]$^{10+}$ (calculated=965.45).

Example 2

Synthesis of Crosslinker Reagents 2d, 2g, 2k, and 2o

Crosslinker reagent 2e was prepared from azelaic acid monobenzyl ester and PEG10000 according to the following scheme:

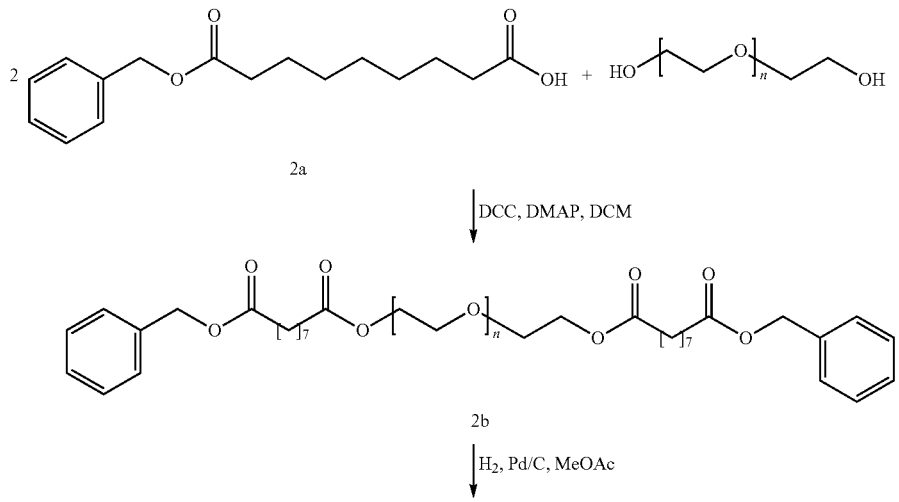

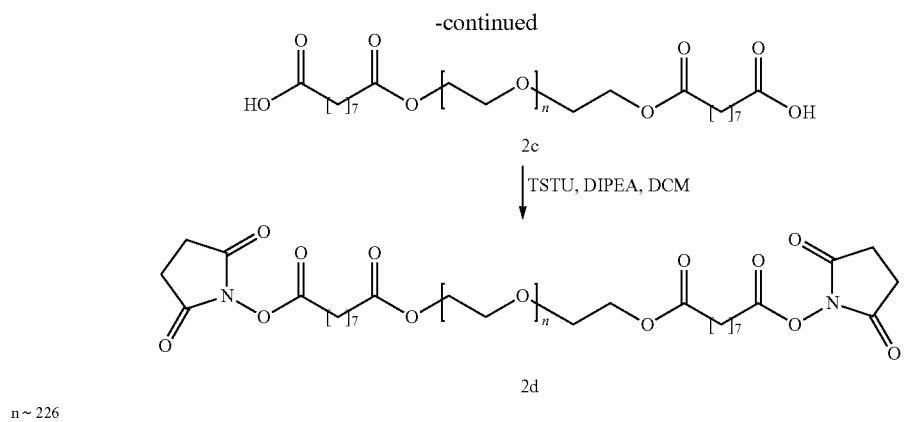

2c

↓ TSTU, DIPEA, DCM

2d n ~ 226

For the synthesis of azelaic acid monobenzyl ester 2a, a mixture of azelaic acid (37.6 g, 200 mmol), benzyl alcohol (21.6 g, 200 mmol), p-toluenesulfonic acid (0.80 g, 4.2 mmol), and 240 mL toluene was refluxed for 7 h in a Dean-Stark apparatus. After cooling down, the solvent was evaporated and 300 mL sat. aqueous $NaHCO_3$ solution were added. This mixture was extracted with 3×200 mL MTBE. The combined organic phases were dried over $Na_2SO_4$ and the solvent was evaporated. The product was purified on 2×340 g silica using ethyl acetate/heptane (10:90→25:75) as eluent. The eluent was evaporated and the residue was dried in vacuo over night.

Yield 25.8 g (46%) colorless oil 2a.

MS: m/z 279.16=$[M+H]^+$ (calculated=279.16).

For synthesis of compound 2b, azelaic acid monobenzyl ester 2a (3.90 g, 14.0 mmol) and PEG 10000 (40.0 g, 4.00 mmol) were dissolved in 64 mL dichloromethane and cooled with an ice bath. A solution of DCC (2.89 g, 14.0 mmol) and DMAP (0.024 g, 0.020 mmol) in 32 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 65 mL dichloromethane and diluted with 308 mL MTBE at room temperature. The mixture was stored over night at −20° C. The precipitate was collected by filtration through a glass filter Por. 3, and washed with 250 mL of cooled MTBE (−20° C.). The product was dried in vacuo over night.

Yield 40.8 g (97%) white powder 2b.

MS: m/z 835.50=$[M+14H]^{14+}$ (calculated=835.56).

For synthesis of compound 2c, compound 2b (40.6 g, 3.86 mmol) was dissolved in methyl acetate (250 mL) and 203 mg of palladium on charcoal was added. Under a hydrogen atmosphere of ambient pressure, the mixture was stirred overnight at room temperature. The reaction mixture was filtered through a pad of celite and the filtrate was evaporated and dried in vacuo over night.

Yield 37.2 g (93%) glassy solid 2c.

MS: m/z 882.53=$[M+13H]^{13+}$ (calculated=882.51).

For synthesis of compound 2d, compound 2c (32.0 g, 3.10 mmol) and TSTU (3.73 g, 12.4 mmol) were dissolved in 150 mL dichloromethane at room temperature. Then DIPEA (1.60 g, 12.4 mmol) was added and the mixture was stirred for 1 h. The resulting suspension was filtered and the filtrate was diluted with 170 mL dichloromethane, washed with 140 mL of a solution of 750 g water/197 g NaCl/3 g NaOH. The organic phase was dried over $MgSO_4$ and the solvent was evaporated in vacuo.

The residue was dissolved in 200 mL toluene, diluted with 180 mL MTBE at room temperature and stored over night at −20° C. The precipitate was collected by filtration through a glass filter Por. 3, and washed with 100 mL of cooled MTBE (−20° C.). The product was dried in vacuo over night.

Yield 28.8 g (88%) white powder 2d.

MS: m/z 795.47=$[M+15H]^{15+}$ (calculated=795.54).

Crosslinker reagent 2g was prepared from azelaic acid monobenzyl ester and PEG6000 according to the following scheme:

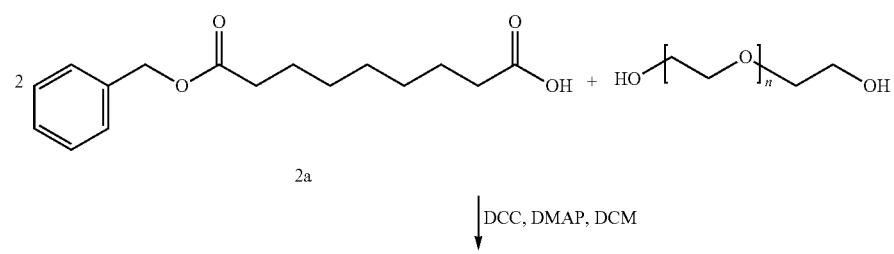

2a

↓ DCC, DMAP, DCM

-continued

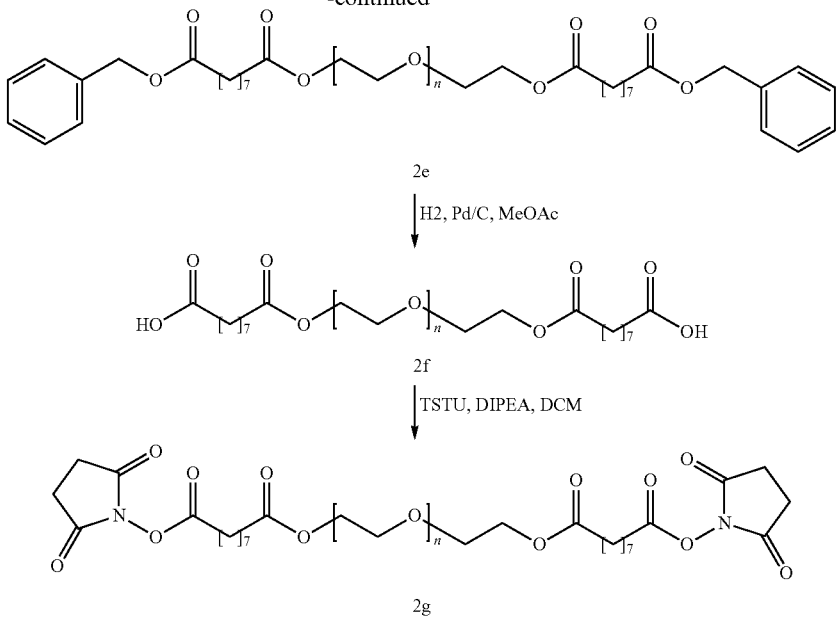

n ~ 135

For synthesis of compound 2e, azelaic acid monobenzyl ester 2a (6.50 g, 23.3 mmol) and PEG 6000 (40.0 g, 6.67 mmol) were dissolved in 140 mL dichloromethane and cooled with an ice bath. A solution of DCC (4.81 g, 23.3 mmol) and DMAP (0.040 g, 0.33 mmol) in 40 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 70 mL dichloromethane and diluted with 300 mL MTBE at room temperature. The mixture was stored over night at −20° C. The precipitate was collected by filtration through a glass filter Por. 3, and washed with 500 mL of cooled MTBE (−20° C.). The product was dried in vacuo over night.

Yield 41.2 g (95%) white powder 2e.

MS: m/z 833.75=$[M+8H]^{8+}$ (calculated=833.74).

For synthesis of compound 2f, compound 2e (41.2 g, 6.32 mmol) was dissolved in methyl acetate (238 mL) and ethanol (40 mL), then 400 mg of palladium on charcoal was added. Under a hydrogen atmosphere of ambient pressure, the mixture was stirred overnight at room temperature. The reaction mixture was filtered through a pad of celite and the filtrate was evaporated and dried in vacuo over night.

Yield 38.4 g (96%) glassy solid 2f.

MS: m/z 750.46=$[M+9H]^{9+}$ (calculated=750.56).

For synthesis of compound 2g, compound 2f (38.2 g, 6.02 mmol) and TSTU (7.25 g, mmol) were dissolved in 130 mL dichloromethane at room temperature. Then DIPEA (3.11 g, 24.1 mmol) was added and the mixture was stirred for 1 h. The resulting suspension was filtered, the filtrate was diluted with 100 mL dichloromethane and washed with 200 mL of a solution of 750 g water/197 g NaCl/3 g NaOH. The organic phase was dried over $MgSO_4$ and the solvent was evaporated in vacuo.

The residue was dissolved in 210 mL toluene, diluted with 430 mL MTBE at room temperature and stored over night at −20° C. The precipitate was collected by filtration through a glass filter Por. 3, and washed with 450 mL of cooled MTBE (−20° C.). The product was dried in vacuo over night.

Yield 35.8 g (91%) white powder 2g.

MS: m/z 857.51=$[M+8H]^{8+}$ (calculated=857.51).

Crosslinker reagent 2k was prepared from isopropylmalonic acid monobenzyl ester and PEG10000 according to the following scheme:

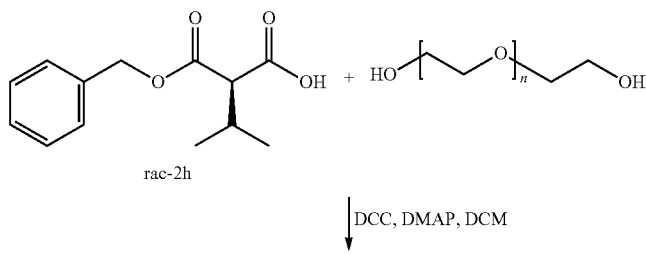

rac-2h

DCC, DMAP, DCM

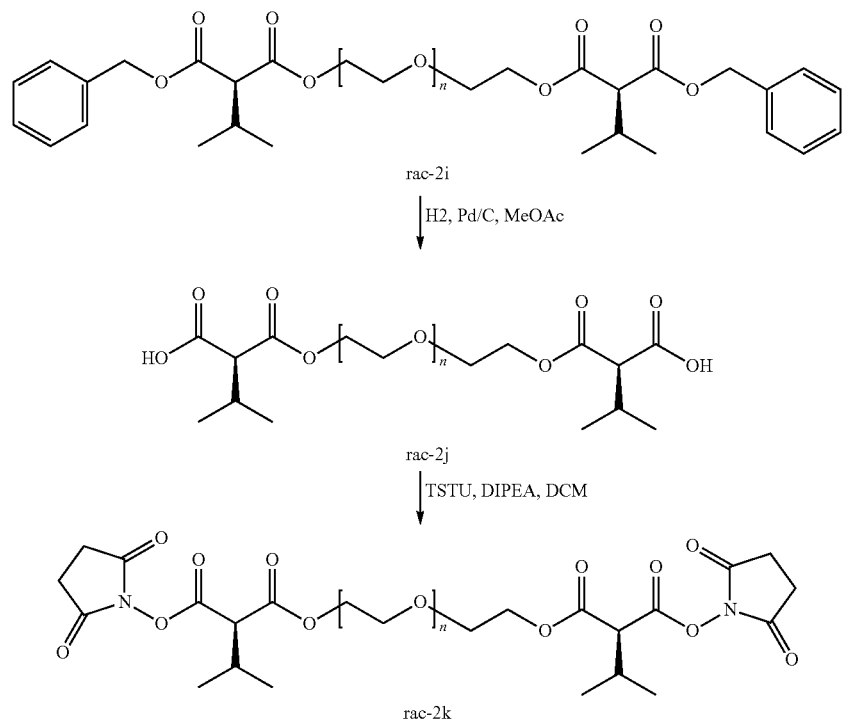

rac-2k n ~ 226

For the synthesis of isopropylmalonic acid monobenzyl ester rac-2h, isopropylmalonic acid (35.0 g, 239 mmol), benzyl alcohol (23.3 g, 216 mmol) and DMAP (1.46 g, 12.0 mmol) were dissolved in 100 mL acetonitrile. Mixture was cooled to 0° C. with an ice bath. A solution of DCC (49.4 g, 239 mmol) in 150 mL acetonitrile was added within 15 min at 0° C. The ice bath was removed and the reaction mixture was stirred over night at room temperature, then the solid was filtered off. The filtrate was evaporated at 40° C. in vacuo and the residue was dissolved in 300 mL MTBE. This solution was extracted with 2×300 mL sat. aqueous $NaHCO_3$ solution, then the combined aqueous phases were acidified to pH=1-3 using 6 N hydrochloric acid. The resulting emulsion was extracted with 2×300 mL MTBE and the solvent was evaporated. The combined organic phases were washed with 200 mL sat. aqueous NaCl and dried over $MgSO_4$. The product was purified on 340 g silica using ethyl acetate/heptane (10:90→20:80) as eluent. The eluent was evaporated and the residue was dried in vacuo over night.

Yield 9.62 g (17%) colorless oil rac-2h.

MS: m/z 237.11=$[M+H]^+$ (calculated=237.11).

For synthesis of compound 2i, isopropylmalonic acid monobenzyl ester rac-2h (945 mg, 4.00 mmol) and PEG 10000 (10.0 g, 4.00 mmol) were dissolved in 20 mL dichloromethane and cooled with an ice bath. A solution of DCC (825 mg, 4.00 mmol) and DMAP (6 mg, 0.05 mmol) in 10 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 20 mL dichloromethane and diluted with 150 mL MTBE at room temperature. The mixture was stored over night at −20° C. The precipitate was collected by filtration through a glass filter Por. 3, and washed with 500 mL of cooled MTBE (−20° C.). The product was dried in vacuo over night.

Yield 9.63 g (92%) white powder 2i.

MS: m/z 742.50=$[M+16H]^{16+}$ (calculated=742.51).

For synthesis of compound 2j, compound 2i (3.38 g, 0.323 mmol) was dissolved in methyl acetate (100 mL) and 105 mg of palladium on charcoal was added. Under a hydrogen atmosphere of ambient pressure, the mixture was stirred overnight at room temperature. The reaction mixture was filtered through a pad of celite and the filtrate was evaporated and dried in vacuo over night.

Yield 3.25 g (98%) glassy solid 2j.

MS: m/z 731.25=$[M+16H]^{16+}$ (calculated=731.25).

For synthesis of compound 2k, compound 2j (3.10 g, 0.302 mmol) and TSTU (0.364 g, 1.21 mmol) were dissolved in 15 mL dichloromethane at room temperature. Then DIPEA (0.156 g, 1.21 mmol) was added and the mixture was stirred for 45 min. The resulting suspension was filtered and the filtrate was washed with 2×10 mL of a 0.5 M phosphate buffer pH=6.5. The organic phase was dried over $MgSO_4$ and the solvent was evaporated in vacuo. The residue was dissolved in 20 mL toluene, diluted with 10 mL MTBE at room temperature and stored over night at −20° C. The precipitate was collected by filtration through a glass filter Por. 3, and washed with 250 mL of cooled MTBE (−20° C.). The product was dried in vacuo over night.

Yield 2.66 g (84%) white powder 2k.

MS: m/z 743.37=$[M+16H]^{16+}$ (calculated=743.38).

Crosslinker reagent rac-2o was prepared from cis-1,4-cyclohexanedicarboxylic acid and PEG10000 according to the following scheme:

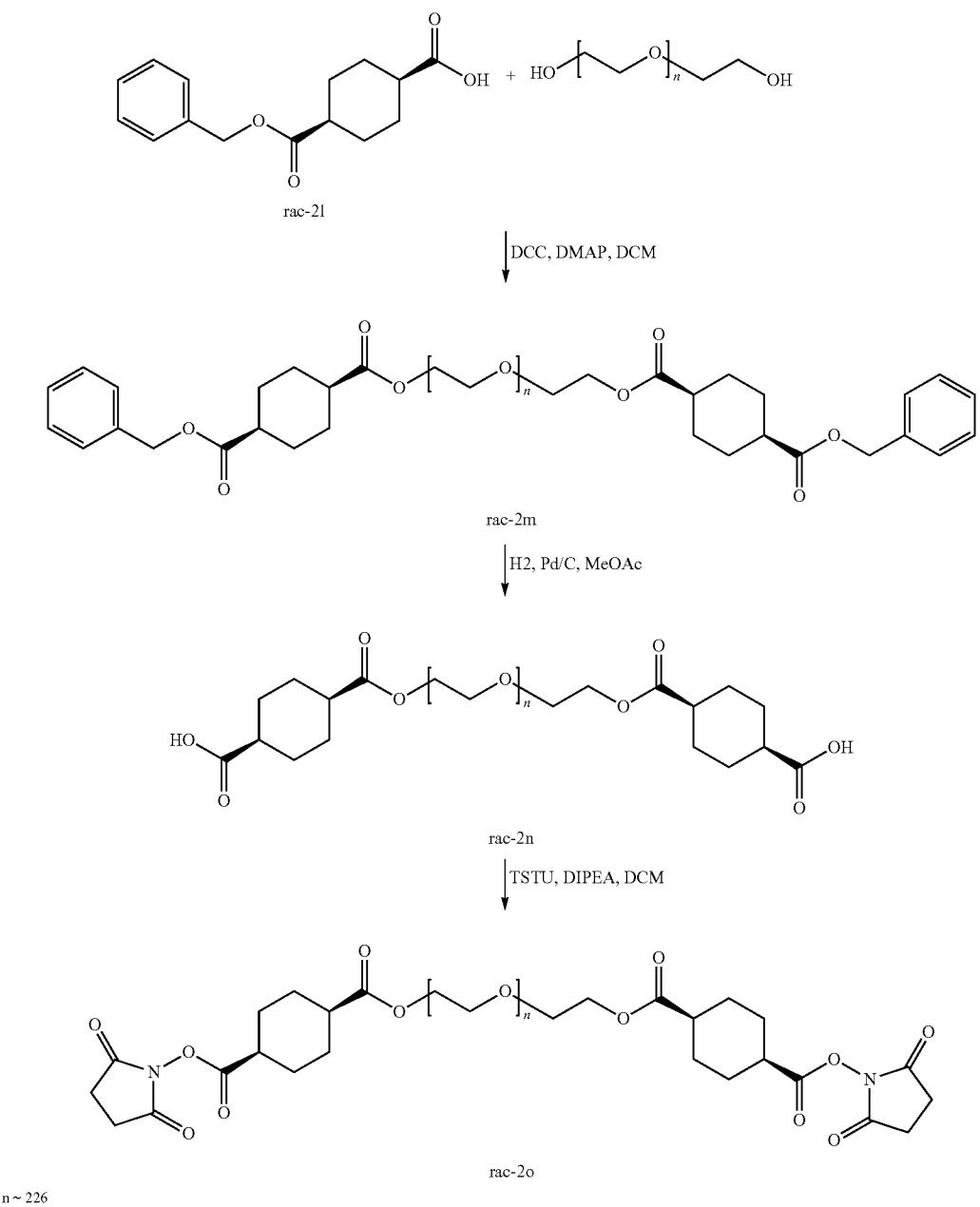

n ~ 226

For the synthesis of cis-1,4-cyclohexanedicarboxylic acid monobenzyl ester rac-21, cis-1,4-cyclohexanedicarboxylic acid (20.0 g, 116 mmol), benzyl alcohol (11.3 g, 105 mmol) and DMAP (710 mg, 5.81 mmol) were dissolved in 200 mL THF. Mixture was cooled to 0° C. with an ice bath. A solution of DCC (49.4 g, 239 mmol) in 100 mL THF was added within 15 min at 0° C. The ice bath was removed and the reaction mixture was stirred over night at room temperature, then the solid was filtered off. The filtrate was evaporated at 40° C. and the residue was dissolved in 300 mL MTBE. This solution was extracted with 2×300 mL sat. aqueous NaHCO$_3$ solution, then the combined aqueous phases were acidified to pH=1-3 using 6 N hydrochloric acid. The resulting emulsion was extracted with 2×300 mL MTBE and the solvent was evaporated. The combined organic phases were washed with 200 mL sat. aqueous NaCl and dried over MgSO$_4$. The product was purified on 340 g silica using ethyl acetate/heptane (10:90→20:80) as eluent. The eluent was evaporated and the colorless oily residue crystallized during drying in vacuo over night.

Yield 4.82 g (16%) colorless crystals rac-21.

MS: m/z 263.13=[M+H]$^+$ (calculated=263.13).

For synthesis of compound 2m, cis-1,4-cyclohexanedicarboxylic acid monobenzyl ester rac-21 (2.10 g, 8.00 mmol) and PEG 10000 (20.0 g, 10.0 mmol) were dissolved in 50 mL dichloromethane and cooled with an ice bath. A solution of DCC (1.65 g, 8.00 mmol) and DMAP (0.012 g, 0.10 mmol) in 25 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 55 mL dichloromethane and diluted with 300 mL MTBE at room temperature. The mixture was stored over night at −20° C. The precipitate was collected by filtration through a glass filter Por. 3, and washed with 250 mL of cooled MTBE (−20° C.). The product was dried in vacuo over night.

Yield 18.2 g (87%) white powder 2m.
MS: m/z 745.76=$[M+16H]^{16+}$ (calculated=745.77).

For synthesis of compound 2n, compound 2m (9.00 g, 0.857 mmol) was dissolved in methyl acetate (100 mL) and 157 mg of palladium on charcoal was added. Under a hydrogen atmosphere of ambient pressure, the mixture was stirred overnight at room temperature. The reaction mixture was filtered through a pad of celite and the filtrate was evaporated and dried in vacuo over night.

Yield 8.83 g (100%) glassy solid 2n.
MS: m/z 734.50=$[M+16H]^{16+}$ (calculated=734.50).

For synthesis of compound 2o, compound 2n (8.92 g, 0.864 mmol) and TSTU (1.04 g, 3.64 mmol) were dissolved in 35 mL dichloromethane at room temperature. Then DIPEA (0.447 g, 3.46 mmol) was added and the mixture was stirred for 45 min. The resulting suspension was filtered and the filtrate was washed with 2×10 mL of a 0.5 M phosphate buffer pH=6.5. The organic phase was dried over $MgSO_4$ and the solvent was evaporated in vacuo.

The residue was dissolved in 50 mL toluene, diluted with 25 mL MTBE at room temperature and stored over night at −20° C. The precipitate was collected by filtration through a glass filter Por. 3, and washed with 400 mL of cooled MTBE (−20° C.). The product was dried in vacuo over night.

Yield 7.62 g (84%) white powder 2o.
MS: m/z 702.60=$[M+16H]^{16+}$ (calculated=702.59).

Example 3

Preparation of Hydrogel Beads 3a, 3b, 3c, and 3d Containing Free Amino Groups

In a cylindrical 250 mL reactor with bottom outlet, diameter 60 mm, equipped with baffles, an emulsion of 218 mg Cithrol™ DPHS in 100 mL undecane was stirred with an isojet stirrer, diameter 50 mm at 580 rpm, at ambient temperature. A solution of 250 mg 1a and 2205 mg 2d in 22.1 g DMSO was added and stirred for 10 min at RT to form a suspension. 1.1 mL TMEDA were added to effect polymerization. The mixture was stirred for 16 h. 1.7 mL of acetic acid were added and then after 10 min 100 mL of a 15 wt % solution of sodium chloride in water was added. After 10 min, the stirrer was stopped and phases were allowed to separate. After 2 h the aqueous phase containing the hydrogel was drained.

For bead size fractionation, the water-hydrogel suspension was diluted with 40 mL ethanol and wet-sieved on 125, 100, 75, 63, 50, 40, and 32 μm steel sieves using a Retsch AS200 control sieving machine for 15 min. Sieving amplitude was 1.5 mm, water flow 300 mL/min. Bead fractions that were retained on the 63 and 75 μm sieves were pooled and washed 3 times with 0.1% AcOH, 10 times with ethanol and dried for 16 h at 0.1 mbar to give 670 mg of 3a as a white powder.

Amino group content of the hydrogel was determined to be 0.145 mmol/g by conjugation of a Fmoc-amino acid to the free amino groups on the hydrogel and subsequent Fmoc-determination.

3b was prepared as described for 3a except for the use of 350 mg 1a, 2548 mg 2g, 26.1 g DMSO, 257 mg Cithrol™ DPHS, 1.5 mL TMEDA, and 2.4 mL acetic acid, yielding 550 mg 3b as a white powder, free amino groups 0.120 mmol/g.

3c was prepared as described for 3a except for the use of 250 mg 1a, 3019 mg rac-2k, 32.7 g DMSO, 290 mg Cithrol™ DPHS, 1.1 mL ml TMEDA, and 1.7 mL acetic acid, yielding 770 mg 3c as a white powder, free amino groups 0.126 mmol/g.

3d was prepared as described for 3a except for the use of 250 mg 1a, 2258 mg rac-2o, 22.6 g DMSO, 222 mg Cithrol™ DPHS, 1.1 mL ml TMEDA, and 1.7 mL acetic acid, yielding 186 mg 3d as a white powder, free amino groups 0.153 mmol/g.

Example 4

Synthesis of Linker Reagent 4c

Linker reagent 4c was synthesized according to the following scheme:

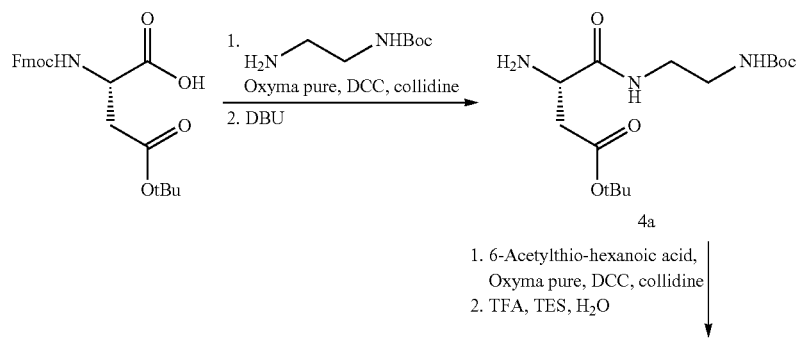

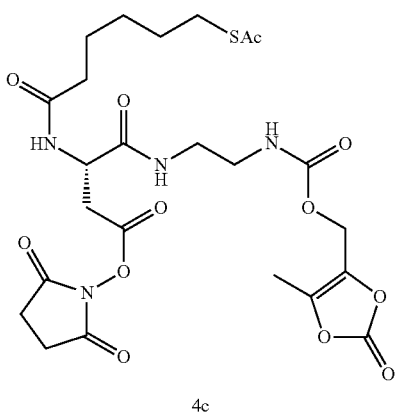

4c

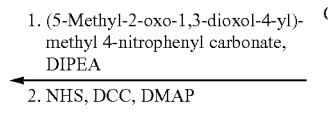

1. (5-Methyl-2-oxo-1,3-dioxol-4-yl)-methyl 4-nitrophenyl carbonate, DIPEA
2. NHS, DCC, DMAP

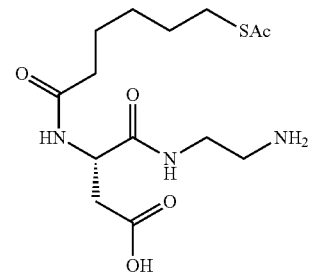

4b

Synthesis of 4a:

Fmoc-L-Asp(OtBu)-OH (1.00 g, 2.43 mmol) was dissolved with DCC (0.70 g, 3.33 mmol) in DCM (25 mL). Oxyma pure (0.51 g, 3.58 mmol) and collidine (0.50 mL, 3.58 mmol) were added in one portion and a solution of N-Boc-ethylenediamine (0.41 g, 2.56 mmol) in DCM (15 mL) was added slowly. After stirring the mixture for 90 min at RT the formed precipitate was filtered off and the filtrate washed with aqueous HCl (0.1 M, 50 mL). The aqueous layer was extracted with DCM (2×20 mL) and the combined organic fractions were washed with sat. aqueous NaHCO$_3$ (3×25 mL) and brine (1×50 mL), dried over Na$_2$SO$_4$, filtered and concentrated in vacuo. The crude solid was purified by flash chromatography. The intermediate N-boc-N'—(N-fmoc-4-tert.-butyl-L-aspartoyl)-ethylenediamine was obtained as white solid (0.98 g, 1.77 mmol, 73%).

MS: m/z 554.29=[M+H]$^+$, (calculated=554.29).

N-boc-N'—(N-fmoc-4-tert.-butyl-L-aspartoyl)-ethylenediamine (0.98 g, 1.77 mmol) was dissolved in THF (15 mL), DBU (0.31 mL) was added and the solution was stirred for 12 min at RT. The reaction was quenched with AcOH (0.5 ml), concentrated in vacuo and the residue purified by flash chromatography to give 4a (0.61 g, 1.77 mmol, 73% over 2 steps) as white solid.

MS: m/z 332.38=[M+H]$^+$, (calculated=332.22).

Synthesis of 4b:

6-Acetylthiohexanoic acid (0.37 g, 1.95 mmol) was dissolved in DCM (19.5 mL) and Oxyma pure (0.35 g, 2.48 mmol) and DCC (0.40 g, 1.95 mmol) added in one portion. The solution was stirred for 30 min at RT, filtered, and the filtrate added to a solution of 4a (0.61 g, 1.77 mmol) in DCM (10.5 mL). DIPEA (0.46 mL, 2.66 mmol) was added to the solution and the reaction stirred for 2 h at RT. The solution was washed with aqueous H$_2$SO$_4$ (0.1 M, 2×30 mL), sat. aqueous NaHCO$_3$ (2×20 mL) and brine (1×20 mL). The organic layer was dried over Na$_2$SO$_4$, filtered and concentrated in vacuo. The crude material was purified by flash chromatography to give N-boc-N'—(N-6-acetylthiohexyl-4-tert.-butyl-L-aspartoyl)-ethylenediamine (0.65 g, 1.30 mmol, 73% over 2 steps) as white solid.

MS: m/z 504.27=[M+H]$^+$, (calculated=504.28).

N-boc-N'—(N-6-Acetylthiohexyl-4-tert.-butyl-L-aspartoyl)-ethylenediamine (0.60 g, 1.18 mmol) was dissolved in TFA (5 mL) and TES (0.13 mL) and water (0.13 ml) were added. The mixture was stirred for 30 min at RT. TFA was removed in a stream of N$_2$, and crude 4b dissolved in H$_2$O/ACN 1:1 and purified by RP-HPLC.

Yield: 0.39 g, 0.85 mmol (TFA salt), 72%.

MS: m/z 348.25=[M+H]$^+$, (calculated=348.16).

Synthesis of 4c:

4b (TFA salt, 0.38 g, 0.80 mmol) was dissolved in DMF (5 mL) and (5-methyl-2-oxo-1,3-dioxol-4-yl)-methyl 4-nitrophenyl carbonate (0.26 g, 0.88 mmol) and DIPEA (0.28 mL, 1.6 mmol) were added. The resulting suspension was diluted with DCM (5 mL) and stirred for 3 h at RT. More DIPEA (0.28 mL 1.6 mmol) was added and stirring continued for 2 h. DCM was concentrated in vacuo, the residue diluted with H$_2$O/ACN 3:1 and purified by RP-HPLC to give N-(5-methyl-2-oxo-1,3-dioxol-4-yl)-methyl-oxo carbonyl-N'—(N-6-acetylthio hexyl-L-aspartyl)-ethylenediamine (0.31 g, 0.62 mmol, 77%) as colorless oil.

MS: m/z 504.16=[M+H]$^+$, (calculated=504.17).

N-(5-methyl-2-oxo-1,3-dioxol-4-yl)-methyl oxocarbonyl-N'—(N-6-acetylthiohexyl-L-aspartyl)-ethylenediamine (150 mg, 0.30 mmol) was dissolved in DCM (17.5 mL) and NHS (41 mg, 0.36 mmol), DCC (74 mg, 0.36 mmol) and DMAP (4 mg, 0.03 mmol) were added in one portion. The reaction was stirred for 1 h at RT and the resulting suspension filtered. The precipitate was washed with a small amount of DCM and the combined filtrates concentrated in vacuo. 4c was purified by RP-HPLC to give a colorless oil (144 mg, 0.24 mmol, 80%).

MS: m/z 601.18=[M+H]$^+$, (calculated=601.18).

Example 5

Preparation of Maleimide Functionalized Hydrogel Beads 5a 259.3 mg of dry hydrogel beads 3a was incubated for 15 min in 10 mL 1% n-propylamine in NMP and subsequently washed two times with 1% n-propylamine in NMP and two times with 2% DIPEA in NMP. 171 mg of maleimide-NH-PEG$_{12}$-PFE was dissolved in 1 mL NMP and added to the washed hydrogel beads 3a. The hydrogel suspension was incubated for 2 h at room temperature. Resulting maleimide functionalized hydrogel beads 5a were washed five times each with NMP followed by 20 mM succinate, 1 mM Na$_2$EDTA, 0.01% Tween20, pH 3.0, followed by water, followed by 0.1% acetic acid, 0.01% Tween20.

Maleimide functionalized hydrogel beads 5b, 5c, and 5d were prepared accordingly using 3b, 3c, and 3d.

Example 6

Synthesis of Transient Lucentis-Linker-Hydrogel Prodrug 6c 4.6 mg Lucentis (depicted in the scheme below as Lucentis-NH$_2$) (460 µL of 10 mg/mL Lucentis in 10 mM histidine, 10 wt % α,α-trehalose, 0.01% Tween20, pH 5.5) was buffer exchanged to 10 mM sodium phosphate, 2.7 mM potassium chloride, 140 mM sodium chloride, pH 7.4 and the concentration of Lucentis was adjusted to 16.4 mg/mL. 6 mg of Linker reagent 4c was dissolved in 100 µL DMSO to yield a concentration of 100 mM. 1 molar equivalent of linker reagent 4c relative to the amount of Lucentis was added to the Lucentis solution. The reaction mixture was mixed carefully and incubated for 5 min at room temperature. Subsequently, 2 additional molar equivalents of linker reagent 4c were added to the Lucentis solution in 1 molar equivalent steps and after addition of each equivalent the reaction mixture was incubated for 5 min at room temperature yielding a mixture of unmodified Lucentis and the protected Lucentis-linker monoconjugate 6a.

The pH of the reaction mixture was adjusted to pH 6.5 by addition of 1 M sodium citrate, pH 5.0 and Na$_2$EDTA was added to a final concentration of 5 mM. To remove the protecting groups of 6a 0.5 M NH$_2$OH (dissolved in 10 mM sodium citrate, 140 mM sodium chloride, 5 mM Na$_2$EDTA, pH 6.5) was added to a final concentration of 45 mM and the deprotection reaction was incubated at room temperature for 4 h yielding the Lucentis-linker monoconjugate 6b. The mixture of Lucentis and Lucentis-linker monoconjugate 6b was buffer exchanged to 10 mM sodium phosphate, 2.7 mM potassium chloride, 140 mM sodium chloride, 5 mM Na$_2$EDTA, 0.01% Tween 20, pH 6.5 and the overall concentration of the two Lucentis species was adjusted to 11.8 mg/mL. The content of Lucentis-linker monoconjugate 6b in the mixture was 20% as determined by ESI-MS.

4 mg of the Lucentis/Lucentis-linker monoconjugate 6b mixture in 10 mM sodium phosphate, 2.7 mM potassium chloride, 140 mM sodium chloride, 5 mM Na$_2$EDTA, 0.01% Tween 20, pH 6.5 were added to 1 mg of maleimide functionalized hydrogel beads 5a and incubated overnight at room temperature yielding transient Lucentis-linker-hydrogel prodrug 6c.

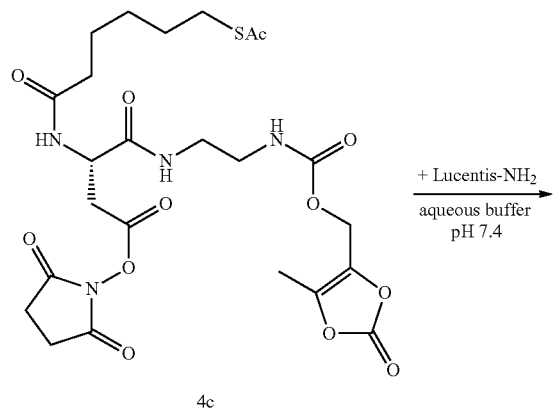

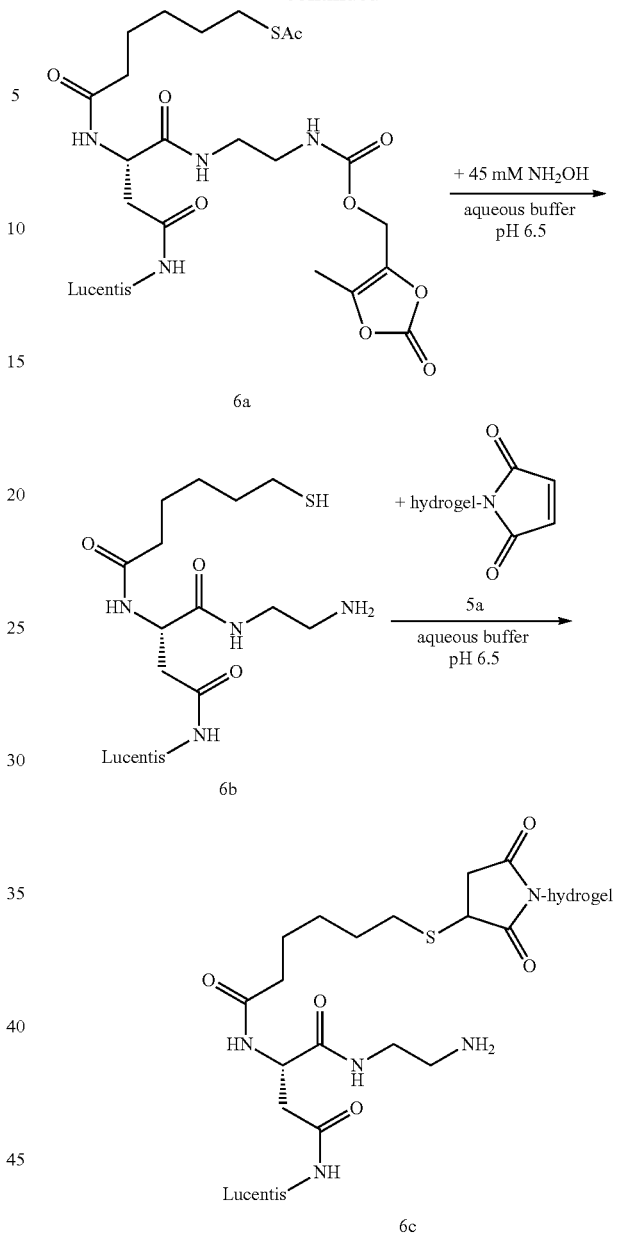

Example 7

In Vitro Release Kinetics Determination of In Vitro Half-Life

Lucentis-linker-hydrogel prodrug 6c (containing approximately 1 mg Lucentis) was washed five times with 60 mM sodium phosphate, 3 mM Na$_2$EDTA, 0.01% Tween20, pH 7.4 and finally suspended in 1 mL of the aforementioned buffer. The suspension was incubated at 37° C. The buffer of the suspension was exchanged after different time intervals and analyzed by HPLC-SEC at 220 nm. Peaks corresponding to liberated Lucentis were integrated and the total of liberated Lucentis was plotted against total incubation time. Curve fitting software was applied to determine first-order cleavage rates.

Example 8

Synthesis of Linker Reagent 8e

Linker reagent 8e was synthesized according to the following scheme:

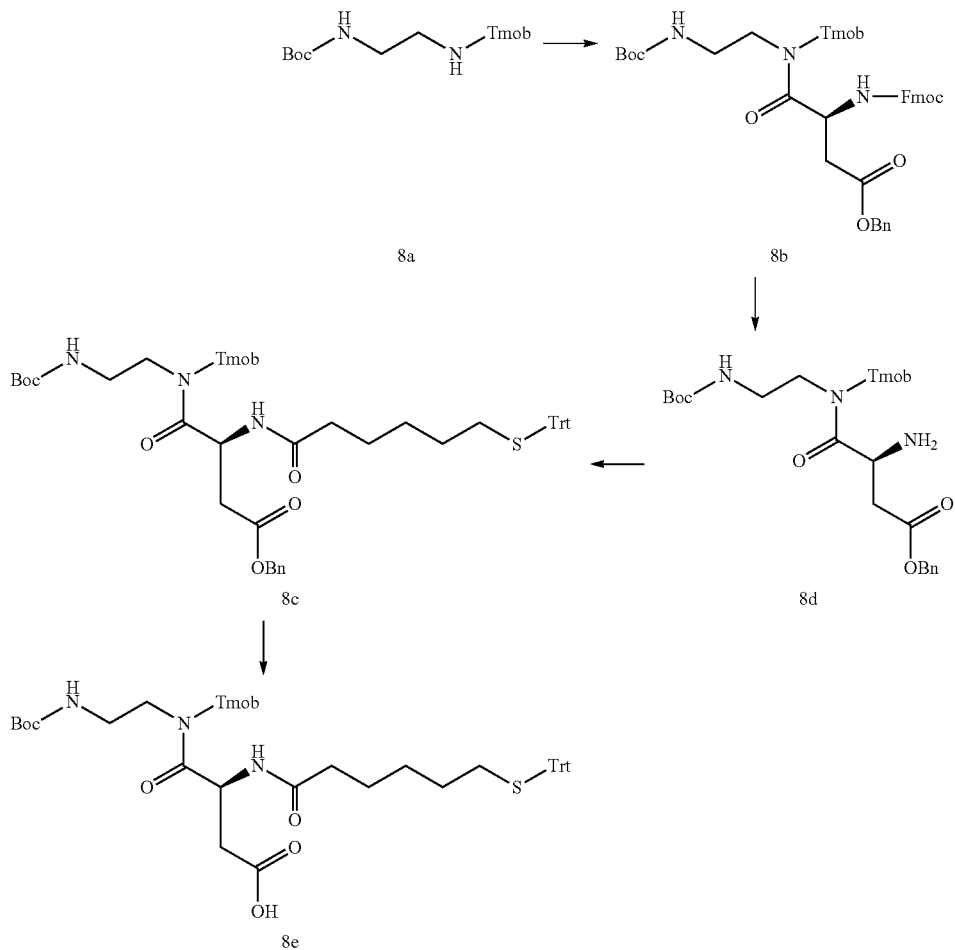

To a solution of N-Boc-ethylenediamine (2.08 g, 12.98 mmol) and NaCNBH$_3$ (775 mg, 12.33 mmol) in MeOH (20 mL, anhydrous) a solution of 2,4,6-trimethoxybenzaldehyde (2.29 g, 11.68 mmol) in 40 mL anhydrous MeOH/DCM (1:1 v/v) was added over 2 h via syringe pump. The mixture was stirred for 90 min, acidified with 0.4 M HCl (60 mL) and stirred further 15 min. The reaction mixture was extracted with ethyl acetate (5×). The combined organic phases were washed with saturated NaHCO$_3$ and brine and dried over Na$_2$SO$_4$. Solvents were removed in vacuo and the residue was dried in high vacuum (<0.1 mbar). Crude N-Boc-N'-Tmob-ethylenediamine 8a was used in the next reaction step without further purification. Yield: 3.70 g (10.87 mmol, 84%) of a colorless solid. MS: m/z 341.21=[M+H]$^+$, (calculated=341.21).

A solution of 8a (1.7 g, 4.99 mmol) in DCM (40 ml, anhydrous, mol. sieve) was added to a solution of DCC (1.34 g, 6.50 mmol), Oxyma pure (995 mg, 7.00 mmol), Fmoc-L-Asp(OBn)-OH (2.22 g, 4.98 mmol) and 2,4,6-collidine (1.24 mL, 9.53 mmol) in DCM (40 ml, anhydrous, mol. sieve). The reaction mixture was stirred for 3 h at RT. The precipitate was filtered off and the filtrate was washed with 0.1 M HCl, sat. NaHCO$_3$ and brine. Organic phase was dried over Na$_2$SO$_4$ and solvents were removed in vacuo. The crude material was purified by flash chromatography to give 8b (3.19 g, 4.15 mmol, 83%) as off white solid. MS: m/z 768.35=[M+H]$^+$, (calculated=768.35).

To a solution of 8b (8.59 g, 11.19 mmol) in THF (98 mL) DBU (2 mL) was added. The solution was stirred for 12 min at RT, and the solvent was concentrated in vacuo. Flash chromatography afforded 4.89 g 8c (8.96 mmol, 80%). MS: m/z 546.28=[M+H]$^+$, (calculated=546.28).

6-Tritylmercaptohexanoic acid (2.04 g, 5.22 mmol) was dissolved in DCM (20 mL, anhydrous, mol. sieve) and DCC (1.08 g, 5.22 mmol) and Oxyma pure (945 mg, 6.65 mmol) were added. After 30 min, 8c (2.59 g, 4.75 mmol) and DIPEA (1.24 mL, 7.12 mmol) were added. The reaction mixture was stirred for 22 h at RT. The mixture was extracted with 1 N H$_2$SO$_4$ (2×), sat. NaHCO$_3$ (2×) and brine. The organic phase was dried over Na$_2$SO$_4$, concentrated in vacuo and 8d was purified by flash chromatography. Yield: 4.10 g (4.47 mmol, 94%). MS: m/z 940.12=[M+Na]$^+$, (calculated=940.43).

To a solution of 8d (4.10 g, 4.47 mmol) in i-PrOH (60 mL), water (20 mL) and LiOH (322 mg, 13.41 mmol) was added and the reaction mixture was stirred for 1 h at RT. Toluene (300 mL) was added and the organic phase was with 0.1 N HCl and with brine. The organic phase was dried over Na$_2$SO$_4$, filtrated and concentrated in vacuo. 8e was purified by flash chromatography. Yield: 3.53 g (4.26 mmol, 95%). MS: m/z 827.93=[M+H]$^+$, (calculated=828.39).

Example 9

Synthesis of Linker Reagent 9c

Linker reagent 9c was synthesized according to the following scheme:

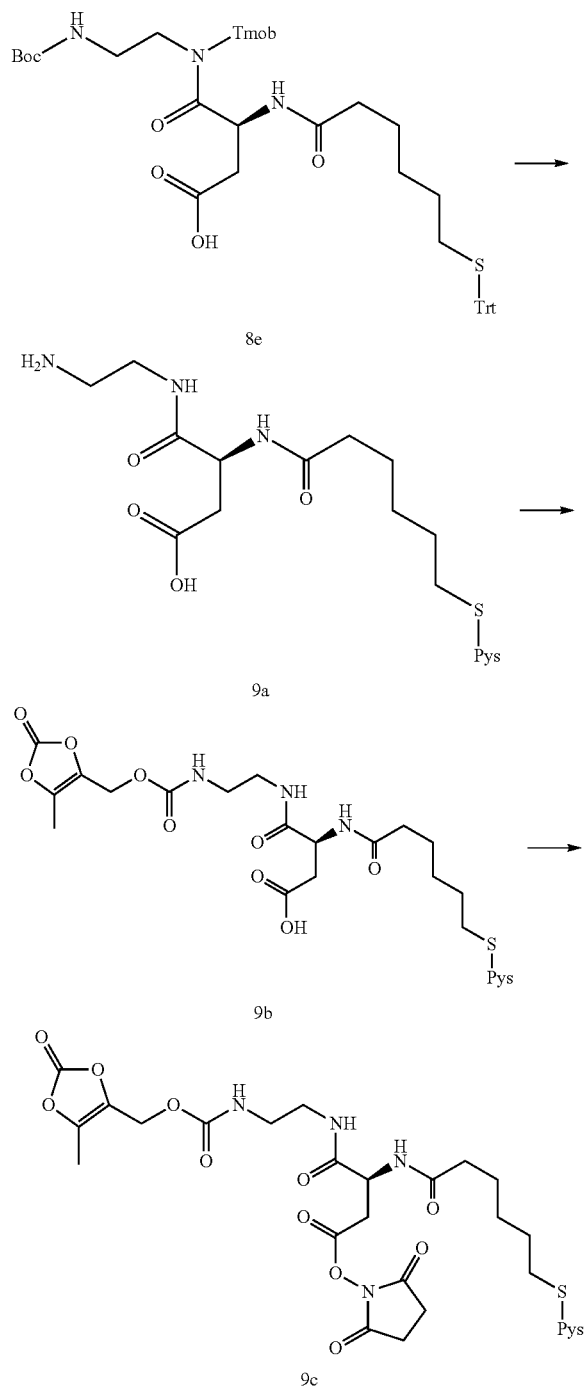

8e (300 mg, 0.36 mmol) was dissolved in HFIP/water/TES (39:1:1 v/v/v, 4.1 mL). Under stirring TFA (0.35 mL) was added and the reaction stirred for 75 min. The solvents were evaporated in a stream of argon. The residue was partitioned between water (20 mL) and DCM (40 mL). The water phase was collected, the DCM phase washed with water (5 mL) and both water phases combined. The pH of the resulting solution was adjusted with pH 7.4 sodium phosphate buffer (0.5 M, 5 mL) and a solution of 2,2'-dithiodipyridine in 1 mL was added and the resulting suspension stirred for 30 min. The mixture was lyophilized and the residue suspended in ACN/water (7:3 v/v, 9 mL) and filtered. The filtrate was purified by RP-HPLC to give 9a. Yield: 90 mg, 0.17 mmol (TFA salt), 47%, MS: m/z 415.25=[M+H]$^+$, (calculated=415.15).

9a (90 mg, 0.17 mmol) was dissolved in DCM (1.2 mL) and (5-methyl-2-oxo-1,3-dioxol-4-yl)-methyl 4-nitrophenyl carbonate (138 mg, 0.47 mmol) and 2,4,6-collidine (129 µL, 0.98 mmol) was added with stirring. DMF (1 mL) was added to facilitate dissolution of the formed precipitate. After 2 h and 8 h DIPEA (19 µL, 0.11 mmol, each) was added and the reaction stirred for 48 h. The reaction was quenched with AcOH (38 µL) and DCM evaporated in a stream of nitrogen. The residue was diluted with ACN/water/TFA (1:1:0.002 v/v/v) and purified by RP-HPLC to give 9b. Yield: 64 mg, 0.11 mmol, 65%, MS: m/z 571.09=[M+H]$^+$, (calculated=571.15).

9b (32 mg, 56 µmol) was dissolved in DCM. With stirring NHS (8 mg, 67 µmol), DCC (14 mg, 67 µmol) and DMAP (0.7 mg, 6 mmol) were added. The reaction was stirred and after 1.5 h and 3.5 h DCC was added (3.5 mg, 11 µmol and 2.3 mg, 7 µmol, respectively). The solvent was evaporated in a stream of argon and the residue suspended in water/ACN/TFA (1:9:0.01 v/v/v, 3 mL) and filtered. The filtrate was purified by RP-HPLC to give 9c (28 mg, 42 µmol, 75%). MS: m/z 668.17=[M+H]$^+$, (calculated=668.17).

Example 10

Synthesis of Linker Reagent 10f

Linker reagent 10f was synthesized according to the following scheme:

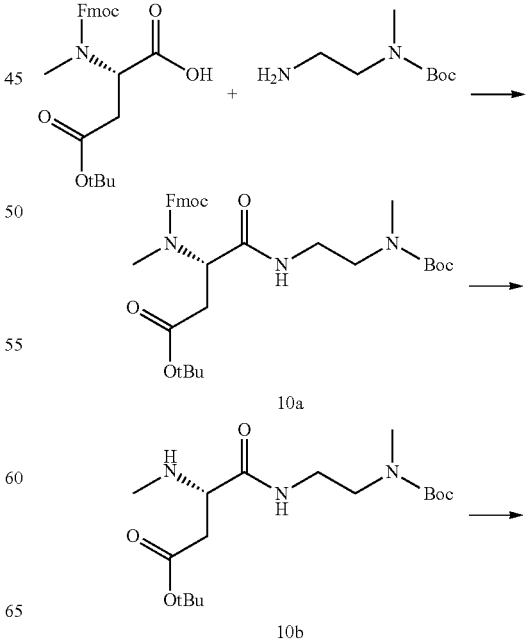

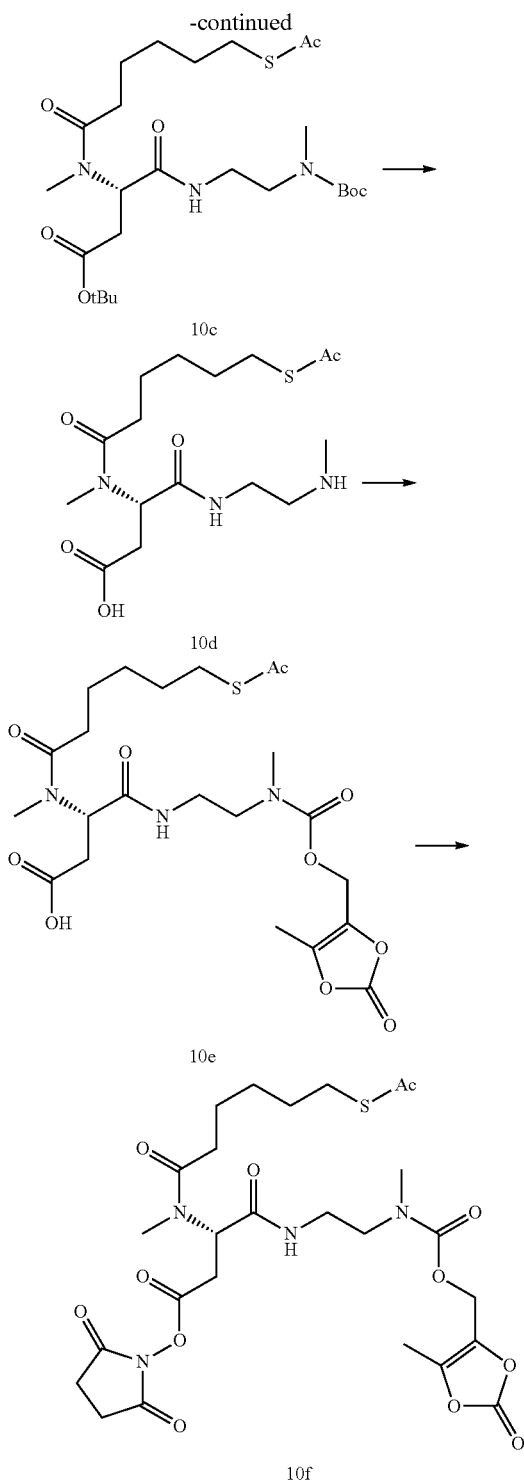

10c

10d

10e

10f

Fmoc-N-Me-L-Asp(OtBu)-OH (1 g, 2.35 mmol) was dissolved in DCM (35 mL) and DCC (0.68 g, 3.29 mmol), Oxyma pure (0.5 g, 3.53 mmol) and 2,4,6-collidine (0.49 mL, 3.76 mmol) were added. N-Boc-N-methyl-ethylenediamine was dissolved in DCM (15 mL) and added slowly by syringe to the reaction mixture. The reaction was stirred for 16 h, the precipitate filtered off and the filtrate washed with 0.1 M HCl (50 mL). The water layer was reextracted twice with DCM (20 mL). The organic layers were combined and washed with sat. sodium bicarbonate solution (1×50 mL, 2×25 mL) and brine (1×50 mL). The organic phase was dried over $Na_2SO_4$, concentrated in vacuo and 10a was purified by flash chromatography. Yield: 1.36 g (2.33 mmol, 99%). MS: m/z 582.32=[M+H]$^+$, (calculated=582.32).

10a (1.36 g, 2.33 mmol) was dissolved in THF (20 mL) and DBU (0.4 mL) was added and the reaction stirred for 12 min. AcOH (0.5 mL) was added and the mixture concentrated in vacuo and 10b was purified by flash chromatography. Yield: 0.82 g (2.28 mmol, 98%). MS: m/z 360.25=[M+H]$^+$, (calculated=360.25).

6-Acetylmercaptohexanoic acid (0.49 g, 2.58 mmol) was dissolved in DCM (25 mL) and DCC (0.53 g, 2.58 mmol), Oxyma pure (0.47 g, 3.19 mmol) were added. The reaction was stirred for 45 min and filtered using a syringe with frit into a solution of 10b (0.82 g, 2.28 mmol) in DCM (12 mL). DIPEA (0.61 mL, 3.42 mmol) was added and the reaction stirred. Due to insufficient conversion Oxyma pure (0.2 g, 1.4 mmol) and DIPEA (0.25 mL, 1.4 mmol) were added and the reaction stirred for 16 h. Due to insufficient conversion 6-acetylmercaptohexanoic acid (0.49 g, 2.58 mmol), DCC (0.53 g, 2.58 mmol) and Oxyma pure (0.47 g, 3.19 mmol) were stirred for 30 min and filtered into the reaction. DIPEA (0.6 mL, 3.42 mmol) was added and the reaction stirred for 2.5 h. The reaction mixture was washed with 0.1 M $H_2SO_4$ (20 mL), saturated sodium bicarbonate solution (2×20 mL) and brine (20 mL). The organic phase was dried over $Na_2SO_4$, concentrated in vacuo and 10c was purified by flash chromatography. Yield: 0.74 g (1.39 mmol, 60%). MS: m/z 532.30=[M+H]$^+$, (calculated=532.31).

10c (0.74 g, 1.39 mmol) was dissolved in TFA/TES/water (95:2.5:2.5 v/v/v, 5.25 mL) and stirred for 30 min. The mixture was concentrated in vacuo and purified by RP-HPLC to give 10d (0.38 g, 0.78 mmol, 56%) MS: m/z 376.19=[M+H]$^+$, (calculated=376.19). 10d (0.38 g, 0.78 mmol) was dissolved in DCM (7 mL) and (5-methyl-2-oxo-1,3-dioxol-4-yl)-methyl 4-nitrophenyl carbonate (0.35 g, 1.17 mmol) and 2,4,6-collidine (0.45 mL, 3.51 mmol) were added and the reaction stirred. After 1 h 2,4,6-collidine (0.2 mL, 1.56 mmol) was added and the reaction stirred for 20 h. The reaction was concentrated in vacuo and purified by RP-HPLC to give 10e (0.26 g, 0.49 mmol, 63%) MS: m/z 532.20=[M+H]$^+$, (calculated=532.20).

10e (0.26 g, 0.49 mmol) was dissolved in DCM (3.6 mL) and DCC (0.12 g, 0.59 mmol), NHS (68 mg, 0.59 mmol) and DMAP (6 mg, 0.05 mmol) were added. The reaction was stirred for 1 h. The resulting suspension was filtered and the precipitate washed with DCM (2 mL). The filtrate was purified by flash chromatography to give 10f as white foam. Yield: 0.27 g (0.43 mmol, 87%). MS: m/z 629.21=[M+H]$^+$, (calculated=629.21).

Example 11

Synthesis of Linker Reagent 11d

Linker reagent 11d was synthesized according to the following scheme:

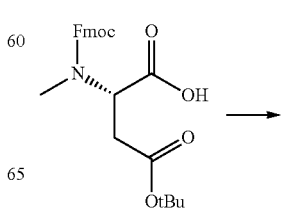

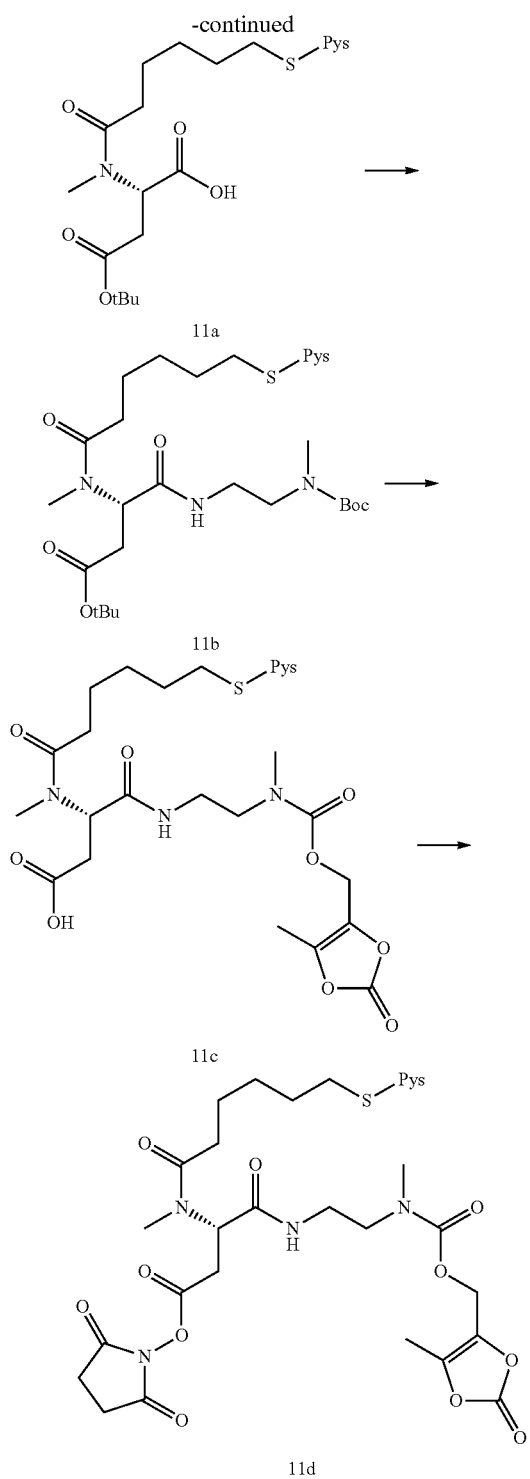

11a

11b

11c

11d

2-Chlorotritylchloride resin (1.4 mmol/g, 357 mg, 0.5 mmol) was weighted into a 10 mL syringe with frit. The resin was swollen twice with 2 mL DCM. N-Fmoc-N-methyl-L-aspartate(OtBu)-OH (532 mg, 1.25 mmol and DIPEA (305 µL, 1.75 mmol) were dissolved in DCM (3 mL) and drawn into the syringe. The syringe was agitated for 1 h. MeOH (0.5 mL) was drawn into the syringe and the syringe agitated for 30 min. The resin was washed 5 times with DCM (4 mL) and 5 times with DMF (4 mL). The resin was agitated 3 times for 5 min with DMF:DBU:piperidine (96:2:2 v/v/v, 4 mL). The resin was washed 5 times with DMF (4 mL). 6-tritylmercaptohexanoic acid (488 mg, 1.25 mmol) and HATU (475 mg, 1.25 mmol) were dissolved in DMF (3 mL) and DIPEA (436 µL, 2.5 mmol) added. After 1 min preincubation the solution was drawn into the syringe and the syringe agitated for 1 h. The resin was washed 5 times with DMF (4 mL), 5 times with DCM (4 mL) and twice with MeOH (4 mL) and dried in vacuo. A solution of HFIP/TES/acetic acid (90/5/5 v/v/v, 3 mL each) were drawn into the syringe and the syringe agitated twice for 30 min. The solvent of the collected filtrates was evaporated in a stream of nitrogen. The residue was suspended in ACN/water (1:1 v/v, 5 mL) and filtered off. 2,2'-dithiodipyridine (220 mg, 1 mmol) in ACN (0.5 mL) was added to the filtrate. pH of the reaction was adjusted to 7 with pH 7.4 sodium phosphate buffer (0.5 M, 1.2 mL) and stirred for 15 min. The product was directly purified by RP-HPLC to give 11a (117 mg, 0.27 mmol, 53%) MS: m/z 443.30=[M+H]$^+$, (calculated=443.17).

11a (117 mg, 0.27 mmol) was dissolved in DCM (2.4 mL). PyBOP (166 mg, 0.32 mmol), DIPEA (185 µL, 1.06 mmol) and N-Boc-N-methylethylenediamine (57 µL, 0.32 mmol) were added and the reaction stirred for 45 min. Acetic acid (185 µL) was added and the solvents removed in a stream of nitrogen. The residue was dissolved with ACN/water/TFA (2:1:0.003 v/v/v) and purified by RP-HPLC to give 11b (135 mg, 0.23 mmol, 85%) MS: m/z 599.27=[M+H]$^+$, (calculated=599.29).

11b (135 mg, 0.23 mmol) was dissolved in TFA/TES/water (95:2.5:2.5 v/v/v, 5 mL). After 15 min the solvents were evaporated in a stream of nitrogen. The residue was diluted with ACN/water 1:1 and lyophilized. The residue was dissolved in DCM (1.5 mL), and (5-methyl-2-oxo-1,3-dioxol-4-yl)-methyl 4-nitrophenyl carbonate (80 mg, 0.27 mmol) was added. With stirring DIPEA (78 µL, 0.46 mmol) was slowly added until the reaction stayed light yellow colored. More DIPEA (39 µL, 0.23 mmol) was added and the reaction stirred for 1 h. After addition of DIPEA (20 µL, 0.12 mmol) the reaction was stirred for 30 min. Acetic acid (140 µL) were added and the solvents removed in a stream of nitrogen. The residue was diluted with ACN/water/TFA (1:1:0.002 v/v/v, 3 mL) and purified by RP-HPLC to give 11c (69 mg, 0.12 mmol, 51%). MS: m/z 599.19=[M+H]$^+$, (calculated=599.19).

11c (69 mg, 0.12 mmol) was dissolved in DCM and NHS (16 mg, 0.14 mmol), DCC (29 mg, 0.14 mmol) and DMAP (1.4 mg, 0.012 mmol) were added and the reaction stirred for 75 min. The solvent was evaporated in a stream of nitrogen and the residue was suspended in ACN/water/TFA (1:1:0.002 v/v/v, 3.5 mL) and filtered. The filtrate was purified by RP-HPLC to give 11d (60 mg, 0.09 mmol, 75%). MS: m/z 696.20=[M+H]$^+$, (calculated=696.20).

Example 12

Synthesis of Linker Reagent 12e

Linker reagent 12e was synthesized according to the following scheme:

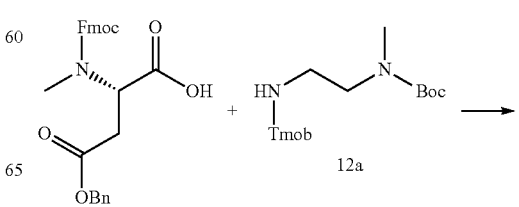

12a

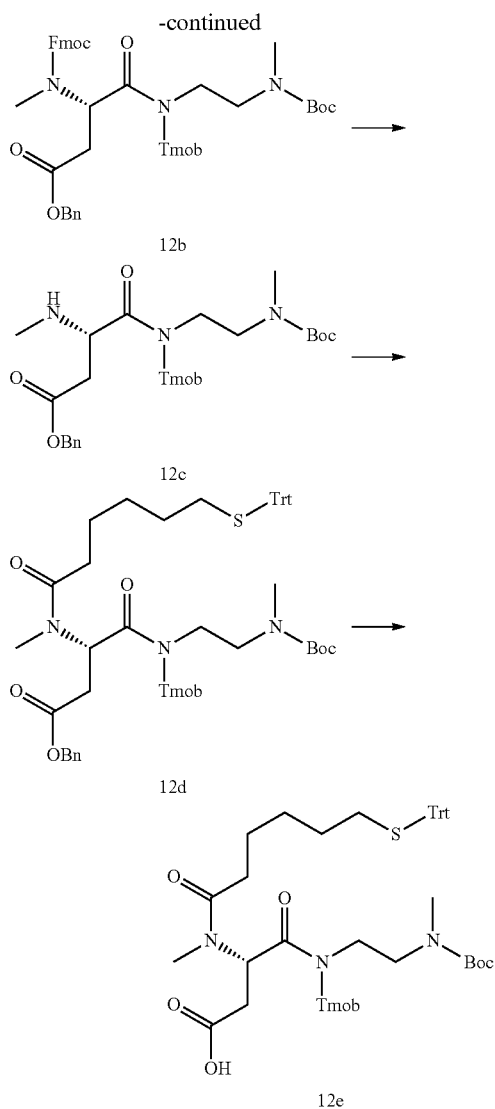

12b

12c

12d

12e

To a solution of N-Boc-N-methylethylenediamine (2 g, 11.48 mmol) and NaCNBH$_3$ (819 mg, 12.63 mmol) in MeOH (20 mL) was added 2,4,6-trimethoxybenzaldehyde (2.08 mg, 10.61 mmol) portion wise. The mixture was stirred at RT for 90 min, acidified with 3 M HCl (4 mL) and stirred further 15 min. The reaction mixture was added to saturated NaHCO$_3$ solution (200 mL) and extracted 5× with CH$_2$Cl$_2$. The combined organic phases were dried over Na$_2$SO$_4$ and the solvents were evaporated in vacuo. The resulting N-Boc-N-methyl-N'-tmob-ethylenediamine (12a) was completely dried in high vacuum and used in the next reaction step without further purification. Yield: 3.76 g (11.48 mmol, 89% purity, 12a: double Tmob protected product=8:1). MS: m/z 355.22=[M+H]$^+$, (calculated=355.23).

To a solution of 12a (2 g, 5.65 mmol) in CH$_2$Cl$_2$ (24 ml) COMU (4.84 g, 11.3 mmol), N-Fmoc-N-methyl-L-Asp (OBn)-OH (2.08 g, 4.52 mmol) and 2,4,6-collidine (2.65 mL, 20.34 mmol) were added. The reaction mixture was stirred for 3 h at RT, diluted with CH$_2$Cl$_2$ (250 mL) and washed 3× with 0.1 M H$_2$SO$_4$ (100 mL) and 3× with brine (100 mL). The aqueous phases were re-extracted with CH$_2$Cl$_2$ (100 mL). The combined organic phases were dried over Na$_2$SO$_4$, filtrated and the residue concentrated to a volume of 24 mL. 12b was purified using flash chromatography. Yield: 5.31 g (148%, 6.66 mmol) MS: m/z 796.38=[M+H]$^+$, (calculated=796.38).

To a solution of 12b [5.31 g, max. 4.51 mmol ref. to N-Fmoc-N-Me-L-Asp(OBn)-OH] in THF (60 mL) DBU (1.8 mL, 3% v/v) was added. The solution was stirred for 12 min at RT, diluted with CH$_2$Cl$_2$ (400 mL) and washed 3× with 0.1 M H$_2$SO$_4$ (150 mL) and 3× with brine (150 mL). The aqueous phases were re extracted with CH$_2$Cl$_2$ (100 ml). The combined organic phases were dried over Na$_2$SO$_4$ and filtrated. 12c was isolated upon evaporation of the solvent and used in the next reaction without further purification. MS: m/z 574.31=[M+H]$^+$, (calculated=574.31).

12c (5.31 g, 4.51 mmol, crude) was dissolved in acetonitrile (26 mL) and COMU (3.87 g, 9.04 mmol), 6-tritylmercaptohexanoic acid (2.12 g, 5.42 mmol) and 2,4,6-collidine (2.35 mL, 18.08 mmol) were added. The reaction mixture was stirred for 4 h at RT, diluted with CH$_2$Cl$_2$ (400 mL) and washed 3× with 0.1 M H$_2$SO$_4$ (100 mL) and 3× with brine (100 mL). The aqueous phases were re extracted with CH$_2$Cl$_2$ (100 mL). The combined organic phases were dried over Na$_2$SO$_4$, filtrated and 12d was isolated upon evaporation of the solvent. Product 7i was purified using flash chromatography. Yield: 2.63 g (62%, 94% purity) MS: m/z 856.41=[M+H]$^+$, (calculated=856.42).

To a solution of 12d (2.63 g, 2.78 mmol) in i-PrOH (33 mL) and H$_2$O (11 mL) was added LiOH (267 mg, 11.12 mmol) and the reaction mixture was stirred for 70 min at RT. The mixture was diluted with CH$_2$Cl$_2$ (200 mL) and washed 3× with 0.1 M H$_2$SO$_4$ (50 mL) and 3× with brine (50 mL). The aqueous phases were re-extracted with CH$_2$Cl$_2$ (100 mL). The combined organic phases were dried over Na$_2$SO$_4$, filtrated and 12e was isolated upon evaporation of the solvent. 12e was purified using flash chromatography. Yield: 2.1 g (88%) MS: m/z 878.4=[M+Na]$^+$, (calculated=878.40).

Example 13

Synthesis of Linker Reagent 13g

Linker reagent 13g was synthesized according to the following scheme:

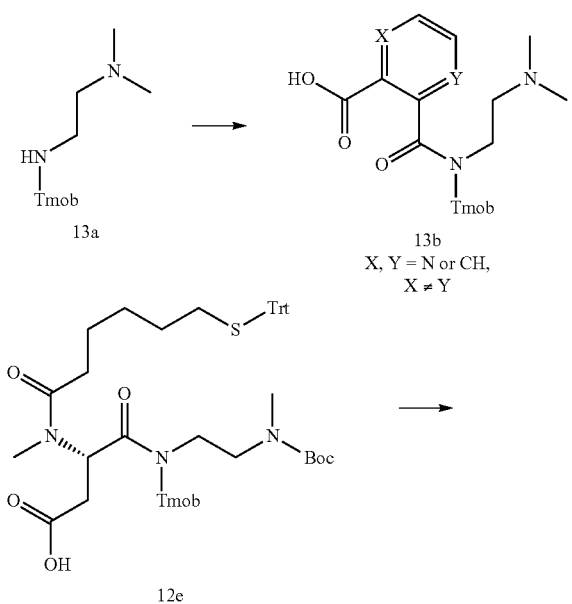

13a

13b
X, Y = N or CH,
X ≠ Y

12e

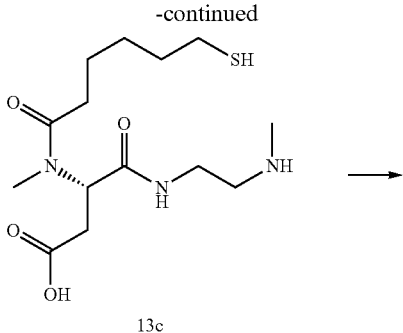

13c

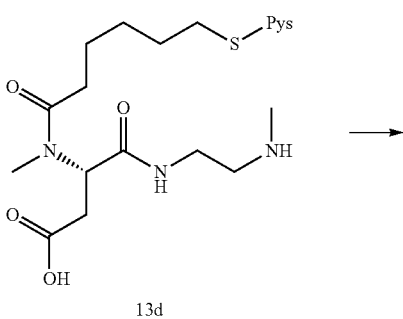

13d

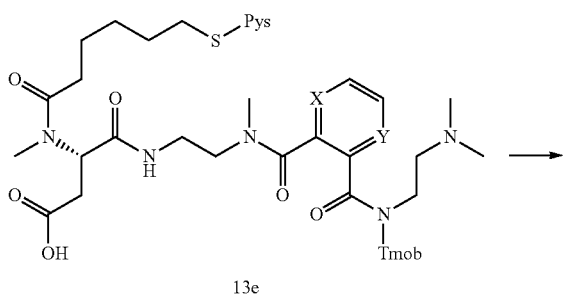

13e

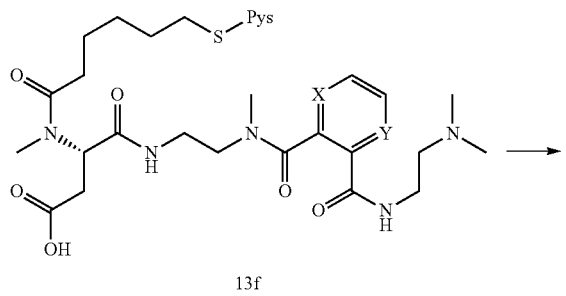

13f

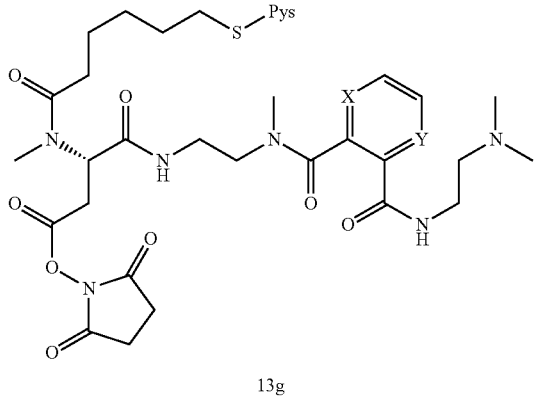

13g

To a solution of N,N-dimethylethylenediamine (441 mg, 5 mmol) and NaCNBH$_3$ (439 mg, 7 mmol) in MeOH (21 mL) was added a solution of 2,4,6-trimethoxybenzaldehyde (1.34 g, 6.85 mmol) in DCM and MeOH (17 mL each) with a syringe. The mixture was stirred at RT for 60 min, acidified with 0.5 M HCl (50 mL) and stirred further 15 min. The reaction mixture was brought to pH>12 by adding 1 M NaOH and extracted 4 times with ethyl acetate (1×100 mL, 3×50 mL). The combined organic phases were dried over MgSO$_4$ and the solvents were evaporated in vacuo. The resulting N,N-dimethyl-N'-tmob-ethylenediamine (13a) was completely dried in high vacuum and used in the next reaction step without further purification. Yield: 1.63 g (contains double Tmob protected product). MS: m/z 269.19=[M+H]$^+$, (calculated=269.19).

13a (268 mg, ca 0.83 mmol) was dissolved in THF (5 mL) and 2,3-pyridinedicarboxylic anhydride (149 mg, 1 mmol), DIPEA (362 µL, 2.08 mmol) and DMF (1 mL) were added. The solution was stirred for 15 min, quenched with AcOH (362 µL) and the THF removed in a stream of nitrogen. The residue was diluted with ACN/water/TFA (1:1:0.002 v/v/v, 4 mL) and purified by RP-HPLC to give 13b (244 mg, 0.46 mmol, 55%). MS: m/z 418.20=[M+H]$^+$, (calculated=418.20).

12e (500 mg, 0.58 mmol) was dissolved in TFA/TES/DTT/water (85:5:5:5 v/v/v/v, 10 mL) and stirred for 4 h. The solvents were removed in a stream of nitrogen and the residue suspended in ACN/water and filtered. The filtrate was purified by RP-HPLC to give 13c (71 mg, 0.21 mmol, 36%). MS: m/z 334.43=[M+H]$^+$, (calculated=334.18).

13c (71 mg, 0.21 mmol) was dissolved in ACN/water (1:1, 1 mL) and 2,2'-dithiodipyridine (93 mg, 0.42 mmol) in ACN/water (1:1, 1 mL, suspension) and pH 7.4 sodium phosphate buffer (0.5 M, 1 mL) were added. The resulting solution was stirred for 15 min and directly purified by RP-HPLC to give 13d (64 mg, 0.15 mmol, 68%). MS: m/z 443.30=[M+H]$^+$, (calculated=443.18).

13b (91 mg, 0.22 mmol) was dissolved in DMF (1 mL) and PyBOP (113 mg, 0.22 mmol) was added. DIPEA (50 µL, 0.29 mmol) was added and the solution stirred for 15 min. 13d (64 mg, 0.145 mmol) was dissolved in DCM (1.5 mL) and added to the DMF solution. The reaction was stirred for 100 min and AcOH (50 µL) was added. DCM was removed in a stream of nitrogen and the residue dissolved in ACN/water/TFA and purified by RP-HPLC to give 13e (26 mg, 31 µmol, 21%). MS: m/z 842.14=[M+H]$^+$, (calculated=842.36).

13e (26 mg, 31 µmol) was dissolved in HFIP/TES/water (39:1:1 v/v/v, 1 mL) and TFA (83 µL) was added with stirring. After 90 min the solvents were evaporated in vacuo and the residue purified by RP-HPLC to give 13f (11 mg, 17 µmol, 54%). MS: m/z 662.28=[M+H]$^+$, (calculated=662.28).

13f (11 mg, 17 µmol) was dissolved in DCM (1.5 mL), DCC (4.2 mg, 20 µmol), NHS (2.3 mg, 20 µmol) and DMAP (0.2 mg, 1 µmol) were added and the suspension stirred. After 1 h and 2 h the aforementioned amount of DCC and NHS were added again. After 3 h the solvent was evaporated in a stream of nitrogen. The residue was suspended in ACN/water/TFA (1:1:0.002, 3 mL) and filtered. The filtrate was purified by RP-HPLC to give 13g (14 mg, 16 µmol (TFA salt), 94%). MS: m/z 759.30=[M+H]$^+$, (calculated=759.30).

Example 14

Synthesis of Linker Reagent 14f

Linker reagent 14f was synthesized according to the following scheme:

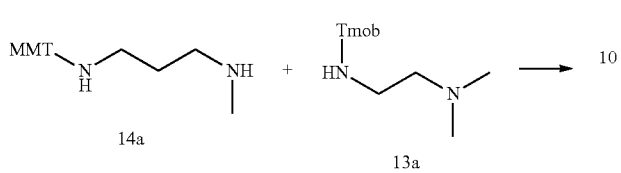

14a + 13a

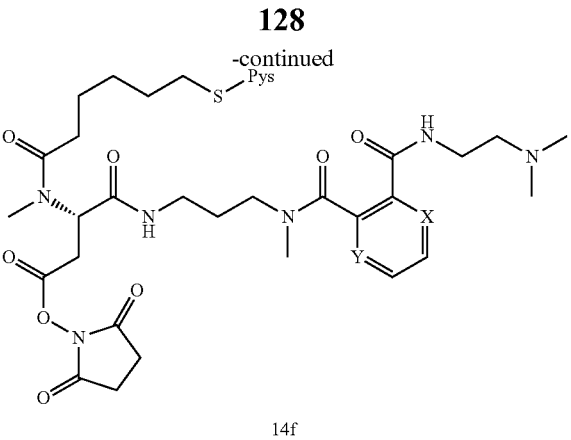

14f

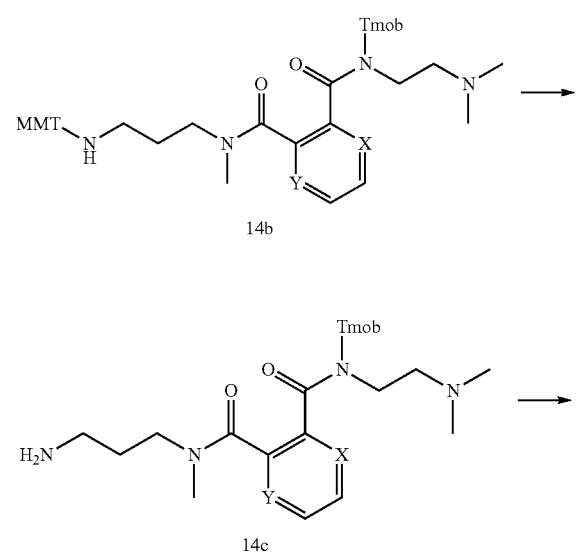

14b

14c

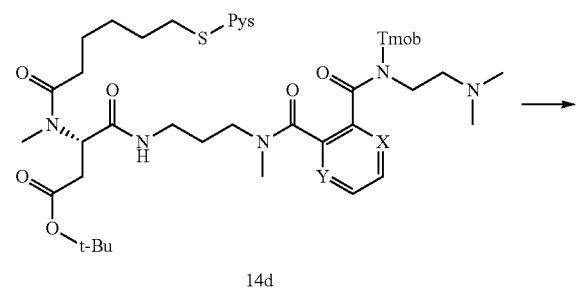

14d

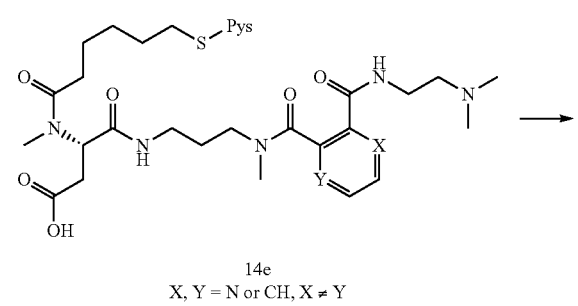

14e

X, Y = N or CH, X ≠ Y

A solution of p-monomethoxytrityl chloride (1.54 g, 5 mmol) in DCM (10 mL) was slowly added with stirring to a solution of 3-(methylamino)propylamine (4.4 g, 50 mmol) in DCM (10 mL). After 2 h diethyl ether (166 mL) was added. Brine (100 mL) was mixed with NaOH (4 M, 80 μL) and the reaction washed with this mixture (3×33 mL). The organic layer was washed with brine (30 mL), dried with MgSO$_4$ and concentrated in vacuo. Yield (14a): 1.79 g (4.95 mmol, 99%).

14a (0.36 g, 1 mmol) was dissolved in THF (7 mL) and DIPEA (0.44 ml, 2.5 mmol) and a solution of quinolinic anhydride (0.18 g, 1.2 mmol) in THF (3 mL) were added with stirring. After 30 min a solution of 13a (0.54 g, 2 mmol) in DMF (2 mL) and PyBOP (0.78 g, 1.5 mmol) were added and the reaction stirred for 1 h. The reaction was diluted with ethyl acetate (50 mL) and washed with NaOH (1 M, 20 mL). The aqueous phase was reextracted with ethyl acetate (2×20 mL) and the collected organic phases combined and concentrated in vacuo and purified using flash chromatography to give 14b (0.4 g, 0.53 mmol, 53%) MS: m/z 760.41=[M+H]$^+$, (calculated=760.41).

14b (0.4 g, 0.53 mmol) was dissolved in ACN (3 mL) and HCl (0.4 M, 3 mL) was added and the solution stirred for 4 h. The reaction was quenched with NaOH (1 M, 15 mL) and extracted with DCM (5×30 mL). The combined organic phase was dried over MgSO$_4$, concentrated in vacuo and 14c was purified by flash chromatography. Yield: 0.32 g (0.42 mmol, 81%, MMT salt) MS: m/z 488.31=[M+H]$^+$, (calculated=488.29).

11a (49 mg, 0.11 mmol) and 14c (114 mg, 0.15 mmol) were dissolved in DCM (1.4 mL) and PyBOP (62 mg, 0.12 mmol) and DIPEA (38 μL, 0.22 mmol) were added with stirring. After 2 h AcOH (40 μL) was added and the solvents evaporated in vacuo. The residue was dissolved in ACN/water/TFA (1:1:0.002 v/v/v, 5 mL) and purified by RP-HPLC to give 14d (104 mg, 0.1 mmol TFA salt, 92%). MS: m/z 912.19=[M+H]$^+$, (calculated=912.44).

14d (104 mg, 0.1 mmol) was dissolved in HFIP/TES/water (39:1:1 v/v/v, 3 mL) and TFA (0.25 mL) was added with stirring. After 2 h TFA (0.25 mL) was added with stirring and the reaction stirred further for 20 h. The mixture was concentrated in vacuo and the residue dissolved in ACN/water/TFA (1:1:0.002 v/v/v, 3 mL) and purified by RP-HPLC to give 14e (28 mg, 35 μmol TFA salt, 35%). MS: m/z 676.13=[M+H]$^+$, (calculated=676.30).

14e (25 mg, 32 µmol) was dissolved in DCM (2 mL) and DCC (10 mg, 48 µmol), NHS (5.5 mg, 48 µmol) and DMAP (0.4 mg, 3.2 µmol) were added and the suspension stirred. After 1.5 h the aforementioned amount of DCC and NHS were added again. After 3 h the solvent was evaporated in a stream of nitrogen. The residue was suspended in ACN/water/TFA (1:1:0.002 v/v/v, 4 mL) and filtered. The filtrate was purified by RP-HPLC to give 14f (28 mg, 31.6 µmol TFA salt, 99%). MS: m/z 773.31=[M+H]$^+$, (calculated=773.31).

Example 15

Synthesis of Linker Reagent 15f

Linker reagent 15f was synthesized according to the following scheme:

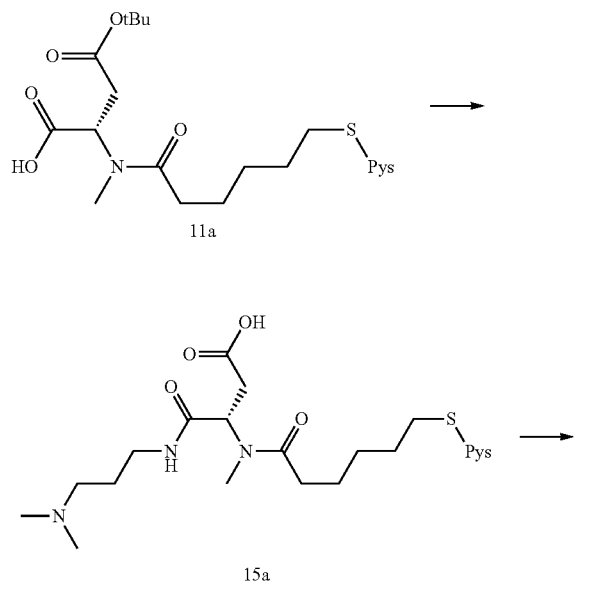

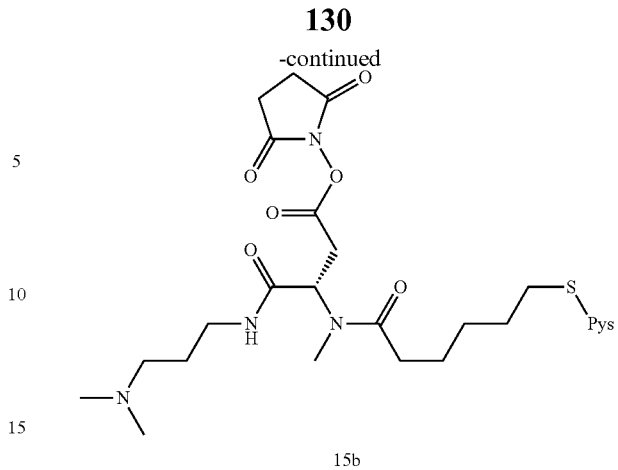

To a solution of 11a (0.29 g, 0.65 mmol) and PyBOP (0.34 g, 0.65 mmol) in ACN (5 mL) DIPEA (0.57 mL, 3.27 mmol) was added. This mixture was stirred at room temperature for one minute, before N,N-dimethylaminopropane-1,3-diamine (0.12 mL, 0.98 mmol) was added. After 30 min AcOH (0.7 mL) was added to quench the reaction. This mixture was diluted with water and purified by RP-HPLC. The obtained intermediate was dissolved in TFA (3 mL) and the mixture was stirred for 30 min before TFA was removed by a stream of N$_2$. The residue was dried in vacuo over night to give 15a (0.42 g, 0.61 mmol (2×TFA salt), 93%) as colorless oil, which was used without any further purification. MS: m/z=471.21=[M+H]$^+$, (calculated 471.21).

To a solution of 15a (0.23 mg, 0.33 mmol) in DCM (5 mL) DMAP (8 mg, 65 µmol), NHS (75 mg, 0.65 mmol) and DCC (135 mg, 0.65 mmol) were added. After stirring for 3 h the reaction was quenched by addition of AcOH (10 µL). The solvent was removed by a stream of N$_2$ and the residue was suspended in H$_2$O/ACN/TFA (1:1:0.002 v/v/v) and filtered. The filtrate was purified by RP-HPLC to give 15b (83 mg, 0.10 mmol (2×TFA salt), 32%) as a colorless oil. MS: m/z=568.23=[M+H]$^+$, (calculated 568.23).

Example 16

Synthesis of Purification Tag 16e

Purification tag 16e was synthesized according to the following scheme:

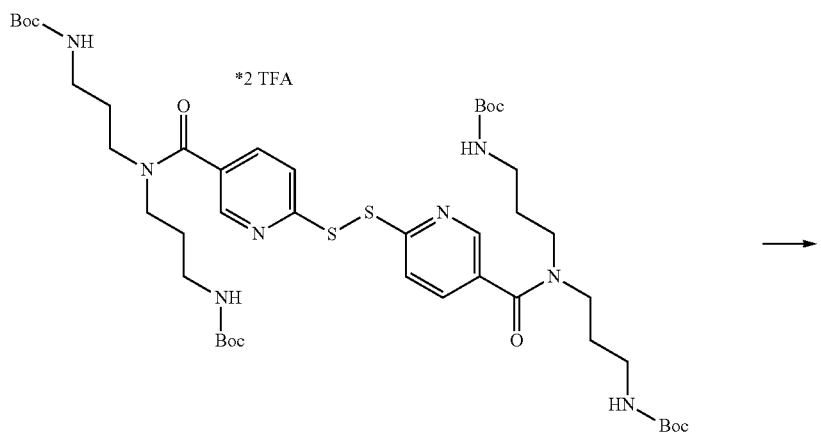

-continued
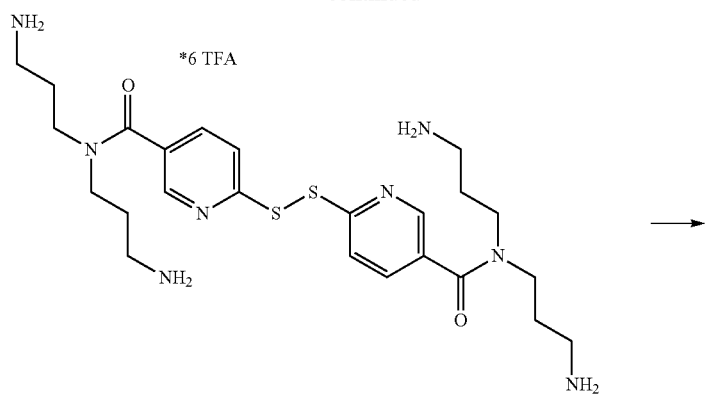
16b
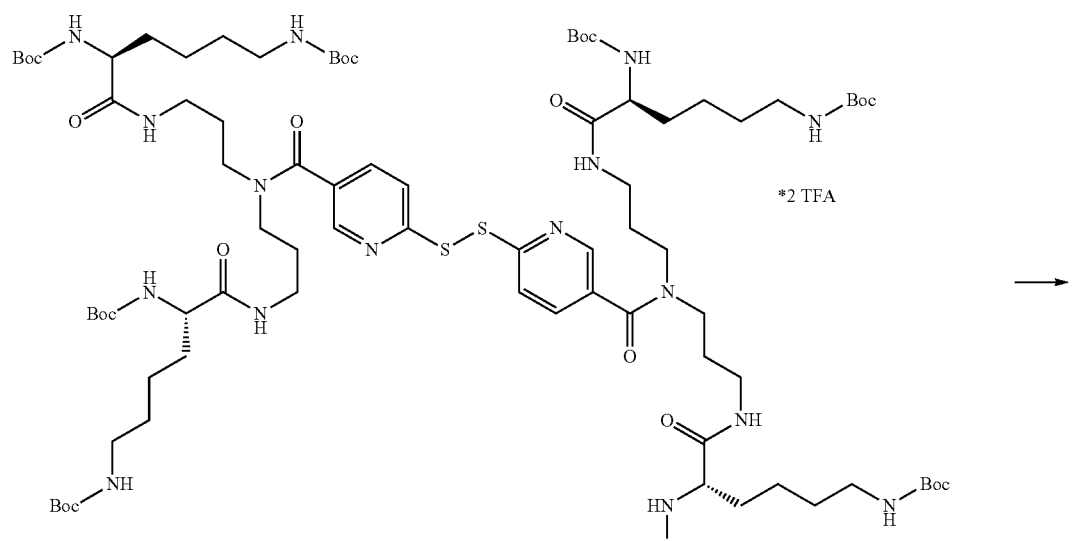
16c
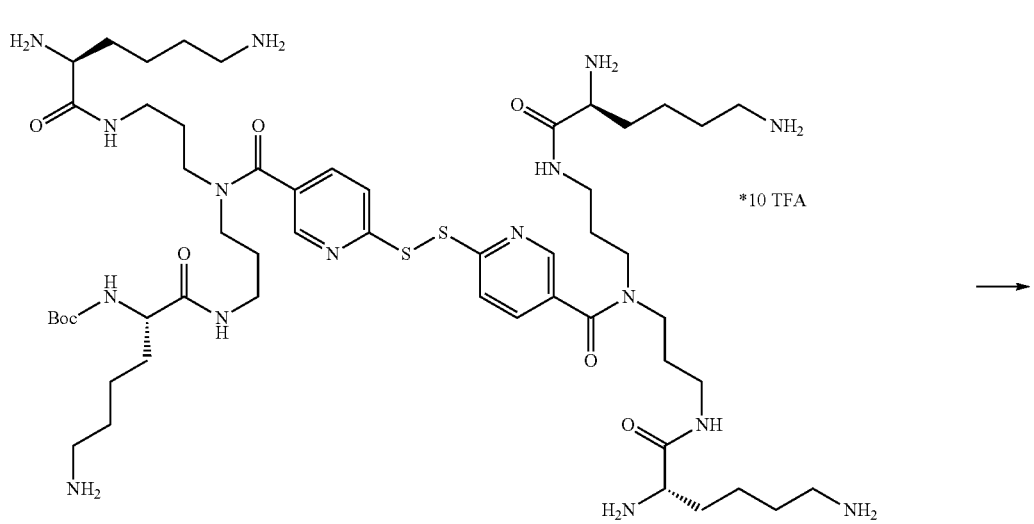
16d

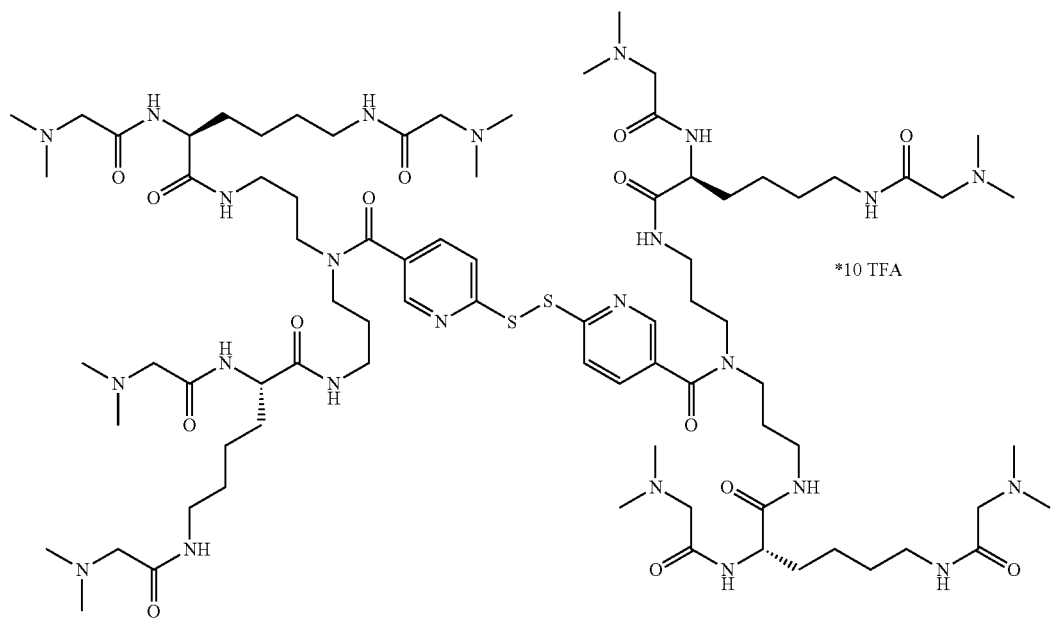

16e

To a suspension of 6,6'-dithiodinicotinic acid (0.62 g, 2 mmol) in ACN (20 mL) were added PyBOP (2.08 g, 4 mmol) and DIPEA (1.29 g, 1.74 mL, 10 mmol) and the mixture was stirred for 1 min. The obtained brown solution was added to a solution of 1,9-bis-Boc-1,5,9-triazanonane (1.99 g, 6 mmol) in a mixture of ACN (20 mL) and DMF (5 mL) and stirred for 2 h. The reaction mixture was diluted with EtOAc (150 mL) and the organic layer was washed with aq. HCl (10 mM, 5×100 mL), saturated NaHCO$_3$ solution (3×100 mL) and brine (100 mL), subsequently. After drying over MgSO$_4$ and filtration, the solvent was removed in vacuo and the crude residue was purified by flash chromatography to give 16a (1.92 g, max. 2 mmol) as a light yellow foam. The product contains a small, non-separable amount of tripyrrolidine phosphoramide, which is removed in the next step. MS: m/z=935.47=[M+H]$^+$, (calculated 935.47).

16a (1.92 g, max. 2 mmol) was dissolved in TFA (10 mL) and the solution was stirred for 10 min. The reaction mixture was added dropwise to ice-cold diethyl ether (160 mL) to precipitate the product. The resulting suspension was centrifuged at 7000×G and 2° C. for 3 min. The supernatant was discarded and the precipitate was dissolved in methanol (10 mL). This solution was added dropwise to ice-cold diethyl ether (160 mL) and the formed suspension was centrifuged at 7000×G and 2° C. for 3 min. After discarding the supernatant the precipitation procedure was accomplished two more times like described above. The remaining oily precipitate was dried in vacuo to give 16b (1.77 g, 1.45 mmol (6×TFA salt), 73%) as a light brown, very hygroscopic powder. MS: m/z=535.26=[M+H]$^+$, (calculated 535.26).

To a solution of 16b (3.30 g, 2.7 mmol) in DMF (90 mL) were added DIPEA (5.4 mL, 31 mmol) and Boc-L-Lys (Boc)-OSu (5.62 g, 12.7 mmol). The mixture was stirred for 14 h before it was diluted with ethyl acetate (600 mL). The organic layer was washed with aq. HCl (10 mM, 5×300 mL), sat. NaHCO$_3$ solution (3×300 mL) and brine (300 mL) and was dried over MgSO$_4$. After filtration the solvent was removed in vacuo and the crude residue was purified by flash chromatography to give 16c (5.52 g, max. 2.7 mmol) as light yellow foam with 90% purity. MS: m/z=924.54=[M+2H]$^{2+}$, (calculated 924.53).

16c (5.52 g, max. 2.7 mmol) was dissolved in TFA (20 mL). After stirring for 15 min the product was precipitated by adding the reaction mixture dropwise to ice-cold diethyl ether (160 mL). The resulting suspension was centrifuged at 7000×G and 2° C. for 3 min. The supernatant was discarded and the precipitate was dissolved in methanol (10 mL). This solution was added dropwise to ice-cold diethyl ether (160 mL) and the formed suspension was centrifuged at 7000×G and 2° C. for 3 min. After discarding the supernatant the precipitation procedure was accomplished two more times like described above. The remaining oily precipitate was dried in vacuo to give 16d (4.96 g, 2.27 mmol (10×TFA salt), 84%) as a light brown, hygroscopic powder. MS: m/z=1046.64=[M+H]$^+$, (calculated 1046.64).

To a solution of 16d (1.53 g, 0.7 mmol) in dry DMF (20 mL) was added a solution of N,N-dimethylglycine (1.16 g, 11.2 mmol), PyBOP (5.83 g, 11.2 mmol) and DIPEA (3.23 g, 4.36 mL, 25 mmol) in DMF (35 mL) and stirred for 1 h. The mixture was then concentrated in vacuo to an approximate volume of 10 mL. To this residue water was added to a total volume of 100 mL and the solution was acidified to pH 1-2 by adding TFA. The turbid mixture was centrifuged at 5000×G and 2° C. for 3 minutes. The oily precipitate was discarded and the supernatant was purified by RP-HPLC to give 16e (1.05 g, 0.37 mmol (10×TFA salt), 53%) as a colorless oil. MS: m/z=864.54=[M+2H]$^{2+}$, (calculated 864.54).

Example 17

Synthesis of Linker Reagent 17g

Linker reagent 17g was synthesized according to the following scheme:

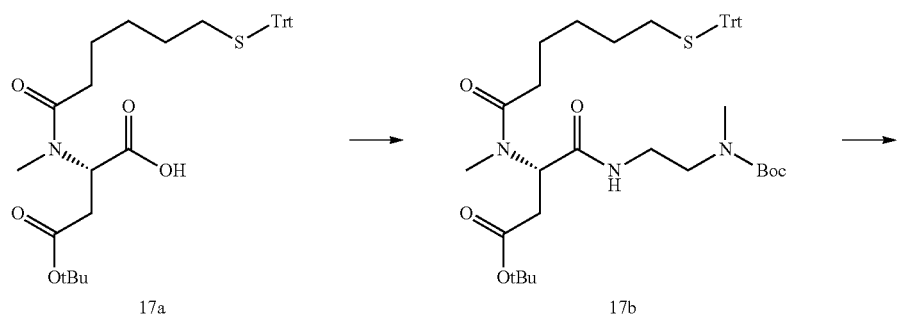
17a → 17b
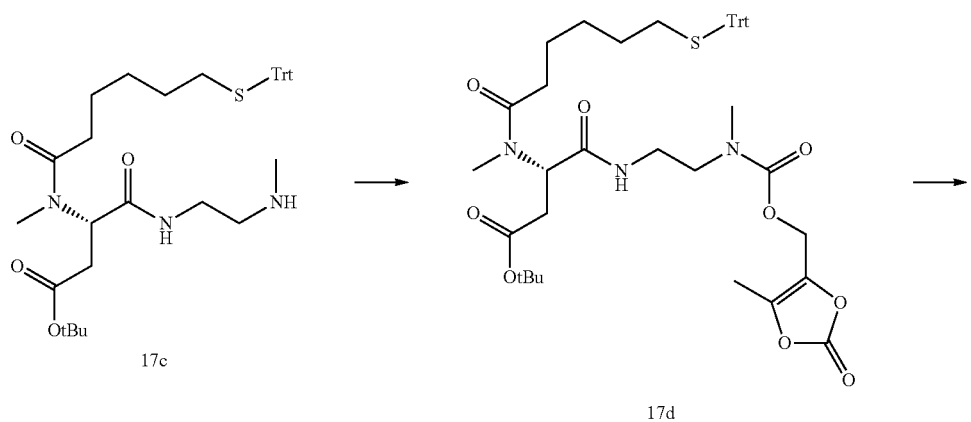
17c → 17d
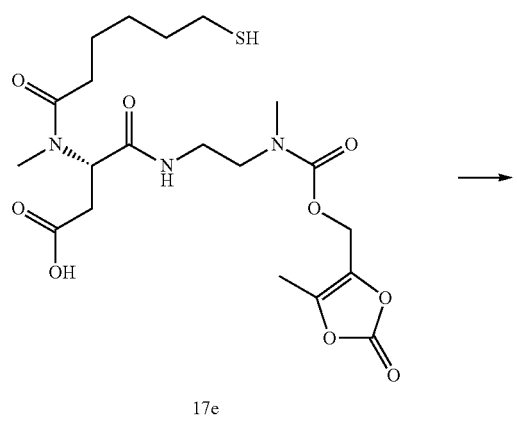
17e →
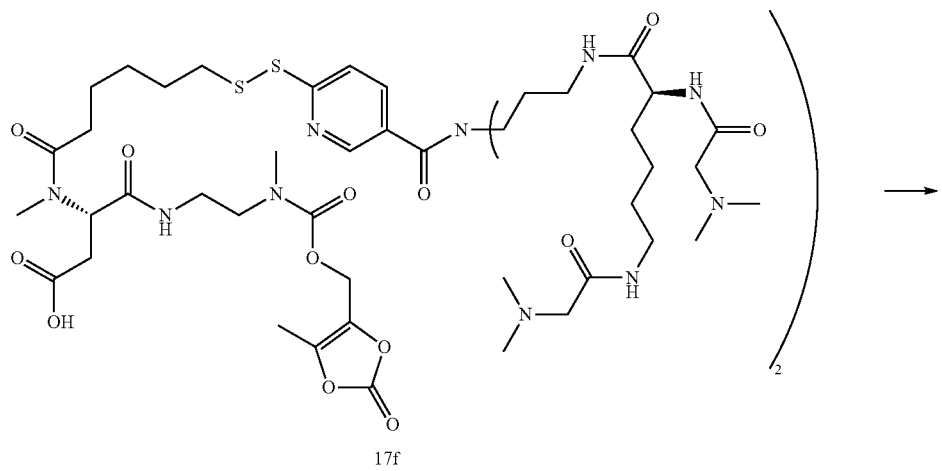
17f →

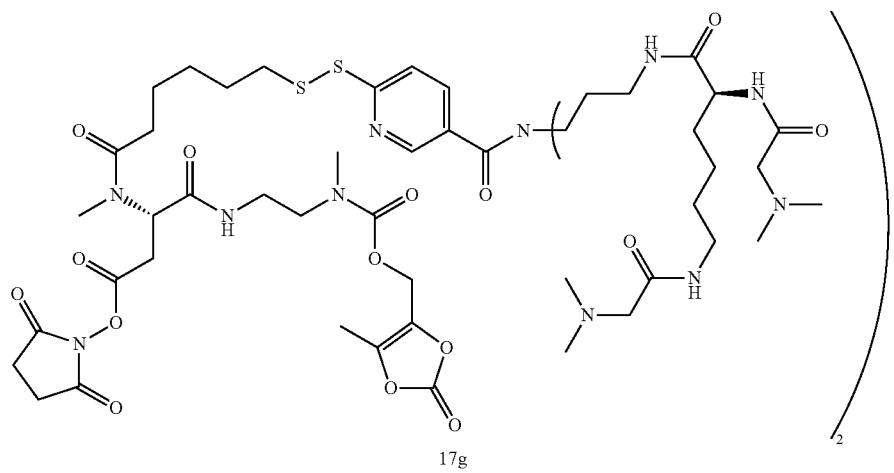

17g

2-Chlorotritylchloride resin (1.4 mmol/g, 1.43 g, 2 mmol) was weighted into a 20 ml syringe with frit. The resin was swollen twice with 10 mL DCM. N-Fmoc-N-methyl-L-Asp (OtBu)-OH (1.06 g, 2.5 mmol) was dissolved in DCM (6 mL) and drawn into the syringe. DIPEA (436 µL, 2.5 mmol) was dissolved in DCM (1 mL) and drawn into the syringe. The syringe was agitated for 5 min. DIPEA (654 µL, 3.75 mmol) was dissolved in DCM (1 mL) and drawn into the syringe. The syringe was agitated for 1 h. MeOH (2 mL) was drawn into the syringe and the syringe agitated for 30 min. The resin was washed 5 times with DMF (10 mL). The resin was agitated 3 times for 5 min with DMF:DBU:piperidine (96:2:2 v/v/v 7 mL). The resin was washed 5 times with DMF (5 mL). 6-Tritylmercaptohexanoic acid (1.95 g, 5 mmol) and PyBOP (2.6 g, 5 mmol) were dissolved in DMF (6 mL) and DIPEA (3.5 mL, 20 mmol) added. After 1 min preincubation the solution was drawn into the syringe and the syringe agitated for 3 h. The resin was washed 5 times with DMF (7 mL), 5 times with DCM (7 mL). A solution of HFIP/DCM (¼ v/v, 8 mL each) were drawn into the syringe and the syringe agitated 3 times for 30 min. The collected filtrates were concentrated in vacuo. Crude 17a (0.84 g, 1.45 mmol, 73%) was used without further purification in the next step. MS: m/z 598.18=[M+Na]$^+$, (calculated=598.26).

17a (1.67 g, 2.9 mmol) was dissolved in DCM (20 mL) and N-Boc-N-methylethylenediamine (0.62 mL, 3.48 mmol) and PyBOP (1.81 g, 3.48 mmol) were added. DIPEA (2.02 mL, 11.6 mmol) was added and the reaction stirred for 1 h. AcOH (2 mL) was added, the mixture diluted with DCM (40 mL) and washed with water (2×20 mL). The organic layer was dried over MgSO$_4$ and concentrated in vacuo and the crude residue was purified by flash chromatography to give 17b (1.74 g, 2.38 mmol, 82%). MS: m/z=754.19=[M+Na]$^+$, (calculated 754.39).

17b (1.74 g, 2.38 mmol) and triphenylmethanol (0.62 g, 2.38 mmol) were dissolved in DCM (7.2 mL) and TFA (7.2 mL) was added with stirring. The reaction was stirred for 90 min and the solvents were removed in a stream of nitrogen over 45 min. The residue was co-evaporated with DCM. The residue was suspended in ACN/water/TFA (2:1:0.003 v/v/v, 14 mL) and filtered. The filtrate was purified by RP-HPLC to give 17c (0.9 g, 1.3 mmol TFA salt, 55%). MS: m/z 576.20=[M+H]$^+$, (calculated=576.29).

17c (0.9 g, 1.3 mmol) was dissolved in DCM (20 mL) and (5-methyl-2-oxo-1,3-dioxol-4-yl)-methyl 4-nitrophenyl carbonate (0.46 g, 1.56 mmol) was added. DIPEA (0.45 mL, 2.6 mmol) was slowly added and the reaction stirred for 30 min. DIPEA (0.11 mL, 0.65 mmol) was added and the reaction stirred for 30 min. Again, DIPEA (0.11 mL, 0.65 mmol) was added and the reaction stirred for 60 min. AcOH (0.68 mL) was added and the mixture concentrated in vacuo and the crude residue was purified by flash chromatography to give 17d (1.04 g, max. 1.3 mmol). MS: m/z=754.28=[M+Na]$^+$, (calculated 754.28).

17d (1.04 g, max. 1.3 mmol) was dissolved in HFIP/TES/water (39:1:1 v/v/v, 8.2 mL) and TFA (0.66 mL) was added. After stirring for 15 min the reaction was concentrated in vacuo, the residue suspended in ACN/water/TFA (1:1:0.002 v/v/v 12 mL) and filtered. The filtrate was purified by RP-HPLC to give 17e (0.32 g, 0.65 mmol, 50%). MS: m/z 490.19=[M+H]$^+$, (calculated=490.19).

17e (181 mg, 0.37 mmol) was dissolved in ACN/water/TFA (1:1:0.002 v/v/v, 3 mL). 16e (1.05 g, 0.37 mmol (10×TFA salt) was dissolved in ACN/water (1:1 v/v, 20 mL). Both solutions were combined and pH 7.4 sodium phosphate (0.5 M, 4 mL) was added and the mixture stirred for 30 min. The pH of the solution was adjusted to ca. pH 2 by addition of ACN/water/TFA (1:1:0.22 v/v/v) and ACN was removed in vacuo. The residue was purified by RP-HPLC to give 17f (0.47 g, 0.24 mmol 5×TFA salt, 65%). MS: m/z 676.86=[M+2H]$^{2+}$, (calculated=676.86).

17f (0.18 g, 94 µmol) was dissolved in ACN (6 mL) and NHS (92 mg, 0.8 mmol) and DCC (166 mg, 0.8 mmol) were added and the reaction stirred for 1 h. The solvent was removed in vacuo and the residue suspended in ACN/water/TFA (0.15:0.85:0.001 v/v/v, 6 mL) and filtered. The filtrate was purified by RP-HPLC to give 17g (129 mg, 64 µmol 5×TFA salt, 68%). MS: m/z 725.37=[M+H]$^+$, (calculated=725.37).

Example 18
Synthesis of Linker Reagent 18i
Linker reagent 18i was synthesized according to the following scheme:
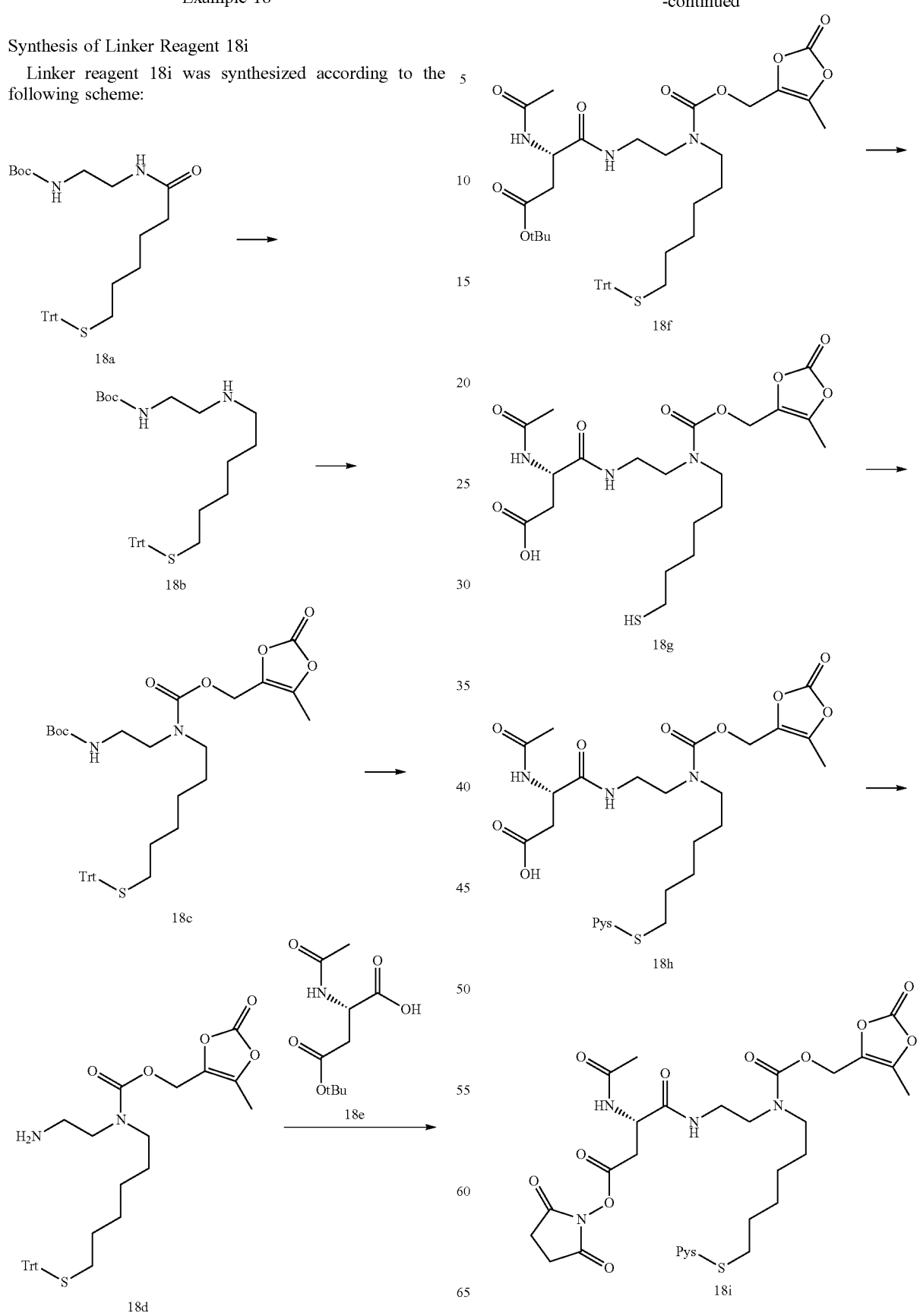

N-Boc-ethylenediamine (0.77 g, 4.8 mmol) was dissolved in DCM (15 mL) and 6-tritylmercaptohexanoic acid (2.25 g, 5.76 mmol) and PyBOP (3.0 g 5.76 mmol) were added with stirring. DIPEA (2.52 ml, 14.4 mmol) was added and the reaction stirred for 1 h. The reaction was diluted with diethyl ether (150 mL) and washed with slightly basic brine (3×30 mL, prepared from 100 mL brine and 3 mL 0.1 M aq. NaOH). The organic phase was washed once more with brine (30 mL), dried over $Na_2SO_4$ and concentrated in vacuo and purified using flash chromatography to give 18a as a white foam. Yield: 2.55 g (4.79 mmol, 99%) MS: m/z 555.24=[M+Na]$^+$, (calculated=555.27).

18a (2.55 g, 4.79 mmol) was dissolved in THF (26 mL) and transferred into an oven-dried argon filled round-bottom flask. Borane-THF complex in THF (1 M, 17.7 mL, 17.71 mmol) was added and the reaction stirred for 15 h. MeOH (5.4 mL) was added slowly and N,N'-dimethyl ethylenediamine (3.11 mL, 28.8 mmol) was added and the reaction refluxed for 2.5 h. After cooling the reaction was diluted with ethyl acetate and washed with sat. sodium bicarbonate solution (2×125 mL) and brine (1×125 mL). The organic phase was dried over $Na_2SO_4$, concentrated in vacuo to give 18b which was used without further purification in the next step. Yield: 2.38 g (4.59 mmol, 96%) MS: m/z 519.27=[M+H]$^+$, (calculated=519.31).

18b (1.19 g 2.29 mmol) was dissolved in DCM and (5-methyl-2-oxo-1,3-dioxol-4-yl)-methyl 4-nitrophenyl carbonate (1.02 g, 3.44 mmol) and 2,4,6-collidine (1.36 mL, 10.32 mmol) were added and the reaction stirred for 23 h. The reaction was concentrated in vacuo and purified using flash chromatography to give 18c. Yield: 1.19 g (1.77 mmol, 79%) MS: m/z 697.18=[M+Na]$^+$, (calculated=697.29).

18c (0.5 g, 0.74 mmol) was dissolved in DCM (2.5 mL) and triphenylmethanol (0.19 g, 0.74 mmol) and TFA (2.5 mL) were added. The reaction was stirred for 40 min, concentrated in a stream of argon and dried in vacuo (<0.1 mbar). The residue was dissolved in ACN/water (7:3 v/v, 10 mL) and purified by RP-HPLC to give 18d (0.50 g, 0.84 mmol, 114%). MS: m/z 575.33=[M+H]$^+$, (calculated=575.26).

2-Chlorotritylchloride resin (1.22 mmol/g, 0.87 g, 1 mmol) was weighted into a 10 ml syringe with frit. The resin was swollen with 5 mL DCM and washed with DCM (5×4 mL). N-Fmoc-L-Asp(OtBu)-OH (1.1 g, 2.7 mmol) was dissolved in DCM (5 mL) and DIPEA (0.66 mL, 3.78 mmol) was added and the solution drawn into the syringe. The syringe was agitated for 1 h. MeOH (0.5 mL) was drawn into the syringe and the syringe agitated for 15 min. The resin was washed 5 times with DCM (4 mL) and 5 times with DMF (5 mL). The resin was agitated 3 times for 5 min with DMF:DBU:piperidine (96:2:2 v/v/v 4 mL). The resin was washed 5 times with DMF (4 mL). Acetic anhydride (0.51 mL, 5.4 mmol) and DIPEA (1.9 mL, 10.8 mmol) were dissolved in DMF (6 mL) and the solution was drawn into the syringe and the syringe agitated for 15 min. The resin was washed 5 times with DMF (4 mL), 5 times with DCM (4 mL). A solution of HFIP/DCM (¼ v/v, 5 mL each) were drawn into the syringe and the syringe agitated 3 times for 10 min. The collected filtrates were concentrated in vacuo. Crude 18e (0.29 g, 1.23 mmol, 114%) was used without further purification in the next step. MS: m/z 254.38=[M+Na]$^+$, (calculated=254.12).

18e (65 mg, 0.28 mmol) was dissolved in DCM (3 mL) and PyBOP (0.18 g, 0.34 mmol) and DIPEA (0.15 mL, 0.84 mmol) were added. 18d (0.18 g, 0.31 mmol) was dissolved in DCM (3 mL) and added to the reaction. The reaction was stirred for 1 h and concentrated in vacuo. The residue was purified by RP-HPLC to give 18f (97 mg, 0.12 mmol, 44%). MS: m/z 810.02=[M+Na]$^+$, (calculated=810.34).

18f (97 mg, 0.12 mmol) was dissolved in TFA/TES/water (92:2.5:2.5 v/v/v, 3 mL) and the reaction stirred vigorously for 3 h while a stream of argon was passed through the solution. After 3 h the solvents were removed in a stream of argon and the residue was purified by RP-HPLC to give 18g (16 mg, 33 µmol, 27%). MS: m/z 490.21=[M+H]$^+$, (calculated=490.19).

18g (16 mg, 33 µmol) was dissolved in ACN/water (1:1 v/v, 3 mL) and a solution of 2,2'-dithiodipyridine (14 mg, 65 µmol) in ACN (0.1 mL) was added followed by pH 7.4 sodium phosphate buffer (0.5 M, 0.1 mL). The reaction was stirred for 4.5 h and the product directly purified by RP-HPLC to give 18h (14 mg, 23 µmol, 71%). MS: m/z 598.98=[M+H]$^+$, (calculated=599.19).

18h (14 mg, 23 µmol) was dissolved in DCM (3 mL) and NHS (3 mg, 28 µmol), DCC (6.5 mg, 30 µmol) and DMAP (0.3 mg, 2 µmol) were added. The reaction was stirred for 1.5 h and the solvent removed in a stream of argon. The residue was suspended in ACN/water/TFA (9:1:0.01 v/v/v, 3 mL) and filtered. The filtrate was purified by RP-HPLC to give 18i (17 mg, 23 µmol, 100%). MS: m/z 696.20=[M+H]$^+$, (calculated=696.20).

Example 19

Synthesis of Crosslinker Reagents 19c, 19g

Crosslinker reagent 19c was prepared from suberic acid monobenzyl ester 2a and PEG6000 accordingly to the following scheme:

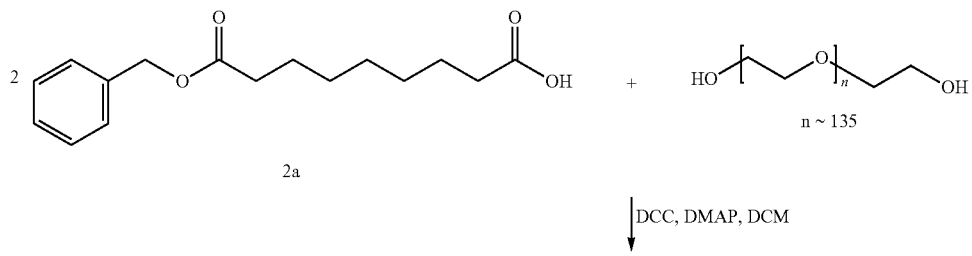

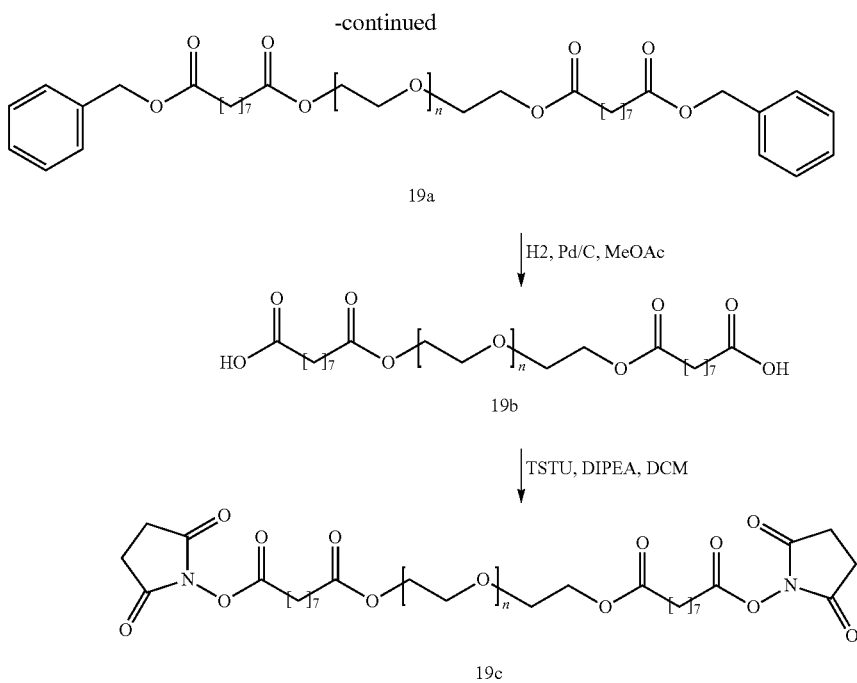

19a

↓ H2, Pd/C, MeOAc

19b

↓ TSTU, DIPEA, DCM

19c

For synthesis of compound 19a, azelaic acid monobenzyl ester 2a (6.50 g, 23.3 mmol) and PEG 6000 (40.0 g, 6.67 mmol) were dissolved in 140 mL dichloromethane and cooled with an ice bath. A solution of DCC (4.81 g, 23.3 mmol) and DMAP (0.040 g, 0.33 mmol) in 40 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 70 mL dichloromethane and diluted with 300 mL MTBE at room temperature. The mixture was stored over night at −20° C. The precipitate was collected by filtration through a glass filter Por. 3, and washed with 500 mL of cooled MTBE (−20° C.). The product was dried in vacuo over night.

Yield 41.2 g (95%) white powder 19a.

MS: m/z 833.75=[M+8H]$^{8+}$ (calculated=833.74).

For mass spectra of polydisperse PEG containing compounds, one single mass peak was selected.

For synthesis of compound 19b, compound 19a (41.2 g, 6.32 mmol) was dissolved in methyl acetate (238 mL) and ethanol (40 mL), then 400 mg of palladium on charcoal was added. Under a hydrogen atmosphere of ambient pressure, the mixture was stirred overnight at room temperature. The reaction mixture was filtered through a pad of celite and the filtrate was evaporated and dried in vacuo over night.

Yield 38.4 g (96%) glassy solid 19b.

MS: m/z 750.46=[M+H]$^{9+}$ (calculated=750.56).

For mass spectra of polydisperse PEG containing compounds, one single mass peak was selected.

For synthesis of compound 19c, compound 19b (38.2 g, 6.02 mmol) and TSTU (7.25 g, mmol) were dissolved in 130 mL dichloromethane at room temperature. Then DIPEA (3.11 g, 24.1 mmol) was added and the mixture was stirred for 1 h. The resulting suspension was filtered, the filtrate was diluted with 100 mL dichloromethane and washed with 200 mL of a solution of 750 g water/197 g NaCl/3 g NaOH. The organic phase was dried over MgSO$_4$ and the solvent was evaporated in vacuo.

The residue was dissolved in 210 mL toluene, diluted with 430 mL MTBE at room temperature and stored over night at −20° C. The precipitate was collected by filtration through a glass filter Por. 3, and washed with 450 mL of cooled MTBE (−20° C.). The product was dried in vacuo over night.

Yield 35.8 g (91%) white powder 19c.

MS: m/z 857.51=[M+8H]$^{8+}$ (calculated=857.51).

For mass spectra of polydisperse PEG containing compounds, one single mass peak was selected.

Crosslinker reagent 19g was prepared from isopropylmalonic acid monobenzyl ester and PEG8000 according to the following scheme:

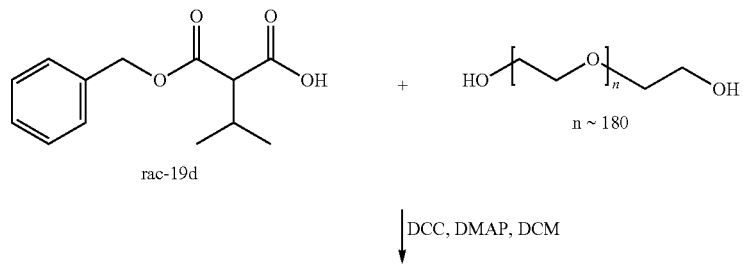

rac-19d

↓ DCC, DMAP, DCM

-continued

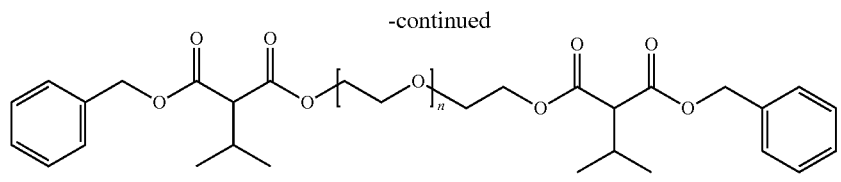

rac-19e

↓ H2, Pd/C, MeOAc

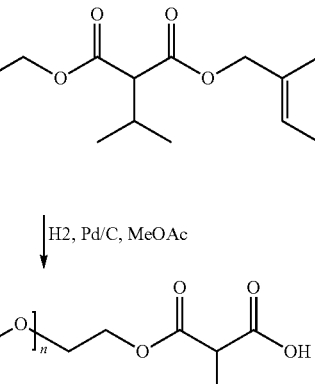

rac-19f

↓ TSTU, DIPEA, DCM

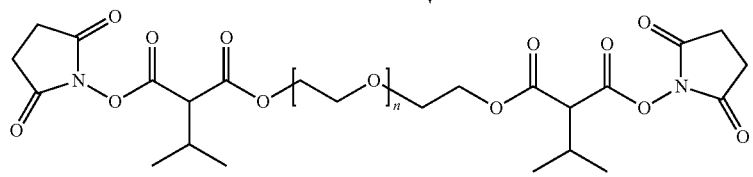

rac-19g

For the synthesis of isopropylmalonic acid monobenzyl ester rac-19d, isopropylmalonic acid (35.0 g, 239 mmol), benzyl alcohol (23.3 g, 216 mmol) and DMAP (1.46 g, 12.0 mmol) were dissolved in 100 mL acetonitrile. Mixture was cooled to 0° C. with an ice bath. A solution of DCC (49.4 g, 239 mmol) in 150 mL acetonitrile was added within 15 min at 0° C. The ice bath was removed and the reaction mixture was stirred over night at room temperature, then the solid was filtered off. The filtrate was evaporated at 40° C. in vacuo and the residue was dissolved in 300 mL MTBE. This solution was extracted with 2×300 mL sat. aqueous NaHCO$_3$ solution, then the combined aqueous phases were acidified to pH=1-3 using 6 N hydrochloric acid. The resulting emulsion was extracted with 2×300 mL MTBE and the solvent was evaporated. The combined organic phases were washed with 200 mL sat. aqueous NaCl and dried over MgSO$_4$. The product was purified on 340 g silica using ethyl acetate/heptane (10:90→20:80) as eluent. The eluent was evaporated and the residue was dried in vacuo over night.

Yield 9.62 g (17%) colorless oil rac-19d.

MS: m/z 237.11=[M+H]$^+$ (calculated=237.11).

For synthesis of compound rac-19e, isopropylmalonic acid monobenzyl ester rac-19d (2.25 g, 9.50 mmol) and PEG 8000 (19.0 g, 2.38 mmol) were dissolved in 100 mL dichloromethane and cooled with an ice bath. A solution of DCC (1.96 g, 9.50 mmol) and DMAP (14 mg, 0.12 mmol) in 10 mL dichloromethane was added. The ice bath was removed and mixture was stirred at room temperature overnight. The resulting suspension was cooled to 0° C. and the solid was filtered off. The solvent was evaporated in vacuo.

The residue was dissolved in 40 mL dichloromethane and diluted with 270 mL MTBE at room temperature. The mixture was stored over night at −20° C. The precipitate was collected by filtration through a glass filter Por. 3, and washed with 500 mL of cooled MTBE (−20° C.). The product was dried in vacuo over night.

Yield 18.5 g (92%) white powder rac-19e.

MS: m/z 737.43=[M+13H]$^{13+}$ (calculated=737.42).

For mass spectra of polydisperse PEG containing compounds, one single mass peak was selected.

For synthesis of compound rac-19f, compound rac-19e (18.4 g, 2.18 mmol) was dissolved in methyl acetate (160 mL) and 254 mg of palladium on charcoal was added. Under a hydrogen atmosphere of ambient pressure, the mixture was stirred overnight at room temperature. The reaction mixture was filtered through a pad of celite and the filtrate was evaporated and dried in vacuo over night.

Yield 17.7 g (98%) glassy solid rac-19f.

MS: m/z 723.51=[M+13H]$^{13+}$ (calculated=723.55).

For mass spectra of polydisperse PEG containing compounds, one single mass peak was selected.

For synthesis of compound rac-19g, compound rac-19f (13.6 g, 1.65 mmol) and TSTU (1.96 g, 6.60 mmol) were dissolved in 60 mL dichloromethane at room temperature. Then DIPEA (852 mg, 6.60 mmol) was added and the mixture was stirred for 45 min. The resulting suspension was filtered, the filtrate was diluted with 70 mL ethyl acetate and washed with 70 mL of a 0.5 M phosphate buffer pH=6.5. The organic phase was dried over MgSO$_4$ and the solvent was evaporated in vacuo. The residue was dissolved in 80 mL toluene, the remaining solid was filtered off and washed with 20 mL of toluene. The combined toluene fractions were diluted with 35 mL MTBE at room temperature and stored over night at −20° C. The precipitate was collected by filtration through a glass filter Por. 3, and washed with 600 mL of cooled MTBE (−20° C.). The product was dried in vacuo over night.

Yield 12.1 g (87%) white powder rac-19g.

MS: m/z 738.51=[M+13H]$^{13+}$ (calculated=738.49).

For mass spectra of polydisperse PEG containing compounds, one single mass peak was selected.

Example 20

Preparation of Hydrogel Beads 20a Containing Free Amino Groups 20a was prepared as described for 3c except applying a stirrer speed of 560 rpm, the use of 398 mg 1b, 2690 mg 19c, 27.8 g DMSO, 274 mg Cithrol™ DPHS, 1.8 mL TMEDA, 2.7 mL acetic acid, yielding 0.22 g on the 50 μm sieve, 0.33 g on the 63 μm sieve, and 0.52 g on the 75 μm sieve of 20a as a white powder, free amino groups 0.152 mmol/g.

Preparation of Hydrogel Beads 20b Containing Free Amino Groups.

20b was prepared as described for 3c except applying a stirrer speed of 580 rpm, the use of 250 mg 1b, 2168 mg rac-19g, 21.8 g DMSO, 215 mg Cithrol™ DPHS, 1.1 mL TMEDA, 1.7 ml, acetic acid, yielding 0.09 g on the 50 μm sieve, 0.17 g on the 63 μm sieve, and 0.54 g on the 75 μm sieve of 20b as a white powder, free amino groups 0.154 mmol/g.

Example 21

Preparation of a Maleimide Containing Histidine-Tag 21

0.78 g of RINK amide MBHA resin (100-200 mesh, 0.64 mmol/g amines) were transferred into a 20 mL syringe equipped with a frit and swollen in 10 mL DCM. The solvent was expelled and the resin was washed three times with NMP, the solvent was discarded each time. The resin was treated for 15 minutes and 5 min, respectively, with 5 mL 20% piperidine in DMF to remove the Fmoc protection group, the solvent was discarded each time. The resin was washed ten times with NMP. 775 mg Fmoc-His(Trt)-OH and 475 mg HATU were dissolved in 3 mL 0.5M HOAT in DMF and 850 μL DIPEA were added. The solution was drawn into the syringe and the suspension was allowed to incubate under gentle shaking for 3 h at ambient temperature. The solvent was discarded and the resin was washed five times with NMP. The Fmoc-protecting group was removed as described above. The next five couplings were each performed using a coupling solution of 620 mg Fmoc-His(Trt)-OH, 77 mg HOBt, 160 mg TBTU and 850 μL DIPEA in 3 mL NMP. The reaction was each time allowed to go for 1 hour at ambient temperature under gentle shaking followed by washing with NMP and Fmoc-deprotection. Afterwards, the resin was treated with a solution of 385 mg Fmoc-Ado-OH, 475 mg HATU, 850 μL DIPEA dissolved in 3 mL 0.5M HOAt in DMF for 1 h at ambient temperature followed by washing with NMP and Fmoc deprotection. The resin was treated with 169 mg maleimido propionic acid, 475 mg HATU, 850 μL DIPEA in 3 mL 0.5 M HOAt in DMF for eight hours at ambient temperature under gentle shaking. The solvent was discarded and the resin washed five times with NMP and ten times with DCM. The solvent was discarded each time. Finally, the resin was treated with each time 5 mL of a solution of 95% TFA/2.5% TIPS/2.5% water for two times 30 min and two times one hour. The solution was expelled into separate 50 mL Falcon tubes and the TFA evaporated under a continuous nitrogen stream. To the residue, 45 mL of ice cold ether were added and the Falcon tube was centrifugated and the supernatant discarded. The precipitate was taken up in 50% ACN/water and purified via prep. HPLC and lyophilized to give 21.

Yield 0.15 g (26%).

MS: m/z 1136.49=[M+H]$^+$ (calculated=1136.49).

Example 22

Preparation of PEGylated Hydrogel Beads in DMSO 22

Dry hydrogel beads as e.g. described in 3c were transferred into a syringe equipped with a frit and NMP (5 mL/100 mg hydrogel beads) was added. The hydrogel was allowed to swell for 10 min at ambient temperature under gentle shaking. The solvent was expelled and the hydrogel washed ten times with each time DMSO, followed by ten washes with each time 1% TMEDA/DMSO (5 mL/100 mg hydrogel beads), the solvent was each time discarded. 0.2 eq (based on amine content of the hydrogel beads) PEG-NHS were dissolved in a solution containing 2 eq (based on amine content of the hydrogel beads) TMEDA in DMSO at 37° C. for 15 min. The solution was drawn into the syringe and the resulting hydrogel suspension was allowed to incubate under gentle shaking. The solvent was expelled and the hydrogel was washed five times with DMSO (5 mL/100 mg hydrogel beads), followed by five washing cycles with 0.1% acetic acid/0.01% Tween 20 (5 mL/100 mg hydrogel beads). Fresh 0.1% acetic acid/0.01% Tween 20 was pulled into the syringe to give a suspension of 10 mg/mL hydrogel based on initial weight. Amine content of the hydrogel beads was determined as described above. Based on equation (2) this refers to the degree of PEGylation.

Example 22a was prepared according to the procedure described above using 50 mg of hydrogel 20a and 60.8 mg 40 kDA PEG-NHS to give PEGylated hydrogel beads with an amine content of 0.141 mmol/g.

Example 22b was prepared according to the procedure described above using 51.3 mg of hydrogel 20b and 59.5 mg 40 kDA PEG-NHS to give PEGylated hydrogel beads with an amine content of 0.118 mmol/g.

Example 23

Preparation of Maleimide Functionalized Hydrogel Beads 23

PEGylated hydrogel beads as a suspension of 10 mg/mL based on initial weight of hydrogel beads prior to PEGylation were transferred into a syringe equipped with a frit. The solvent was expelled and the hydrogel washed ten times with water (5 mL/100 mg hydrogel beads), the solvent was discarded each time. The hydrogel beads were then washed ten times with NMP and five times with 2% DIPEA in NMP. 5 eq of Mal-PEG$_6$-Pfp (based on amine content of the hydrogel beads) were dissolved in NMP (1 mL/50 mg reagent) and added to the washed hydrogel beads. The hydrogel suspension was incubated for 2 h at room temperature. Resulting maleimide functionalized hydrogel beads were washed five times each with NMP and afterwards with 0.1% acetic acid/0.01% Tween20.

Maleimide content of hydrogel beads was determined by conjugation of a Fmoc-cysteine to the maleimide groups on the hydrogel and subsequent Fmoc-determination as described by Gude, M., J. Ryf, et al. (2002) *Letters in Peptide Science* 9(4): 203-206.

Example 23a was prepared according to the procedure described above using 35 mg of 22a (based on initial dry weight of 20a) and 13 mg Mal-PEG$_6$-Pfp.

Example 23b was prepared according to the procedure described above using 35 mg of 22b (based on initial dry weight of 20b) and 17 mg Mal-PEG$_6$-Pfp.

Example 24

Synthesis of Transient Lucentis-Linker-Hydrogel Prodrug 80 mg Lucentis (depicted in the scheme below as Lucentis-NH$_2$) (2000 µL of 40 mg/mL Lucentis in 10 mM histidine, 10 wt % α,α-trehalose, 0.01% Tween20, pH 5.5) was buffer exchanged to 10 mM sodium phosphate, 2.7 mM potassium chloride, 140 mM sodium chloride, pH 7.4 and the concentration of Lucentis was adjusted to 13.5 mg/mL. 6 mg of Linker reagent 4c was dissolved in 100 µL DMSO to yield a concentration of 100 mM. 1 molar equivalent of linker reagent 4c relative to the amount of Lucentis was added to the Lucentis solution. The reaction mixture was mixed carefully and incubated for 5 min at room temperature. Subsequently, 1.3 additional molar equivalents of linker reagent 4c were added to the Lucentis solution yielding a mixture of unmodified Lucentis and the protected Lucentis-linker monoconjugate 24a.

The pH of the reaction mixture was adjusted to pH 6.5 by addition of 1 M sodium citrate, pH 5.0 and Na$_2$EDTA was added to a final concentration of 5 mM. To remove the protecting groups of 24a 0.5 M NH$_2$OH (dissolved in 10 mM sodium citrate, 140 mM sodium chloride, 5 mM Na$_2$EDTA, pH 6.5) was added to a final concentration of 45 mM and the deprotection reaction was incubated at room temperature for 4 h yielding the Lucentis-linker monoconjugate 24b. The mixture of Lucentis and Lucentis-linker monoconjugate 24b was buffer exchanged to 10 mM sodium phosphate, 2.7 mM potassium chloride, 140 mM sodium chloride, 5 mM Na$_2$EDTA, 0.01% Tween 20, pH 6.5 and the overall concentration of the two Lucentis species was adjusted to 12.1 mg/mL.

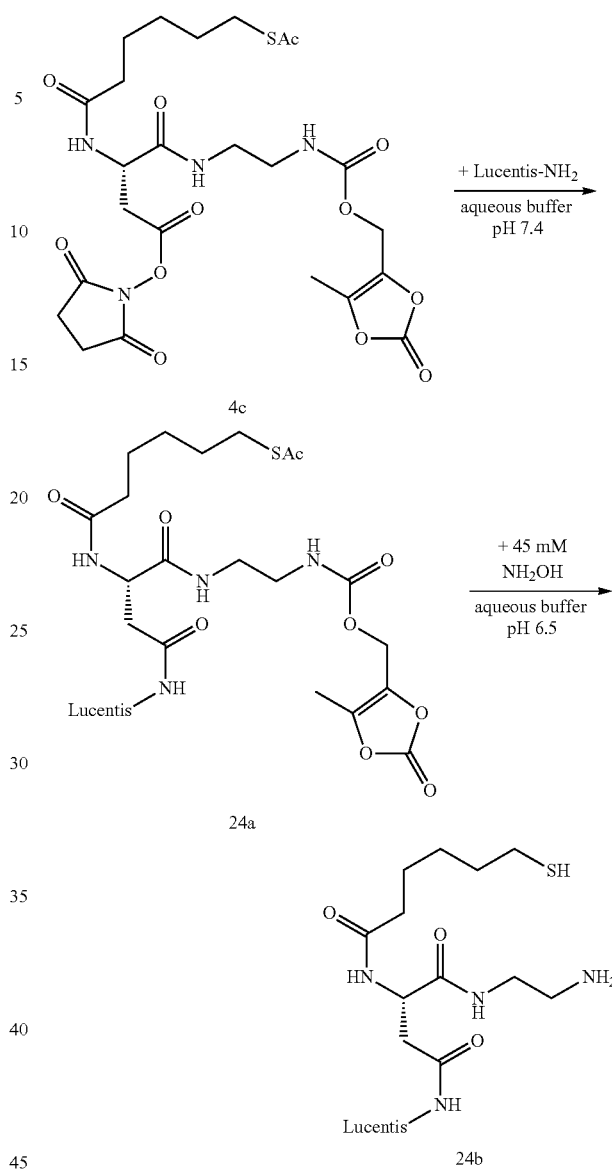

Example 25

Synthesis of Transient Lucentis-Linker-Hydrogel Prodrug 25a 20 mg of the Lucentis/Lucentis-linker monoconjugate 24b mixture in 10 mM sodium phosphate, 2.7 mM potassium chloride, 140 mM sodium chloride, 5 mM Na$_2$EDTA, 0.01% Tween 20, pH 6.5 were added to 2.5 mg of maleimide functionalized hydrogel beads 5a and incubated overnight at room temperature yielding transient Lucentis-linker-hydrogel prodrug 25a.

Example 25b was prepared according to the procedure described for 25a using 2.5 mg (based on dry weight of 20a) 23a.

Example 25c was prepared according to the procedure described for 25b using 2.5 mg (based on dry weight of 20b) 23b.

Example 26

Blocked Hydrogel Beads 26

Hydrogel beads were synthesized according to the procedure described in example 3c and functionalized with maleimide groups according to the procedure described in example 5a. Afterwards, 4 mL of the hydrogel suspension at 10 mg/mL were transferred into a 20 mL syringe equipped with a frit. The solvent was expelled and the hydrogel washed 10 times with 5 mL 10 mM histidine/10 wt % α,α-trehalose/0.01% Tween20/pH 5.5. The solvent was expelled and 5 mL 1 mM β-mercaptoethanol in 10 mM histidine/10 wt % α,α-trehalose/0.01% Tween20/pH 5.5 were drawn into the syringe. The resulting suspension was allowed to incubate at ambient temperature under gentle shaking for 5 min. The solvent was discarded and the hydrogel treated 9 additional times with 5 mL 1 mM β-mercaptoethanol in 10 mM histidine/10 wt % α,α-trehalose/0.01% Tween20/pH 5.5. The solvent was each time discarded. The hydrogel beads were then washed 10 times with each time 5 mL 10 mM histidine/10 wt % α,α-trehalose/0.01% Tween20/pH 5.5, the solvent was discarded each time. The hydrogel beads were then washed ten times with each time 5 mL PBS-T/pH 7.4, the solvent was discarded each time. Finally, fresh PBS-T/pH 7.4 was drawn into the syringe and the suspension transferred into a Falcon tube to give 26.

Example 27

Antibody Binding to Lucentis Hydrogel Beads 27

20 μL of hydrogel suspensions 25a-c (35 volume-%) in PBS-T buffer were mixed with 400 μL first antibody solution in PBS-T with 1% BSA (Sigma, A3059) and incubated for 1 h at 200 rpm in 1.5 mL Eppendorf tubes. For Lucentis hydrogel beads a 1:100 dilution of antibody ab771 (Anti-human IgG Fab fragment antibody [4A11] (ab771)—Abcam, Cambridge, UK) was used. Hydrogel beads were sedimented through a centrifugation step at 100 g for 1 min in a tabletop centrifuge. The supernatant was removed by pipetting and care was taken not to remove any hydrogel beads. Washing of the beads was accomplished via two rounds of washing steps, which included addition of 1 mL PBS-T buffer, centrifugation at 100 g for 1 min and careful removal of the supernatant by pipetting. 400 μL of the secondary antibody in PBS-T with 1% BSA (Sigma, A3059) were added to the beads and incubated for 1 h at 200 rpm. For Lucentis hydrogel beads a 1:50 dilution of antibody ab97041 (Goat Anti-Mouse IgG H&L (Phycoerythrin) pre-adsorbed (ab97041)—Abcam, Cambridge, UK) was used. The supernatant was removed by pipetting and care was taken not to remove any hydrogel beads. Washing of the beads was accomplished via four rounds of washing steps, which included addition of 1 mL PBS-T buffer, centrifugation at 100 g for 1 min and careful removal of the supernatant by pipetting. The washed beads were resuspended in 200 μL PBS-T and transferred completely into black 96-well plates (black, non-binding, Art. no. 655900, Greiner bio-one GmbH, 72636 Frickenhausen, Germany). The fluorescence intensity was determined with a Tecan Infinite M200 fluorescence plate reader (Excitation 495 nm, Emission 575 nm, Number of flashes 25, Integration time 20 μs, Multiple reads per well 5×5 (Border 250 μm), Optimal gain).

Data Analysis

Determination of antibody binding to PEG-modified Lucentis hydrogel beads was achieved in comparison with a standard curve of unmodified Lucentis hydrogel beads 25a. The unmodified Lucentis hydrogel beads were mixed with placebo hydrogel beads 26 in different ratios. The plot (percentage of unmodified Lucentis hydrogel beads versus fluorescence intensity) was fitted in a linear fashion. The percentage of antibody binding to PEGylated Lucentis hydrogel beads was back-calculated according to the obtained calibration curve.

Results

| Lucentis Hydrogel | Residual antibody binding [% in relation to unmodified Lucentis hydrogel] | DevMean - residual antibody binding |
|---|---|---|
| 25b | 6.2 | 1.9 |
| 25c | 5.3 | 0.2 |

Definitions: DevMean = Deviation from mean = $|\mu - X|$, $\mu$ = mean value

Example 28

In Vitro Release Kinetics—Determination of In Vitro Half-Life 28a 50.3 mg of dense Lucentis-linker-hydrogel prodrug suspension 25a (containing approximately 1.68 mg Lucentis) was washed five times with 60 mM sodium phosphate, 3 mM Na$_2$EDTA, 0.01% Tween20, pH 7.4 and finally suspended in 1 mL of the aforementioned buffer. The suspension was incubated at 37° C. The buffer of the suspension was exchanged after different time intervals and analyzed by HPLC-SEC at 220 nm. Peaks corresponding to liberated Lucentis were integrated and the total of liberated Lucentis was plotted against total incubation time. Curve fitting software was applied to determine first-order cleavage rates.

Release Kinetic of 28a:

| t [d] | Lucentis release [μg] | Lucentis release [%] |
|---|---|---|
| 0 | 0 | 0 |
| 4.85 | 141.0 | 8.4 |
| 12.9 | 262.2 | 15.6 |

Example 28b was prepared according to the procedure described in 28a but with 35.0 mg of dense Lucentis-linker-hydrogel prodrug suspension 25b (containing approximately 1.14 mg Lucentis).

Release Kinetic of 28b:

| t [d] | Lucentis release [μg] | Lucentis release [%] |
|---|---|---|
| 0 | 0 | 0 |
| 4.85 | 96.9 | 8.5 |
| 12.9 | 172.7 | 15.1 |

Example 28c was prepared according to the procedure described in 28a but with 25.3 mg of dense Lucentis-linker-hydrogel prodrug suspension 25c (containing approximately 0.73 mg Lucentis).

Release Kinetic of 28c:

| t [d] | Lucentis release [μg] | Lucentis release [%] |
|---|---|---|
| 0 | 0 | 0 |
| 4.85 | 51.8 | 7.3 |
| 12.9 | 96.5 | 13.5 |

Example 29

Preparation of Thiol Functionalized Hydrogel Beads 29

100 mg of dry hydrogel beads as described in 3c with an amine content of 0.097 mmol/g were transferred into a 20 mL syringe equipped with a frit. The hydrogel was swollen in NMP and the solvent was discarded. The hydrogel was washed with five times with each time 5 mL NMP, the solvent was discarded each time. The hydrogel beads were washed five times with each time 5 mL 2% DIPEA in NMP, the solvent was discarded each time. The hydrogel beads were washed five times with 5 mL DMSO, the solvent was discarded each time. 17.7 mg OPSS-PEG$_{12}$-NHS were dissolved in 1 mL DMSO and drawn into the syringe. The suspension was allowed to incubate for 2 hours under gentle shaking at ambient temperature. The solvent was expelled and the hydrogel beads washed five times with each time 5 mL DMSO and five times each time 5 mL 15 mM succinate/100 mM NaCl/5 mM EDTA/pH 4.0, the solvent was each time discarded. 10 mL 15 mM succinate/100 mM NaCl/5 mM EDTA/pH 4.0 buffer were drawn into the syringe and the resulting suspension was transferred into a Falcon Tube. 10 µL Tween20 were added. 1 mL of this hydrogel suspension was transferred into a 5 mL syringe equipped with a frit and the solvent was expelled. The hydrogel beads were incubated with 1 mL of a 50 mM TCEP solution in water for 10 min at ambient temperature under gentle shaking. The solvent was expelled and the hydrogel beads were washed five times with each time 1 mL of a 50 mM TCEP solution in water, the solvent was discarded each time. The hydrogel beads were washed ten times with 1 mL 15 mM succinate/100 mM NaCl/5 mM EDTA/0.01% Tween20/pH 4.0, the solvent was each time discarded. 1 mL 15 mM succinate/100 mM NaCl/5 mM EDTA/0.01% Tween20/pH 4.0 was drawn into the syringe to give 29 as a hydrogel suspension of 10 mg/mL based on initial dry weight of the hydrogel beads.

Example 30

Preparation of a Thiol Functionalized Histidine Tag 30

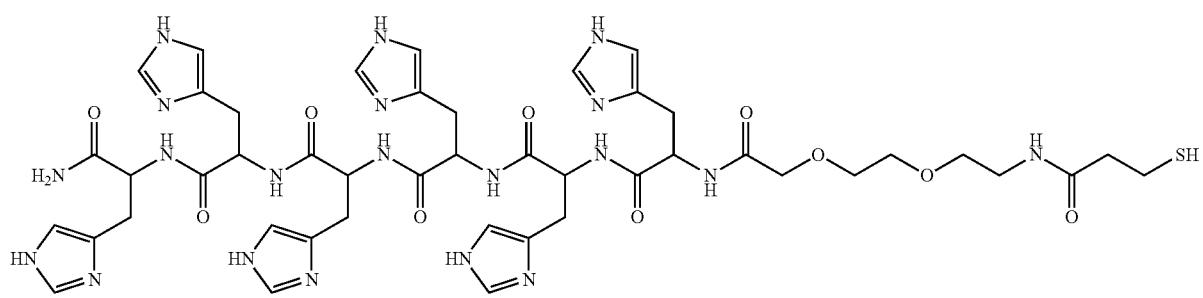 [SMILES: NC(=O)C(Cc1c[nH]cn1)NC(=O)C(Cc1c[nH]cn1)NC(=O)C(Cc1c[nH]cn1)NC(=O)C(Cc1c[nH]cn1)NC(=O)C(Cc1c[nH]cn1)NC(=O)C(Cc1c[nH]cn1)NC(=O)COCCOCCNC(=O)CCS]

0.2 g of Rink amide MBHA resin (100-200 mesh, 0.64 mmol/g amines) were transferred into a 5 ml, syringe equipped with a frit and swollen in 2 mL DMF for 10 min. The solvent was expelled and the resin was washed five times with 5 mL DMF, the solvent was discarded each time. The resin was treated for two times 15 minutes with 5 mL 20% piperidine in DMF, the solvent was discarded each time to remove the Fmoc protecting group. The resin was washed ten times with 2 mL DMF. 198 mg Fmoc-His(Trt)-OH and 146 mg HATU were dissolved in 1 mL 0.5M HOAT in DMF and 223 µL DIPEA were added. The solution was drawn into the syringe and the suspension was allowed to incubate under gentle shaking for 1.5 hours at ambient temperature. The solvent was discarded and the resin was treated again for 1.5 hours with a solution of 198 mg Fmoc-His(Trt)-OH, 146 mg HATU and 223 µL DIPEA in 1 mL 0.5M HOAT in DMF. The solvent was discarded and the resin was washed ten times with 2 mL DMF each time, the solvent was each time discarded. The Fmoc-protecting group was removed as described above. The next five couplings were each performed using a coupling solution of 198 mg Fmoc-His(Trt)-OH, 146 mg HATU and 223 µL DIPEA in 1 mL 0.5M HOAt in DMF. The reaction was each time allowed to go for 1.5 hours at ambient temperature under gentle shaking followed by washing with DMF and Fmoc-deprotection. Afterwards, the resin was treated with a solution of 123 mg Fmoc-Ado-OH, 122 mg HATU, 223 µL DIPEA dissolved in 1 mL 0.5M HOAt in DMF for 1.5 hours at ambient temperature followed by washing with DMF and Fmoc deprotection. The resin was treated with 112 mg 3-(tritylthio-)propionic acid, 122 mg HATU and 223 µL DIPEA in 1 mL 0.5 M HOAt in DMF for one hour at ambient temperature under gentle shaking. The solvent was discarded and the resin washed ten times with DMF and ten times with DCM. The solvent was discarded each time. The resin was treated with each time 3 mL of a solution of 95% TFA/2.5% TIPS/2.5% water for two times 30 min and once for one hour. The solution was expelled into separate 50 mL Falcon tubes and the TFA evaporated under a continuous nitrogen stream. To the residue, 45 mL of ice cold ether were added and the Falcon tube was centrifugated and the supernatant discarded. The precipitate was taken up in 50% ACN/water and purified via prep. HPLC and lyophilized to give 30.

Yield 8.1 mg (6%).
MS: m/z 1073.46=[M+H]$^+$ (calculated=1073.46).

Example 31

Preparation of 2-(2-pyridyldisulfanyl)ethanol 31

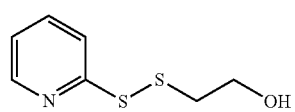 [SMILES: OCCSSc1ccccn1]

250 mg aldrithiol-2 were dissolved in 10 mL 50 mM phosphate/ACN pH 7.4 and 95 µL 2-mercaptoethanol were added. The solution was allowed to stir for 5 min at ambient temperature. Then, additional 50 mg of aldrithiol-2 were added. The solution was stirred for 16 h at ambient temperature. The crude product was purified via prep. HPLC and lyophilized to give 31.

Yield 140.6 mg (55%).

MS: m/z 188.02=[M+H]$^+$ (calculated=188.02).

Example 32

Blocking of Thiol Functionalized Hydrogel 32

4 mg (based on dry weight of the initial hydrogel) of thiol functionalized hydrogel beads 29 were transferred as a suspension of 10 mg/mL in 15 mM succinate/100 mM NaCl/5 mM EDTA/0.01% Tween20/pH 4.0 into a 5 mL syringe equipped with a frit. The solvent was expelled and 322 μL of a 5 mM solution of 31 in 15 mM succinate/100 mM NaCl/5 mM EDTA/0.01% Tween20/pH 4.0 was drawn into the syringe. The suspension was allowed to incubate at ambient temperature under gentle shaking for 16 h. The solvent was expelled and the hydrogel beads were washed ten times with 2 mL 15 mM succinate/100 mM NaCl/5 mM EDTA/0.01% Tween20/pH 4.0, the solvent was discarded each time.

Example 33

Synthesis of Transient Lucentis-Linker-Hydrogel Prodrug 33d 360 mg Lucentis (depicted in the scheme below as Lucentis-NH$_2$) (9 mL of 40 mg/mL Lucentis in 10 mM histidine, 10 wt % α,α-trehalose, 0.01% Tween20, pH 5.5) was buffer exchanged to 10 mM sodium phosphate, 2.7 mM potassium chloride, 140 mM sodium chloride, pH 7.4 and the concentration of Lucentis was adjusted to 20 mg/mL. Linker reagent 11d was dissolved in DMSO to yield a concentration of 100 mM. 5 molar equivalents of linker reagent 11d relative to the amount of Lucentis were added to the Lucentis solution in 2, 2, and 1 molar equivalent steps. The reaction mixture was mixed carefully after each linker reagent addition and incubated for 5 min at room temperature yielding a mixture of unmodified Lucentis and the protected Lucentis-linker monoconjugate 33a.

The pH of a quarter of the reaction mixture was adjusted to pH 6.5 by addition of 1 M sodium citrate, pH 5.0 and Na$_2$EDTA was added to a final concentration of 5 mM. To remove the (5-methyl-2-oxo-1,3-dioxol-yl)-methyl oxocarbonyl protecting group of 33a 0.5 M NH$_2$OH (dissolved in 10 mM sodium citrate, 140 mM sodium chloride, 5 mM Na$_2$EDTA, pH 6.5) was added to a final concentration of 45 mM and the deprotection reaction was incubated at room temperature for 135 min yielding the Lucentis-linker monoconjugate 33b. The mixture of Lucentis and Lucentis-linker monoconjugate 33b was buffer exchanged to 15 mM succinic acid, 100 mM sodium chloride, 5 mM Na$_2$EDTA, pH 4.0 and subsequently concentrated to a concentration of 15 mg/mL. The protein solution was cooled to 4° C. and 1 molar equivalent of 25 mM DTT in 15 mM succinic acid, 100 mM sodium chloride, 5 mM Na$_2$EDTA, pH 4.0 with respect to the overall Lucentis content was added to remove the Pys protecting group yielding the Lucentis-linker monoconjugate 33c. The mixture of unmodified Lucentis and the Lucentis-linker monoconjugate 33c was buffer exchanged to 15 mM succinic acid, 100 mM sodium chloride, 5 mM Na$_2$EDTA, pH 4.0 and subsequently concentrated to a concentration of 28.7 mg/mL. The content of Lucentis-linker monoconjugate 33c in the mixture was 15% as determined by Ellman's assay.

79.7 mg of the Lucentis/Lucentis-linker monoconjugate 33c mixture in 15 mM succinic acid, 100 mM sodium chloride, 5 mM Na$_2$EDTA, pH 4.0 was added to 5.1 mg of maleimide functionalized hydrogel beads 5c, the pH was adjusted to pH 5 by addition of 0.5 M succinic acid, pH 6.0 and incubated overnight at room temperature yielding transient Lucentis-linker-hydrogel prodrug 33d. Excess maleimides were blocked by eight incubation steps with 1 molar equivalent (with respect to maleimide content of maleimide functionalized hydrogel beads 5c) 1 mM 2-mercaptoethanol in 15 mM succinic acid, 100 mM sodium chloride, 5 mM Na$_2$EDTA, pH 4.0 for 15 min at room temperature. In vitro release kinetic analysis to determine in vitro half-life of 33d was performed according to Example 7.

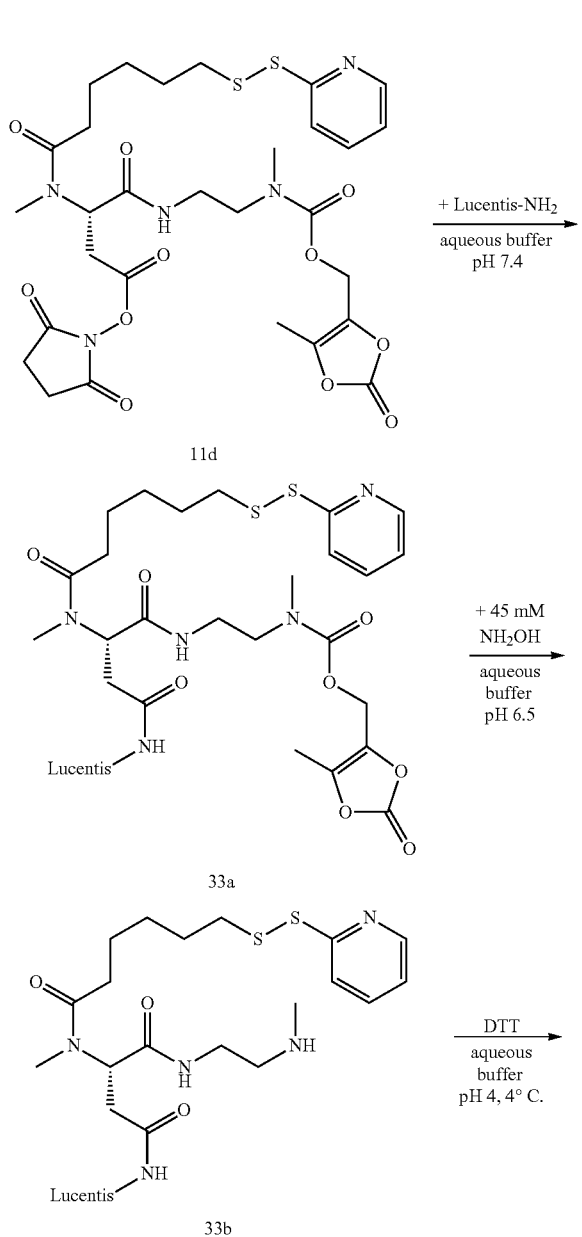

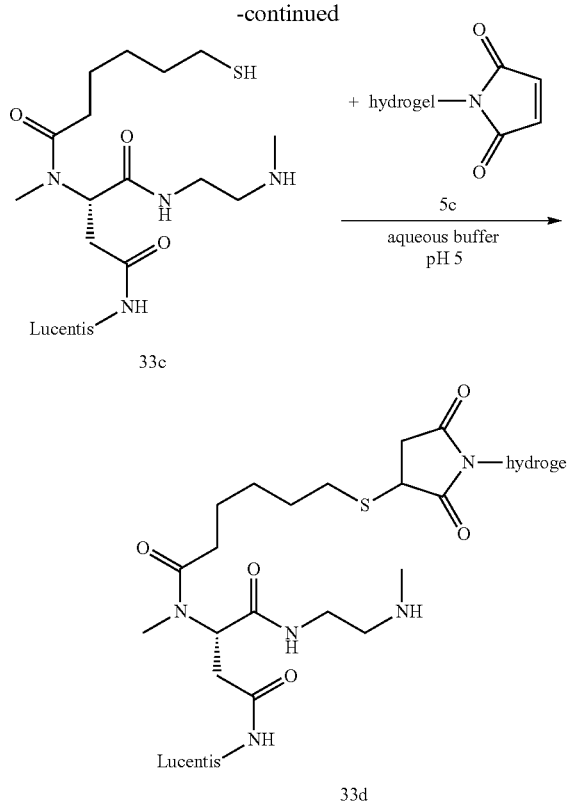

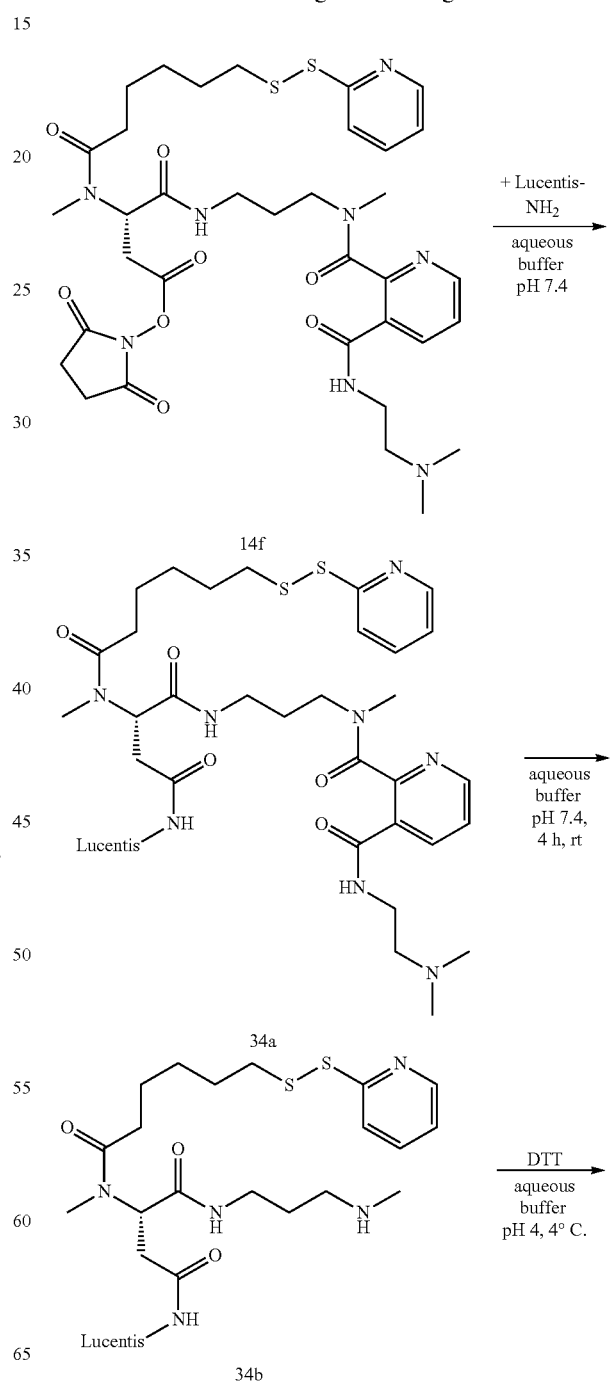

cinic acid, 100 mM sodium chloride, 5 mM Na₂EDTA, pH 4.0 and subsequently concentrated to a concentration of 17.2 mg/mL.

To 106.5 mg of the Lucentis/Lucentis-linker monoconjugate 34c mixture in 15 mM succinic acid, 100 mM sodium chloride, 5 mM Na₂EDTA, pH 4.0 1 molar equivalent with respect to the overall Lucentis content of maleimide containing histidine-tag 21 was added and the pH was adjusted to pH 5 by addition of 0.5 M succinic acid, pH 6.0. Incubation at room temperature for 4.5 h yielded the Lucentis-linker-histidine-tag conjugate 34d, which was purified by cation exchange chromatography from Lucentis and the excess maleimide containing histidine-tag 21.

Example 34

Synthesis of Transient Lucentis-Linker-Histidine-Tag Conjugate 34d 120 mg Lucentis (depicted in the scheme below as Lucentis-NH₂) (3 mL of 40 mg/mL Lucentis in 10 mM histidine, 10 wt % α,α-trehalose, 0.01% Tween20, pH 5.5) was buffer exchanged to 60 mM sodium phosphate, 100 mM sodium chloride, pH 7.4 and the concentration of Lucentis was adjusted to 20 mg/mL. Linker reagent 14f (only 1 regioisomer is depicted in the scheme below) was dissolved in DMSO to yield a concentration of 100 mM. 2 molar equivalents of linker reagent 14f relative to the amount of Lucentis were added to the Lucentis solution. The reaction mixture was mixed carefully and incubated for 5 min at room temperature. Subsequently, 1 additional molar equivalent of linker reagent 14f was added. Additional incubation for 5 min at room temperature yielded a mixture of unmodified Lucentis and the protected Lucentis-linker monoconjugate 34a. Incubation at room temperature for 4 h led to a quantitative conversion of Lucentis-linker monoconjugate 34a to Lucentis-linker monoconjugate 34b.

The mixture of Lucentis and Lucentis-linker monoconjugate 34b was buffer exchanged to 15 mM succinic acid, 100 mM sodium chloride, 5 mM Na₂EDTA, pH 4.0 and the protein concentration was adjusted to 11.8 mg/mL. The protein solution was cooled to 4° C. and 1 molar equivalent of 25 mM DTT in 15 mM succinic acid, 100 mM sodium chloride, 5 mM Na₂EDTA, pH 4.0 with respect to the overall Lucentis content was added to remove the Pys protecting group yielding the Lucentis-linker monoconjugate 34c. The mixture of unmodified Lucentis and the Lucentis-linker monoconjugate 34c was buffer exchanged to 15 mM suc-

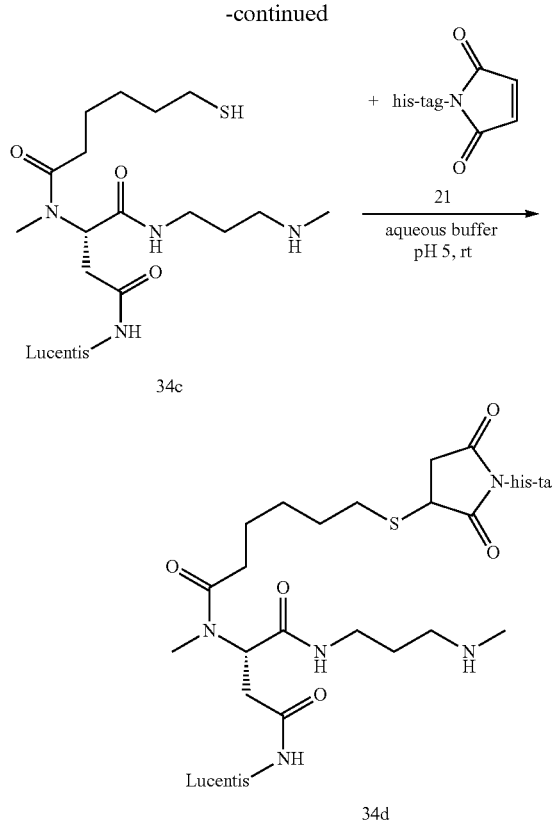

Example 35

In Vitro Release Kinetics—Determination of In Vitro Half-Life of Transient Histidine-Tag Conjugates Cation exchange chromatography purified Lucentis-linker-histidine-tag conjugate 34d was buffer exchanged to 60 mM sodium phosphate, 3 mM Na$_2$EDTA, 0.01% Tween20, pH 7.4 and the concentration was adjusted to 1 mg/mL. After incubation at 37° C. for different time intervals 200 µg protein sample was analyzed by cation exchange chromatography. Amount of released Lucentis was determined by comparison of the peak areas of released Lucentis and Lucentis-linker-histidine-tag conjugate 34d and plotted against incubation time. Curve fitting software was applied to determine first-order cleavage rates.

Example 36

Synthesis and Purification of Transient Tagged Lucentis-Linker Monoconjugate 36b 400 mg Lucentis (depicted in the scheme below as Lucentis-NH$_2$) (10 mL of 40 mg/mL Lucentis in 10 mM histidine, 10 wt % α,α-trehalose, 0.01% Tween20, pH 5.5) was buffer buffer exchanged to 60 mM sodium phosphate, 100 mM sodium chloride, pH 7.4 and the concentration of Lucentis was adjusted to 20.8 mg/mL. Linker reagent 17g was dissolved in DMSO to yield a concentration of 100 mM. 4.5 molar equivalents of linker reagent 17g relative to the amount of Lucentis were added to the Lucentis solution. The reaction mixture was mixed carefully and incubated for 5 min at room temperature yielding a mixture of unmodified Lucentis and the protected, tagged Lucentis-linker monoconjugate 36a.

The mixture of Lucentis and protected, tagged Lucentis-linker monoconjugate 36a was buffer exchanged to 60 mM sodium phosphate, 100 mM sodium chloride, pH 6.5. To remove the (5-methyl-2-oxo-1,3-dioxol-yl)-methyl oxocarbonyl protecting group of 36a 0.5 M NH$_2$OH (dissolved in 10 mM sodium citrate, 140 mM sodium chloride, 5 mM Na$_2$EDTA, pH 6.5) was added to a final concentration of 45 mM and the deprotection reaction was incubated at room temperature for 2.5 h yielding the tagged Lucentis-linker monoconjugate 36b which was separated from unmodified Lucentis by cation exchange chromatography.

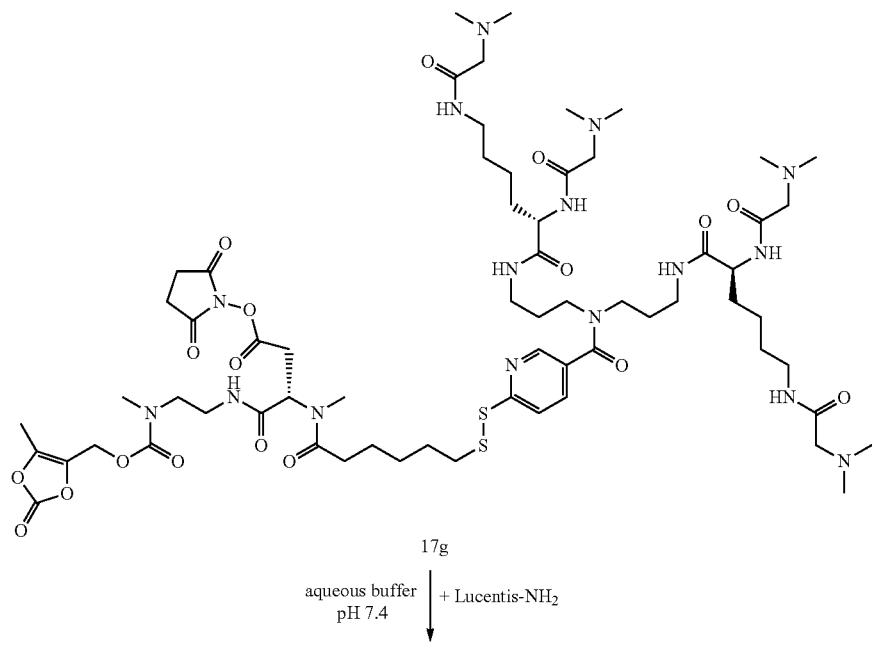

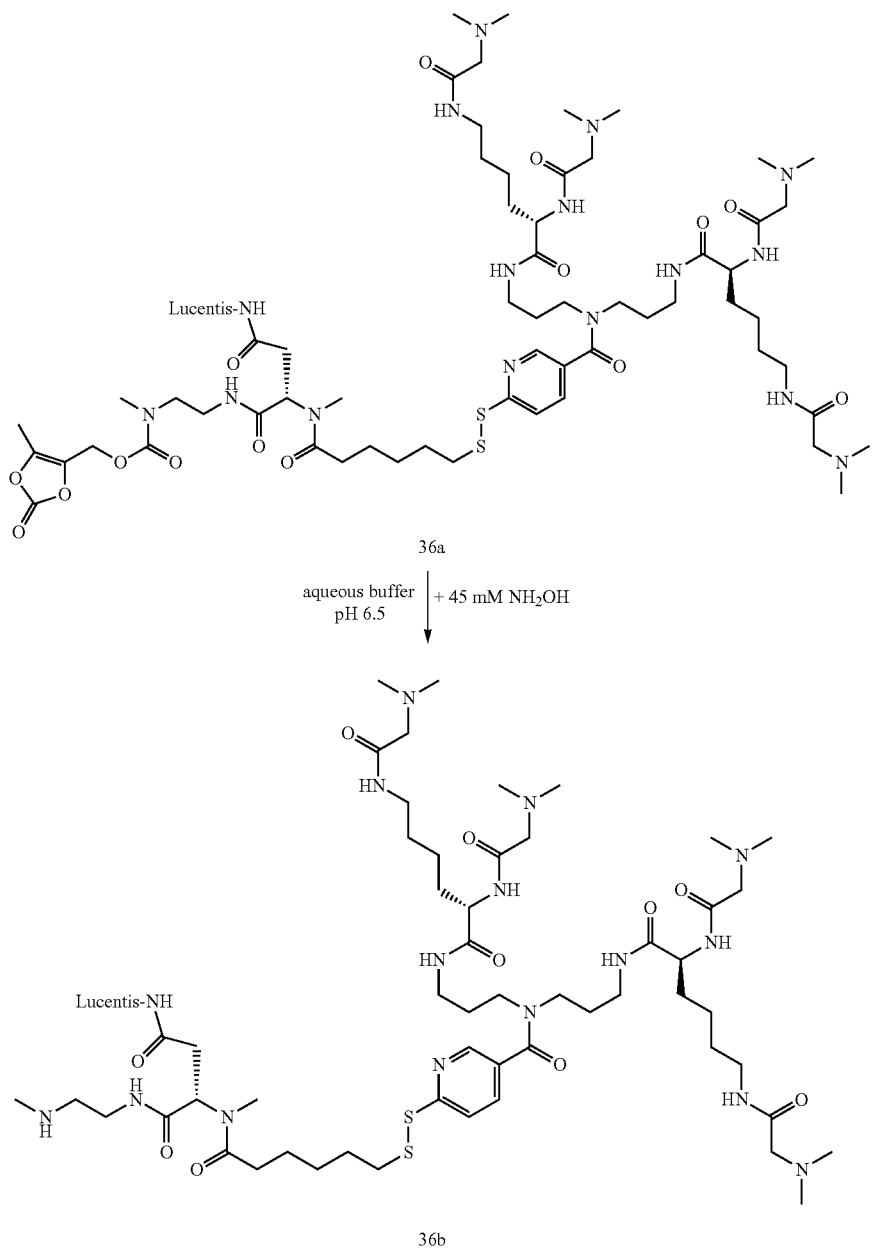

Example 37

Synthesis of Transient Lucentis-Linker-Hydrogel Prodrug 37a Using Thiol/Activated Disulfide Conjugation Chemistry

61.5 mg of the Lucentis/Lucentis-linker monoconjugate 33b mixture (c=41 mg/mL) in 15 mM succinic acid, 100 mM sodium chloride, 5 mM $Na_2EDTA$, pH 4.0 was added to 6.6 mg of thiol functionalized hydrogel beads 29. The hydrogel loading reaction was incubated for 60 h at 4° C. followed by 16 h at room temperature yielding transient Lucentis-linker-hydrogel prodrug 37a.

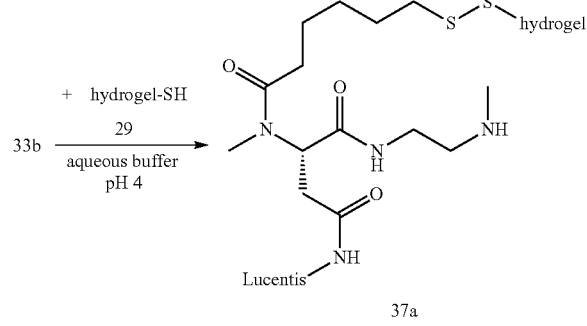

Example 38

Synthesis of Transient Lucentis-Linker-Hydrogel Prodrug 38a Using Thiol/Maleimide Conjugation Chemistry 10 mg Lucentis-linker monoconjugate 34c at a concentration of 20 mg/mL is added to 5 mg maleimide functionalized hydrogel 5c and the reaction mixture is incubated at pH 5 and room temperature overnight yielding the transient Lucentis-linker-hydrogel prodrug 38a. Excess maleimides are blocked by eight incubation steps with 1 molar equivalent (with respect to maleimide content of maleimide functionalized hydrogel beads 5c) 1 mM 2-mercaptoethanol in 15 mM succinic acid, 100 mM sodium chloride, 5 mM $Na_2EDTA$, pH 4.0 for 15 min at room temperature.

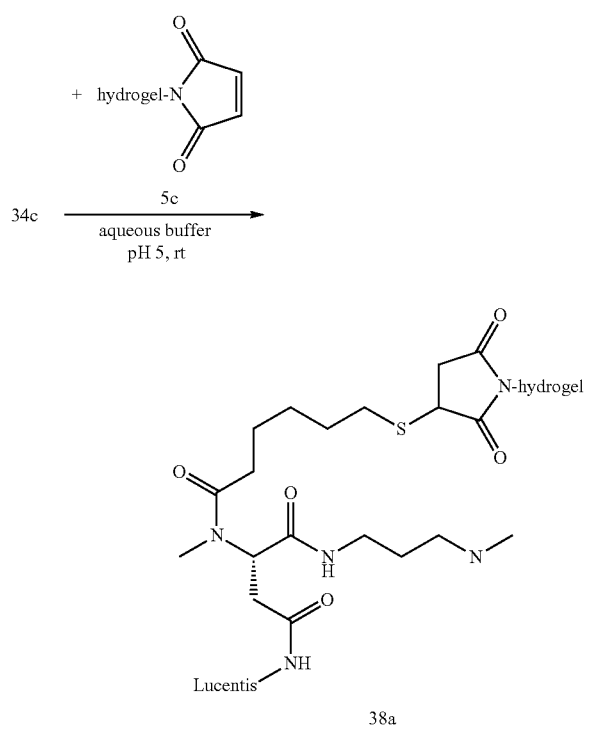

Example 39

Synthesis of Transient Lucentis-Linker-Hydrogel Prodrug 39a Using Thiol/Activated Disulfide Conjugation Chemistry 50 mg of the Lucentis/Lucentis-linker monoconjugate 34b mixture at an overall Lucentis concentration of 40 mg/mL in 15 mM succinic acid, 100 mM sodium chloride, 5 mM $Na_2EDTA$, pH 4.0 is added to 5 mg of thiol functionalized hydrogel beads 29 and the reaction mixture is incubated at room temperature overnight yielding the transient Lucentis-linker-hydrogel prodrug 39a. Excess thiol groups on the hydrogel are blocked by incubation with 5 molar equivalents (with respect to thiol content of thiol functionalized hydrogel beads 29) 1 mM solution of 31 in 15 mM succinic acid, 100 mM sodium chloride, 5 mM $Na_2EDTA$, pH 4.0 for 16 h at room temperature.

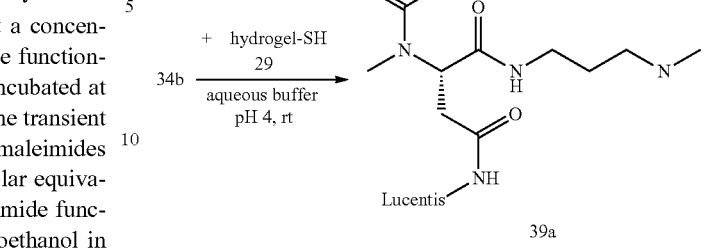

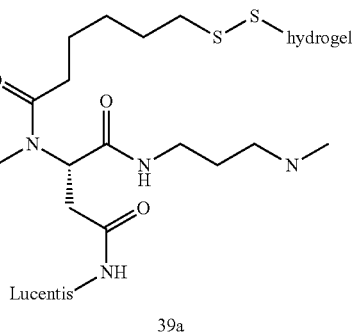

Example 40

Synthesis of Transient Lucentis-Linker-Histidine-Tag Conjugate 40a

Transient Lucentis-linker-histidine-tag conjugate 40a was prepared according to Example 33 using linker reagent 9c. Instead of maleimide functionalized hydrogel 5c 1 molar equivalent with respect to overall Lucentis content of maleimide functionalized histidine-tag 21 was used.

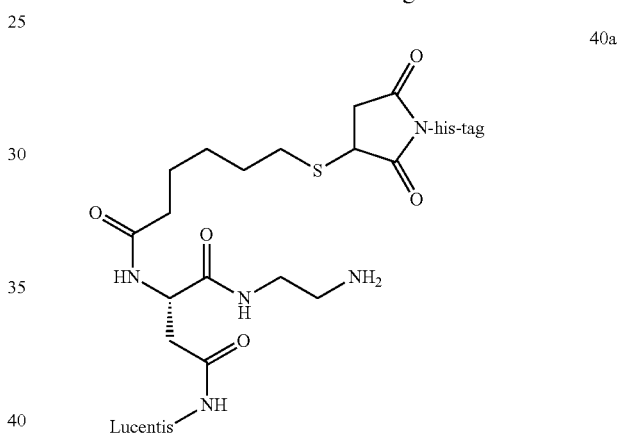

Example 41

Synthesis of Transient Lucentis-Linker-Histidine-Tag Conjugate 41a

Transient Lucentis-linker-histidine-tag conjugate 41a was prepared according to Example 34 using linker reagent 13g.

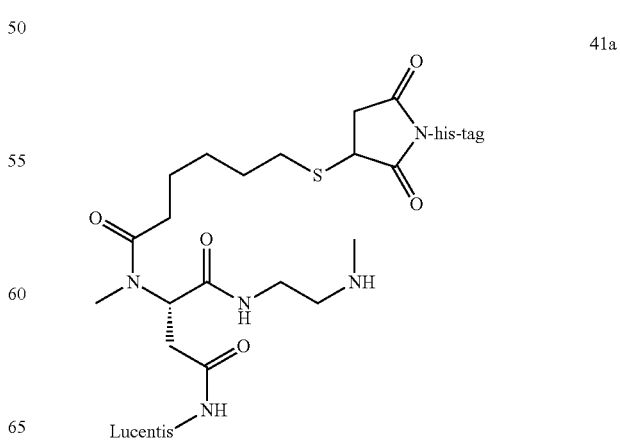

Example 42

Synthesis of Transient Lucentis-Linker-Hydrogel Prodrug 42a

Transient Lucentis-linker-hydrogel prodrug 42a was prepared according to Example 33 using linker reagent 15b. Due to the absence of the (5-methyl-2-oxo-1,3-dioxol-yl)-methyl oxocarbonyl protecting group no hydroxylamine assisted deprotection step was performed.

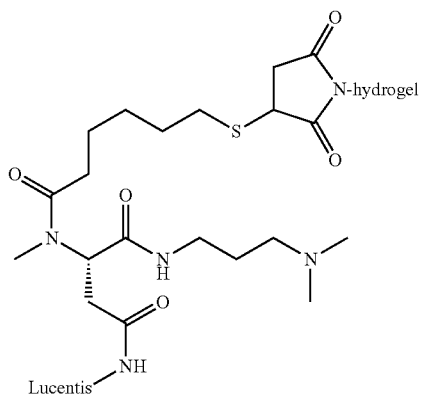

42a

Example 43

Synthesis of Transient Lucentis-Linker-Hydrogel Prodrug 43a

Transient Lucentis-linker-hydrogel prodrug 43a was prepared according to Example 33 using linker reagent 18i.

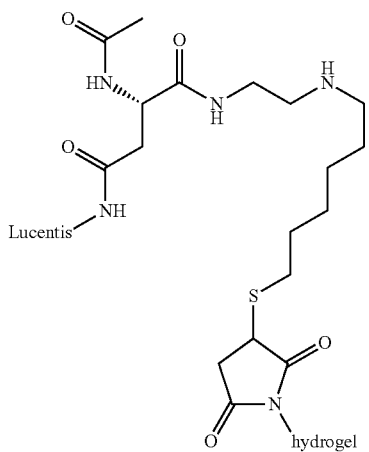

43a

TABLE 1

Half-lives of synthesized Lucentis-linker-hydrogel prodrugs and Lucentis-linker-histidine tag conjugates.

| Prodrug/Conjugate | Half-life at pH 7.4 and 37° C./d |
|---|---|
| 6c | 37 |
| 40a | 37 |
| 33d | 6 |
| 41a | 5 |
| 34d | 30 |
| 42a | 28 |
| 43a | 17 |

Example 44

Synthesis of Transient Lucentis-Linker-Hydrogel Prodrug 44a 1147 mg of the Lucentis/Lucentis-linker monoconjugate 6b mixture in 10 mM sodium phosphate, 2.7 mM potassium chloride, 140 mM sodium chloride, 5 mM $Na_2EDTA$, 0.01% Tween 20, pH 6.5 were added to 153 mg of maleimide functionalized hydrogel beads 5c and incubated overnight at room temperature yielding transient Lucentis-linker-hydrogel prodrug 44a.

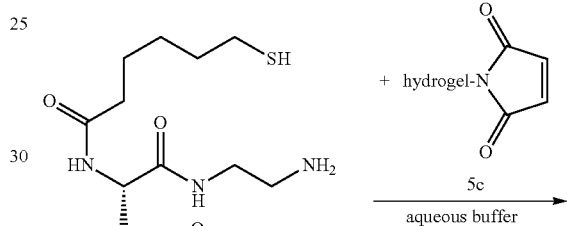

6b

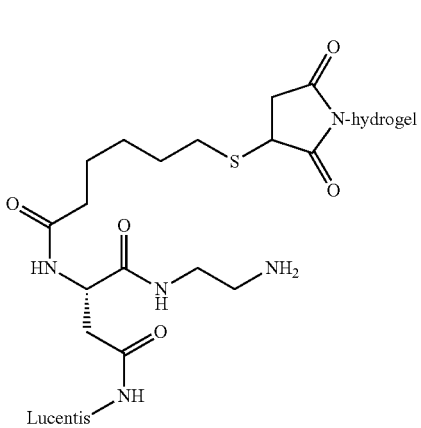

44a

Example 45

Evaluation of Binding Affinity of Lucentis Released from Lucentis-Linker-Hydrogel Prodrug 44a Active VEGF binding concentration of the Lucentis released from Lucentis-linker-hydrogel prodrug 44a was measured on a Biacore surface plasmon resonance system (Biacore T200, Pharmacia, Piscataway, N.J.). VEGF was covalently immobilized onto the carboxymethylated dextran sensor chip (CM5) using the amine coupling kit (GE Healthcare). The binding of Lucentis to VEGF was determined by monitoring the change in the resonance units before and after injection for 180 s. The active VEGF binding concentration was determined using a standard calibration curve prepared from serial dilution of reference material from 5 µg/ml to 0.156 µg/ml. The ratio of this active binding concentration by the total protein concentration determined by Bradford assay or UV-Vis absorbance gives the percent binding.

For Lucentis-linker-hydrogel prodrug 44a it was shown that Lucentis released after 28 days and after more than 120 days showed 80±10% binding.

Example 46

Ranibizumab Measurements and Analysis

For both groups, a qualified ligand-binding assay was designed to measure the concentrations of ranibizumab in rabbit vitreous matrix. For the Lucentis-linker-hydrogel prodrug 44a qualification, the hydrogel was determined to not interfere with ranibizumab quantitation at all concentrations tested. The assay used recombinant human VEGF-A to capture ranibizumab in rabbit vitreous samples. Bound ranibizumab was detected using an anti-human F(ab')2 conjugated to horseradish peroxidase (HRP), and a peroxidase substrate (TMB) was used for color development. The drug level was quantitated using absorbance spectrophotometry using a microplate reader. The concentration of ranibizumab in the study samples was calculated from the standard curve, and the minimum quantifiable concentration (MQC) in rabbit vitreous matrix was 1.5 ng/mL. The vitreous concentrations were plotted and analyzed using MATLAB software.

TABLE 2

Ranibizumab concentrations (ng/mL) measured in vitreous humor after a 0.5 mg/eye intravitreal dose of Ranibizumab

| Time point (day) | Animal | Eye[a] | Individual Animals ng/mL | Mean (ng/mL) | Std Dev of Mean |
|---|---|---|---|---|---|
| 0.25 | A1001 | L | 192186 | 201106 | 45418 |
| 0.25 | A1001 | R | 231717 | | |
| 0.25 | A1002 | L | 239944 | | |
| 0.25 | A1002 | R | 140579 | | |
| 2 | B1003 | L | 151619 | 153967 | 24199 |
| 2 | B1003 | R | 124811 | | |
| 2 | B1004 | L | 155490 | | |
| 2 | B1004 | R | 183949 | | |
| 7 | C1005 | L | 37730 | 58209 | 17247 |
| 7 | C1005 | R | 50149 | | |
| 7 | C1006 | L | 73097 | | |
| 7 | C1006 | R | 71859 | | |
| 11 | D1007 | L | 17493 | 17855 | 4869 |
| 11 | D1007 | R | 13029 | | |
| 11 | D1008 | L | 16311 | | |
| 11 | D1008 | R | 24587 | | |
| 14 | E1009 | L | 14788 | 11332 | 2983 |
| 14 | E1009 | R | 9484 | | |
| 14 | E1010 | L | 12768 | | |
| 14 | E1010 | R | 8288 | | |

[a]L = left eye, R = right eye

TABLE 3

Ranibizumab concentrations (ng/mL) measured in the vitreous humor following a 1.7 mg/eye intravitreal dose of Lucentis-linker-hydrogel prodrug 44a.

| Time point (day) | Animal | Eyes[a] | Individual Animals ng/mL | Mean (ng/mL) | Std Dev of Mean |
|---|---|---|---|---|---|
| 0.25 | A2001 | L | 8097 | 10449 | 2771 |
| 0.25 | A2001 | R | 14261 | | |
| 0.25 | A2002 | L | 8744 | | |
| 0.25 | A2002 | R | 10696 | | |
| 2 | B2003 | L | 41525 | 37010 | 5387 |
| 2 | B2003 | R | 34128 | | |
| 2 | B2004 | L | 41534 | | |
| 2 | B2004 | R | 30854 | | |
| 7 | C2005 | L | 61395 | 64741 | 4887 |
| 7 | C2005 | R | 68766 | | |
| 7 | C2006 | L | 59709 | | |
| 7 | C2006 | R | 69094 | | |
| 11 | C2007 | L | 52090 | 44180 | 7745 |
| 11 | C2007 | R | 34221 | | |
| 11 | C2008 | L | 48043 | | |
| 11 | C2008 | R | 42367 | | |
| 14 | E2009 | L | 46066 | 46112 | 8243 |
| 14 | E2009 | R | 35003 | | |
| 14 | E2010 | L | 48671 | | |
| 14 | E2010 | R | 54706 | | |
| 21 | F2011 | L | NO SAMPLE[b] | ND | ND |
| 21 | F2011 | R | LTR | | |
| 21 | F2012 | L | LTR | | |
| 21 | F2012 | R | LTR | | |
| 24 | G2013 | L | 15259 | 12901 | 7308 |
| 24 | G2013 | R | 2514 | | |
| 24 | G2014 | L | 19609 | | |
| 24 | G2014 | R | 14224 | | |
| 28 | H2015 | L | LTR | | ND |
| 28 | H2015 | R | LTR | ND | |
| 28 | H2016 | L | 23589 | | |
| 28 | H2016 | R | 23284 | | |

[a]L = left eye, R = right eye
[b]no sample in tube
LTR = lower than reportable
ND = not determined Abbreviations aq. aqueous
Asp aspartate
Boc tert-butyloxycarbonyl
CIEC cationic ion exchange chromatography
COMU (1-Cyano-2-ethoxy-2-oxoethylidenaminooxy)dimethylamino-morpholino-carbenium hexafluorophosphate
DBU 1,8-diazabicyclo(5.4.0)undec-7-ene
DCC dicyclohexylcarbodiimide
DCM dichloromethane
DIPEA diisopropylethylamine
DMAP dimethylaminopyridine
DMF dimethylformamide
DMSO dimethylsulfoxide
DTT dithiothreitol
EDTA ethylenediaminetetraacetic acid
Fmoc fluorenylmethyloxycarbonyl
HATU 1-[Bis(dimethylamino)methylene]-1H-1,2,3-triazolo[4,5-b]pyridinium 3-oxid hexafluorophosphate
HFIP hexafluoroisopropanol
HPLC high performance liquid chromatography
iPrOH isopropanol
Lys lysine
max. maximal
Maleimide-NH-PEG12-PFE N-(3-maleimidopropyl)-39-amino-4,7,10,13,16,19,22,25,28,31,34,37-dodecaoxa-nonatriacontanoic acid pentafluorophenyl ester Me methyl
MeOAc methyl acetate
MeOH methanol
MES 2-(N-morpholino)ethanesulfonic acid
MMT 4-methoxytriphenylmethyl
MS mass spectrometry
MTBE methyl-tert-butyl ether
NHS N-hydroxysuccinimide
Oxyma Pure ethyl 2-cyano-2-(hydroxyimino)acetate
PEG polyethyleneglycol
Pys 2-pyridinesulfenyl
PyBOP benzotriazol-1-yl-oxytripyrrolidinophosphonium hexafluorophosphate
RP-HPLC reversed phase high performance liquid chromatography
RT room temperature
sat. saturated
Su N-hydroxysuccinimidyl
tBu and t-Bu tert.-butyl
TAN 1,5,9-triazanonane
TES triethylsilane
TFA trifluoroacetic acid
THF tetrahydrofurane
TLC thin layer chromatography
TMEDA N,N,N',N'-tetramethylethylene diamine
Tmob 2,4,6-trimethoxybenzyl
Trt trityl
TSTU O—(N-succinimidyl)-N,N,N',N'-tetramethyluronium tetrafluoroborate

The invention claimed is:
1. A method for the treatment of one or more ocular conditions, the method comprising:
  intraocularly administering, by injecting into the aqueous humor, the vitreous body, or the lens of an eye, a pharmaceutical composition comprising:
    one or more pharmaceutically acceptable excipient(s); and
    a VEGF neutralizing carrier-linked prodrug comprising a VEGF neutralizing biologically active moiety covalently and reversibly bound to a reversible prodrug linker moiety, wherein the reversible prodrug linker moiety is attached to a hydrogel carrier moiety, either directly or via a spacer moiety;
  wherein the step of intraocularly administering comprises two intraocular administrations of the prodrug; and
  wherein a time period between the two intraocular administrations of the VEGF neutralizing prodrug is at least 10 weeks.
2. The method of claim 1;
  wherein the carrier of the carrier-linked prodrug is a PEG-based hydrogel.
3. The method of claim 1;
  wherein the prodrug comprised in the pharmaceutical composition has a concentration of 5 to 200 mg prodrug/ml pharmaceutical composition.
4. The method of claim 1;
  wherein the composition comprises 8 to 80 weight percent of VEGF neutralizing biologically active moiety based on the total weight of the prodrug.
5. The method of claim 1;
  wherein the injection is carried out with an injection volume ranging from 10 to 200 µl per injection.
6. The method of claim 1;
  wherein the VEGF neutralizing prodrug comprises in bound form at least one biologically active moiety selected from the group of drugs consisting of:
    antisense RNA, antisense DNA, ribozymes, and RNAi molecules targeting a VEGF nucleic acid;
    anti-VEGF aptamers, anti-VEGF antibodies, anti-VEGF antibody fragments, DARPins, and soluble VEGF receptor decoys that prevent binding of a VEGF to its cognate receptor;
    antisense, ribozymes, and RNAi molecules targeting a cognate VEGF receptor (VEGFR) nucleic acid;
    anti-VEGFR aptamers and anti-VEGFR antibodies that bind to a cognate VEGFR receptor;
    anti-VEGFR antibody fragments that bind to a cognate VEGFR receptor; and
    VEGFR tyrosine kinase inhibitors.
7. The method of claim 1;
  wherein the VEGF neutralizing prodrug comprises in bound form at least one biologically active moiety selected from the group consisting of ranibizumab, bevacizumab, pegaptanib, aflibercept, MP0112, KH902, ESBA1008, AL 39324, ALG-1001, and bevasiranib.
8. The method of claim 1;
  wherein the VEGF neutralizing prodrug comprises in bound form ranibizumab.
9. The method of claim 1;
  wherein the VEGF neutralizing prodrug comprises a moiety of formula (F-i):

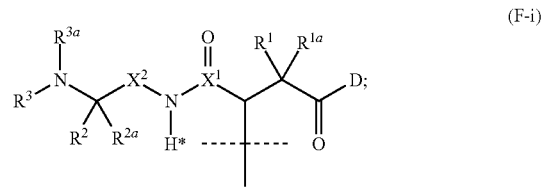

(F-i)

wherein:
  D is ranibizumab;
  the dashed line indicates attachment to the carrier or to the optional spacer moiety;
  $X^1$ is C or S(O);
  $X^2$ is $C(R^7, R^{7a})$ or $C(R^7, R^{7a})$—$C(R^8, R^{8a})$;
  $R^1$, $R^{1a}$, $R^2$, $R^{2a}$, $R^3$, $R^{3a}$, $R^7$, $R^{7a}$, $R^8$, and $R^{8a}$ are independently selected from the group consisting of H and $C_{1-4}$ alkyl;
  optionally, one or more of the pair(s) $R^{1a}/R^{4a}$, $R^{1a}/R^{5a}$, $R^{4a}/R^{5a}$, $R^{4a}/R^{5a}$, $R^{7a}/R^{8a}$ form a chemical bond;
  optionally, one or more of the pair(s) $R^1/R^{1a}$, $R^2/R^{2a}$, $R^4/R^{4a}$, $R^5/R^{5a}$, $R^7/R^{7a}$, $R^8/R^{8a}$ are joined together with the atom to which they are attached to form a $C_{3-7}$ cycloalkyl or a 4-membered to 7-membered heterocyclyl;
  optionally, one or more of the pair(s) $R^1/R^4$, $R^1/R^5$, $R^1/R^6$, $R^4/R^5$, $R^7/R^8$, $R^2/R^3$ are joined together with the atoms to which they are attached to form a ring A;
  optionally, $R^3/R^{3a}$ are joined together with the nitrogen atom to which they are attached to form a 4-membered to 7-membered heterocycle;
  A is selected from the group consisting of phenyl, naphthyl, indenyl, indanyl, tetralinyl, $C_{3-10}$ cycloalkyl, 4-membered to 7-membered heterocyclyl, and 8-membered to 11-membered heterobicyclyl; and optionally, the moiety of formula (F-i) is further substituted, provided that the hydrogel marked with the asterisk in formula (F-i) is not replaced by a substituent, and that $R^3$ and $R^{3a}$ are independently of each other H or are connected to N through an $SP^3$-hybridized carbon atom.

10. The method of claim 9;

wherein $X^1$ is C.

11. The method of claim 9;

wherein the VEGF neutralizing prodrug comprises a moiety of formula (f-ii):

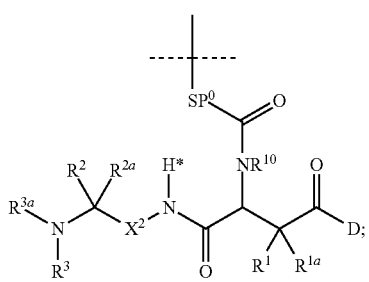

(F-ii)

wherein:
the dashed line indicates attachment to the carrier;
$R^1$, $R^{1a}$, $R^2$, $R^{2a}$, $R^3$, $R^{3a}$, $X^2$, and D are used as defined in claim 9;
$R^{10}$ is selected from H and $C_{1-6}$ alkyl; and
$SP^9$ is a further spacer moiety, which together with the moiety —$NR^{10}C(O)$— forms the optional spacer moiety; and
wherein the moiety of formula (F-ii) is optionally further substituted, provided that the hydrogel marked with the asterisk in formula (F-ii) is not replaced by a substituent and that $R^3$ and $R^{3a}$ are independently of each other H or are connected to N through an $SP^3$-hybridized carbon atom.

12. The method of claim 9;

wherein $R^1$ and $R^{1a}$ are both H.

13. The method of claim 9;

wherein the VEGF neutralizing prodrug comprises a moiety of formula (F-iiia) or (F-iiib):

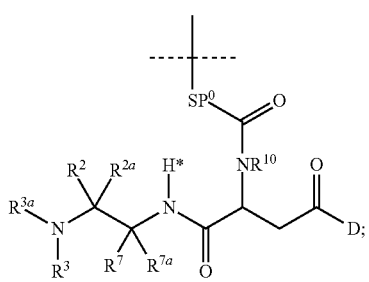

(F-iiia)

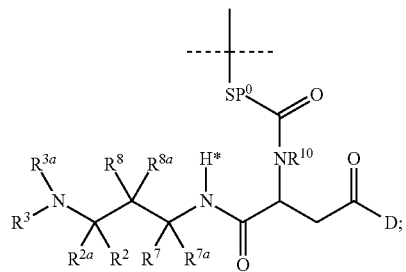

(F-iiib)

wherein:
the dashed line indicates attachment to the carrier;
$R^2$, $R^{2a}$, $R^3$, $R^{3a}$, $R^7$, $R^{7a}$, $R^8$, $R^{8a}$, $X^2$, and D are used as defined in claim 9; and
$R^{10}$ is selected from H and $C_{1-6}$ alkyl; and
$SP^9$ is a further spacer moiety, which together with the moiety —$NR^{10}C(O)$— forms the optional spacer moiety; and
wherein the moiety of formula (F-iiia) or (F-iiib) is optionally further substituted, provided that the hydrogen marked with the asterisk in formula (F-iiia) and (F-iiib) is not replaced by a substituent, and that $R^3$ and $R^{3a}$ are independently of each other H or are connected to N through an $SP^3$-hybridized carbon atom.

14. The method of claim 9;

wherein the VEGF neutralizing prodrug comprises a moiety of formula (F-iva) or (F-ivb):

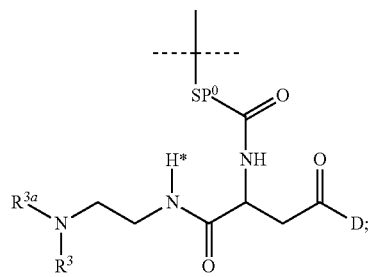

(F-iva)

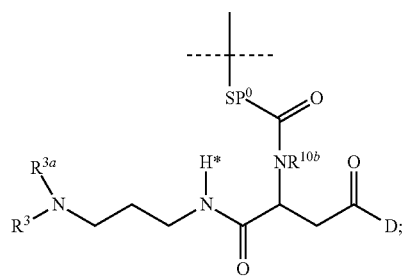

(F-ivb)

wherein:
the dashed line indicates attachment to the carrier;
$R^3$ and $R^{3a}$ are used as defined in claim 9;
$R^{10b}$ is $C_{1-6}$ alkyl; and
$SP^0$ is a further spacer moiety, which together with the moiety —$NHC(O)$— or —$NR^{10}C(O)$— forms the optional spacer moiety; and wherein the moiety of formula (F-iva) or (F-ivb) is optionally further substituted, provided that the hydrogen marked with the asterisk is not replaced by a substituent and that $R^3$ and $R^{3a}$ are independently of each other H or are connected to N through an $SP^3$-hybridized carbon atom.

15. The method of claim 9;
wherein:
$R^3$ is H; and
$R^{3a}$ is methyl.

16. The method of claim 9;
wherein $R^3$ and $R^{3a}$ of are both H.

17. The method of claim 1;
wherein the ocular condition is a disease characterized by ocular neovascularization.

18. The method of claim 17;
wherein the disease characterized by ocular neovascularization is an ocular disease selected from the group consisting of optic disc neovascularization, iris neovascularization, retinal neovascularization, choroidal neovascularization, corneal neovascularization, vitreal neovascularization, glaucoma, pannus, pterygium, macular edema, macular degeneration, age-related macular degeneration, diabetic retinopathy, diabetic retinal ischemia, diabetic macular edema, vascular retinopathy, retinal degeneration, retrolental fibroplasias, retinoblastoma, retinopathy of prematurity of macular degeneration, corneal graft neovascularization, central retinal vein occlusion, pathological myopia, ocular tumors, uveitis, inflammatory diseases of the eye, and proliferative vitreoretinopathy.

19. The method of claim 1;
wherein the pharmaceutical composition further comprises at least one drug in its free form selected from the group consisting of:
   antisense RNA, antisense DNA, ribozymes, and RNAi molecules targeting a VEGF nucleic acid;
   anti-VEGF aptamers, anti-VEGF antibodies, anti-VEGF antibody fragments, DARPins, anticalins, lipocalins, and soluble VEGF receptor decoys that prevent binding of a VEGF to its cognate receptor;
   antisense, ribozymes, and RNAi molecules targeting a cognate VEGF receptor (VEGFR) nucleic acid;
   anti-VEGFR aptamers and anti-VEGFR antibodies that bind to a cognate VEGFR receptor;
   anti-VEGFR antibody fragments that bind to a cognate VEGFR receptor; and
   VEGFR tyrosine kinase inhibitors.

20. The method of claim 1;
wherein the pharmaceutical composition further comprises one or more additional prodrug(s), which one or more additional prodrug(s) comprise(s) in bound form at least one biologically active moiety selected from the group consisting of:
   antisense RNA, antisense DNA, ribozymes, and RNAi molecules targeting a VEGF nucleic acid;
   anti-VEGF aptamers, anti-VEGF antibodies, anti-VEGF antibody fragments, DARPins, anticalins, lipocalins, and soluble VEGF receptor decoys that prevent binding of a VEGF to its cognate receptor;
   antisense, ribozymes, and RNAi molecules targeting a cognate VEGF receptor (VEGFR) nucleic acid;
   anti-VEGFR aptamers and anti-VEGFR antibodies that bind to a cognate VEGFR receptor;
   anti-VEGFR antibody fragments that bind to a cognate VEGFR receptor; and
   VEGFR tyrosine kinase inhibitors.

21. The method of claim 1;
wherein the carrier of the carrier-linked prodrug is a hyaluronic-acid-based hydrogel.

\* \* \* \* \*